United States Patent
Kubo et al.

[11] Patent Number: 6,143,764
[45] Date of Patent: Nov. 7, 2000

[54] QUINOLINE AND QUINAZOLINE DERIVATIVES INHIBITING PLATELET-DERIVED GROWTH FACTOR RECEPTOR AUTOPHOSPHORYLATION AND PHARMACEUTICAL COMPOSITIONS CONTAINING THE SAME

[75] Inventors: Kazuo Kubo; Shinichi Ohyama; Toshiyuki Shimizu; Tsuyoshi Nishitoba; Shinichiro Kato; Hideko Murooka; Yoshiko Kobayashi, all of Takasaki, Japan

[73] Assignee: Kirin Beer Kabushiki Kaisha, Tokyo-to, Japan

[21] Appl. No.: 09/068,660

[22] PCT Filed: Nov. 5, 1996

[86] PCT No.: PCT/JP96/03229

§ 371 Date: May 6, 1998

§ 102(e) Date: May 6, 1998

[87] PCT Pub. No.: WO97/17329

PCT Pub. Date: May 15, 1997

[30] Foreign Application Priority Data

Nov. 7, 1995 [JP] Japan .................................. 7-313555
Feb. 23, 1996 [JP] Japan .................................. 8-62121

[51] Int. Cl.⁷ .................. A61K 31/47; A61K 31/535; C07D 413/00; C07D 215/16; C07D 215/20
[52] U.S. Cl. .................. 514/312; 514/235.2; 514/253; 544/128; 544/235; 544/238; 544/363; 544/405; 154/155; 154/154
[58] Field of Search .................. 546/154, 155; 544/128, 238, 363, 405, 235; 514/253, 312, 235.2

[56] References Cited

U.S. PATENT DOCUMENTS 5,821,244  10/1998  Schaper .................. 514/248

FOREIGN PATENT DOCUMENTS 08507539  8/1996  Japan .
2636636   7/1997  Japan .
98/13350  4/1998  WIPO .

OTHER PUBLICATIONS

CA 122:9884, Schaper, 1994.
CA 120:299513, Kawashima, 1993.
CA 99:88018, Gall–Istok, 1983.
CA 76:42038, Wright, 1971.

Primary Examiner—D. Margaret Seaman
Attorney, Agent, or Firm—Foley & Lardner

[57] ABSTRACT

The present invention relates to novel quinoline derivatives and quinazoline derivatives represented by the following formula (I):

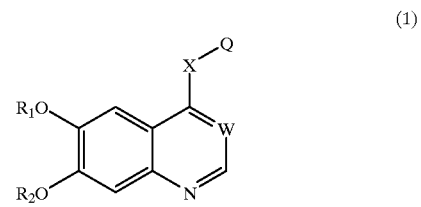

[wherein $R_1$ and $R_2$ are each independently H or $C_1$–$C_4$-alkyl, or $R_1$ and $R_2$ together form $C_1$–$C_3$-alkylene, X is O, S or $CH_2$, W is CH or N, and Q is a substituted aryl group or substituted heteroaryl group] and their pharmaceutically acceptable salts, having platelet-derived growth factor receptor autophosphorylation inhibitory activity, to pharmaceutical compositions containing these compounds, and to methods for the treatment of diseases associated with abnormal cell growth such as tumors.

52 Claims, No Drawings

QUINOLINE AND QUINAZOLINE DERIVATIVES INHIBITING PLATELET-DERIVED GROWTH FACTOR RECEPTOR AUTOPHOSPHORYLATION AND PHARMACEUTICAL COMPOSITIONS CONTAINING THE SAME

This application is a 371 of PCT/JP96/03229, filed Nov. 5, 1996.

FIELD OF THE INVENTION

The present invention relates to novel quinoline derivatives and quinazoline derivatives having an inhibitory action against abnormal cell growth and to their pharmaceutically acceptable salts. More specifically, the present invention relates to novel quinoline derivatives and quinazoline derivatives having an inhibitory action against autophosphorylation of the platelet-derived growth factor receptor and to their pharmaceutically acceptable salts.

BACKGROUND OF THE INVENTION

Growth factors such as insulin, the epidermal growth factor and the platelet-derived growth factor (hereinafter referred to as PDGF) have an important role in cell growth. In particular, PDGF is known to be a powerful cell growth factor related to the control of cell growth and division (Cell 46, 155 (1986)). However, in diseases or pathophysiological situations such as leukemia, cancers, psoriasis, glomerular nephritis, organofibrosis, atherosclerosis, restenosis after percutaneous coronary angioplasty or bypass surgery and rheumatoid arthritis, abnormal production of PDGF or PDGF receptor occurs at the pathophysiological sites, and abnormal cell growth is observed at the pathophysiological sites in such diseases. Namely, this is an excess of cell growth signals associated with overproduction of the PDGF or PDGF receptors. Thus, it is necessary to suppress cell growth signal transduction to improve these pathophysiological situations.

In one trial, it was reported that abnormal cell growth in pathophysiological situations was suppressed by administration of an anti-PDGF antibody (J. Exp. Med. 175, 1413 (1992)); however, there are problems such as in vivo stability and methods of administration as a therapeutic agent because the anti-PDGF antibody is a protein molecule.

On the other hand, in cells, PDGF is known to bind to the PDGF receptor to activate tyrosine kinase present in this receptor. This receptor tyrosine kinase relates to intracellular signal transduction via autophosphorylation of the receptor itself and plays an important role in cell growth. In pathophysiological situations, this intracellular signal transduction is considered to be excessive. Therefore, inhibition of PDGF receptor autophosphorylation can be considered as another possible strategy to suppress cell growth signal transduction.

Examples of suppressing cell growth using the PDGF receptor autophosphorylation inhibitors, which are low molecular weight compounds, are described in the literature (Cancer Research 54, 6106 (1994); Proc. Natl. Acad. Sci. USA. 92, 2558 (1995)). Therefore, PDGF receptor autophosphorylation inhibitors could be useful in many diseases such as leukemia, cancers, psoriasis, glomerular nephritis, organofibrosis, atherosclerosis, restenosis after percutaneous coronary angioplasty or bypass surgery and rheumatoid arthritis.

Examples of previously known PDGF receptor autophosphorylation inhibitors include 3-arylquinolines (J. Med. Chem. 37, 2627 (1994); J. Med. Chem. 37, 2129 (1994) and Publication of Japanese Patent Laid-open No. 94/507643), 3-arylquinoxalines (Cancer Research 54, 6106 (1994)), and 4-pyridyl-2-arylpyrimidines (Proc. Natl. Acad. Sci. USA. 92, 2558 (1995)).

However, as far as the present inventors know, compounds which have a structure in which an aryl group or heteroaryl group is bonded to position 4 of the quinoline backbone or quinazoline backbone via one oxygen atom, sulfur atom or carbon atom and which have a PDGF receptor autophosphorylation inhibitory activity are not known.

Furthermore, as to previously known quinoline derivatives, {4-[(7-chloro-4-quinolinyl)oxy]phenyl}(4-fluorophenyl)methanone is described in Publication of Examined Japanese Patent Application No. 89/246263. This known compound is used as a fungicide, and there are no reports as to its PDGF receptor autophosphorylation inhibitory activity.

Furthermore, 4-arylquinoline derivatives are described in J. Med. Chem. 14, 1060 (1971), Acta Chim. Hung 112, 241 (1983), Publication of Examined Japanese Patent Application No. 88/51375, German Patent No. 3101544, Publication of Examined Japanese Patent Application No. 89/246263, and U.S. Pat. No. 3,936,461. These known compounds are each reported as an antihypertensive agent or intermediate for its production, agent to prevent harmful organisms (preservative), plant growth control agent, fungicide or anti-angina agent, respectively, and there are no reports as to their PDGF receptor autophosphorylation inhibitory activity.

Consequently, the development of novel compounds having the PDGF receptor autophosphorylation inhibitory activity would be of great industrial benefit.

A major objective of the present invention is to provide novel compounds having the PDGF receptor autophosphorylation inhibitory activity.

DISCLOSURE OF THE INVENTION

As a result of intensive studies to attain the abovementioned objective, the present inventors found that compounds having a structure in which an aryl group or heteroaryl group is bound to position 4 of the quinoline backbone or quinazoline backbone via one oxygen atom, sulfur atom or carbon atom best serve the objective, and thus came to complete the present invention based on this finding.

Namely, the present invention is to provide quinoline derivatives and quinazoline derivatives represented by the following formula (I), and pharmaceutically acceptable salts thereof:

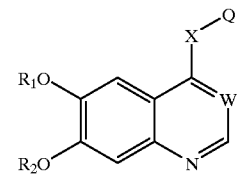

(1)

{wherein $R_1$ and $R_2$ are each independently H, $C_1$–$C_5$-alkyl, or $R_1$ and $R_2$ together form $C_1$–$C_3$-alkylene, and W is CH or N, 1. when W is CH, (a) X is O or S, and Q is a phenyl group represented by formula (II):

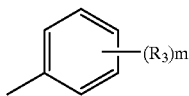
(II)

[wherein m is 1, 2 or 3, $R_3$ is each independently CN, OH, halogen, $C_1$–$C_5$-alkyl, $C_1$–$C_4$-alkoxy or $C_2$–$C_4$-acyl], a group represented by formula (III):

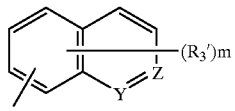
(III)

[wherein m is as defined as described above, $R_3'$ is each independently OH, $C_1$–$C_5$-alkyl, $C_1$–$C_4$-alkoxy, and Y and Z are both or each independently N or CH], or a group represented by formula (IV):

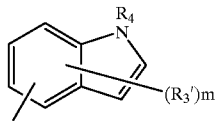
(IV)

[wherein m and $R_3'$ are as defined as described above, and $R_4$ is H, $C_1$–$C_5$-alkyl or $C_2$–$C_4$-acyl], and
(b) X is O, S or $CH_2$, and Q is a group represented by formula (V):

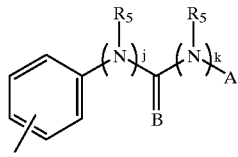
(V)

[wherein j and k are each independently 0 or 1, $R_5$ is each independently H or $C_1$–$C_4$-alkyl, A is $C_1$–$C_8$-alkyl, $C_1$–$C_5$-alkenyl, cyclic ($C_3$–$C_{10}$) alkyl, $C_1$–$C_4$-alkoxycarbonyl, phenyl, naphthyl, furyl, thienyl, benzoyl, substituted benzoyl, $C_2$–$C_4$-acyl, or 5- or 6-membered monocyclic or 9- or 10-membered bicyclic heteroaryl group having 1 or 2 nitrogen atoms and optionally having another hetero atom selected from the group consisting of nitrogen, oxygen and sulfur atoms, these alkyl group, aryl group and heteroaryl group represented by A may have 1 to 5 substituting groups selected from the group consisting of CN, $NO_2$, OH, $NH_2$, halogen, $C_1$–$C_5$-alkyl, cyclic ($C_3$–$C_{10}$) alkyl, $C_1$–$C_4$-alkoxy, $C_1$–$C_4$-alkoxycarbonyl, $C_1$–$C_5$-acyl, $C_1$–$C_5$-acyloxy, $C_1$–$C_3$-alkylenedioxy, $C_1$–$C_4$-alkylamino, di-($C_1$–$C_4$-alkyl) amino, $CO_2H$, $CONH_2$, N-($C_1$–$C_4$-alkyl)amido, N,N-di-($C_1$–$C_4$-alkyl)amido, $C_2$–$C_4$-alkylamido, trifluoromethyl, $C_1$–$C_4$-alkylthio, phenyl, substituted phenyl, phenoxy, substituted phenoxy, phenylthio, substituted phenylthio, phenyl ($C_1$–$C_4$-alkyl), substituted phenyl($C_1$–$C_4$-alkyl), pyridyl, pyrazinyl, pyrimidinyl, pyridazinyl, pyrrolidinyl, piperidinyl, piperazinyl, homopyperazinyl, morpholinyl, quinolyl, quinazolinyl, benzoyl, substituted benzoyl and $C_2$–$C_4$-acyl, and B is O, S, NH, NCN, $NR_6$ or $NOR_6$ (wherein $R_6$ is $C_1$–$C_5$-alkyl), 2. when W is N, X is O, S or $CH_2$, and Q is represented by formula (V):

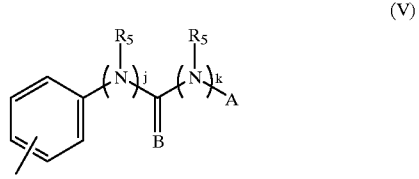
(V)

[wherein j, k, $R_5$, A and B are defined as described as above]}.

BEST MODE FOR CARRYING OUT THE INVENTION

1. Compounds of the present invention

Compounds of the present invention are represented by the abovementioned formula (I), wherein $R_1$, $R_2$, W, X, Q, $R_3$, $R_3'$, $R_4$, $R_5$, $R_6$, Y, Z, A, B, m, j and k are defined as described above.

Examples of specific substituents applicable in the present specification are as follows:

Halogen: chloro, bromo, fluoro, iodo;

$C_1$–$C_5$-alkyl: methyl, ethyl, ethyl, propyl, isopropyl, butyl, isobutyl, s-butyl, t-butyl, pentyl, isopentyl, neopentyl, t-pentyl;

cyclic ($C_3$–$C_{10}$) alkyl: cyclopropyl, cyclobutyl, cyclopentyl, cyclohexyl, cycloheptyl, cyclooctyl, adamantyl;

$C_1$–$C_4$-alkoxycarbonyl: methoxycarbonyl, ethoxycarbonyl, propoxycarbonyl, isopropoxycarbonyl, butoxycarbonyl, isobutoxycarbonyl, s-butoxycarbonyl, t-butoxycarbonyl;

$C_1$–$C_3$-alkylenedioxy: methylenedioxy, ethylenedioxy, propylenedioxy;

$C_1$–$C_4$-alkoxy: methoxy, ethoxy, propoxy, isopropoxy, butoxy, isobutoxy, s-butoxy, t-butoxy;

$C_2$–$C_4$-acyl: acetyl, propionyl, butylyl;

$C_1$–$C_4$-alkylamino: methylamino, ethylamino, propylamino, isopropylamino, butylamino, isobutylamino, s-butylamino, t-butylamino;

di-($C_1$–$C_4$-alkyl) amino: dimethylamino, diethylamino, dipropylamino, dibutylamino;

$C_2$–$C_4$-alkylamido: acetamido, propionamido, butylamido;

$C_1$–$C_4$-alkylthio: methylthio, ethylthio, propylthio, isopropylthio, butylthio, isobutylthio, s-butylthio, t-butylthio;

substituted phenyl: a phenyl group substituted by 1 to 3 groups selected from the group consisting of CN, $NO_2$, OH, $NH_2$, halogen, $C_1$–$C_4$-alkyl, cyclic ($C_3$–$C_{10}$)alkyl, $C_1$–$C_4$-alkoxy, $C_1$–$C_4$-alkoxycarbonyl, $C_1$–$C_3$-alkylenedioxy, $C_1$–$C_4$-alkylamino, di-($C_1$–$C_4$-alkyl)amino, $C_2$–$C_4$-alkylamido, trifluoromethyl, $C_1$–$C_4$-alkylthio, phenyl, phenoxy, phenylthio, phenyl($C_1$–$C_4$-alkyl), benzoyl and $C_2$–$C_4$-acyl;

substituted phenoxy: a phenoxy group substituted by 1 to 3 groups selected from the group consisting of CN, $NO_2$, OH, $NH_2$, halogen, $C_1$–$C_4$-alkyl, cyclic ($C_3$–$C_{10}$)alkyl, $C_1$–$C_4$-alkoxy, $C_1$–$C_4$-alkoxycarbonyl, $C_1$–$C_3$-alkylenedioxy, $C_1$–$C_4$-alkylamino, di-($C_1$–$C_4$-alkyl)amino, $C_2$–$C_4$-alkylamido, trifluoromethyl, $C_1$–$C_4$-alkylthio, phenyl, phenoxy, phenylthio, phenyl($C_1$–$C_4$-alkyl), benzoyl and $C_2$–$C_4$-acyl;

substituted phenylthio: a phenylthio group substituted by 1 to 3 groups selected from the group consisting of CN, NO$_2$, OH, NH$_2$, halogens, C$_1$–C$_4$-alkyl, cyclic (C$_3$–C$_{10}$) alkyl, C$_1$–C$_4$-alkoxy, C$_1$–C$_4$-alkoxycarbonyl, C$_1$–C$_3$-alkylenedioxy, C$_1$–C$_4$-alkylamino, di-(C$_1$–C$_4$-alkyl)amino, C$_2$–C$_4$-alkylamido, trifluoromethyl, C$_1$–C$_4$-alkylthio, phenyl, phenoxy, phenylthio, phenyl(C$_1$–C$_4$-alkyl), benzoyl and C$_2$–C$_4$-acyl;

substituted benzoyl: a benzoyl group substituted by 1 to 3 groups selected from the group consisting of CN, NO$_2$, OH, NH$_2$, halogens, C$_1$–C$_4$-alkyl, cyclic (C$_3$–C$_{10}$)alkyl, C$_1$–C$_4$-alkoxy, C$_1$–C$_4$-alkoxycarbonyl, C$_1$–C$_3$-alkylenedioxy, C$_1$–C$_4$-alkylamino, di-(C$_1$–C$_4$-alkyl)amino, C$_2$–C$_4$-alkylamido, trifluoromethyl, C$_1$–C$_4$-alkylthio, phenyl, phenoxy, phenylthio, phenyl(C$_1$–C$_4$-alkyl), benzoyl and C$_2$–C$_4$-acyl.

The compounds represented by formula (I) may be acid addition salts and base addition salts thereof. The compounds of the present invention include these addition salts. Further, the compounds of the present invention, including these addition salts, include hydrates thereof.

Examples of the acid addition salts include salts with inorganic acids such as hydrochloric acid, sulfuric acid, phosphoric acid, hydrobromic acid and nitric acid, and salts with organic acid such as maleic acid, fumaric acid, malic acid, oxalic acid, tartaric acid, succinic acid, citric acid, acetic acid, lactic acid, methanesulfonic acid and p-toluenesulfonic acid.

Further, examples of the base addition salts include salts with alkaline metal compounds (e.g., sodium hydroxide and potassium hydroxide), salts with alkaline earth metal compounds (e.g., calcium hydroxide and magnesium hydroxide), ammonium salts and salts with organic bases (e.g., triethylamine, ethanolamine).

Further, when these addition salts are used as drugs, the acids and bases naturally have to be pharmaceutically acceptable.

Representative examples of the compounds of formula (I) of the present invention are shown in Table 1. They are preferred embodiments of compound groups.

TABLE 1

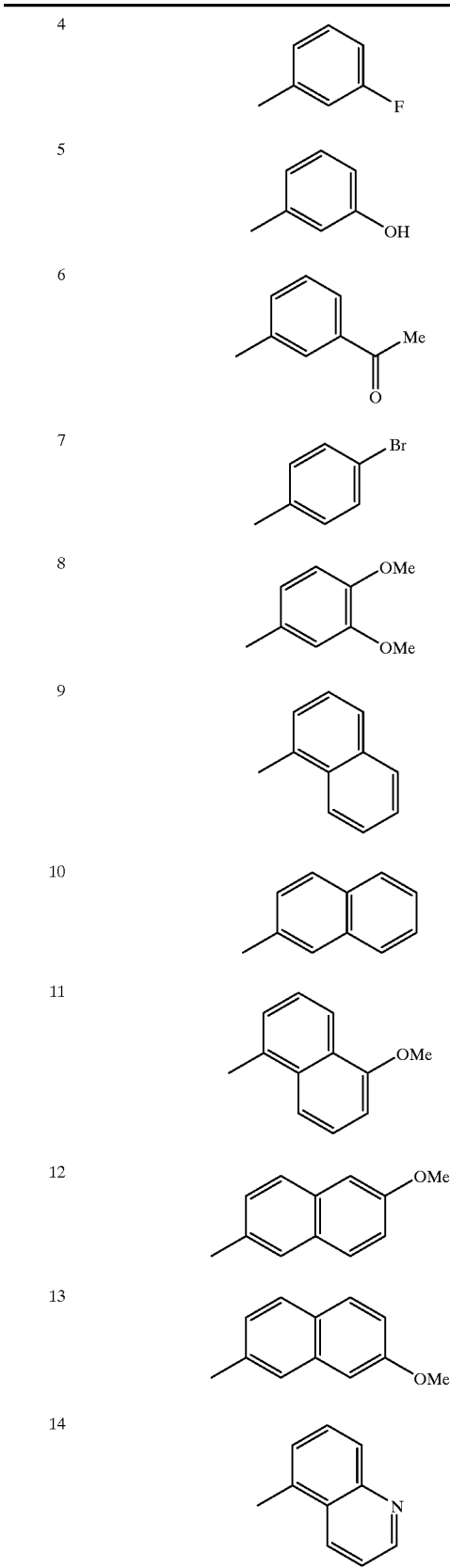

TABLE 1-continued
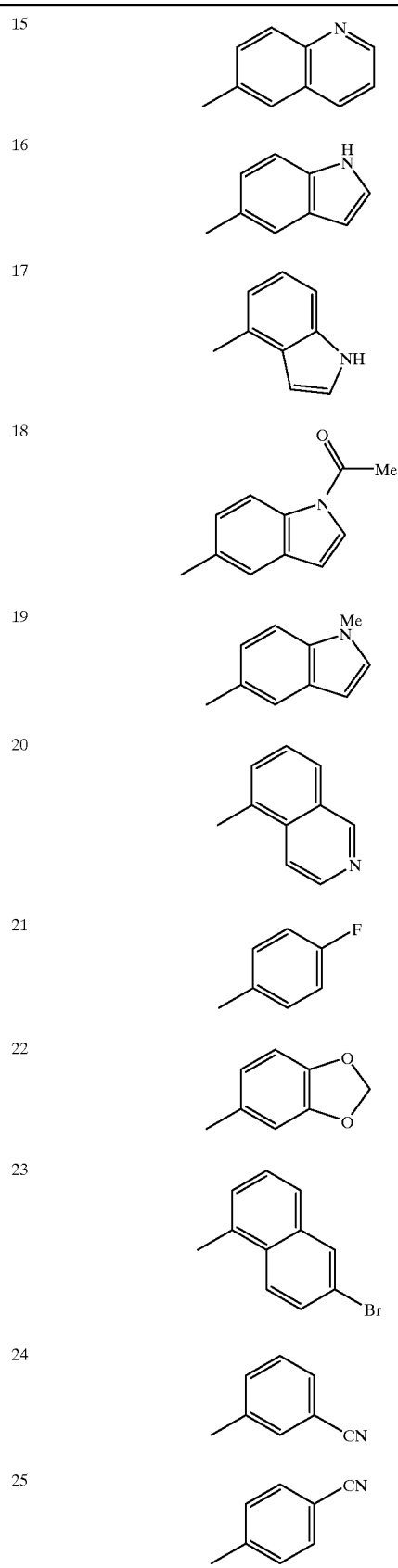
TABLE 1-continued
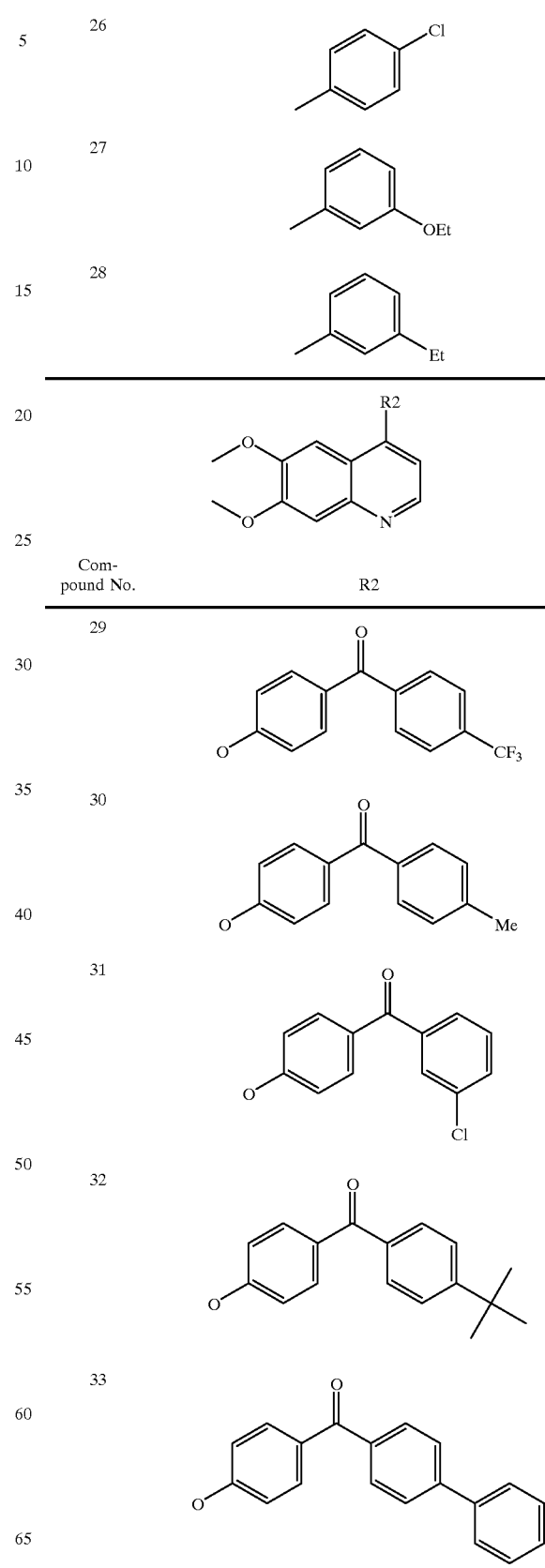

TABLE 1-continued
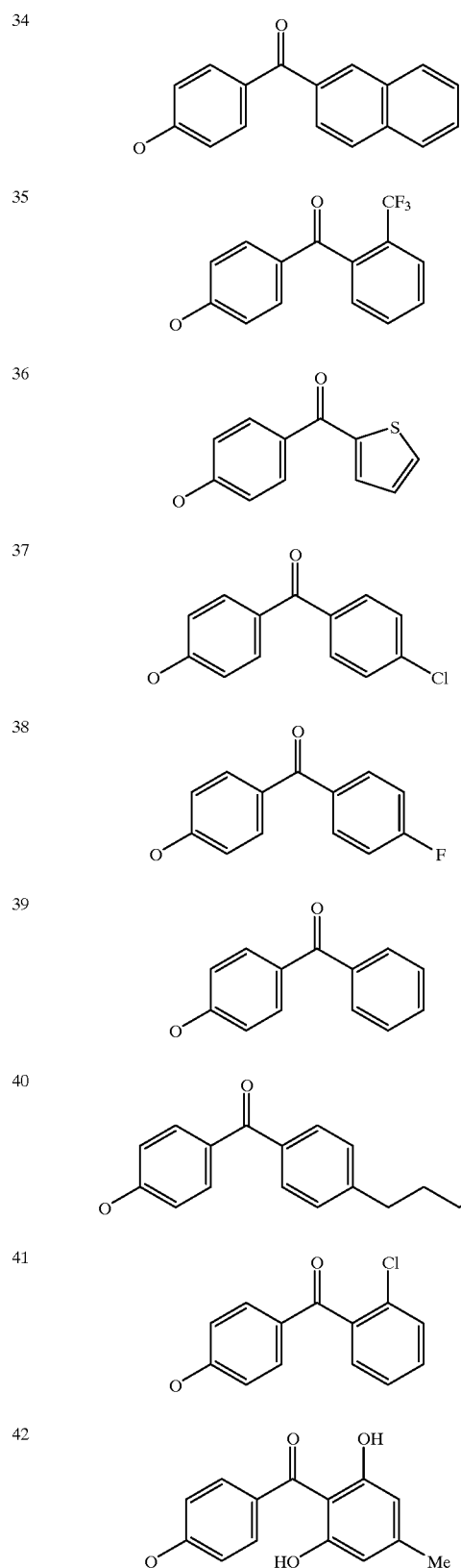
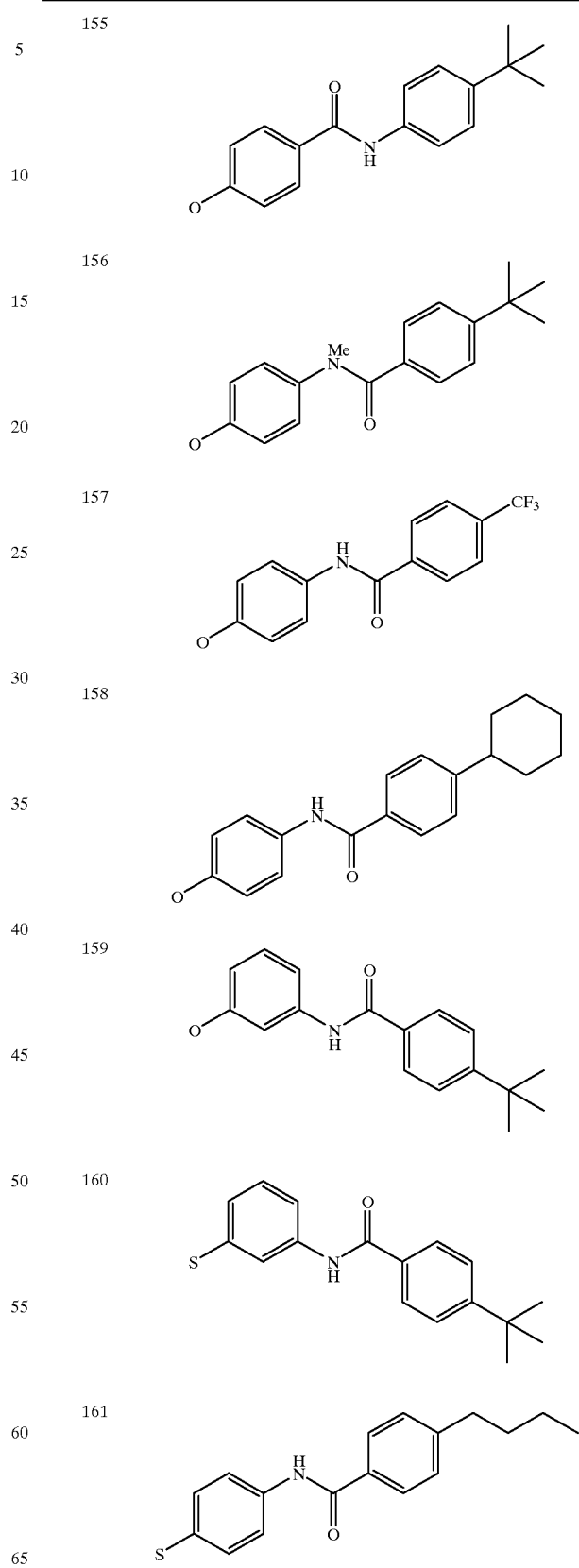

TABLE 1-continued
| 162 | 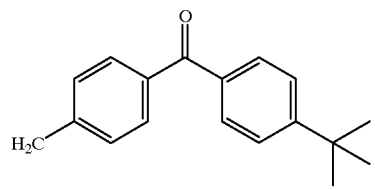 |
| 176 | 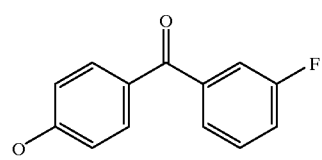 |
| 177 | 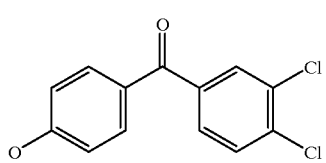 |
| 178 | 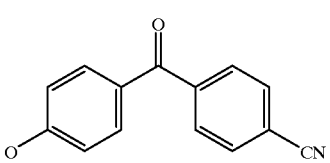 |
| 179 | 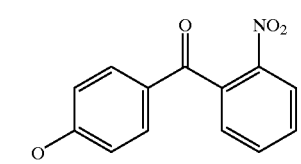 |
| 180 | 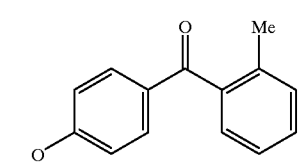 |
| 181 | 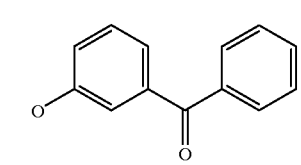 |
| 182 | 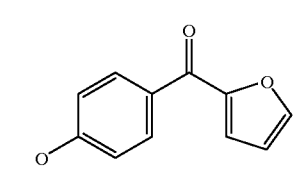 |
| 183 | 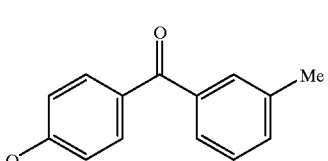 |
TABLE 1-continued
| 184 | 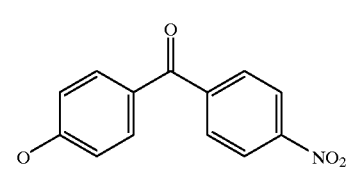 |
| 185 | 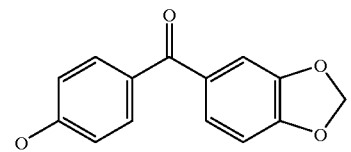 |
| 186 | 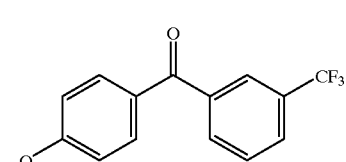 |
| 187 | 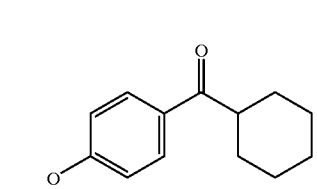 |
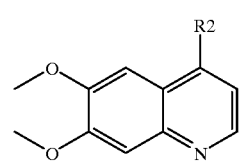
| Compound No. | R2 |
| --- | --- |
| 284 | 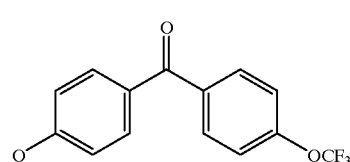 |
| 285 | 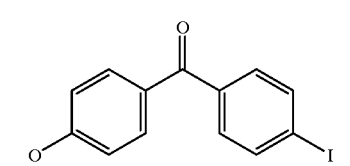 |
| 286 | 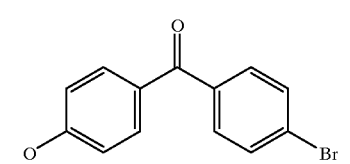 |

TABLE 1-continued
| | |
|---|---|
| 287 | 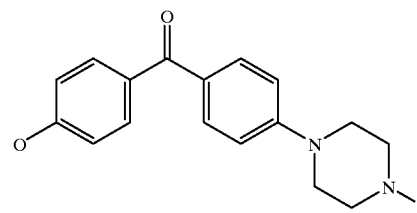 |
| 288 | 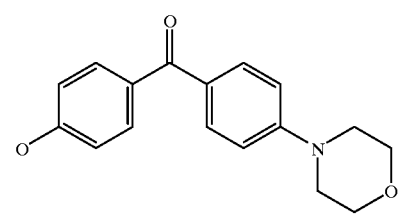 |
| 289 | 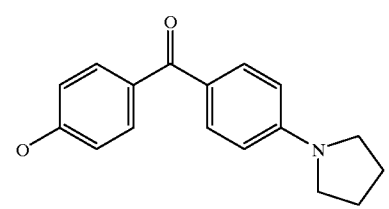 |
| 290 | 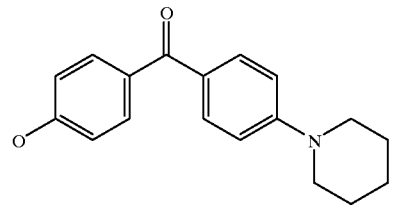 |
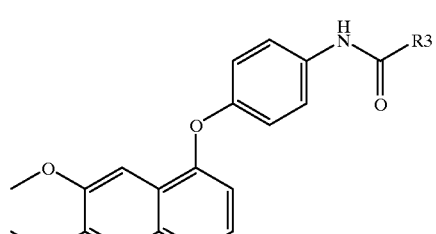
| Compound No. | R3 |
|---|---|
| 43 | 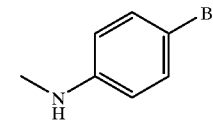 |
| 44 | 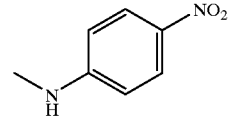 |
| 45 | 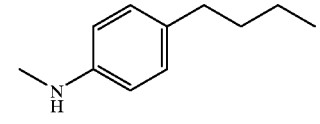 |
| 46 | 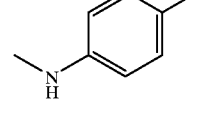 |
| 47 | 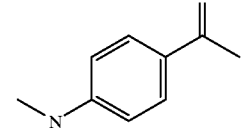 |
| 48 | 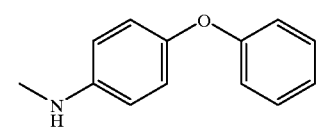 |
| 49 | 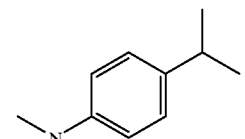 |
| 50 | 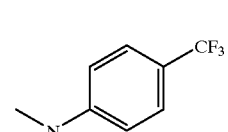 |
| 51 | 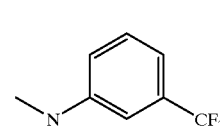 |
| 52 | 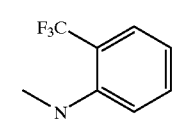 |
| 53 | |
| 54 | |

TABLE 1-continued
| | |
|---|---|
| 55 | 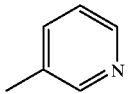 |
| 56 | 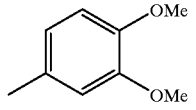 |
| 57 | 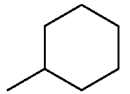 |
| 58 | 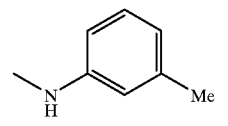 |
| 59 | 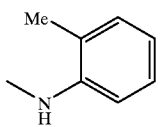 |
| 60 | 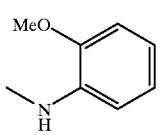 |
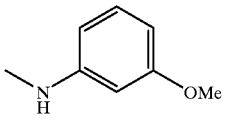
| Compound No. | R3 |
|---|---|
| 61 | 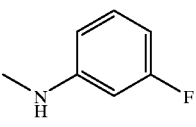 |
| 62 | 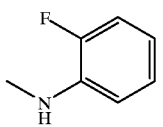 |
| 63 | 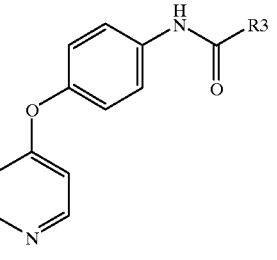 |
TABLE 1-continued
| | |
|---|---|
| 64 | 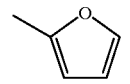 |
| 65 | |
| 66 | |
| 67 | |
| 68 | |
| 69 | |
| 70 | |
| 71 | |
| 72 | |
| 73 | |
| 74 | |
| 75 | 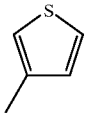 |

TABLE 1-continued
| # | Structure |
|---|---|
| 76 | 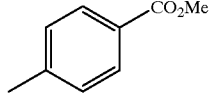 4-methylbenzoate (CO₂Me) |
| 77 | 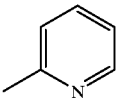 2-methylpyridine |
| 78 | 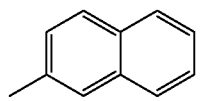 6-methylnaphthalene |
| 79 | 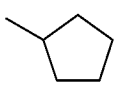 methylcyclopentane |
| 80 | 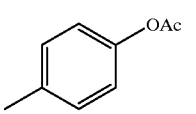 4-methylphenyl acetate (OAc) |
| 81 | 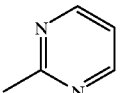 2-methylpyrimidine |
| 82 | 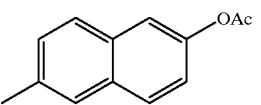 6-methyl-2-naphthyl acetate |
| 83 | 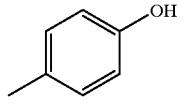 4-methylphenol |
| 84 | 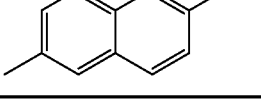 6-methyl-2-naphthol |
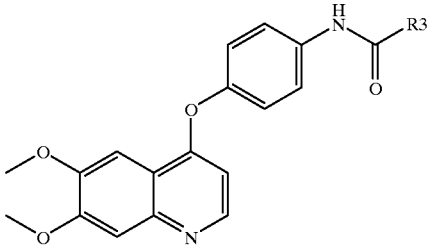
| Compound No. | R3 |
|---|---|
| 163 | 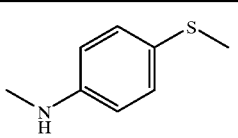 |
TABLE 1-continued
| # | Structure |
|---|---|
| 164 | 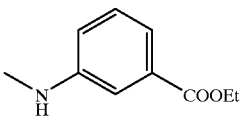 |
| 165 | 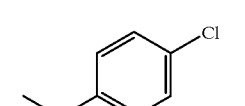 |
| 166 | 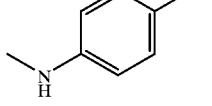 |
| 167 | 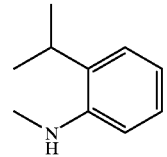 |
| 168 | 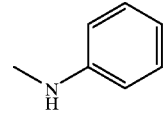 |
| 169 | 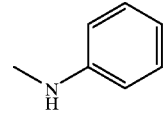 |
| 170 | 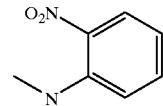 |
| 171 | 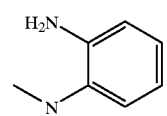 |
| 172 | 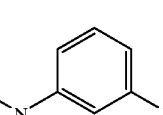 |
| 173 | 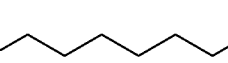 |
| 174 | 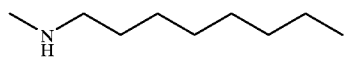 |

TABLE 1-continued
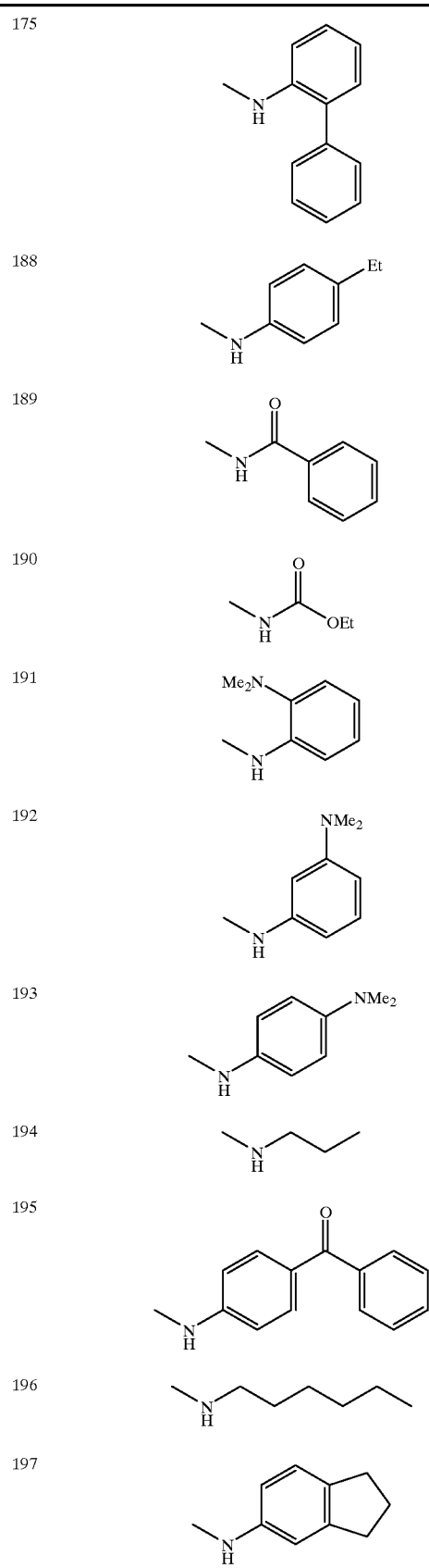
TABLE 1-continued
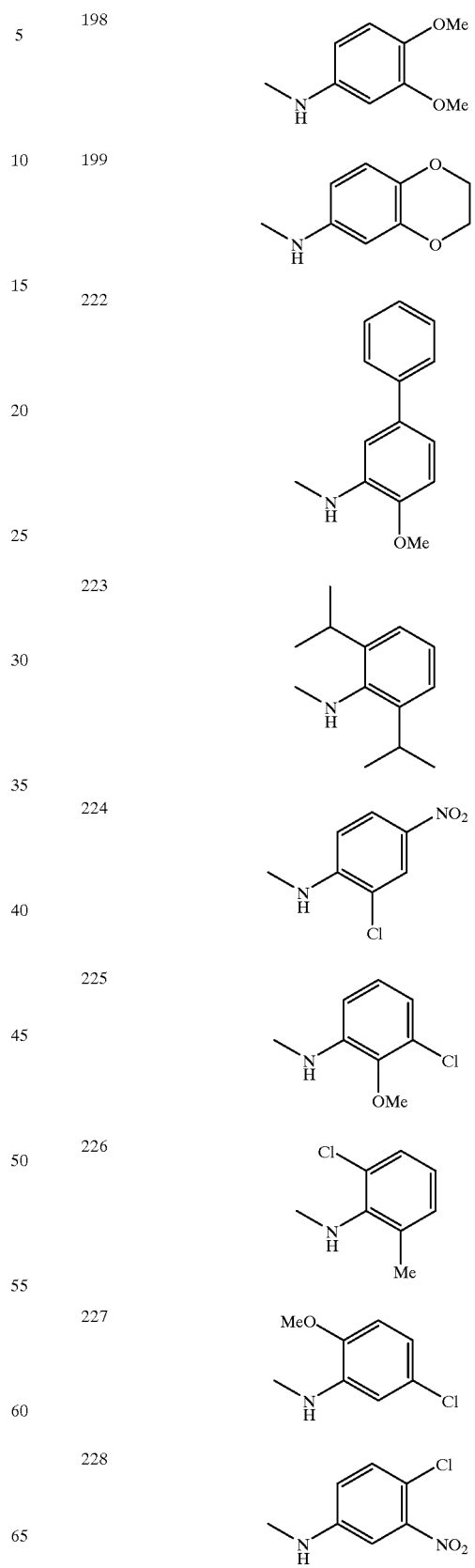

TABLE 1-continued
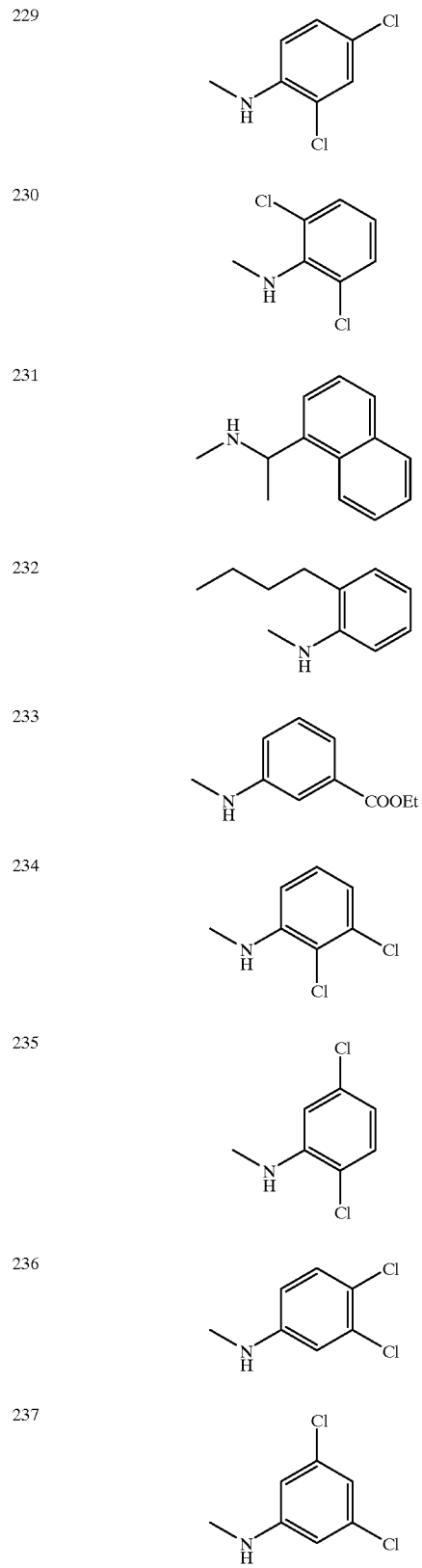
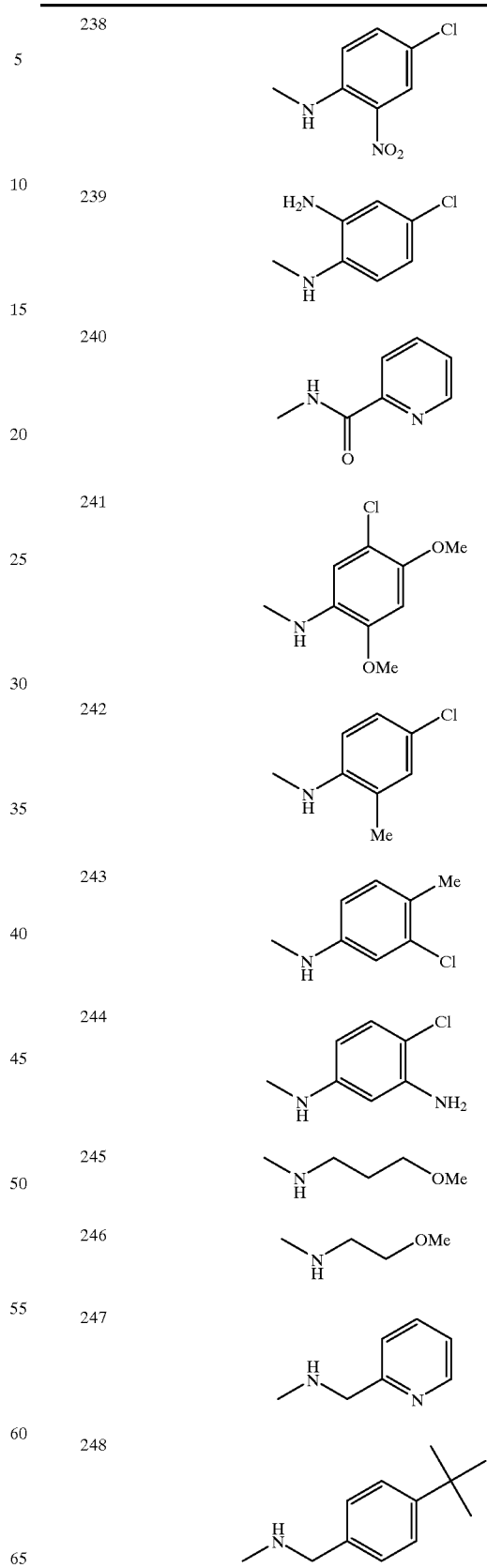

TABLE 1-continued
| | |
|---|---|
| 249 | 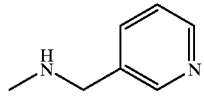 |
| 250 | 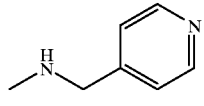 |
| 251 | 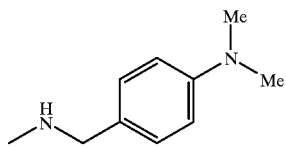 |
| 252 | 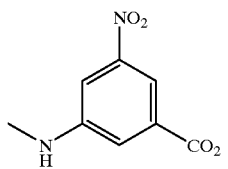 |
| 253 | 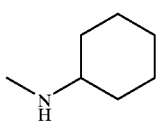 |
| 254 | 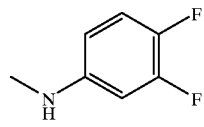 |
| 255 | 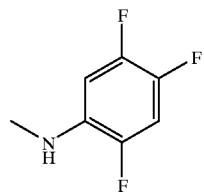 |
| 256 | 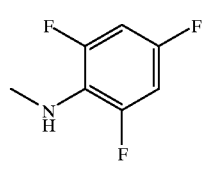 |
| 257 | 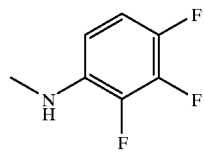 |
| 258 | 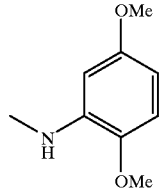 |
| 259 | 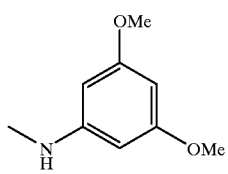 |
| 260 | 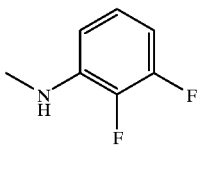 |
| 261 | 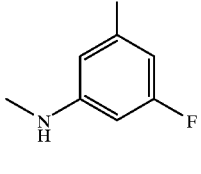 |
| 262 | 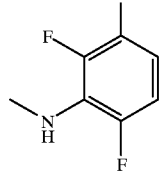 |
| 263 | 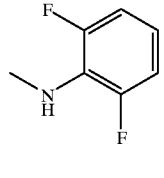 |
| 264 | 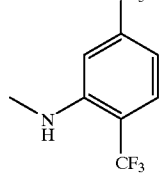 |
| 265 | 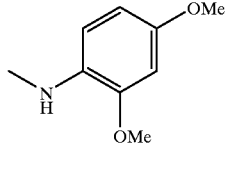 |

TABLE 1-continued
| 266 | 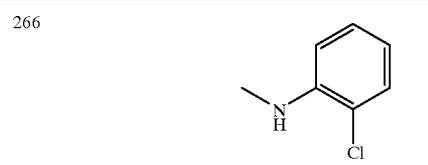 |
| 267 | 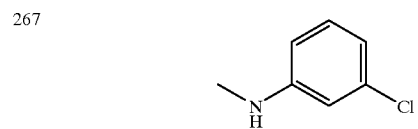 |
| 268 | 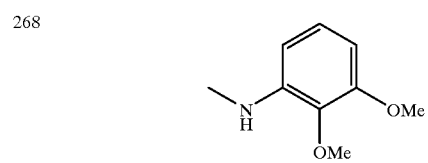 |
| 269 | 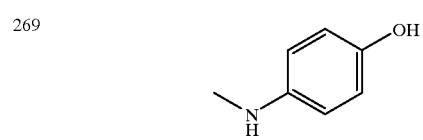 |
| 270 | 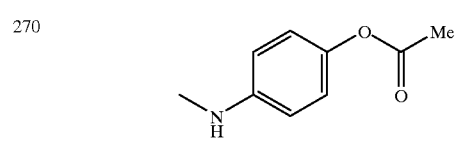 |
| 271 | 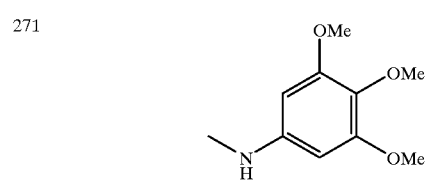 |
| 272 | 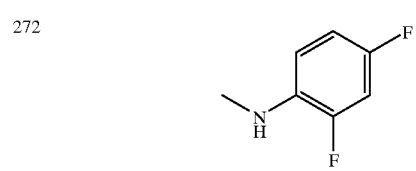 |
| 273 | 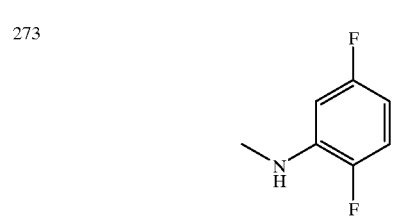 |
| 274 | 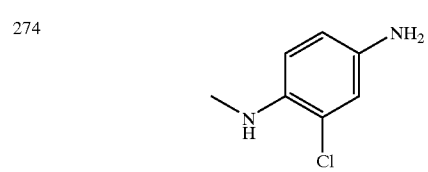 |
| 275 | 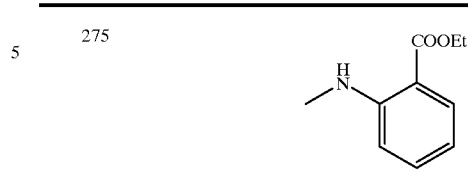 |
| 276 | 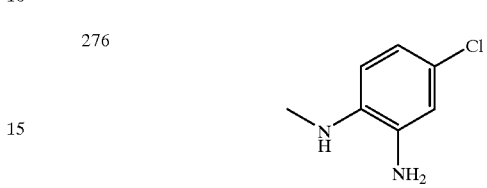 |
| 277 | 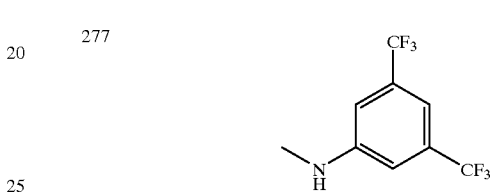 |
| 278 |  |
| 279 | 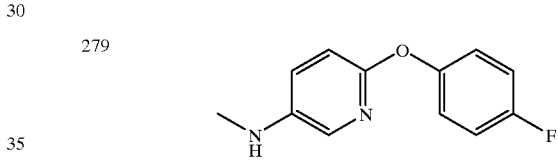 |
| 280 | 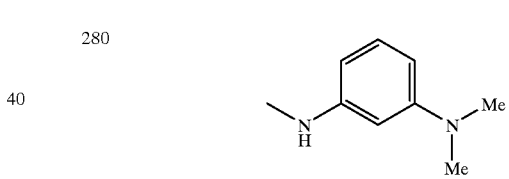 |
| 281 |  |
| 282 | 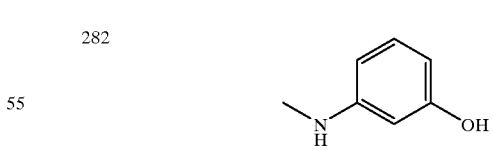 |

TABLE 1-continued

| Compound No. | Structure |
|---|---|
| 283 | 3-(methylamino)benzoic acid (m-NHMe-C6H4-COOH) |

Core structure for compounds 85-92:
6,7-dimethoxyquinoline-4-yl-O-(3-NHC(O)R4-phenyl)

| Compound No. | R4 |
|---|---|
| 85 | -NH-(4-F-C6H4) |
| 86 | -NH-(3-F-C6H4) |
| 87 | -NH-(2-F-C6H4) |
| 88 | -NH-(4-Me-C6H4) |
| 89 | -NH-(3-Me-C6H4) |
| 90 | -NH-(2-Me-C6H4) |
| 91 | -NH-(4-n-Bu-C6H4) |
| 92 | -NH-(4-CF3-C6H4) |
| 93 | -NH-(3-CF3-C6H4) |
| 94 | -NH-(2-CF3-C6H4) |
| 95 | -NH-(4-OMe-C6H4) |
| 96 | -NH-(3-OMe-C6H4) |
| 97 | -NH-(2-OMe-C6H4) |
| 98 | -NH-(2-Cl-C6H4) |

Core structure for compounds 99-101:
6,7-dimethoxyquinazolin-4-yl-O-(4-NHC(O)R5-phenyl)

| Compound No. | R5 |
|---|---|
| 99 | -NH-(4-OMe-C6H4) |
| 100 | -NH-(4-F-C6H4) |
| 101 | -NH-(4-Br-C6H4) |

TABLE 1-continued

| # | Structure |
|---|---|
| 102 | 4-nitro-N-methylaniline |
| 103 | 4-butyl-N-methylaniline |
| 104 | N-methylbenzene-1,4-diamine |
| 105 | 1-(4-(methylamino)phenyl)ethanone |
| 106 | N-methyl-4-phenoxyaniline |
| 107 | 4-isopropyl-N-methylaniline |
| 108 | N-methyl-4-(trifluoromethyl)aniline |
| 109 | N-methyl-3-(trifluoromethyl)aniline |
| 110 | N-methyl-2-(trifluoromethyl)aniline |
| 111 | N,3-dimethylaniline |
| 112 | N,2-dimethylaniline |
| 113 | 2-methoxy-N-methylaniline |
| 114 | 3-methoxy-N-methylaniline |
| 115 | 3-fluoro-N-methylaniline |
| 116 | 2-fluoro-N-methylaniline |
| 214 | N-methylcyclopentanamine |
| 215 | N-methylcyclohexanamine |
| 216 | N-methylcycloheptanamine |
| 217 | N-methylpropan-2-amine |
| 218 | N-methylpropan-1-amine |
| 219 | N-methyl-2-methylpropan-1-amine |
| 220 | N-methylbutan-1-amine |
| 221 | N-methylpentan-1-amine |

TABLE 1-continued
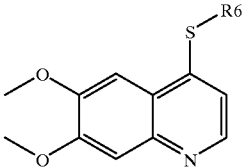
| Compound No. | R6 |
|---|---|
| 117 | 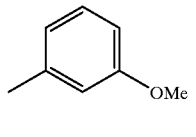 |
| 118 | 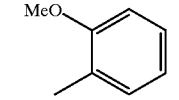 |
| 119 | 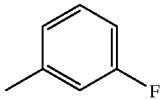 |
| 120 | 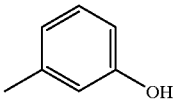 |
| 121 | 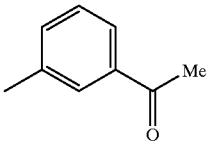 |
| 122 | 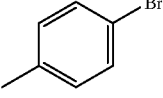 |
| 123 | 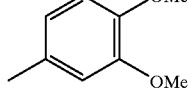 |
| 124 | 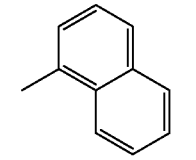 |
| 125 | 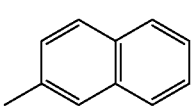 |
| 126 | 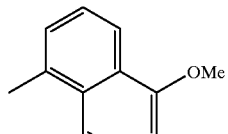 |
TABLE 1-continued
| 127 | 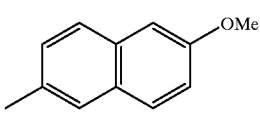 |
|---|---|
| 128 | 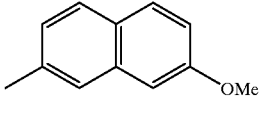 |
| 129 | 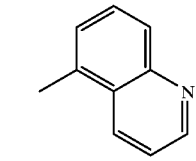 |
| 130 | 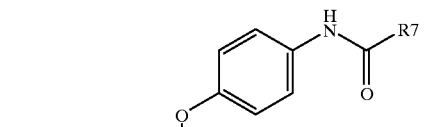 |
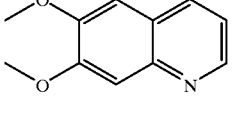
| Compound No. | R7 |
|---|---|
| 131 | 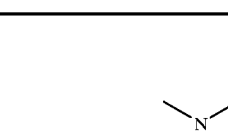 |
| 132 | 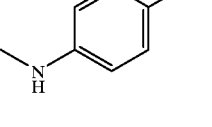 |
| 133 | 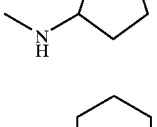 |
| 134 | 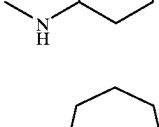 |
| 135 | 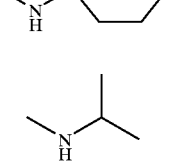 |

TABLE 1-continued

| Compound No. | R8 |
|---|---|
| 136 | *N-methyl isobutylamine* |
| 137 | *N-methyl isopentylamine* |
| 138 | *N-methyl propylamine* |
| 139 | *N-methyl butylamine* |
| 140 | *N-methyl 2-methylbutylamine* |

Structure: 6,7-dimethoxy-4-(2-(HN-C(=O)-R8)phenoxy)quinoline

| Compound No. | R8 |
|---|---|
| 141 | 4-fluorophenyl-NHMe |
| 142 | 3-fluorophenyl-NHMe |
| 143 | 2-fluorophenyl-NHMe |
| 144 | 4-methylphenyl-NHMe |
| 145 | 3-methylphenyl-NHMe |
| 146 | 2-methylphenyl-NHMe |
| 147 | 4-butylphenyl-NHMe |
| 148 | 4-(CF₃)phenyl-NHMe |
| 149 | 3-(CF₃)phenyl-NHMe |
| 150 | 2-(CF₃)phenyl-NHMe |
| 151 | 4-methoxyphenyl-NHMe |
| 152 | 3-methoxyphenyl-NHMe |
| 153 | 2-methoxyphenyl-NHMe |
| 154 | 2-chlorophenyl-NHMe |

Structure: 6,7-dimethoxy-4-(4-R9-phenoxy)quinoline

| Compound No. | R9 |
|---|---|

TABLE 1-continued

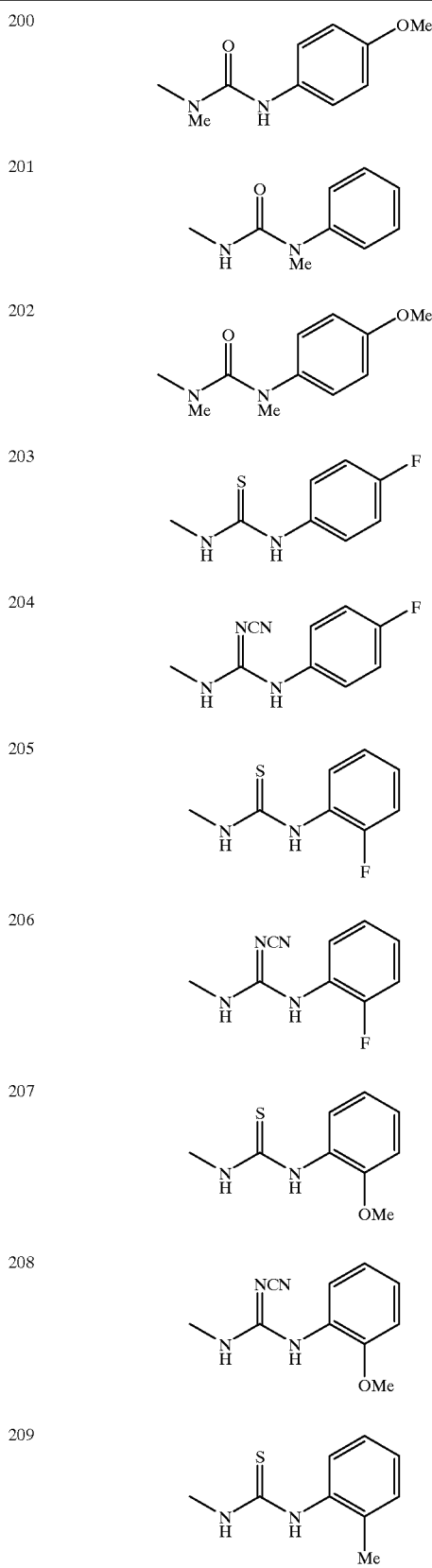

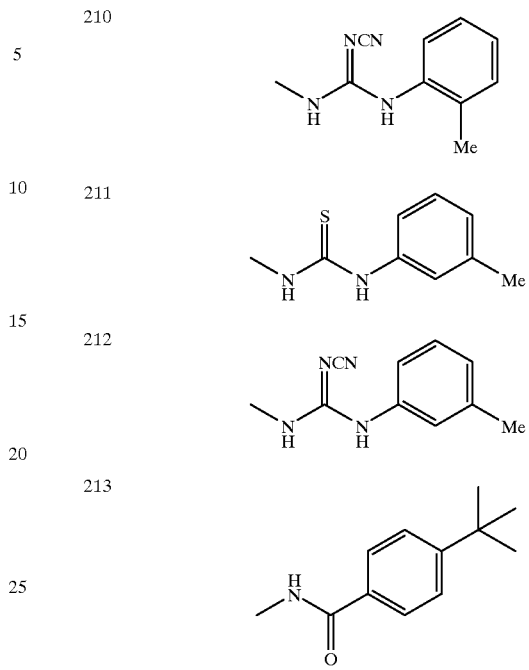

II. Methods of producing compounds of the present invention

Compounds of the present invention can be synthesized, for example, according to the methods described below. However, it should be understood that methods of producing compounds of the present invention are not limited to these methods.

Although all of the compounds of the present invention are novel compounds which are not described in the literature, they can be produced using known chemical techniques. Further, the raw materials used for the production may be commercially available or synthesized by customary methods, if necessary. For example, 4-chloroquinoline derivatives can be synthesized by various known methods. For example, the method described in Org. Synth. Col. Vol. 3, 272 (1955) and Acta Chim. Hung. 112, 241 (1983) can be used. Many quinoline derivatives used in Examples hereinafter can be produced according to the following reaction scheme:

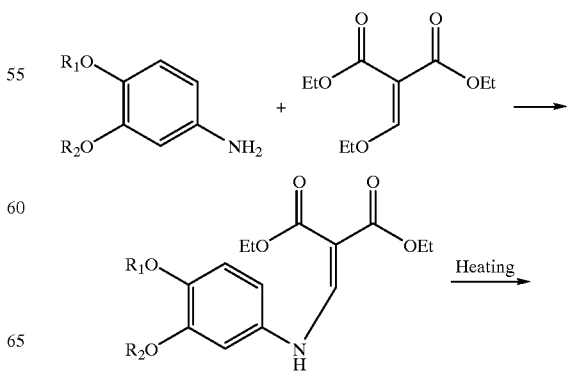

-continued

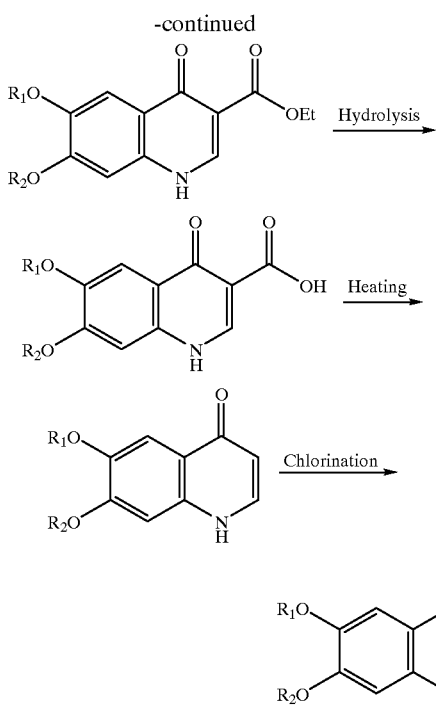

4-Chloroquinazoline derivatives can also be synthesized by various known methods. For example, the methods described in Dai Yuki Kagaku (Comprehensive Organic Chemistry), Vol. 17, 150, edited by Kotake, Asakura Shoten (1967) can be used. Many quinazoline material compounds used in Examples hereinafter can be produced according to the following reaction scheme:

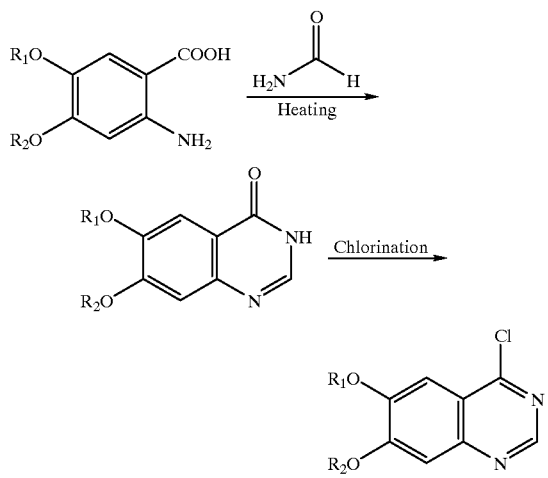

General methods of producing compounds of the present invention will be explained as follows:

1. Compounds of formula (I) wherein Q is represented by formula (II), formula (III) or formula (IV)
a. Synthesis of a compound wherein X is O:

A compound of formula (I) wherein X is O is produced by condensation of an aryl compound or heteroaryl compound having a hydroxyl group with a 4-chloroquinoline derivative.

b. Synthesis of compounds wherein X is S:

A compound of formula (I) wherein X is S is produced in the same manner as described for a compound wherein X is O, by condensation of an aryl compound or heteroaryl compound having a thiol group with a 4-chloroquinoline derivative.

2. Compounds of formula (I) wherein Q is represented by formula (V) wherein both j and k are 0
a. Synthesis of a compound wherein X is O:

A Friedel-Crafts acylation reaction is carried out with phenol with a protected hydroxyl group by an appropriate protecting group in the presence of a Lewis acid (e.g., rare earth trifluoromethanesulfonate, in particular, scandium (III) trifluoromethanesulfonate or ytterbium (III) trifluoromethanesulfonate) described in literatures (e.g., J. Chem. Soc., Chem. Commun., 1157 (1993); Synlett, 1157 (1994)) to obtain an acylated compound. Next, the protecting group of the hydroxyl group of the acylated compound is removed, and the resultant compound is reacted with a 4-chloroquinoline derivative or 4-chloroquinazoline derivative at a temperature between 80 and 200° C., preferably between 130 and 180° C. in no solvent or in the presence of an appropriate polar solvent for 1 minute to 5 hours, preferably for 10 minutes to 1 hour to obtain the target compound.

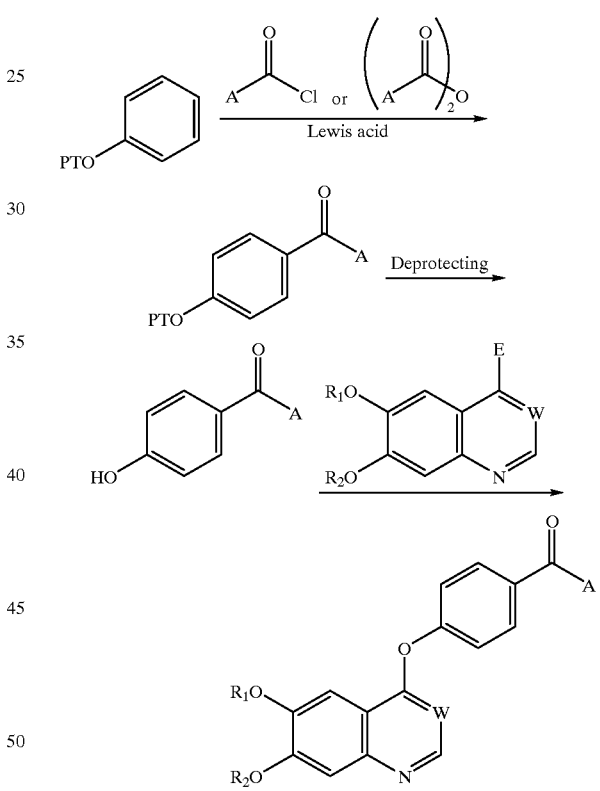

[In the formulas, A, $R_1$, $R_2$ and W are defined as described above, E is a leaving group (e.g., halogen, methanesulfonate, p-toluenesulfonate or trifluoromethanesulfonate, preferably chlorine), and PT is a protecting group (e.g., methyl or methoxymethyl)].

b. Synthesis of a compound wherein X is S:

For example, an acylthiophenol derivative can be synthesized by the following method described in the literature (Org. Syn. 51, 139 (1971)). Namely, an acylphenol derivative which can be synthesized as described in a. above is reacted with N,N-dimethylthiocarbamoylchloride to synthesize an O-aryl-N,N-dimethylthiocarbamate derivative. This derivative is heated (for example, at 200–300° C.) so that an S-aryl-N,N-dimethylthiocarbamate derivative with rearranged oxygen and sulfur is formed in situ, which is then treated under alkaline conditions to yield the corresponding acylthiophenol derivative. Next, in the same manner as described for producing a compound wherein X is O, or in a polar solvent (e.g., N,N-dimethylformamide), the acylthiophenol derivative is reacted with a 4-chloroquinoline derivative or 4-chloroquinazoline derivative with sodium hydroxide at a temperature between 80 and 150° C. to obtain the target compound.

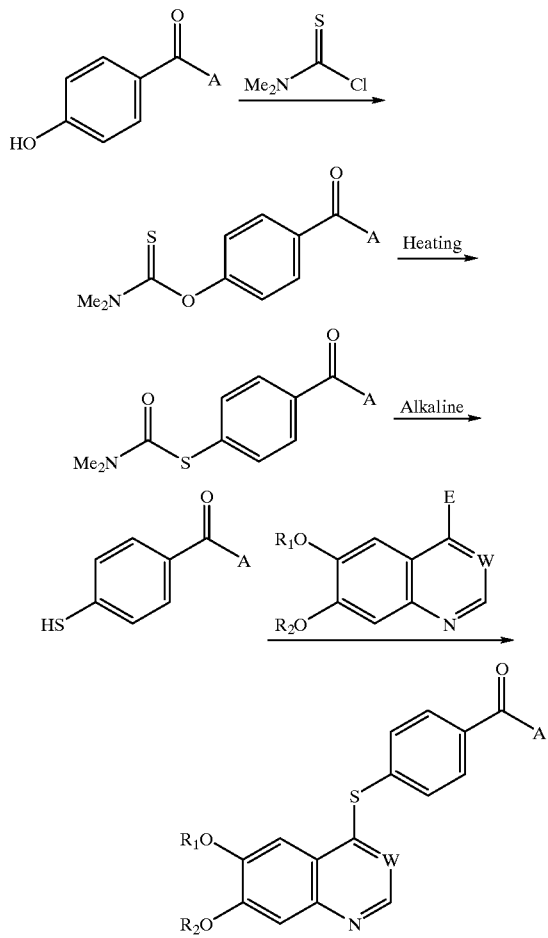

[In the formulas, A, $R_1$, $R_2$, W and E are defined as described above].

c. Synthesis of a compound wherein X is $CH_2$:

A compound represented by formula (I) wherein X is $CH_2$ can be synthesized using the method described by R. Cutler et al. (J. Am. Chem. Soc. 71, 3375 (1949)). In the present method, a 4-chloroquinoline derivative or 4-chloroquinazoline derivative is added to 4-bromophenylacetonitrile sodium salt in an appropriate organic solvent (e.g., toluene), then refluxed, and the diarylsubstituted acetonitrile so obtained is isolated and purified. The purified product is dissolved in an acidic solvent (e.g., aqueous sulfuric acid) and refluxed for 1–20 hours to obtain a 4-(4-bromobenzyl)quinoline derivative or said quinazoline derivative. Next, using the method of J. K. Stille et al. (J. Org. Chem. 48, 4634 (1983)), the 4-(4-bromobenzyl) quinoline derivative or said quinazoline derivative is reacted with alkyllithium in an appropriate solvent (e.g., tetrahydrofuran) to form an organic lithium compound in situ. Trialkyltin chloride is then added to yield an organic tin compound, and the resulting compound and an acid chloride are refluxed with heat in an appropriate organic solvent (e.g., chloroform) in the presence of a catalytic amount of a palladium complex (e.g., bis(triphenylphosphine)palladium (II) chloride) to produce the target compound.

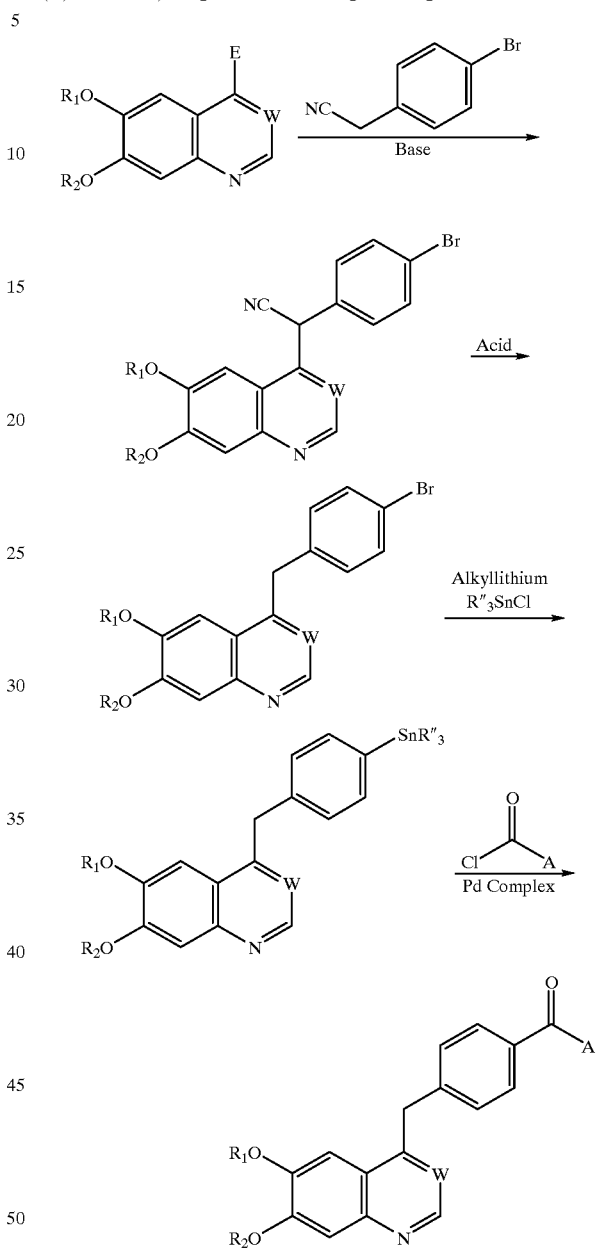

[In the formulas, A, $R_1$, $R_2$, W and E are defined as described above, and R″ is methyl or butyl].

3. Compounds of formula (I) wherein Q is represented by formula (V) wherein B is O, and j is 1 and k is 0, or j is 0 and k is 1 a. Synthesis of a compound wherein X is O:

A 4-chloroquinoline derivative or 4-chloroquinazoline derivative is reacted with nitrophenol in an appropriate solvent or no solvent to synthesize a 4-(nitrophenoxy) quinoline derivative or said quinazoline derivative. The resulting derivative is then stirred in an appropriate solvent (e.g., N,N-dimethylformamide) in the presence of a catalyst (e.g., palladium hydroxide/carbon) under a hydrogen atmosphere to obtain the 4-(aminophenoxy)quinoline derivative or said quinazoline derivative. The resulting derivative can be amidated using carboxylic acids or their derivatives to produce the target compound according to known methods. Further, its N-alkylamides can be produced by reaction with an alkyl halide in an appropriate solvent (e.g., N,N-dimethylformamide) in the presence of a base (e.g., sodium hydride).

Further, analogously, a 4-(carboxyphenoxy)quinoline derivative or said quinazoline derivative can be obtained by reacting a hydroxybenzoic acid ester with a 4-chloroquinoline derivative or 4-chloroquinazoline derivative, followed by acid or base hydrolysis. The resultant derivative can be amidated using an alkylamine or arylamine to produce the target compound according to known methods. Further, its N-alkylamides can be produced by the abovementioned method.

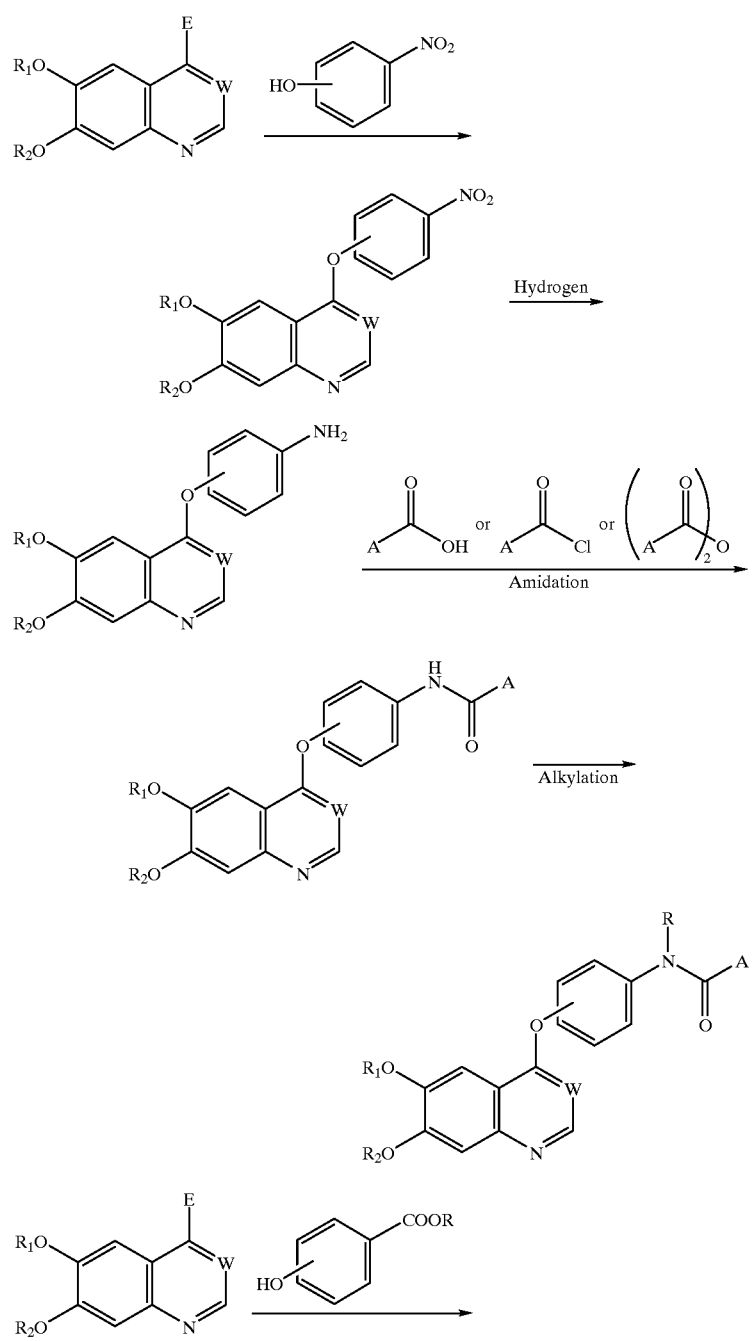

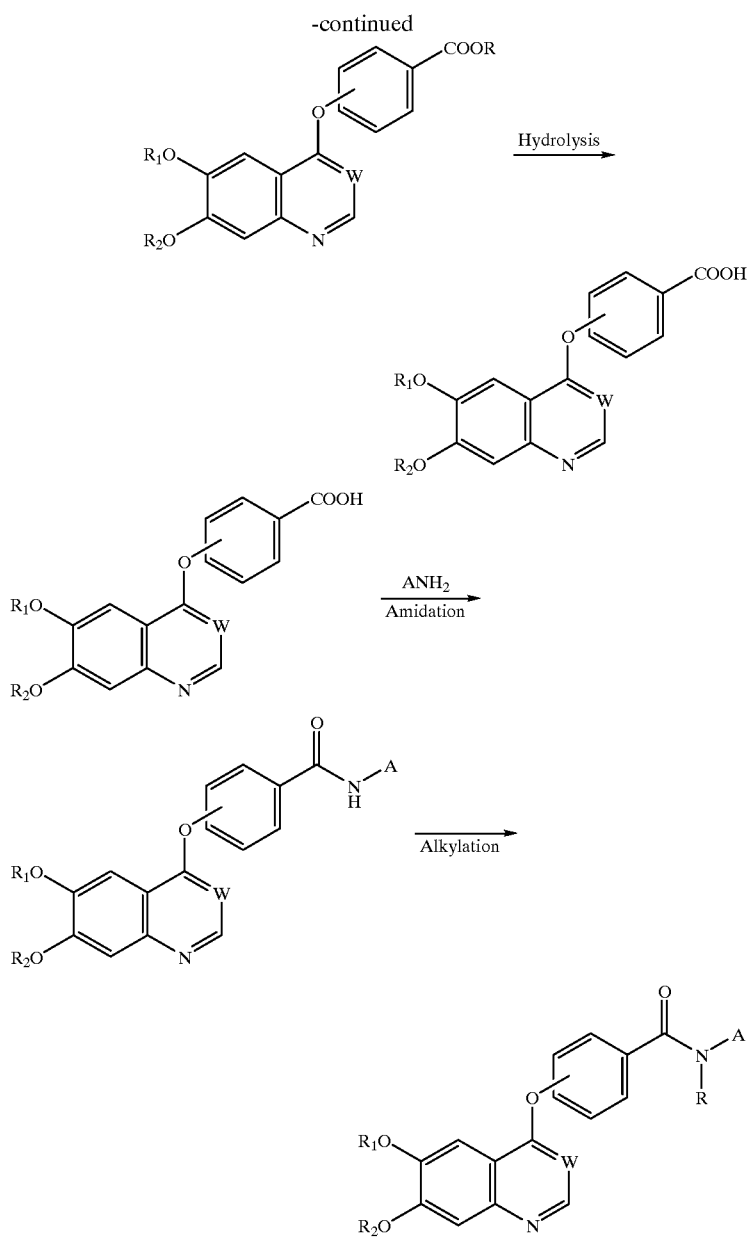

[In the formulas, A, $R_1$, $R_2$, W and E are defined as described above, and R is methyl, ethyl, propyl, isopropyl, butyl, isobutyl, s-butyl or t-butyl.]

b. Synthesis of a compound wherein X is S:

A 4-(aminophenylthio)quinoline derivative or said quinazoline derivative is obtained by reacting a 4-chloroquinoline derivative or 4-chloroquinazoline derivative with aminothiophenol in an appropriate solvent or no solvent. The resulting derivative can be amidated using carboxylic acids or their derivative to produce the target compound according to known methods. Further, its N-alkylamides can be produced by reaction with an alkyl halide in an appropriate solvent (e.g., N,N-dimethylformamide) in the presence of a base (e.g., sodium hydride).

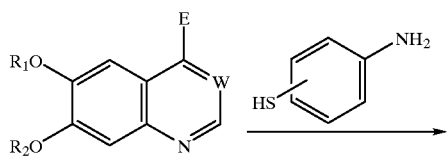

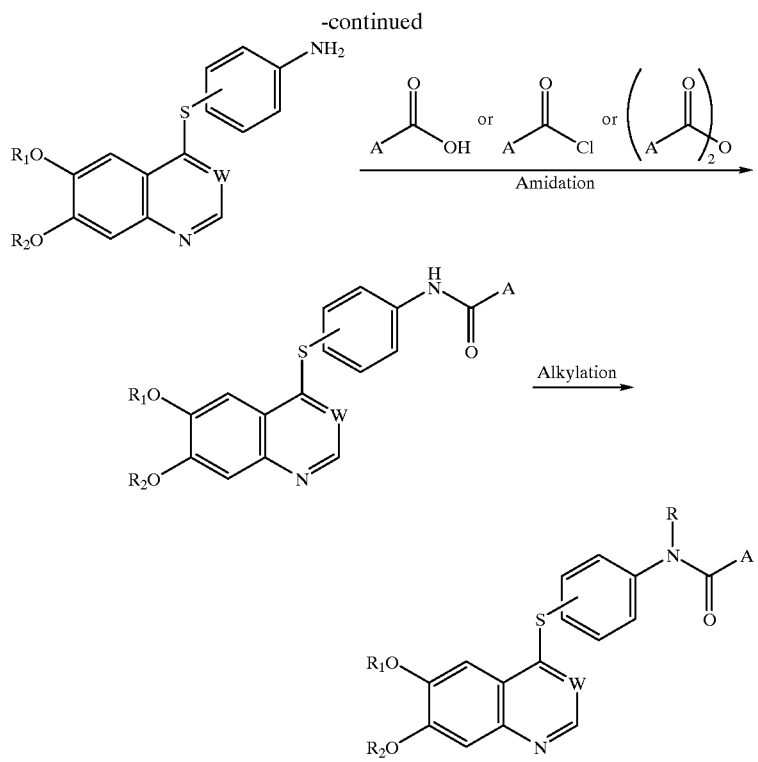

[In the formulas, A, $R_1$, $R_2$, W, E and R are defined as described above.]

c. Synthesis of a compound wherein X is $CH_2$:

A compound represented by formula (I) wherein X is $CH_2$ can be synthesized by the method described by R. Cutler et al. (J. Am. Chem. Soc. 71, 3375 (1949)). In this method, a base (e.g., sodium hydride) is added to aminophenylacetonitrile with a protected amino group (e.g., by a benzyl group) in an appropriate organic solvent (e.g., toluene), a 4-chloroquinoline derivative or 4-chloroquinazoline derivative is added, and the mixture is refluxed. The diarylsubstituted acetonitrile so obtained is isolated and purified, then dissolved in an acidic solvent (e.g., aqueous sulfuric acid) and refluxed for 1–20 hours, and then the protecting group is removed to obtain a 4-(aminobenzyl)quinoline derivative or 4-(aminobenzyl)quinazoline derivative. The resulting derivative can be amidated using carboxylic acids or their derivative to produce the target compound according to known methods. Further, its N-alkylamides can be produced by reaction with an alkyl halide in an appropriate solvent (e.g., N,N-dimethylformamide) in the presence of a base (e.g., sodium hydride).

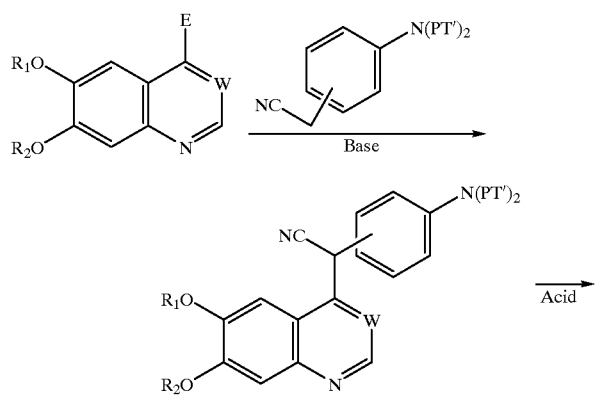

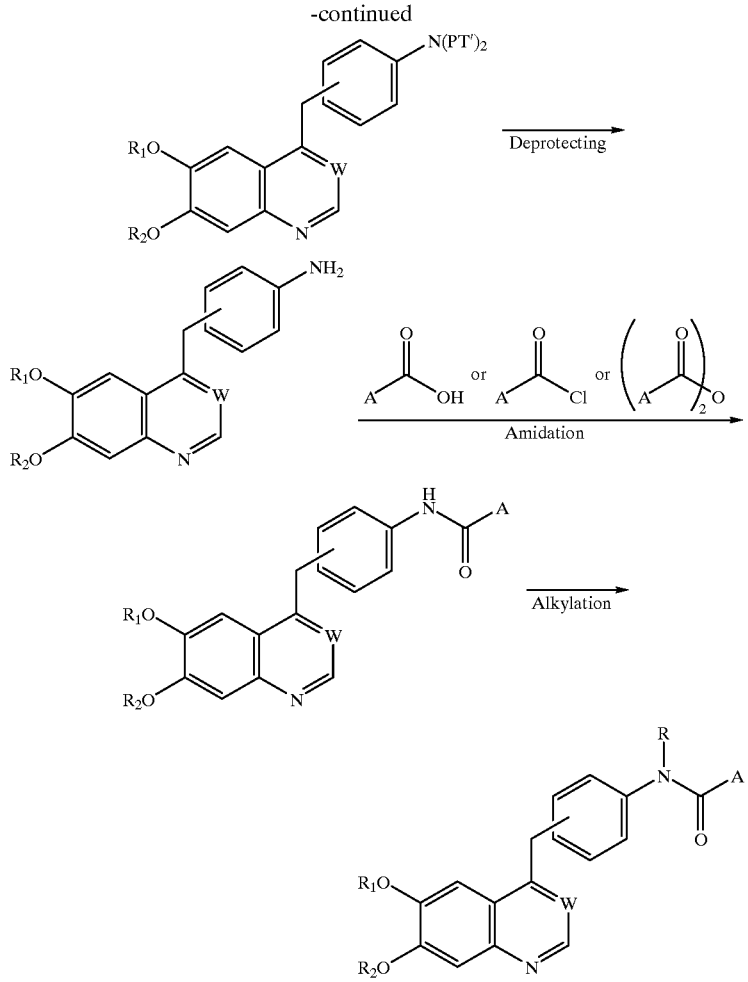

[In the formulas, A, $R_1$, $R_2$, W, E and R are defined as described above, and PT' is a protecting group (e.g., benzyl group.]

4. Compounds of formula (I) in which Q is represented by formula (V) wherein both j and k are 1 a. Synthesis of a compound wherein B is O:

A compound wherein B is O can be produced by reacting one of the abovementioned intermediates with an isocyanate derivative or carbamate derivative according to known methods.

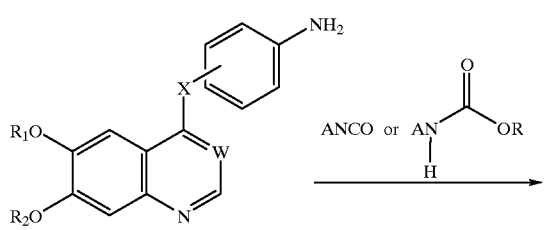

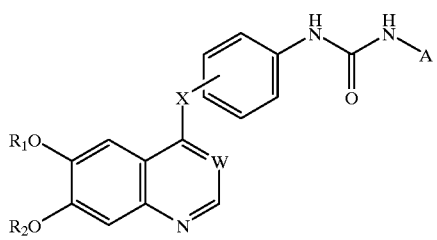

[In the formulas, A, $R_1$, $R_2$, W and R are defined as described above, and X is O, S or $CH_2$.]

b. Synthesis of a compound wherein B is S:

A compound wherein B is S can be produced by reacting one of the abovementioned intermediates with an isocyanate derivative or thiocarbamate derivative according to known methods.

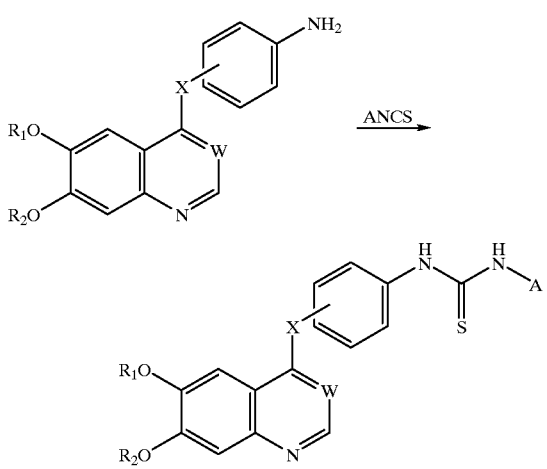

[In the formulas, A, $R_1$, $R_2$ and W are defined as described above, and X is O, S or $CH_2$.]

c. Synthesis of a compound wherein B is NCN:

A compound wherein B is NCN can be produced according to the method described by H. J. Petersen et al. (J. Med. Chem. 21, 773 (1978)).

In this method, the compound obtained in the abovementioned a. is refluxed in the presence of a triphosphorus compound (e.g., triphenylphosphine), a base (e.g., triethylamine) and carbon tetrachloride in an appropriate organic solvent (e.g., methylene chloride) to produce the corresponding carbodiimide, and then the carbodiimide is reacted with cyanamide to obtain the target compound. Alternatively, the target compound can be produced by reacting the compound obtained in the abovementioned b. with cyanamide in the presence of a condensation reagent (e.g., dicyclohexylcarbodiimide) and a base (e.g., ethyldiisopropylamine) in an appropriate organic solvent (e.g., ether).

Salts of the quinoline derivatives or quinazoline derivatives obtained by the methods of the abovementioned 1–4 can be produced by general methods which are conventionally used to produce salts.

III. Use of compounds of the present invention

Intracellular signal transduction mediated by growth factor receptor autophosphorylation is involved in various pathophysiological situations including neoplastic or other abnormal cell growth. Since quinoline derivatives and quinazoline derivatives of the present invention and their pharmaceutically acceptable salts have an inhibitory activity on platelet-derived growth factor (PDGF) receptor autophophorylation, they are expected to be useful as a therapeutic agent to treat various diseases which are caused by abnormal cell growth generated by PDGF receptor autophosphorylation due to an excessive amount of PDGF (e.g., leukemia, cancers, psoriasis, glomerular nephritis, organofibrosis, atherosclerosis, restenosis after percutaneous coronary angioplasty or bypass surgery and rheumatoid arthritis).

Pharmaceutical compositions which contain compounds of the present invention as an effective component, namely medicinal compositions, can be administered to human and other animals either orally or non-orally (e.g., intravenous, intramuscular, subcutaneous, rectal or endermic administration). Accordingly, medicinal compositions which contain compounds of the present invention as an effective component are prepared into a suitable dosage form depending on the method of administration.

Examples of oral preparations include tablets, capsules, powders, granules and syrups, and examples of non-oral preparations include injections, rectal agents, oily suppositories and aqueous suppositories.

These various pharmaceutical preparations can be produced using ordinally excipients, disintegrating agents, binding agents, lubricating agents, coloring agents, diluents or release controlling agents.

Examples of excipients are lactose, glucose, corn starch, sorbitol, and crystalline cellulose; examples of disintegrat-

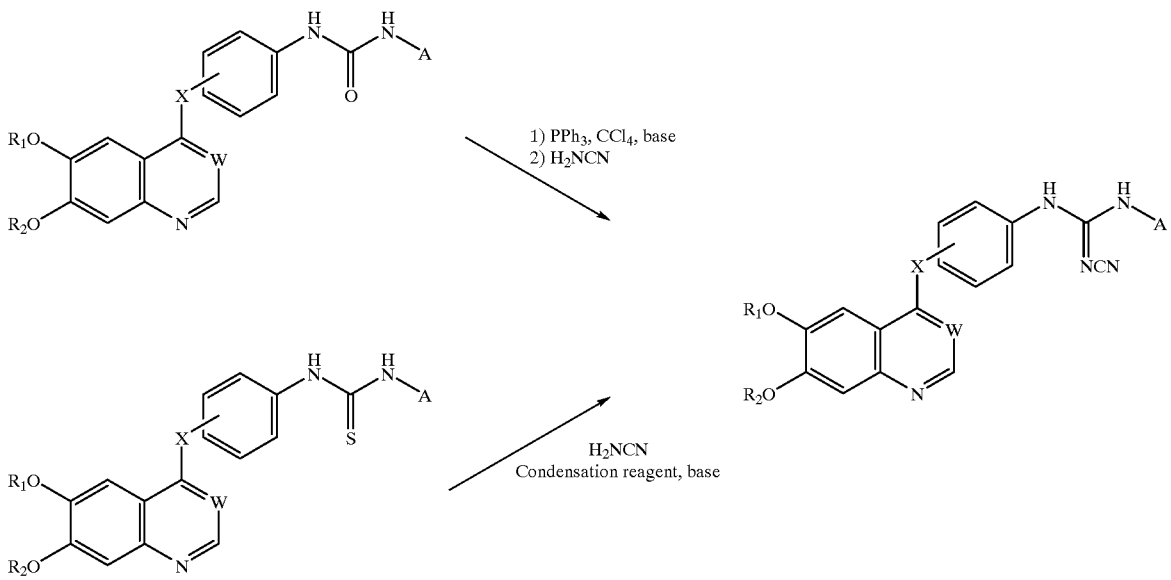

[In the formulas, A, $R_1$, $R_2$ and W are defined as described above, and X is O, S or $CH_2$.]

ing agents are starch, sodium alginate, gelatine powder, calcium carbonate, calcium citrate and dextrine; examples of bonding agents are dimethylcellulose, polyvinyl alcohol, polyvinyl ether, methycellulose, ethylcellulose, gum arabic, gelatine, hydroxypropylcellulose and polyvinylpyrrolidone; examples of lubricating agents are talc, magnesium stearate, polyethylene glycol and hydrogenated vegetable oils.

Further, the abovementioned injectable agents can be produced by adding buffering agents, pH controlling agents, stabilizing agents or the like, if necessary.

Contents of the compounds of the present invention in the medicinal formulations vary depending on their dosage form, but they are generally between about 0.5 and 50% by wight, preferably between about 1 and 20% by weight of the total.

The particular dose for each individual patient is determined as a function of age, body weight and sex of the patient, type or severity of the disease to be treated. For example, a daily dose of between 1 and 100 mg/kg of body weight, preferably between 1 and 50 mg/kg of body weight, is administered one or more times.

EXAMPLES

The present invention is illustrated in greater detail by the following Examples and Test Examples. The numbers in parentheses at the end of title compound in the Examples correspond to the compound numbers given in Table 1.

Example 1 (Reference Example)

6-Methoxy-2-naphthol

Potassium carbonate (1.244 g) was added to a solution of commercially available 2,6-dihydroxynaphthalene (961 mg) in N,N-dimethylformamide (100 ml), and the admixture was stirred at room temperature for 30 minutes. Dimethyl sulfate (1.14 ml) was slowly added dropwise to the mixture and the resulting mixture was further stirred at room temperature overnight. The reaction mixture thus prepared was neutralized with a 2N HCl solution and then partitioned between water and ethyl acetate, and the ethyl acetate layer was dried with anhydrous magnesium sulfate. After removing the solvent by distillation under reduced pressure, the resulting residue was purified by column chromatography on silica gel (eluting with chloroform/ethyl acetate) to obtain 307 mg of the title compound (yield: 29%).

$^1$H-NMR (CDCl$_3$, 90 MHz): δ 3.89 (s, 3H), 7.00~7.18 (m, 4H), 7.53~7.70 (m, 2H)

Mass spectrometry data (FD-MS, m/z): 174 (M$^+$)

Example 2

6,7-Dimethoxy-4-(6-methoxy-2-naphthyloxy) quinoline [12]

4-Chloro-6,7-dimethoxyquinoline (75 mg) and 6-methoxy-2-naphthol (174 mg) obtained in Example 1 were mixed and stirred at 180° C. for 30 minutes, and the reaction mixture was then purified by thin layer chromatography on silica gel (eluting with hexane/acetone (2/1)) to obtain 71 mg of the title compound (yield: 59%).

$^1$H-NMR (CDCl$_3$, 90 MHz): δ 3.96 (s, 3H), 4.07 (s, 3H), 4.08 (s, 3H), 6.53 (d, J=5.71 Hz, 1H), 7.18~7.36 (m, 3H), 7.56~7.91 (m, 5H), 8.50 (br, 1H)

Mass spectrometry data (FD-MS, m/z): 361 (M$^+$)

Example 3

6,7-Dimethoxy-4-(2-naphthyloxy)quinoline [10]

4-Chloro-6,7-dimethoxyquinoline (45 mg) and commercially available β-naphthol (144 mg) were mixed and stirred at 180° C. for 2 hours, and the reaction mixture was then purified in the same manner as described in Example 2 to obtain 45 mg of the title compound (yield: 68%).

$^1$H-NMR (CDCl$_3$, 90 MHz): δ 4.05 (s, 3H), 4.06 (s, 3H), 6.52 (d, J=5.28 Hz, 1H), 7.27~7.61 (m, 6H), 7.75~8.00 (m, 3H), 8.50 (br, 1H)

Mass spectrometry data (FD-MS, m/z): 331 (M$^+$)

Example 4

6,7-Dimethoxy-4-(7-methoxy-2-naphthyloxy) quinoline [13]

4-Chloro-6,7-dimethoxyquinoline (89 mg) and commercially available 7-methoxy-2-naphthol (209 mg) were mixed and stirred at 180° C. for 30 minutes, and the reaction mixture was then purified in the same manner as described in Example 2 to obtain 59 mg of the title compound (yield: 41%).

$^1$H-NMR (CDCl$_3$, 90 MHz): δ 3.92 (s, 3H), 4.05 (s, 3H), 4.07 (s, 3H), 6.54 (d, J=5.49 Hz, 1H), 7.10~7.24 (m, 3H), 7.49~7.91 (m, 5H), 8.49 (d, J=5.49, 1H)

Mass spectrometry data (FD-MS, m/z): 361 (M$^+$)

Example 5 (Reference Example)

5-Methoxy-1-naphthol

Using commercially available 1,5-dihydroxynaphthalene, the synthesis and purification were carried out in the same manner as described in Example 1 to obtain the title compound (yield: 28%).

$^1$H-NMR (CDCl$_3$, 90 MHz): δ 4.00 (s, 3H), 6.79~6.89 (m, 2H), 7.30~7.48 (m, 2H), 7.69~7.90 (m, 2H)

Mass spectrometry data (FD-MS, m/z): 174 (M$^+$)

Example 6

6,7-Dimethoxy-4-(5-methoxy-1-naphthyloxy) quinoline [11]

4-Chloro-6,7-dimethoxyquinoline (85 mg) and 5-methoxy-1-naphthol (67 mg) obtained in Example 5 were mixed and stirred at 180° C. for 20 minutes, and the reaction mixture was then purified in the same manner as described in Example 2 to obtain 19 mg of the title compound (yield: 14%).

$^1$H-NMR (CDCl$_3$, 90 MHz): δ 4.04 (s, 3H), 4.08 (s, 6H), 6.31 (d, J=5.27 Hz, 1H), 6.83~6.92 (m, 1H), 7.34~7.61 (m, 4H), 7.75 (s, 1H), 8.20~8.29 (s, 1H), 8.43 (brs, 1H)

Mass spectrometry data (FD-MS, m/z): 361 (M$^+$)

Example 7

6,7-Dimethoxy-4-(4-indolyloxy)quinoline [17]

4-Chloro-6,7-dimethoxyquinoline (112 mg) and commercially available 4-hydroxyindole (200 mg) were mixed and stirred at 180° C. for 30 minutes. The reaction mixture was neutralized with saturated aqueous sodium hydrogen carbonate and then partitioned between water and chloroform, and the chloroform layer was dried with anhydrous magnesium sulfate. After removing the solvent by reduced-pressure distillation, the resulting residue was purified by thin layer chromatography on silica gel eluting with chloroform/ethyl acetate (3/1) to obtain 51 mg of the title compound (yield: 32%).

¹H-NMR (CDCl₃, 90 MHz): δ 3.95 (s, 3H), 3.96 (s, 3H), 6.08~6.13 (m, 1H), 6.35 (d, J=5.28 Hz, 1H), 6.83~6.93 (m, 1H), 7. 29~7.45 (m, 5H), 7.62 (s, 1H), 8.40 (d, J=5.05 Hz, 1H)

Mass spectrometry data (FD-MS, m/z): 320 (M⁺)

Example 8

6,7-Dimethoxy-4-(3,4-dimethoxyphenoxy)quinoline [8]

4-Chloro-6,7-dimethoxyquinoline (90 mg) and commercially available 3,4-dimethoxyphenol (187 mg) were mixed and stirred at 180° C. for 30 minutes, and the mixture was then purified by column chromatography on silica gel eluting with hexane/acetone to obtain 26 mg of the title compound (yield: 19%).

¹H-NMR (CDCl₃, 500 MHz): δ 3.87 (s, 3H), 3.93 (s, 3H), 4.05 (s, 3H), 4.06 (s, 3H), 6.45 (d, J=4.9 Hz, 1H), 6.75 (dd, J=2.4 Hz, 9.2 Hz, 1H), 6.75 (d, J=2.4 Hz, 1H), 6.93 (d, J=9.2 Hz, 1H), 7.42 (s, 1H), 7.57 (s, 1H), 8.48 (d, J=4.9 Hz, 1H)

Mass spectrometry data (FD-MS, m/z): 341 (M⁺)

Example 9

6,7-Dimethoxy-4-(6-quinolyloxy)quinoline [15]

Using 4-chloro-6,7-dimethoxyquinoline (90 mg) and commercially available 6-hydroxyquinoline (176 mg), reaction and purification were carried out in the same manner as described in Example 8 to obtain 62 mg of the title compound (yield: 46%).

¹H-NMR (CDCl₃, 500 MHz): δ 4.05 (s, 3H), 4.06 (s, 3H), 6.56 (d, J=5.5 Hz, 1H), 7.44~7.62 (m, 5H), 8.13 (d, J=8.5 Hz, 1H), 8.22 (d, J=9.2 Hz, 1H), 8.53 (d, J=4.9 Hz, 1H), 8.94 (d, J=4.3 Hz, 1H)

Mass spectrometry data (FD-MS, m/z): 332 (M⁺)

Example 10

6,7-Dimethoxy-4-(3-fluorophenoxy)quinoline [4]

4-Chloro-6,7-dimethoxyquinoline (100 mg) and commercially available 3-fluorophenol (0.20 ml) were mixed and stirred at 180° C. for 30 minutes. The reaction mixture was neutralized with saturated aqueous sodium hydrogen carbonate and then partitioned between water and ethyl acetate, and the ethyl acetate layer was washed with brine and then dried with anhydrous sodium sulfate. After removing the solvent by reduced-pressure distillation, the resulting residue was purified by column chromatography on silica gel eluting with hexane/ethyl acetate and then with chloroform to obtain 125 mg of the title compound (yield: 94%).

¹H-NMR (CDCl₃, 500 MHz): δ 4.04 (s, 3H), 4.06 (s, 3H), 6.56 (d, J=4.9 Hz, 1H), 6.93 (d, J=9.2 Hz, 1H), 6.95~7.05 (m, 2H), 7.39~7.45 (m, 1H), 7.47 (s, 1H), 7.50 (s, 1H), 8.53 (d, J=4.3 Hz, 1H)

Mass spectrometry data (FD-MS, m/z): 299 (M⁺)

Example 11

6,7-Dimethoxy-4-(3-hydroxyphenoxy)quinoline [5]

4-Chloro-6,7-dimethoxyquinoline (300 mg) and commercially available resorcinol monoacetate (0.835 ml) were mixed and stirred at 180° C. for 30 minutes. The reaction mixture was neutralized with saturated aqueous sodium hydrogen carbonate and then partitioned between water and ethyl acetate, and the ethyl acetate layer was washed with brine and then dried with anhydrous sodium sulfate. After removing the solvent by reduced-pressure distillation, the resulting residue was crystallized with chloroform to obtain 37 mg of the title compound (yield: 9%).

¹H-NMR (CDCl₃, 500 MHz): δ 4.01 (s, 3H), 4.02 (s, 3H), 6.48 (t, J=2.4 Hz, 1H), 6.59 (d, J=5.5 Hz, 1H), 6.77 (dd, J=2.4 Hz, 7.3 Hz, 1H), 6.82 (dd, J=2.4 Hz, 8.6 Hz, 1H), 7.33 (t, J=7.9 Hz, 1H), 7.39 (s, 1H), 7.47 (s, 1H), 8.40 (d, J=5.5 Hz, 1H)

Mass spectrometry data (FD-MS, m/z): 297 (M⁺)

Example 12

6,7-Dimethoxy-4-(4-bromophenoxy)quinoline [7]

4-Chloro-6,7-dimethoxyquinoline (1.00 g) and commercially available 4-bromophenol (115 mg) were mixed and stirred at 180° C. for 40 minutes. The reaction mixture was neutralized with saturated aqueous sodium hydrogen carbonate and then partitioned between water and chloroform, and the chloroform layer was washed with brine and dried with sodium sulfate. After removing the solvent by reduced-pressure distillation, the resulting residue was purified by column chromatography on silica gel, eluting in sequence with hexane/acetone, chloroform and chloroform/methanol, to obtain 1.20 g of the title compound (yield: 76%).

¹H-NMR (CDCl₃, 500 MHz): 4.04 (s, 3H), 4.05 (s, 3H), 6.48 (d, J=4.9 Hz, 1H), 7.08 (d, J=8.5 Hz, 2H), 7.43 (s, 1H), 7.51 (s, 1H), 7.58 (d, J=8.5 Hz, 2H), 8.51 (d, J=4.9 Hz, 1H)

Mass spectrometry data (FD-MS, m/z): 359 (M⁺), 361 (M⁺+2)

Example 13

6,7-Dimethoxy-4-(2-methoxyphenoxy)quinoline [1]

4-Chloro-6,7-dimethoxyquinoline (102 mg) and commercially available 2-methoxyphenol (0.5 ml) were mixed and stirred at 150° C. for 8 hours. The reaction mixture was neutralized with saturated aqueous sodium hydrogen carbonate and then partitioned between water and ethyl acetate, and the ethyl acetate layer was washed with brine and then dried with sodium sulfate. After removing the solvent by reduced-pressure distillation, the resulting residue was purified by column chromatography on silica gel eluting first with hexane/ethyl acetate and then with chloroform/methanol to obtain 76 mg of the title compound (yield: 54%).

¹H-NMR (CDCl₃, 90 MHz): δ 3.78 (s, 3H), 4.05 (s, 3H), 4.05 (s, 3H), 6.31 (d, J=5.3 Hz, 1H), 6.9~7.4 (m, 4H), 7.42 (s, 1H), 7.63 (s, 1H), 8.45 (d, J=5.3 Hz, 1H)

Mass spectrometry data (FAB-MS, m/z): 312 (M⁺+1)

Example 14

6,7-Dimethoxy-4-(3-methoxyphenoxy)quinoline [2]

4-Chloro-6,7-dimethoxyquinoline (103 mg) and commercially available 3-methoxyphenol (158 mg) were mixed and stirred at 160° C. for 9 hours. The reaction mixture was neutralized with saturated aqueous sodium hydrogen carbonate and then partitioned between water and ethyl acetate, and the ethyl acetate layer was washed with brine and then dried with sodium sulfate. After removing the solvent by reduced-pressure distillation, the resulting residue was purified by chromatography on silica gel eluting with hexane/ethyl acetate to obtain 29 mg of the title compound (yield: 52%).

$^1$H-NMR (CDCl$_3$, 90 MHz): δ 3.82 (s, 3H), 4.04 (s, 3H), 4.05 (s, 3H), 6.53 (d, J=5.3 Hz, 1H), 6.7~6.9 (m, 3H), 7.35 (t, J=7.0 Hz, 1H), 7.43 (s, 1H), 7.54 (s, 1H), 8.50 (d, J=5.3 Hz, 1H)

Mass spectrometry data (FD-MS, m/z): 311 (M$^+$)

Example 15

6,7-Dimethoxy-4-(4-methoxyphenoxy)quinoline [3]

4-Chloro-6,7-dimethoxyquinoline (103 mg) and commercially available 4-methoxyphenol (286 mg) were mixed and stirred at 150° C. for 6 hours. The reaction mixture was neutralized with saturated aqueous sodium hydrogen carbonate and then partitioned between water and ethyl acetate, and the ethyl acetate layer was washed with brine and dried with anhydrous sodium sulfate. After removing the solvent by reduced-pressure distillation, the resulting residue was purified by column chromatography on silica gel eluting first with hexane/ethyl acetate and then with chloroform/ethyl acetate to obtain 2.21 g of the title compound (yield: 88%).

$^1$H-NMR (CDCl$_3$, 90 MHz): δ 3.85 (s, 3H), 4.05, (s, 3H), 4.05 (s, 3H), 6.41 (d, J=5.3 Hz, 1H), 6.97 (d, J=9.5 Hz, 2H), 7.14 (d, J=9.5 Hz, 2H), 7.43 (s, 1H), 7.58 (s, 1H), 8.46 (d, J=5.3 Hz, 1H)

Mass spectrometry data (FAB-MS, m/z): 312 (M$^+$+1)

Example 16

6,7-Dimethoxy-4-(5-quinolyloxy)quinoline [14]

4-Chloro-6,7-dimethoxyquinoline (50 mg) and commercially available 5-hydroxyquinoline (50 mg) were mixed and stirred at 170° C. for 10 minutes. The reaction mixture was neutralized with saturated aqueous sodium hydrogen carbonate and then partitioned between water and ethyl acetate, and the ethyl acetate layer was washed with brine and then dried with anhydrous sodium sulfate. After removing the solvent by reduced-pressure distillation, the resulting residue was purified by thin layer chromatography on silica gel eluting first with hexane/ethyl acetate (1/1) and then with chloroform/methanol (50/1) to obtain 47 mg of the title compound (yield: 64%).

$^1$ H-NMR (CDCl$_3$, 90 MHz): δ 4.06 (s, 3H), 4.07 (s, 3H), 6.35 (d, J=5.3 Hz, 1H), 7.2~7.5 (m, 3H), 7.68 (s, 1H), 7.7~8.4 (m, 3H), 8.46 (d, J=5.3 Hz, 1H), 8.49 (dd, J=1.76 Hz, 4.17 Hz, 1 H)

Mass spectrometry data (FD-MS, m/z): 332 (M$^+$)

Example 17

6,7-Dimethoxy-4-(1-naphthyloxy)quinoline [9]

4-Chloro-6,7-dimethoxyquinoline (97 mg) and commercially available 1-naphthol (340 mg) were mixed and stirred at 150° C. for 8 hours. The reaction mixture was neutralized with saturated aqueous sodium hydrogen carbonate and then partitioned between water and ethyl acetate, and the ethyl acetate layer was washed with brine and then dried with anhydrous sodium sulfate. After removing the solvent by reduced-pressure distillation, the resulting residue was purified by column chromatography on silica gel eluting first with hexane/ethyl acetate (3/1) and then with chloroform/methanol (100/1), and further purified by thin layer chromatography on silica gel eluting with hexane/ethyl acetate (1/1) to obtain 57 mg of the title compound (yield: 40%).

$^1$H-NMR (CDCl$_3$, 90 MHz): δ 4.05 (s, 3H), 4.05 (s, 3H), 6.32 (d, J=5.3 Hz, 1H), 7.2~7.6 (m, 5H), 7.74 (s, 1H), 7.8~8.0 (m, 3H), 8.35 (d, J=5.3 Hz, 1H)

Mass spectrometry data (FD-MS, m/z): 331 (M$^+$)

Example 18

6,7-Dimethoxy-4-(5-indolyloxy)quinoline [16]

4-Chloro-6,7-dimethoxyquinoline (1.0 g) and commercially available 5-hydroxyindole (1.19 g) were mixed and stirred at 150° C. for 1.5 hours. The reaction mixture was neutralized with saturated aqueous sodium hydrogen carbonate and then partitioned between water and ethyl acetate, and the ethyl acetate layer was washed with brine and then dried with anhydrous sodium sulfate. After removing the solvent by reduced-pressure distillation, the resulting residue was purified by column chromatography on silica gel eluting in sequence with hexane/ethyl acetate, chloroform and chloroform/methanol, to obtain 898 mg of the title compound (yield: 63%).

$^1$H-NMR (CDCl$_3$, 90 MHz): δ 4.05 (s, 3H), 4.07 (s, 3H), 6.42 (d, J=5.3 Hz, 1H), 6.5~6.7 (m, 1H), 6.9~7.6 (m, 5H), 7.67 (s, 1H), 8.44 (d, J=5.3 Hz, 1H), 8.55 (br, 1H)

Mass spectrometry data (FD-MS, m/z): 320 (M$^+$)

Example 19

6,7-Dimethoxy-4-(3-methoxyphenylthio)quinoline [117]

4-Chloro-6,7-dimethoxyquinoline (50 mg) and commercially available 3-methoxybenzenethiol (77 mg) were mixed and stirred at 180° C. for 30 seconds. Purification was carried out in the same manner as described in Example 18 to obtain 72 mg of the title compound (yield: 100%).

$^1$H-NMR (CDCl$_3$, 90 MHz): δ 3.79 (s, 3H), 4.01 (s, 3H), 4.03 (s, 3H), 6.84 (d, J=4.8 Hz, 1H), 6.9~7.5 (m, 6H), 8.45 (d, J=5.1 Hz, 1H)

Mass spectrometry data (FD-MS, m/z): 327 (M$^+$)

Example 20

6,7-Dimethoxy-4-(4-methoxyphenylthio)quinoline [118]

4-Chloro-6,7-dimethoxyquinoline (50 mg) and commercially available 4-methoxybenzenethiol (63 mg) were mixed and stirred at 150° C. for 5 minutes. Purification was carried out in the same manner as described in Example 18, and further crystallization with chloroform gave 80 mg of the title compound (yield: 100%).

$^1$H-NMR (CDCl$_3$, 90 MHz): δ 3.88 (s, 3H), 4.03 (s, 3H), 4.05 (s, 3H), 6.60 (d, J=4.8 Hz, 1H), 7.15 (d, J=8.7 Hz, 2H), 7.38 (s, 1H), 7.39 (s, 1H), 7.52 (d, J=8.8 Hz, 2H), 8.39 (d, J=5.1 Hz, 1H)

Mass spectrometry data (FD-MS, m/z): 327 (M$^+$)

Example 21 (Reference Example)

4-Bromo-1-methoxymethylphenol

Commercially available 4-bromophenol (17.3 g) was dissolved in N,N-dimethylformamide (90 ml), to which sodium hydride (2.64 g) was added while cooled in ice. After stirring at room temperature overnight, chloromethyl methyl ether (8.35 ml) was added, and the admixture was stirred for a further 1 hour. The reaction mixture was partitioned between water and ethyl acetate, and the ethyl acetate layer was dried with anhydrous magnesium sulfate. After removing the solvent by reduced-pressure distillation, the resulting residue was purified by column chromatography on silica gel eluting with hexane/acetone to obtain 18.25 g of the title compound (yield: 84%).

$^1$H-NMR (CDCl$_3$, 90 MHz): δ 3.46 (s, 3H), 5.13 (s, 2H), 6.91 (d, J=9.2 Hz, 2H), 7.38 (d, J=9.2 Hz, 2 H)

Mass spectrometry data (FD-MS, m/z): 216 (M$^+$), 218 (M$^+$+2)

Example 22 (Reference Example)

4-Tri-n-butyltin-1-methoxymethylphenol

4-Bromo-1-methoxymethylphenol (15.99 g) obtained in Example 21 was dissolved in anhydrous tetrahydrofuran (20 ml), the solution was added to commercially available magnesium powder (1.97 g) under argon, and a drop of an iodine solution in anhydrous tetrahydrofuran was added to the solution to start the reaction. When magnesium disappeared and the temperature of the reaction mixture returned to room temperature, commercially available tri-n-butyltin chloride (23.99 g) dissolved in tetrahydrofuran (10 ml) was added slowly dropwise. The reaction mixture was stirred at room temperature for 4 hours and then partitioned between 5% aqueous ammonium chloride and chloroform. The chloroform layer was dried with anhydrous magnesium sulfate and the solvent was then removed by reduced-pressure distillation to obtain 31.39 g of the title compound (yield: 100%).

$^1$H-NMR (CDCl$_3$, 90 MHz): δ 0.80–1.65 (m, 27H), 3.48 (s, 3H), 5.17 (s, 2H), 6.91~7.42 (m, 4H)

Mass spectrometry data (FD-MS, m/z): 428 (M$^+$+1)

Example 23 (Reference Example)

4-Hydroxyphenyl 4-trifluoromethylphenyl ketone

4-Tri-n-butyltin-1-methoxymethylphenol (1.282 g) obtained in Example 22 and commercially available 4-(trifluoromethyl)benzoyl chloride (626 mg) were dissolved in chloroform (5 ml), commercially available bis(triphenylphosphine)palladium (II) chloride (8 mg) was added, and the admixture was refluxed for 5 hours. The reaction mixture was partitioned between water and ether, the ether layer was washed with saturated aqueous potassium fluoride, and the ether layer obtained by partitioning with brine was dried with anhydrous magnesium sulfate. The residue (1.028 g) obtained by removing the solvent by reduced-pressure distillation was dissolved in tetrahydrofuran (2 ml), water (5 ml) and 6 N aqueous hydrochloric acid (12 ml) were added, and the admixture was refluxed for 4.5 hours. The resulting reaction mixture was partitioned between brine and ether, and the ether layer was dried with anhydrous magnesium sulfate. After removing the solvent by reduced-pressure distillation, the resulting residue was purified by column chromatography on silica gel eluting with hexane/acetone to obtain 348 mg of the title compound (yield: 30%).

Mass spectrometry data (FD-MS, m/z): 266 (M$^+$)

Example 24

(4-Trifluoromethylphenyl){4-[(6,7-dimethoxy-4-quinolyl)oxy]phenyl}methanone [29]

4-Chloro-6,7-dimethoxyquinoline (81 mg) and 4-hydroxyphenyl 4-trifluoromethylphenyl ketone (288 mg) obtained in Example 23 were mixed and stirred at 180° C. for 20 minutes, and the reaction mixture was then purified by thin layer chromatography on silica gel eluting with hexane/acetone (2/1) to obtain 98 mg of the title compound (yield: 60%).

$^1$H-NMR (CDCl$_3$, 500 MHz): δ 4.03 (s, 3H), 4.06 (s, 3H), 6.68 (d, J=4.9 Hz, 1H), 7.29 (d, J=8.5 Hz, 2H), 7.46 (s, 1H), 7.47 (s, 1H), 7.78 (d, J=7.9 Hz, 2H), 7.91 (d, J=7.9 Hz, 2H), 7.94 (d, J=9.2 Hz, 2H), 8.59 (d, J=4.9 Hz, 1H),

Mass spectrometry data (FD-MS, m/z): 453 (M$^+$)

Example 25 (Reference Example)

4-Hydroxyphenyl 4-methylphenyl ketone

4-Tri-n-butyltin-1-methoxymethylphenol (1.282 g) obtained in Example 22 and commercially available 4-toluoyl chloride (464 mg) were dissolved in chloroform (5 ml), commercially available bis(triphenylphosphine)palladium(II) chloride (8 mg) was added, and the admixture was refluxed for 8 hours. The reaction mixture was partitioned in the same manner as described in Example 23 and the resulting ether layer was dried with anhydrous magnesium sulfate. The residue (967 mg) obtained by removing the solvent by reduced-pressure distillation was dissolved in tetrahydrofuran (0.5 ml), water (4 ml) and 6 N aqueous hydrochloric acid (10 ml) were added, and the admixture was refluxed for 7 hours. The reaction mixture was treated in the same manner as described in Example 23 to obtain 271 mg of the title compound (yield: 34%).

Mass spectrometry data (FD-MS, m/z): 212 (M$^+$)

Example 26

{4-[(6,7-Dimethoxy-4-quinolyl)oxy]phenyl}(4-methylphenyl)methanone [30]

4-Chloro-6,7-dimethoxyquinoline (89 mg) and 4-hydroxyphenyl 4-methylphenyl ketone (248 mg) obtained in Example 25 were mixed and stirred at 180° C. for 10 minutes, and the reaction mixture was then purified in the same manner as described in Example 24 to obtain 118 mg of the title compound (yield: 74%).

$^1$H-NMR (CDCl$_3$, 500 MHz): δ 2.45 (s, 3H), 4.03 (s, 3H), 4.06 (s, 3H), 6.65 (d, J=5.5 Hz, 1H), 7.27 (d, J=8.6 Hz, 2H), 7.30 (d, J=7.9 Hz, 2H), 7.46 (s, 1H), 7.49 (s, 1H), 7.74 (d, J=7.9 Hz, 2H), 7.91 (d, J=8.5 Hz, 2H), 8.57 (d, J=4.9 Hz, 1H)

Mass spectrometry data (FD-MS, m/z): 399 (M$^+$)

Example 27 (Reference Example)

3-Chlorophenyl 4-hydroxyphenyl ketone

4-Tri-n-butyltin-1-methoxymethylphenol (1.282 g) obtained in Example 22 and commercially available 3-chlorobenzoyl chloride (525 mg) were dissolved in chloroform (5 ml), commercially available bis(triphenylphosphine)palladium(II) chloride (8 mg) was added, and the admixture was refluxed for 7 hours. The reaction mixture was partitioned in the same manner as described in Example 23, and the resulting ether layer was dried with anhydrous magnesium sulfate. A portion (1.563 g) of the residue (1.914 g) obtained by removing the solvent by reduced-pressure distillation was dissolved in tetrahydrofuran (1 ml), water (7 ml) and 6 N aqueous hydrochloric acid (17 ml) were added, and the admixture was refluxed for 8 hours. The reaction mixture was treated in the same manner as described in Example 23 to obtain 313 mg of the title compound (yield: 22%).

Mass spectrometry data (FD-MS, m/z): 232 (M$^+$)

Example 28

(3-Chlorophenyl){4-[(6,7-dimethoxy-4-quinolyl)oxy]phenyl}methanone [31]

4-Chloro-6,7-dimethoxyquinoline (89 mg) and 3-chlorophenyl 4-hydroxyphenyl ketone (279 mg) obtained in Example 27 were mixed and stirred at 180° C. for 20 minutes. The reaction mixture was then purified in the same manner as described in Example 24 to obtain 67 mg of the title compound (yield: 40%).

$^1$H-NMR (CDCl$_3$, 500 MHz): δ 4.05 (s, 3H), 4.01 (s, 3H), 6.71 (d, J=5.5 Hz, 1H), 7.31 (d, J=8.5 Hz, 2H), 7.51 (s, 1H), 7.69 (s, 1H), 7.94 (d, J=8.5 Hz, 2H), 8.12 (s, 1H), 7.37~8.03 (m, 4H)

Mass spectrometry data (FD-MS, m/z): 419 (M$^+$)

Example 29 (Reference Example)

4-t-Butylphenyl 4-methoxyphenyl ketone

To commercially available nitromethane (5 ml) were added commercially available anisole (541 mg), commercially available 4-t-butylbenzoyl chloride (983 mg) and commercially available scandium(III) trifluoromethanesulfonate (492 mg), and the admixture was stirred at 60° C. for 21 hours. The reaction mixture was partitioned between water and chloroform, and the chloroform layer was then dried with anhydrous magnesium sulfate. After removing the solvent by reduced-pressure distillation, the resulting residue was purified by column chromatography on silica gel eluting with hexane/acetone to obtain 862 mg of the title compound (yield: 64%).

Mass spectrometry data (FD-MS, m/z): 268 (M$^+$)

Example 30 (Reference Example)

4-t-Butylphenyl 4-hydroxyphenyl ketone 4-t-Butylphenyl 4-methoxyphenyl ketone (862 mg) obtained in Example 29 was dissolved in N,N-dimethylformamide (35 ml), sodium thiomethoxide (562 mg) was added, and the admixture was refluxed for 3 hours under argon. The reaction mixture was partitioned between 10% aqueous phosphoric acid and ethyl acetate. The ethyl acetate layer was then dried with anhydrous magnesium sulfate and the solvent was removed by reduced-pressure distillation to obtain 794 mg of the title compound (yield: 97%).

$^1$H-NMR (CDCl$_3$, 500 MHz): δ 1.36 (s, 9H), 6.92 (d, J=8.5 Hz, 2H), 7.49 (d, J=8.6 Hz, 2H), 7.72 (d, J=7.9 Hz, 2H), 7.79 (d, J=8.5 Hz, 2H)

Mass spectrometry data (FD-MS, m/z): 254 (M$^+$)

Example 31

(4-t-Butylphenyl){4-[(6,7-dimethoxy-4-quinolyl)oxy]phenyl}methanone [32]

4-Chloro-6,7-dimethoxyquinoline (341 mg) and 4-t-butylphenyl 4-hydroxyphenyl ketone (775 mg) obtained in Example 30 were mixed and stirred at 150° C. for 15 minutes. The reaction mixture was then purified by column chromatography on silica gel eluting with hexane/acetone to obtain 72 mg of the title compound (yield: 11%).

$^1$H-NMR (CDCl$_3$, 500 MHz): δ 1.38 (s, 9H), 4.04 (s, 3H), 4.06 (s, 3H), 6.65 (d, J=5.5 Hz, 1H), 7.27 (d, J=8.6 Hz, 2H), 7.45 (s, 1H), 7.50 (s, 1H), 7.52 (d, J=8.5 Hz, 2H), 7.78 (d, J=8.6 Hz, 2H), 7.94 (d, J=8.6 Hz, 2H), 8.57 (d, J=4.9 Hz, 1H)

Mass spectrometry data (FAB-MS, m/z): 442 (M$^+$+1)

Example 32 (Reference Example)

4-Biphenyl 4-methoxyphenyl ketone

To commercially available nitromethane (50 ml) were added commercially available anisole (3.244 g), commercially available 4-phenylbenzoyl chloride (6.500 g) and commercially available ytterbium(III) trifluoromethanesulfonate (1.861 g), and the admixture was stirred at 60° C. for 24 hours. The reaction mixture was partitioned between water and chloroform, and the chloroform layer was then dried with anhydrous magnesium sulfate. After removing the solvent by reduced-pressure distillation, a portion (1.00 g) of the resulting residue (9.842 g) was purified by column chromatography on silica gel eluting with hexane/acetone to obtain 300 mg of the title compound (yield: 34%).

$^1$H-NMR (CDCl$_3$, 500 MHz): δ 3.90 (s, 3H), 6.98 (d, J=8.5 Hz, 2H), 7.40 (t, J=7.3 Hz, 1H), 7.48 (t, J=7.3 Hz, 2H), 7.65 (d, J=7.3 Hz, 2H), 7.76 (d, J=8.6 Hz, 2H), 7.85 (d, J=8.5 Hz, 2H), 7.87 (d, J=9.2 Hz, 2H)

Mass spectrometry data (FD-MS, m/z): 288 (M$^+$)

Example 33 (Reference Example)

4-Biphenyl 4-hydroxyphenyl ketone

4-Biphenyl 4-methoxyphenyl ketone (267 mg) obtained in Example 32 was dissolved in N,N-dimethylformamide (20 ml), sodium thiomethoxide (162 mg) was added, and the admixture was refluxed under argon for 3 hours. The reaction mixture was partitioned between 10% aqueous phosphoric acid and ethyl acetate. The ethyl acetate layer was washed with 0.5 N aqueous silver nitrate and then dried with anhydrous magnesium sulfate, the solvent was removed by reduced-pressure distillation, and the resulting residue was purified by column chromatography on silica gel eluting with hexane/ethyl acetate to obtain 207 mg of the title compound (yield: 82%).

$^1$H-NMR (CDCl$_3$, 500 MHz): δ 6.91 (d, J=8.5 Hz, 2H), 7.43 (t, J=7.3 Hz, 1H), 7.52 (dd, J=7.3 Hz, 7.9 Hz, 2H), 7.70 (d, J=8.5 Hz, 2H), 7.75 (d, J=7.9 Hz, 2H) 7.77 (d, J=7.9 Hz, 2H), 7.83 (d, J=7.9 Hz, 2H)

Mass spectrometry data (FD-MS, m/z): 274 (M$^+$)

Example 34

{4-[(6,7-Dimethoxy-4-quinolyl)oxy]phenyl}(4-biphenyl)methanone [33]

4-Chloro-6,7-dimethoxyquinoline (65 mg) and 4-biphenyl 4-hydroxyphenyl ketone (79 mg) obtained in Example 33 were mixed and stirred at 180° C. for 30 minutes. The reaction mixture was purified by thin layer chromatography on silica gel eluting with chloroform/ethyl acetate (10/1) to obtain 50 mg of the title compound (yield: 37%).

$^1$H-NMR (CDCl$_3$, 90 MHz): δ 4.11 (s, 3H), 4.14 (s, 3H), 6.74 (d, J=5.3 Hz, 1H), 7.30~8.09 (m, 15H), 8.65 (d, J=5.3 Hz, 1H)

Mass spectrometry data (FAB-MS, m/z): 462 (M$^+$)

Example 35 (Reference Example)

4-Methoxyphenyl 2-naphthyl ketone

To commercially available nitromethane (10 ml) were added commercially available anisole (1.081 g), commercially available 2-naphthoyl chloride (1.906 g) and commercially available ytterbium(III) trifluoromethanesulfonate (620 mg), and the admixture was stirred at 60° C. for 8 hours. The reaction mixture was partitioned between water and chloroform, and the chloroform layer was then dried with anhydrous magnesium sulfate. After removing the solvent by reduced-pressure distillation, the resulting residue was purified by column chromatography on silica gel eluting with hexane/ethyl acetate to obtain 817 mg of the title compound (yield: 31%).

$^1$H-NMR (CDCl$_3$, 500 MHz): δ 3.89 (s, 3H), 6.98 (d, J=9.2 Hz, 2H), 7.53 (t, J=8.6 Hz, 1H), 7.58 (t, J=9.2 Hz, 1H), 7.86~7.93 (m, 6H), 8.21 (s, 1 H)

Mass spectrometry data (FD-MS, m/z): 262 (M$^+$)

Example 36 (Reference Example)

4-Hydroxyphenyl 2-naphthyl ketone

4-Methoxyphenyl 2-naphthyl ketone (735 mg) obtained in Example 35 was dissolved in N,N-dimethylformamide (20 ml), sodium thiomethoxide (491 mg) was added, and the admixture was refluxed under argon for 5 hours. The reaction mixture was treated in the same manner as described in Example 33 to obtain 595 mg of the title compound (yield: 86%).

$^1$H-NMR (CDCl$_3$, 500 MHz): δ 6.93 (d, J=7.6 Hz, 2H), 7.61 (t, J=7.0 Hz, 1H), 7.67 (t, J=7.3 Hz, 1H), 7.74 (d, J=8.5 Hz, 2H), 7.78~7.80 (m, 1H), 8.02~8.10 (m, 3H), 8.25 (s, 1H)

Mass spectrometry data (FD-MS, m/z): 248 (M$^+$)

Example 37

{4-[(6,7-Dimethoxy-4-quinolyl)oxy]phenyl}(2-naphthyl)methanone [34]

4-Chloro-6,7-dimethoxyquinoline (112 mg) and 4-hydroxyphenyl 2-naphthyl ketone (124 mg) obtained in Example 36 were mixed and stirred at 180° C. for 30 minutes. The reaction mixture was partitioned between saturated aqueous sodium hydrogen carbonate and chloroform, and then the chloroform layer was dried with anhydrous magnesium sulfate. After removing the solvent by reduced-pressure distillation, a portion (50 mg) of the resulting residue (227 mg) was purified by thin layer chromatography on silica gel eluting with chloroform/ethyl acetate (5/1) to obtain 11 mg of the title compound (yield: 23%).

$^1$H-NMR (CDCl$_3$, 90 MHz): 4.05 (s, 3H), 4.07 (s, 3 H), 6.70 (d, J=5.3 Hz, 1H), 7.35 (s, 1H), 7.48~7.90 (m, 5H), 7.96~8.05 (m, 6H), 8.29 (s, 1H), 8.60 (d, J=5.3 Hz, 1H)

Mass spectrometry data (FAB-MS, m/z): 436 (M$^+$+1)

Example 38 (Reference Example)

4-Methoxyphenyl 2-thienyl ketone

To commercially available nitromethane (10 ml) were added commercially available anisole (1.081 g), commercially available 2-thenoyl chloride (1.466 g) and commercially available ytterbium(III) trifluoromethanesulfonate (620 mg), and the admixture was stirred at 60° C. for 8 hours. The reaction mixture was treated in the same manner as described in Example 35 to obtain 965 mg of the title compound (yield: 44%).

$^1$H-NMR (CDCl$_3$, 500 MHz): δ 3.89 (s, 3H), 6.98 (d, J=8.5 Hz, 2H), 7.16 (dd, J=3.7 Hz, 4.9 Hz, 1H), 7.64 (d, J=3.7 Hz, 1H), 7.68 (d, J=4.9 Hz, 1H), 7.90 (d, J=8.6 Hz, 2H)

Mass spectrometry data (FD-MS, m/z): 218 (M$^+$)

Example 39 (Reference Example)

4-Hydroxyphenyl 2-thienyl ketone

4-Methoxyphenyl 2-thienyl ketone (804 mg) obtained in Example 38 was dissolved in N,N-dimethylformamide (30 ml), sodium thiomethoxide (645 mg) was added, and the admixture was refluxed under argon for 5 hours. The reaction mixture was partitioned in the same manner as described in Example 33. The ethyl acetate layer was dried with anhydrous magnesium sulfate, the solvent was removed by reduced-pressure distillation, and the resulting residue was purified by column chromatography on silica gel eluting with chloroform to obtain 702 mg of the title compound (yield: 93%).

$^1$H-NMR (CDCl$_3$, 500 MHz): δ 6.84 (brs, 1H), 6.93 (d, J=8.5 Hz, 2H), 7.14 (dd, J=3.7 Hz, 4.9 Hz, 1H), 7.64 (d, J=3.7 Hz, 1H), 7.68 (d, J=4.9 Hz, 1H), 7.83 (d, J=8.5 Hz, 2H)

Mass spectrometry data (FD-MS, m/z): 204 (M$^+$)

Example 40

{4-[(6,7-Dimethoxy-4-quinolyl)oxy]phenyl}(2-thienyl)methanone [36]

4-Chloro-6,7-dimethoxyquinoline (112 mg) and 4-hydroxyphenyl 2-thienyl ketone (102 mg) obtained in Example 39 were mixed and stirred at 160° C. for 40 minutes. The reaction mixture was purified in the same manner as described in Example 24 to obtain 34 mg of the title compound (yield: 17%).

$^1$H-NMR (CDCl$_3$, 500 MHz): δ 4.04 (s, 3H), 4.07 (s, 3H), 6.65 (d, J=5.5 Hz, 1H), 7.20 (dd, J=3.7 Hz, 4.9 Hz, 1H), 7.29 (d, J=8.5 Hz, 2H), 7.47 (s, 1H), 7.49 (s, 1H), 7.70 (d, J=3.1 Hz, 1H), 7.75 (d, J=4.9 Hz, 1H), 8.00 (d, J=8.6 Hz, 2H), 8.58 (d, J=5.5 Hz, 1H)

Mass spectrometry data (FAB-MS m/z): 392 (M$^+$+1)

Example 41

(4-Chlorophenyl){4-[(6,7-dimethoxy-4-quinolyl)oxy]phenyl}methanone [37]

4-Chloro-6,7-dimethoxyquinoline (112 mg) and commercially available 4-chlorophenyl 4-hydroxyphenyl ketone (349 mg) were mixed and stirred at 180° C. for 20 minutes. The reaction mixture was purified by thin layer chromatography on silica gel eluting with chloroform/ethyl acetate (5/1) to obtain 26 mg of the title compound (yield: 12%).

$^1$H-NMR (CDCl$_3$, 90 MHz): δ 4.03 (s, 3H), 4.07 (s, 3H), 6.66 (d, J=5.3 Hz, 1H), 7.19~7.34 (m, 2H), 7.44~7.56 (m, 4H), 7.71~7.99 (m, 4H), 8.58 (d, J=5.3 Hz, 1H)

Mass spectrometry data (FD-MS, m/z): 419 (M$^+$)

Example 42

(4-fluorophenyl){4-[(6,7-Dimethoxy-4-quinolyl)oxy]phenyl}methanone [38]

4-Chloro-6,7-dimethoxyquinoline (112 mg) and commercially available 4-fluorophenyl 4-hydroxyphenyl ketone (324 mg) were mixed and stirred at 170° C. for 20 minutes. The reaction mixture was then purified in the same manner as described in Example 41 to obtain 114 mg of the title compound (yield: 57%).

$^1$H-NMR (CDCl$_3$, 500 MHz): δ 4.04 (s, 3H), 4.07 (s, 3H), 6.65 (d, J=5.5 Hz, 1H), 7.18 (d, J=8.5 Hz, 1H), 7.20 (d, J=8.5

Hz, 1H), 7.27 (s, 1H), 7.28 (s, 1H), 7.47 (d, J=8.5 Hz, 2H), 7.86 (d, J=8.5 Hz, 1H), 7.88 (d, J=8.5 Hz, 1H), 7.90 (d, J=8.5 Hz, 2H), 8.58 (d, J=4.9 Hz, 1H)

Mass spectrometry data (FD-MS, m/z): 403 (M$^+$)

Example 43

{4-[(6,7-Dimethoxy-4-quinolyl)oxy]phenyl}(phenyl) methanone [39]

4-Chloro-6,7-dimethoxyquinoline (91 mg) and commercially available 4-hydroxybenzophenone (243 mg) were mixed and stirred at 180° C. for 30 minutes. The reaction mixture was purified in the same manner as described in Example 31 to obtain 38 mg of the title compound (yield: 24%).

$^1$H-NMR (CDCl$_3$, 90 MHz): δ 4.03 (s, 3H), 4.05 (s, 3H), 6.66 (d, J=5.3 Hz, 1H), 7.31~7.99 (m, 11H), 8.57 (d, J=5.3 Hz, 1H)

Mass spectrometry data (FD-MS, m/z): 385 (M$^+$)

Example 44 (Reference Example)

3,5-dimethoxy toluene

Commercially available orcinol (5.77 g) was dissolved in acetonitrile (200 ml), dimethyl sulfate (8.47 ml) and potassium carbonate (12.3 g) were added, and the admixture was refluxed for 2.5 hours. The reaction mixture was poured into ice water and partitioned with chloroform, and the chloroform layer was dried with anhydrous magnesium sulfate. The solvent was removed by reduced-pressure distillation, and the resulting residue was purified by column chromatography on silica gel eluting with hexane/ethyl acetate (5/1) to obtain 5.04 g of the title compound (yield: 82%).

$^1$H-NMR (CDCl$_3$, 500 MHz): δ 2.30 (s, 3H), 3.76 (s, 6H), 6.30 (s, 1H), 6.37 (s, 2H)

Example 45 (Reference Example)

2,6-Dimethoxy-4-methylphenyl 4-methoxyphenyl ketone 3,5-Dimethoxy toluene (1.00 g) obtained in Example 44 was dissolved in anhydrous tetrahydrofuran (10 ml), commercially available 2.5 M n-butyllithium-hexane solution (2.90 ml) was added at −45° C. under nitrogen, and the admixture was stirred for 3 hours. Commercially available 4-methoxybenzoyl chloride (1.23 g) was dissolved in tetrahydrofuran (10 ml), and the resulting solution was added slowly to the admixture at −45° C. The reaction mixture was stirred at room temperature for 1 hour and then partitioned between water and chloroform. The chloroform layer was dried with anhydrous magnesium sulfate, the solvent was removed by reduced-pressure distillation, and the resulting residue was purified by column chromatography on silica gel eluting with hexane/ethyl acetate (5/1) to obtain 384 mg of the title compound (yield: 20%).

$^1$H-NMR (CDCl$_3$, 500 MHz): δ 2.40 (s, 3H), 3.69 (s, 6H), 3.85 (s, 3H), 6.43 (s, 2H), 6.89 (d, J=9.2 Hz, 2H), 7.82 (d, J=9.2 Hz, 2H)

Example 46 (Reference Example)

2,6-Dihydroxy-4-methylphenyl 4-hydroxyphenyl ketone 2,6-Dimethoxy-4-methylphenyl 4-methoxyphenyl ketone (321 mg) obtained in Example 45 was dissolved in anhydrous methylene chloride (10 ml), commercially available boron tribromide (349 ml) was added slowly while cooled in ice, and the admixture was stirred at room temperature overnight. The reaction mixture was poured into ice water and then partitioned with ethyl acetate. The ethyl acetate layer was washed with brine and then dried with anhydrous magnesium sulfate. The solvent was removed by reduced-pressure distillation, and the resulting residue was purified by column chromatography on silica gel eluting with hexane/ethyl acetate to obtain 87 mg of the title compound (yield: 68%).

$^1$H-NMR (CDCl$_3$, 500 MHz): δ 2.16 (s, 3H), 6.16 (s, 2H), 6.79 (d, J=8.6 Hz, 2H), 7.56 (d, J=8.5 Hz, 2H)

Example 47

(2,6-Dihydroxy-4-methylphenyl){4-[6,7-dimethoxy-4-quinolyl)oxy]phenyl}methanone [42]

4-Chloro-6,7-dimethoxyquinoline (61 mg) and 2,6-dihydroxy-4-methylphenyl 4-hydroxyphenyl ketone (100 mg) obtained in Example 46 were dissolved in diethylene glycol dimethyl ether (0.5 ml), and the solution was stirred at 170° C. for 20 minutes. The reaction mixture was partitioned between saturated aqueous sodium hydrogen carbonate and chloroform, and the chloroform layer was washed with brine and then dried with anhydrous magnesium sulfate. The solvent was removed by reduced-pressure distillation, and the resulting residue was purified by column chromatography on silica gel eluting with chloroform/methanol (100/1) to obtain 32 mg of the title compound (yield: 27%).

$^1$H-NMR (DMSO, 500 MHz): δ 2.18 (s, 3H), 3.90 (s, 3H), 3.95 (s, 3H), 6.20 (s, 2H) 6.68 (d, J=4.9 Hz, 1H), 7.32 (d, J=9.2 Hz, 2H), 7.42 (s, 1H), 7.43 (s, 1H), 7.82 (d, J=8.6 Hz, 2H), 8.54 (d, J=5.5 Hz, 1H)

Mass spectrometry data (FD-MS, m/z): 432 (M$^+$+1)

Example 48 (Reference Examples)

6,7-Dimethoxy-4-(4-nitrophenoxy)quinoline

4-Chloro-6,7-dimethoxyquinoline (1.84 g) and commercially available 4-nitrophenol (3.42 g) was mixed and stirred at 170° C. for 50 minutes. After cooling to room temperature in air, aqueous sodium hydrogen carbonate was added to the reaction mixture, and the admixture was extracted 3 times with ethyl acetate, and the ethyl acetate layer was washed with brine and then dried with anhydrous sodium sulfate. The solvent was removed by reduced-pressure distillation, and the resulting residue was purified by column chromatography on silica gel eluting with chloroform/methanol to obtain 4.54 g of the title compound (yield: 89%).

$^1$H-NMR (CDCl$_3$, 500 MHz): δ 4.01 (s, 3H), 4.06 (s, 3H), 6.69 (d, J=4.9 Hz, 1H), 7.27 (d, J=9.1 Hz, 2H), 7.37 (s, 1H), 7.47 (s, 1H), 8.32 (d, J=9.1 Hz, 2H), 8.62 (d, J=4.9 Hz, 1H)

Mass spectrometry data (FD-MS, m/z): 326 (M$^+$)

Example 49 (Reference Example)

6,7-Dimethoxy-4-(4-aminophenoxy)quinoline 6,7-Dimethoxy-4-(4-nitrophenoxy)quinoline (1.00 g) was dissolved in N,N-dimethylformamide/ethyl acetate (30 ml/15 ml), 10% palladium hydroxide-carbon (69 mg) was added, and the admixture was stirred at room temperature under hydrogen for 17 hours. The reaction mixture was filtered using Celite. The filtrate was washed with brine and then dried with anhydrous sodium sulfate. The solvent was removed by reduced-pressure distillation to obtain 799 mg of the title compound (yield: 88%).

$^1$H-NMR (CD$_3$OD, 500 MHz): δ 4.00 (s, 3H), 4.00 (s, 3H), 6.47 (d, J=5.5 Hz, 1H), 6.82 (d, J=8.6 Hz, 2H), 6.96 (d, J=9.2 Hz, 2H), 7.32 (s, 1H), 7.62 (s, 1H), 8.36 (d, J=5.5 Hz, 1H),

Mass spectrometry data (FD-MS, m/z): 296 (M$^+$)

Example 50

N-{4-[6,7-Dimethoxy-4-quinolinyl)oxy]phenyl}-3-pyridinecarboxamide [61]

6,7-Dimethoxy-4-(4-aminophenoxy)quinoline (57 mg) and commercially available nicotinic acid (37 mg) were dissolved in N,N-dimethylformamide (2 ml), 1-ethyl-3-(3'-dimethylaminopropyl)carbodiimide hydrochloride (79 mg) was added, and the admixture was stirred at room temperature for 5 hours. The reaction mixture was partitioned between water and ethyl acetate, and the ethyl acetate layer was washed with brine and then dried with anhydrous sodium sulfate. The solvent was removed by reduced-pressure distillation and the resulting crystallized product was washed with ether to obtain 47 mg of the title compound (yield: 61%).

$^1$H-NMR (CDCl$_3$, 500 MHz): δ 4.05 (s, 3H), 4.06 (s, 3H), 6.49 (d, J=4.9 Hz, 1H), 7.22 (d, J=8.6 Hz, 2H) 7.42 (s, 1H), 7.47 (dd, J=4.9, 7.9 Hz, 1H), 7.56 (s, 1H), 7.77 (d, J=9.2 Hz, 1H), 8.26 (d, J=8.5 Hz, 2H), 8.49 (d, J=4.9 Hz, 1H), 8.79 (d, J=3.7 Hz, 1H), 9.13 (s, 1H)

Mass spectrometry data (FD-MS, m/z): 401 (M$^+$)

Example 51

N-{4-[(6,7-Dimethoxy-4-quinolinyl)oxy]phenyl}-(3,4-dimethoxyphenyl)carboxamide [62]

6,7-Dimethoxy-4-(4-aminophenoxy)quinoline (56 mg) and commercially available 3,4-dimethoxybenzoic acid (60 mg) were dissolved in N,N-dimethylformamide (2 ml), 1-ethyl-3-(3'-dimethylaminopropyl)carbodiimide hydrochloride (81 mg) was added, and the admixture was stirred at room temperature for 22 hours. The reaction mixture was partitioned between water and ethyl acetate, and the ethyl acetate layer was washed with brine and then dried with anhydrous sodium sulfate. The solvent was removed by reduced-pressure distillation, and the resulting residue was purified by column chromatography on silica gel eluting chloroform/acetone (10/1) to obtain 7 mg of the title compound (yield: 8%).

$^1$H-NMR (CDCl$_3$, 500 MHz): δ 3.87 (s, 3H), 3.87 (s, 3H), 4.06 (s, 3H), 4.07 (s, 3H), 6.48 (d, J=5.5 Hz, 1H), 6.63 (d, J=8.5 Hz, 2H), 7.18 (d, J=9.2 Hz, 2H), 7.34 (m, 2H), 7.43 (s, 1H), 7.55 (s, 1H), 7.57 (s, 1H), 7.76 (d, J=8.6 Hz, 2H), 8.48 (d, J=5.5 Hz, 1H)

Mass spectrometry data (FD-MS, m/z): 460 (M$^+$)

Example 52

N-{4-[(6,7-Dimethoxy-4-quinolinyl)oxy]phenyl}-cyclohexanecarboxamide [63]

6,7-Dimethoxy-4-(4-aminophenoxy)quinoline (52 mg) and commercially available cyclohexanecarboxylic acid (46 mg) were dissolved in N,N-dimethylformamide (2 ml), 1-ethyl-3-(3'-dimethylaminopropyl)carbodiimide hydrochloride (84 mg) was added, and the admixture was stirred at room temperature for 22 hours. The reaction mixture was then purified in the same manner as described in Example 51 to obtain 45 mg of the title compound (yield: 64%).

$^1$H-NMR (CDCl$_3$, 500 MHz): δ 1.30 (m, 2H), 1.56 (m, 2H), 1.73 (m, 2H), 1.85 (m, 2H), 1.97 (m, 2H), 2.26 (m, 1H), 4.05 (s, 3H), 4.05 (s, 3H), 6.43 (d, J=5.5 Hz, 1H), 7.14 (d, J=8.5 Hz, 2H), 7.36 (s, 1H), 7.42 (s, 1H), 7.55 (s, 1H), 7.63 (d, J=8.5 Hz, 2H), 8.47 (d, J=5.5 Hz, 1H)

Mass spectrometry data (FD-MS, m/z): 406 (M$^+$)

Example 53

N-{4-[(6,7-Dimethoxy-4-quinolinyl)oxy]phenyl}-2-furancarboxamide [64]

6,7-Dimethoxy-4-(4-aminophenoxy)quinoline (55 mg) and commercially available 2-furancarboxylic acid (32 mg) were dissolved in N,N-dimethylformamide (2 ml), 1-ethyl-3-(3'-dimethylaminopropyl)carbodiimide hydrochloride (91 mg) was added, and the admixture was stirred at room temperature for 22 hours. The reaction mixture was then purified in the same manner as described in Example 51 to obtain 35 mg of the title compound (yield: 48%).

$^1$H-NMR (CDCl$_3$, 500 MHz): δ 4.04 (s, 3H), 4.05 (s, 3H), 6.49 (d, J=4.9 Hz, 1H), 6.57 (dd, J=1.8, 8.7 Hz, 1H), 7.20 (d, J=8.6 Hz, 2H), 7.28 (d, J=7.9 Hz, 1H), 7.42 (s, 1H), 7.51 (s, 1H), 7.56 (s, 1H), 7.77 (d, J=9.2 Hz, 2H), 8.35 (s, 1H), 8.49 (d, J=5.5 Hz, 1H)

Mass spectrometry data (FD-MS, m/z): 390 (M$^+$)

Example 54

N-{4-[(6,7-Dimethoxy-4-quinolinyl)oxy]phenyl}-3-thiophenecarboxamide [65]

6,7-Dimethoxy-4-(4-aminophenoxy)quinoline (54 mg) and commercially available 3-thiophenecarboxylic acid (44 mg) were dissolved in N,N-dimethylformamide (2 ml), 1-ethyl-3-(3-dimethylaminopropyl) carbodiimide hydrochloride (82 mg) was added, and the admixture was stirred at room temperature for 31 hours. The reaction mixture was then purified in the same manner as described in Example 51 to obtain 41 mg of the title compound (yield: 55%).

$^1$H-NMR (CDCl$_3$, 500 MHz): δ 4.02 (s, 3H), 4.04 (s, 3H), 6.46 (d, J=5.5 Hz, 1H), 7.17 (d, J=8.6 Hz, 2H), 7.38 (m, 1H), 7.55 (d, J=1.2 Hz, 1H), 7.56 (s, 1H), 7.73 (d, J=8.6 Hz, 2H), 8.05 (dd, J=1.2, 3.1 Hz, 1H), 8.37 (s, 1H), 8.47 (d, J=5.5 Hz, 1H)

Mass spectrometry data (FD-MS, m/z): 406 (M$^+$)

Example 55

N-{4-[(6,7-Dimethoxy-4-quinolinyl)oxy]phenyl}-(4-nitrophenyl)carboxamide [66]

6,7-Dimethoxy-4-(4-aminophenoxy)quinoline (110 mg) and commercially available 4-nitrobenzoic acid (100 mg) were dissolved in N,N-dimethylformamide (4 ml), 1-ethyl-3-(3'-dimethylaminopropyl)carbodiimide hydrochloride (176 mg) was added, and the admixture was stirred at room temperature for 22 hours. The reaction mixture was then purified in the same manner as described in Example 50 to obtain 126 mg of the title compound (yield: 77%).

$^1$H-NMR (DMSO-d$_6$, 500 MHz): δ 3.94 (s, 3H), 3.95 (s, 3H), 6.49 (d, J=5.5 Hz, 1H), 7.29 (d, J=9.2 Hz, 2H), 7.39 (s, 1H), 7.52 (s, 1H), 7.93 (d, J=9.2 Hz, 2H), 8.21 (d, J=8.6 Hz, 2H), 8.39 (d, J=9.2 Hz, 2H), 8.48 (d, J=5.5 Hz, 1H), 10.7 (s, 1H)

Mass spectrometry data (FD-MS, m/z): 445 (M⁺)

Example 56

N-{4-[(6,7-Dimethoxy-4-quinolinyl)oxy]phenyl}-(N,N-dimethylaminophenyl)carboxamide [67]

6,7-Dimethoxy-4-(4-aminophenoxy)quinoline (51 mg) and commercially available 4-(dimethylamino)benzoic acid (44 mg) were dissolved in N,N-dimethylformamide (2 ml), 1-ethyl-3-(3'-dimethylaminopropyl)carbodiimide hydrochloride (83 mg) was added, and the admixture was stirred at room temperature for 16 hours. The reaction mixture was then purified in the same manner as described in Example 51 to obtain 7 mg of the title compound (yield: 10%).

$^1$H-NMR (CDCl$_3$, 500 MHz): δ 3.06 (s, 6H), 4.05 (s, 3H), 4.06 (s 3H), 6.48 (d, J=4.9 Hz, 1H), 6.71 (d, J=8.6 Hz, 2H), 7.17 (d, J=8.5 Hz, 2H), 7.44 (s, 1H), 7.57 (s, 1H), 7.74 (d, J=8.5 Hz, 2H), 7.81 (d, J=9.2 Hz, 2H), 7.94 (s, 1H), 8.49 (d, J=5.5 Hz, 1H)

Mass spectrometry data (FD-MS, m/z): 443 (M⁺)

Example 57

N-{4-[(6,7-Dimethoxy-4-quinolinyl)oxy]phenyl}-(4-acetylphenyl)carboxamide [68]

6,7-Dimethoxy-4-(4-aminophenoxy)quinoline (54 mg) and commercially available 4-acetylbenzoic acid (46 mg) were dissolved in N,N-dimethylformamide (2 ml), 1-ethyl-3-(3'-dimethylaminopropyl)carbodiimide hydrochloride (87 mg) was added, and the admixture was stirred at room temperature for 22 hours. The reaction mixture was then purified in the same manner as described in Example 50 to obtain 43 mg of the title compound (yield: 53%).

$^1$H-NMR (DMSO-d$_6$, 500 MHz): δ 2.66 (s, 3H), 3.94 (s, 3H), 3.95 (s, 3H), 6.48 (d, J=4.9 Hz, 1H), 7.28 (d, J=9.2 Hz, 2H), 7.39 (s, 1H), 7.52 (s, 1H), 7.94 (d, J=9.2 Hz, 2H), 8.10 (m, 4H), 8.48 (d, J=5.5 Hz, 1H), 10.6 (s, 1H)

Mass spectrometry data (FD-MS, m/z): 442 (M⁺)

Example 58

N-{4-[(6,7-Dimethoxy-4-quinolinyl)oxy]phenyl}-(4-butylphenyl)carboxamide [69]

6,7-Dimethoxy-4-(4-aminophenoxy)quinoline (54 mg) and commercially available 4-butyl benzoate (54 mg) were dissolved in N,N-dimethylformamide (2 ml), 1-ethyl-3-(3'-dimethylaminopropyl)carbodiimide hydrochloride (85 mg) was added, and the admixture was stirred at room temperature for 22 hours. The reaction mixture was then purified in the same manner as described in Example 51 to obtain 65 mg of the title compound (yield: 78%).

$^1$H-NMR (CDCl$_3$, 500 MHz): δ 0.95 (t, J=7.3 Hz, 3H), 1.38 (m, 2H), 1.64 (m, 2H), 2.69 (t, J=8.0 Hz, 2H), 4.05 (s, 3H), 4.06 (s, 3H), 6.48 (d, J=5.5 Hz, 1H), 7.19 (d, J=9.2 Hz, 2H), 7.30 (d, J=8.6 Hz, 2H), 7.42 (s, 1H), 7.57 (s, 1H), 7.75 (d, J=8.6 Hz, 2H), 7.82 (d, J=8.6 Hz, 2H), 8.03 (s, 1H), 8.49 (d, J=5.5 Hz, 1H)

Mass spectrometry data (FD-MS, m/z): 456 (M⁺)

Example 59

N-{4-[(6,7-Dimethoxy-4-quinolinyl)oxy]phenyl}-(4-aminophenyl)carboxamide [70]

{4-[(6,7-Dimethoxy-4-quinolinyl)oxy]phenyl}-(4-nitrophenyl)carboxamide (100 mg) was dissolved in N,N-dimethylformamide/ethyl acetate (9 ml/5 ml), 10% palladium-carbon (69 mg) was added, and the admixture was stirred at room temperature under hydrogen for 22 hours. The reaction mixture was filtered using Celite. The filtrate was then distilled under reduced pressure to remove the solvents, and the resultant residue was purified by column chromatography on silica gel eluting chloroform/acetone to obtain 85 mg of the title compound (yield: 91%).

$^1$H-NMR (DMSO-d$_6$, 500 MHz): δ 3.94 (s, 3H), 3.95 (s, 3H), 5.75 (brs, 2H), 6.46 (d, J=4.9 Hz, 1H), 6.61 (d, J=8.6 Hz, 2H), 7.22 (d, J=9.2 Hz, 2H), 7.39 (s, 1H), 7.52 (s, 1H), 7.73 (d, J=8.5 Hz, 2H), 7.89 (d, J=9.2 Hz, 2H), 8.46 (d, J=5.5 Hz, 1H), 9.90 (s, 1H)

Mass spectrometry data (FD-MS, m/z): 415 (M⁺)

Example 60

N-{4-[(6,7-Dimethoxy-4-quinolinyl)oxy]phenyl}-4-pyridinecarboxamide [71]

6,7-Dimethoxy-4-(4-aminophenoxy)quinoline (53 mg) and commercially available isonicotinic acid (45 mg) were dissolved in N,N-dimethylformamide (2 ml), 1-ethyl-3-(3'-dimethylaminopropyl)carbodiimide hydrochloride (98 mg) was added, and the admixture was stirred at room temperature for 62 hours. The reaction mixture was then purified in the same manner as described in Example 51 to obtain 22 mg of the title compound (yield: 31%).

$^1$H-NMR(DMSO-d$_6$, 500 MHz): δ 3.94 (s, 3H), 3.96 (s, 3H), 6.48 (d, J=5.5 Hz, 1H), 7.29 (d, J=9.2 Hz, 2H), 7.39 (s, 1H), 7.52 (s, 1H), 7.88 (d, J=4.3 Hz, 2H), 7.92 (d, J=8.5 Hz, 2H), 8.48 (d, J=4.9 Hz, 1H), 8.80 (d, J=4.3 Hz, 2H), 10.6 (s, 1H)

Mass spectrometry data (FD-MS, m/z): 401 (M⁺)

Example 61

N-{4-[(6,7-Dimethoxy-4-quinolinyl)oxy]phenyl}-2-thiophenecarboxamide [72]

6,7-Dimethoxy-4-(4-aminophenoxy)quinoline (50 mg) and commercially available 2-thiophenecarboxylic acid (46 mg) were dissolved in N,N-dimethylformamide (2 ml), 1-ethyl-3-(3'-dimethylaminopropyl)carbodiimide hydrochloride (99 mg) was added, and the admixture was stirred at room temperature for 62 hours. The reaction mixture was then purified in the same manner as described in Example 51 to obtain 37 mg of the title compound (yield: 54%).

$^1$H-NMR (CDCl$_3$, 500 MHz): δ 4.02 (s, 3H), 4.04 (s, 3H), 6.46 (d, J=5.5 Hz, 1H), 7.11 (m, 1H), 7.17 (d, J=8.6 Hz, 2H), 7.40 (s, 1H), 7.55 (m, 1H), 7.56 (s, 1H), 7.73 (d, J=8.5 Hz, 2H), 7.73 (m, 1H), 8.38 (s, 1H), 8.48 (d, J=4.9 Hz, 1H)

Mass spectrometry data (FD-MS, m/z): 406 (M⁺)

Example 62

N-{4-[(6,7-Dimethoxy-4-quinolinyl)oxy]phenyl}-4-biphenylcarboxamide [73]

6,7-Dimethoxy-4-(4-aminophenoxy)quinoline (52 mg) was suspended in triethylamine/methylene chloride (3 ml/2 ml), commercially available biphenylcarbonyl chloride (80 mg) was added, and the admixture was stirred at room temperature for 25 hours. Aqueous sodium hydrogen carbonate was added to the reaction mixture, and the resulting admixture was extracted with ethyl acetate. The ethyl acetate layer was washed with brine and then dried with anhydrous sodium sulfate. The solvent was removed by reduced-pressure distillation, and the resulting residue was purified by column chromatography on silica gel eluting with chloroform/acetone and further by washing resulting crystals with acetone to obtain 9 mg of the title compound (yield: 10%).

$^1$H-NMR (DMSO-d$_6$, 500 MHz): δ 3.95 (s, 3H), 3.95 (s, 3H), 6.48 (d, J=5.5 Hz, 1H), 7.28 (d, J=9.2 Hz, 2H), 7.40 (s, 1H), 7.43 (t, J=7.3 Hz, 1H), 7.50~7.53 (m, 3H), 7.77 (d, J=7.3 Hz, 2H), 7.85 (d, J=8.6 Hz, 2H), 7.96 (m, 2H), 8.08 (d, J=8.5 Hz, 2H), 8.48 (d, J=4.9 Hz, 1H), 10.4 (s, 1H)

Mass spectrometry data (FD-MS, m/z): 476 (M$^+$)

Example 63

N-{4-[(6,7-Dimethoxy-4-quinolinyl)oxy]phenyl}-(4-butoxyphenyl)carboxamide [74]

6,7-Dimethoxy-4-(4-aminophenoxy)quinoline (52 mg) was suspended in triethylamine/methylene chloride (3 ml/2 ml), commercially available 4-butoxybenzoyl chloride (0.07 ml) was added, and the admixture was stirred at room temperature for 30 hours. The reaction mixture was then purified in the same manner as described in Example 62 to obtain 34 mg of the title compound (yield: 41%).

$^1$H-NMR (CDCl$_3$, 500 MHz): δ 0.99 (t, J=7.3 Hz, 3H), 1.52 (m, 2H), 1.80 (m, 2H), 4.03 (m, 2H), 4.04 (s, 3H), 4.05 (s, 3H), 6.47 (d, J=4.9 Hz, 1H), 6.95 (d, J=9.2 Hz, 2H), 7.18 (d, J=9.2 Hz, 2H), 7.46 (s, 1H), 7.57 (s, 1H), 7.74 (d, J=9.2 Hz, 2H), 7.86 (d, J=9.2 Hz, 2H), 8.10 (s, 1H), 8.49 (d, J=4.9 Hz, 1H)

Mass spectrometry data (FD-MS, m/z): 472 (M$^+$)

Example 64

N-{4-[(6,7-Dimethoxy-4-quinolinyl)oxy]phenyl}-(4-bromophenyl)carboxamide [75]

6,7-Dimethoxy-4-(4-aminophenoxy)quinoline (52 mg) and commercially available 4-bromobenzoic acid (78 mg) were dissolved in N,N-dimethylformamide (2 ml), 1-ethyl-3-(3'-dimethylaminopropyl)carbodiimide hydrochloride (102 mg) was added, and the admixture was stirred at room temperature for 17 hours. The reaction mixture was then purified in the same manner as described in Example 51 to obtain 43 mg of the title compound (yield: 52%).

$^1$H-NMR (CDCl$_3$, 500 MHz): δ 4.07 (s, 3H), 4.07 (s, 3H), 6.53 (d, J=5.5 Hz, 1H), 7.22 (d, J=9.2 Hz, 2H), 7.37 (s, 1H), 7.50 (s, 1H), 7.62 (s, 1H), 7.65 (d, J=8.6 Hz, 2H), 7.84 (d, J=8.6 Hz, 2H), 7.86 (d, J=8.6 Hz, 2H), 8.41 (d, J=5.5 Hz, 1H)

Mass spectrometry data (FD-MS, m/z): 478 (M$^+$), 480 (M$^+$+2)

Example 65

N-{4-[(6,7-Dimethoxy-4-quinolinyl)oxy]phenyl}-(4-methoxycarbonylphenyl)carboxamide [76]

6,7-Dimethoxy-4-(4-aminophenoxy)quinoline (100 mg) and commercially available monomethylterephthalic acid (130 mg) were dissolved in N,N-dimethylformamide (4 ml), 1-ethyl-3-(3'-dimethylaminopropyl)carbodiimide hydrochloride (227 mg) was added, and the admixture was stirred at room temperature for 18 hours. The reaction mixture was then purified in the same manner as described in Example 51 to obtain 99 mg of the title compound (yield: 64%).

$^1$H-NMR (CDCl$_3$, 500 MHz): δ 3.98 (s, 3H), 4.06 (s, 3H), 4.06 (s, 3H), 6.49 (d, J=4.9 Hz, 1H), 7.22 (d, J=9.2 Hz, 2H), 7.43 (s, 1H), 7.56 (s, 1H), 7.76 (d, J=9.2 Hz, 2H), 7.97 (d, J=8.6 Hz, 2H), 8.18 (d, J=8.6 Hz, 2H), 8.49 (d, J=5.5 Hz, 1H)

Mass spectrometry data (FD-MS, m/z): 458 (M$^+$)

Example 66

N-{4-[(6,7-Dimethoxy-4-quinolinyl)oxy]phenyl}-2-pyridinecarboxamide [77]

6,7-Dimethoxy-4-(4-aminophenoxy)quinoline (50 mg) and commercially available picolinic acid (42 mg) were dissolved in N,N-dimethylformamide (2 ml), 1-ethyl-3-(3'-dimethylaminopropyl)carbodiimide hydrochloride (123 mg) was added, and the admixture was stirred at room temperature for 19 hours. The reaction mixture was then purified in the same manner as described in Example 51 to obtain 38 mg of the title compound (yield: 56%).

$^1$H-NMR (CDCl$_3$, 500 MHz) δ 4.06 (s, 3H), 4.06 (s, 3H), 6.49 (d, J=5.5 Hz, 1H), 7.23 (d, J=8.6 Hz, 2H), 7.43 (s, 1H), 7.51 (m, 1H), 7.58 (s, 1H), 7.89 (d, J=9.2 Hz, 2H), 7.94 (m, 1H), 8.33 (d, J=8.0 Hz, 1H), 8.50 (d, J=5.5 Hz, 1H), 8.64 (dd, J=1.8, 4.9 Hz, 1H)

Mass spectrometry data (FD-MS, m/z): 401 (M$^+$)

Example 67

N-{4-[(6,7-Dimethoxy-4-quinolinyl)oxy]phenyl}-(4-hydroxycarbonylphenyl)carboxamide [78]

{4-[(6,7-Dimethoxy-4-quinolinyl)oxy]phenyl}-(4-methoxycarbonylphenyl)carboxamide was dissolved in methanol (3 ml), 33% aqueous potassium hydroxide (1.5 ml) was added, and the admixture was stirred at room temperature for 2 hours. The reaction mixture was washed 2 times with ethyl acetate, and the water layer was neutralized with dilute hydrocholoric acid and extracted 2 times with chloroform. The chloroform layer was dried with sodium sulfate, and the solvent was then removed by reduced-pressure distillation to obtain 34 mg of the title compound (yield: 45%).

$^1$H-NMR (DMSO-d$_6$, 500 MHz): δ 3.93 (s, 3H), 3.94 (s, 3H), 6.47 (d, J=5.5 Hz, 1H), 7.28 (d, J=9.2 Hz, 2H), 7.39 (s, 1H), 7.51 (s, 1H), 7.92 (d, J=9.2 Hz, 2H), 8.07 (s, 4H), 8.47 (d, J=5.5 Hz, 1H), 10.5 (s, 1H)

Mass spectrometry data (FD-MS, m/z): 444 (M$^+$)

Example 68

N-{4-[(6,7-Dimethoxy-4-quinolinyl)oxy]phenyl}cyclopentanecarboxamide [79]

6,7-Dimethoxy-4-(4-aminophenoxy)quinoline (53 mg) and commercially available cyclopentanecarboxylic acid (66 mg) were dissolved in N,N-dimethylformamide (2 ml), 1-ethyl-3-(3'-dimethylaminopropyl)carbodiimide hydrochloride (110 mg) was added, and the admixture was stirred at room temperature for 17 hours. The reaction mixture was purified in the same manner as described in Example 51 to obtain 35 mg of the title compound (yield: 50%).

$^1$H-NMR (CDCl$_3$, 500 MHz) δ 1.64 (m, 2H), 1.81 (m, 2H), 1.91 (m, 4H), 2.75 (m, 1H), 4.04 (s, 3H), 4.04 (s, 3H), 6.44 (d, J=4.9 Hz, 1H), 7.13 (d, J=9.2 Hz, 2H), 7.45 (s, 1H), 7.55 (m, 1H), 7.65 (d, J=8.6 Hz, 2H), 8.47 (d, J=5.5 Hz, 1H)

Mass spectrometry data (FD-MS, m/z): 392 (M$^+$)

Example 69

N-{4-[(6,7-Dimethoxy-4-quinolinyl)oxy]phenyl}adamantanecarboxamide [81]

6,7-Dimethoxy-4-(4-aminophenoxy)quinoline (51 mg) and commercially available adamantanecarboxylic acid (110 mg) were dissolved in N,N-dimethylformamide (2 ml), 1-ethyl-3-(3'-dimethylaminopropyl)carbodiimide hydrochloride (107 mg) was added, and the admixture was stirred at room temperature for 15 hours. The reaction mixture was purified in the same manner as described in Example 51 to obtain 13 mg of the title compound (yield: 17%).

$^1$H-NMR (CDCl$_3$, 500 MHz): δ 1.82 (m, 6H), 2.00 (m, 6H), 2.13 (m, 3H), 4.05 (s, 3H), 4.05 (s, 3H), 6.44 (d, J=4.9 Hz, 1H), 7.15 (d, J=9.2 Hz, 2H), 7.42 (s, 1H), 7.55 (m, 1H), 7.64 (d, J=9.2 Hz, 2H), 8.46 (d, J=4.9 Hz, 1H),

Mass spectrometry data (FD-MS, m/z): 458 (M$^+$)

Example 70

N-{4-[(6,7-Dimethoxy-4-quinolinyl)oxy]phenyl}-(4-acetoxyphenyl)carboxamide [80]

6,7-Dimethoxy-4-(4-aminophenoxy)quinoline (110 mg) and commercially available 4-acetoxybenzoic acid (207 mg) were dissolved in N,N-dimethylformamide (6 ml), 1-ethyl-3-(3'-dimethylaminopropyl)carbodiimide hydrochloride (223 mg) was added, and the admixture was stirred at room temperature for 7 hours. The reaction mixture was then purified in the same manner as described in Example 51 to obtain 123 mg of the title compound (yield: 72%).

$^1$H-NMR (CDCl$_3$, 500 MHz): δ 2.35 (s, 3H), 4.06 (s, 3H), 4.06 (s, 3H), 6.49 (d, J=4.9 Hz, 1H), 7.21 (d, J=9.2 Hz, 2H), 7.25 (d, J=9.1 Hz, 2H), 7.43 (s, 1H), 7.56 (s, 1H), 7.73 (d, J=9.2 Hz, 2H), 7.87 (s, 1H), 7.93 (d, J=8.6 Hz, 2H), 8.50 (d, J=5.5 Hz, 1H),

Mass spectrometry data (FD-MS, m/z): 458 (M$^+$)

Example 71

N-{4-[(6,7-Dimethoxy-4-quinolinyl)oxy]phenyl}-2-(6-acetoxynaphthyl)carboxamide [82]

6,7-Dimethoxy-4-(4-aminophenoxy)quinoline (51 mg) and commercially available 6-acetoxy-2-naphthoic acid (121 mg) were dissolved in N,N-dimethylformamide (2 ml), 1-ethyl-3-(3'-dimethylaminopropyl)carbodiimide hydrochloride (124 mg) was added, and the admixture was stirred at room temperature for 13 hours. The reaction mixture was then purified in the same manner as described in Example 51 to obtain 66 mg of the title compound (yield: 75%).

$^1$H-NMR (DMSO-d$_6$, 500 MHz): δ 2.38 (s, 3 H), 4.03 (s, 3H), 4.05 (s, 3H), 6.49 (d, J=5.5 Hz, 1H), 7.20 (d, J=9.2 Hz, 2H), 7.30 (dd, J=2.4, 9.2 Hz, 1H), 7.42 (s, 1H), 7.57 (m, 1H), 7.61 (d, J=1.8 Hz, 1H), 7.81 (d, J=9.2 Hz, 2H), 7.86 (d, J=8.6 Hz, 1H), 7.89 (d, J=9.2 Hz, 1H), 7.94 (d, J=8.6 Hz, 1H), 8.38 (s, 1H), 8.49 (d, J=4.9 Hz, 1H)

Mass spectrometry data (FD-MS, m/z): 508 (M$^+$)

Example 72

N-{4-[(6,7-Dimethoxy-4-quinolinyl)oxy]phenyl}-(4-hydroxyphenyl)carboxamide [83]

N-{4-[(6,7-Dimethoxy-4-quinolinyl)oxy]phenyl}-(4-acetoxyphenyl)carboxamide (103 mg) was dissolved in methanol (4 ml), 35% aqueous potassium hydroxide (2 ml) was added, and the admixture was stirred at room temperature for 5 hours. The reaction mixture was partitioned with ethyl acetate/water, and the ethyl acetate layer was washed with brine and then dried with anhydrous sodium sulfate. The solvent was removed by reduced-pressure distillation, and the resulting crystals were washed with ether to obtain 77 mg of the title compound (yield: 82%).

$^1$H-NMR (DMSO-d$_6$, 500 MHz): δ 3.94 (s, 3H), 3.95 (s, 3H), 6.46 (d, J=4.9 Hz, 1H), 6.87 (d, J=8.5 Hz, 2H), 7.24 (d, J=9.2 Hz, 2H), 7.39 (s, 1H), 7.52 (s, 1H), 7.87 (d, J=8.6 Hz, 2H), 7.90 (d, J=9.2 Hz, 2H), 8.47 (d, J=5.5 Hz, 1H), 10.1 (s, 1H)

Mass spectrometry data (FD-MS, m/z): 417 (M$^+$+1)

Example 73

N-{4-[(6,7-Dimethoxy-4-quinolinyl)oxy]phenyl}-2-(6-hydroxynaphthyl)carboxamide [84]

N-{4-[(6,7-Dimethoxy-4-quinolinyl)oxy]phenyl}-2-(6-acetoxynaphthyl)carboxamide (47 mg) was dissolved in methanol (4 ml), 35% aqueous potassium hydroxide (2 ml) was added, and the admixture was stirred at room temperature for 5 hours. The reaction mixture was then purified in the same matter as described in the Example 72 to obtain 37 mg of the title compound (yield: 86%).

$^1$H-NMR (DMSO-d$_6$, 500 MHz): δ 3.95 (s, 3H), 3.95 (s, 3H), 6.49 (d, J=4.9 Hz, 1H), 7.18 (m, 1H), 7.20 (s, 1H), 7.27 (d, J=8.6 Hz, 2H), 7.39 (s, 1H), 7.53 (s, 1H), 7.80 (d, J=8.5 Hz, 1H), 7.92~7.98 (m, 4H), 8.47~8.48 (m, 2H), 10.0 (brs, 1H), 10.4 (s, 1H)

Mass spectrometry data (FD-MS, m/z): 467 (M$^+$+1)

Example 74

N-(4-Methoxyphenyl)-N'-{4-[(6,7-dimethoxy-4-quinolinyl)oxy]phenyl}urea [43]

6,7-Dimethoxy-4-(4-aminophenoxy)quinoline (53 mg) was dissolved in toluene (3 ml) with heat, 4-methoxyphenyl isocyanate (0.2 ml) was added, and the admixture was refluxed with heat for 30 minutes. The separated crystals were filtered and washed with toluene to obtain 54 mg of the title compound (yield: 68%).

$^1$H-NMR (DMSO-d$_6$, 500 MHz): δ 3.72 (s, 3H), 3.94 (s, 3H), 3.95 (s, 3H), 6.44 (d, J=4.9 Hz, 1H), 6.87 (d, J=8.5 Hz, 2H), 7.19 (d, J=9.2 Hz, 2H), 7.37 (d, J=8.5 Hz, 2H), 7.38 (s, 1H), 7.52 (s, 1H), 7.58 (d, J=8.5 Hz, 2H), 8.46 (d, J=5.5 Hz, 1H), 8.50 (s, 1H), 8.73 (s, 1H)

Mass spectrometry data (FD-MS, m/z): 445 (M$^+$)

Example 75

N-(4-Fluorophenyl)-N'-{4-[(6,7-dimethoxy-4-quinolinyl)oxy]phenyl}urea [44]

6,7-Dimethoxy-4-(4-aminophenoxy)quinoline (54 mg) was dissolved in toluene (3 ml) with heat, 4-fluorophenyl isocyanate (0.2 ml) was added, and the admixture was refluxed with heat for 70 minutes. The separated crystals were filtered and washed with toluene to obtain 38 mg of the title compound (yield: 48%).

$^1$H-NMR (DMSO-d$_6$, 500 MHz): δ 3.94 (s, 3H), 3.95 (s, 3H), 6.44 (d, J=4.9 Hz, 1H), 7.12 (m, 2H), 7.19 (m, 2H), 7.38 (s, 1H), 7.47 (m, 2H), 7.51 (s, 1H), 7.59 (d, J=9.2 Hz, 2H), 8.45 (d, J=5.5 Hz, 1H), 8.72 (s, 1H), 8.79 (s, 1H)

Mass spectrometry data (FD-MS, m/z ): 433 (M$^+$)

Example 76

N-(4-Bromophenyl)-N'-{4-[(6,7-dimethoxy-4-quinolinyl)oxy]phenyl}urea [45]

6,7-Dimethoxy-4-(4-aminophenoxy)quinoline (52 mg) was dissolved in toluene (3 ml) with heat, 4-bromophenyl isocyanate (0.2 ml) was added, and the admixture was refluxed with heat for 50 minutes. The separated crystals were filtered and washed with toluene to obtain 56 mg of the title compound (yield: 64%).

$^1$H-NMR (DMSO-$d_6$, 500 MHz): 3.94 (s, 3H), 3.95 (s, 3H), 6.44 (d, J=5.5 Hz, 1H), 7.19 (d, J=9.2 Hz, 2H), 7.39 (s, 1H), 7.45 (m, 4H), 7.51 (s, 1H), 7.59 (d, J=9.2 Hz, 2H), 8.46 (d, J=5.5 Hz, 1H), 8.86 (s, 1H), 8.86 (s, 1H)

Mass spectrometry data (FD-MS, m/z): 493 (M$^+$), 495 (M$^+$+2)

Example 77

N-{4-[(6,7-Dimethoxy-4-quinolinyl)oxy]phenyl}-N'-(4-nitrophenyl)urea [46]

6,7-Dimethoxy-4-(4-aminophenoxy)quinoline (103 mg) was dissolved in toluene (10 ml) with heat, 4-nitrophenyl isocyanate (366 mg) was added, and the admixture was refluxed with heat for 60 minutes. The separated crystals were filtered and washed with toluene to obtain 141 mg of the title compound (yield: 88%).

$^1$H-NMR (DMSO-$d_6$, 500 MHz) δ 3.94 (s, 3H), 3.95 (s, 3H), 6.45 (d, J=5.5 Hz, 1H), 7.23 (d, J=8.6 Hz, 2H), 7.39 (s, 1H), 7.51 (s, 1H), 7.62 (d, J=9.2 Hz, 2H), 7.71 (d, J=9.2 Hz, 2H), 8.20 (d, J=9.2 Hz, 2H), 8.46 (d, J=5.5 Hz, 1H), 9.08 (s, 1H), 9.49 (s, 1H)

Mass spectrometry data (FD-MS, m/z): 460 (M$^+$)

Example 78

N-(4-Butylphenyl)-N'-{4-[(6,7-dimethoxy-4-quinolinyl)oxy]phenyl}urea [47]

6,7-Dimethoxy-4-(4-aminophenoxy)quinoline (50 mg) was dissolved in toluene (3 ml) with heat, 4-butylphenyl isocyanate (0.2 ml) was added, and the admixture was refluxed with heat for 26 minutes. The resulting residue was purified by column chromatography on silica gel eluting with chloroform/acetone (10/1) to obtain 36 mg of the title compound (yield: 45%).

$^1$H-NMR (CDCl$_3$/CD$_3$OD, 500 MHz): δ 0.93 (m, 3H), 1.35 (m, 2H), 1.57 (m, 2H), 2.57 (m, 2H), 4.06 (s, 3H), 4.06 (s, 3H), 6.49 (m, 1H), 7.14 (m, 4H), 7.33~7.62 (m, 6H), 8.39 (m, 1H)

Mass spectrometry data (FD-MS, m/z): 471 (M$^+$)

Example 79

N-(4-aminophenyl)-N'-{4-[(6,7-dimethoxy-4-quinolinyl)oxy]phenyl}urea [48]

N-{4-[(6,7-Dimethoxy-4-quinolinyl)oxy]phenyl}-N'-(4-nitro)phenylurea (111 mg) was dissolved in N,N-dimethylformamide (7 ml), 10% palladium hydroxide-carbon (100 mg) was added, and the admixture was stirred at room temperature under hydrogen for 22 hours. The reaction mixture was filtered using Celite. The filtrate was washed with brine and then dried with anhydrous sodium sulfate. The solvent was removed by reduced-pressure distillation to obtain 66 mg of the title compound (yield: 63%).

$^1$H-NMR (DMSO-$d_6$, 500 MHz): δ 3.94 (s, 3H), 3.94 (s, 3H), 4.74 (brs, 2H), 6.43 (d, J=4.9 Hz, 1H), 6.52 (d, J=8.6 Hz, 2H), 7.08 (d, J=8.6 Hz, 2H), 7.16 (d, J=9.2 Hz, 2H), 7.38 (s, 1H), 7.51 (s, 1H), 7.55 (d, J=9.2 Hz, 2H), 8.14 (s, 1H), 8.45 (d, J=4.9 Hz, 1H), 8.61 (s, 1H)

Mass spectrometry data (FD-MS, m/z): 430 (M$^+$)

Example 80

N-(4-Acetylphenyl)-N'-{4-[(6,7-dimethoxy-4-quinolinyl)oxy]phenyl}urea [49]

6,7-Dimethoxy-4-(4-aminophenoxy)quinoline (51 mg) was dissolved in toluene (3 ml) with heat, 4-acetylphenyl isocyanate (210 mg) was added, and the admixture was refluxed with heat for 20 minutes. The resulting residue was purified by column chromatography on silica gel eluting with chloroform/acetone (10/1) to obtain 50 mg of the title compound (yield: 64%).

$^1$H-NMR (CDCl$_3$/CD$_3$OD, 500 MHz): δ 2.59 (s, 3H), 4.07 (s, 3H), 4.07 (s, 3H), 6.50 (d, J=5.5 Hz, 1H), 7.17 (d, J=8.5 Hz, 2H), 7.36 (s, 1H), 7.58 (s, 1H), 7.58 (d, J=8.5 Hz, 2H), 7.60 (d, J=8.5 Hz, 2H), 7.94 (d, J=8.5 Hz, 2H), 8.40 (d, J=5.5 Hz, 1H)

Mass spectrometry data (FD-MS, m/z): 457 (M$^+$)

Example 81

N-{4-[(6,7-Dimethoxy-4-quinolinyl)oxy]phenyl}-N'-(4-phenoxyphenyl)urea [50]

6,7-Dimethoxy-4-(4-aminophenoxy)quinoline (53 mg) was dissolved in toluene (3 ml) with heat, 4-phenoxyphenyl isocyanate (0.2 ml) was added, and the admixture was refluxed with heat for 30 minutes. The resulting residue was purified by column chromatography on silica gel eluting with chloroform/acetone (10/1) to obtain 55 mg of the title compound (yield: 60%).

$^1$H-NMR (CDCl$_3$/CD$_3$OD, 500 MHz): δ 4.46 (s, 3H), 4.46 (s, 3H), 6.51 (m, 1H), 6.98~7.62 (m, 15H), 8.40 (m, 1H)

Mass spectrometry data (FD-MS, m/z): 507 (M$^+$)

Example 82

N-(4-Isopropylphenyl)-N'-{4-[(6,7-dimethoxy-4-quinolinyl)oxy]phenyl}urea [51]

6,7-Dimethoxy-4-(4-aminophenoxy)quinoline (51 mg) was dissolved in toluene (3 ml) with heat, 4-isopropylphenyl isocyanate (0.2 ml) was added, and the admixture was refluxed with heat for 26 minutes. The resulting residue was purified by column chromatography on silica gel eluting with chloroform/acetone (10/1) to obtain 70 mg of the title compound (yield: 90%).

$^1$H-NMR (CD$_3$OD, 500 MHz): δ 1.18 (d, J=6.7 Hz, 6H), 2.82 (m, 1H), 3.97 (s, 3H), 4.01 (s, 3H), 6.37 (d, J=5.5 Hz, 1H), 7.04 (d, J=8.5 Hz, 2H), 7.11 (d, J=8.5 Hz, 2H), 7.25 (d, J=8.5 Hz, 2H), 7.26 (s, 1H), 7.38 (s, 1H), 7.41 (d, J=9.2 Hz, 2H), 7.54 (s,1H), 7.82 (s, 1H), 8.03 (s, 1H), 8.42 (d, J=5.5 Hz, 1H)

Mass spectrometry data (FD-MS, m/z): 457 (M$^+$)

Example 83

N-(4-Trifluoromethylphenyl)-N'-{4-[(6,7-dimethoxy-4-quinolinyl)oxy]phenyl}urea [52]

6,7-Dimethoxy-4-(4-aminophenoxy)quinoline (53 mg) was dissolved in toluene (3 ml) with heat, 4-trifluoromethylphenyl isocyanate (0.2 ml) was added, and the admixture was refluxed with heat for 10 minutes. The separated crystals were filtered and washed with toluene to obtain 77 mg of the title compound (yield: 88%).

$^1$H-NMR (CDCl$_3$, 500 MHz): δ 4.05 (s, 3H), 4.05 (s, 3H), 6.52 (d, J=5.5 Hz, 1H), 7.18 (d, J=9.2 Hz, 2H), 7.36 (s, 1H), 7.56 (s, 1H), 7.59 (d, J=8.6 Hz, 2H), 7.62 (d, J=8.6 Hz, 2H), 7.63 (s, 1H), 8.40 (d, J=5.5 Hz, 1H)

Mass spectrometry data (FD-MS, m/z): 483 (M$^+$)

Example 84

N-(4-n-Butylphenyl)-N'-{4-[(6,7-dimethoxy-4-quinolyl)oxy]phenyl}urea [147]

6,7-Dimethoxy-4-(2-aminophenoxy)quinoline (56 mg), which was obtained, analogously to Example 49, by reducing 6,7-dimethoxy-4-(2-nitrophenoxy)quinoline obtained in the same manner as described in Example 48, except that 2-nitrophenol was used in place of 4-nitrophenol, was dissolved in toluene (3 ml) with heat, 4-n-butylphenyl isocyanate (0.2 ml) was added, and the admixture was refluxed with heat for 30 minutes. The resulting residue was purified by chromatography on silica gel eluting with chloroform/acetone (10/1) to obtain 45 mg of the title compound (yield: 50%).

$^1$H-NMR (CDCl$_3$, 500 MHz): δ 0.89 (t, J=7.3 Hz, 3H), 1.30 (m, 2H), 1.52 (m, 2H), 2.50 (m, 2H), 3.90 (s, 3H), 3.93 (s, 3H), 6.22 (d, J=4.9 Hz, 1H), 6.87 (d, J=7.3 Hz, 1H), 6.96~7.01 (m, 4H), 7.15 (brs, 1H), 7.28~7.31 (m, 4H), 8.12 (brs, 1H), 8.26 (d, J=4.9 Hz, 1H), 8.58 (d, J=7.9 Hz, 1H)

Mass spectrometry data (FD-MS, m/z): 471 (M$^+$)

Example 85

N-(4-n-Butylphenyl)-N'-{3-[(6,7-dimethoxy-4-quinolyl)oxy]phenyl}urea [91]

6,7-Dimethoxy-4-(3-aminophenoxy)quinoline (51 mg), which was obtained, analogously to Example 49, by reducing 6,7-dimethoxy-4-(3-nitrophenoxy)quinoline obtained in the same manner as described in Example 48, except that 3-nitrophenol was used in place of 4-nitrophenol, was dissolved in toluene (3 ml) with heat, 4-n-butylphenyl isocyanate (0.2 ml) was added, and the admixture was refluxed with heat for 50 minutes. The resulting residue was purified by chromatography on silica gel eluting with chloroform/acetone (10/1) to obtain 26 mg of the title compound (yield: 32%).

$^1$H-NMR (CDCl$_3$, 500 MHz): 60.89 (t, J=7.3 Hz, 3H), 1.30 (m, 2H), 1.52 (m, 2H), 2.51 (m, 2H), 3.95 (s, 1H), 4.00 (s, 1H), 6.49 (d, J=5.5 Hz, 1H), 6.81 (d, J=8.0 Hz, 1H), 7.04 (d, J=7.9 Hz, 2H), 7.2~7.30 (m, 5H), 7.37 (s, 1H), 7.51 (s, 1H) 7.84 (brs, 1H), 8.24 (brs, 1H), 8.43 (d, J=4.9Hz, 1H)

Mass spectrometry data (FD-MS, m/z): 471 (M$^+$)

Example 86

N-n-Butyl-N'-{4-[(6,7-dimethoxy-4-quinolyl)oxy]phenyl}urea [139]

6,7-Dimethoxy-4-(4-aminophenoxy)quinoline (51 mg) was dissolved in toluene (3 ml) with heat, n-butyl isocyanate (0.2 ml) was added, and the admixture was refluxed with heat for 14 hours. The resulting residue was purified by chromatography on silica gel eluting with chloroform/acetone (10/1) to obtain 31 mg of the title compound (yield: 46%).

$^1$H-NMR (CDCl$_3$, 500 MHz): δ 0.93 (t, J=7.8 Hz, 3H), 1.37 (m, 2H), 1.53 (m, 2H), 3.28 (m, 2H), 4.04 (s, 3H), 4.04 (s, 3H), 5.04 (brs, 1H), 6.44 (d, J=5.5 Hz, 1H), 6.98 (brs, 1H), 7.11 (d, J=9.2 Hz, 2H), 7.41 (s, 1H), 7.43 (d, J=9.2 Hz, 2H), 7.55 (s, 1H), 8.46 (d, J=4.9 Hz, 1H)

Mass spectrometry data (FD-MS, m/z): 395 (M$^+$)

Example 87

N-{4-[6,7-Dimethoxy-4-quinolyl)oxy]phenyl}-(4-trifluoromethylphenyl)carboxamide [157]

6,7-Dimethoxy-4-(4-aminophenoxy)quinoline (53 mg) and commercially available 4-trifluoromethanebenzoic acid (102 mg) were dissolved in N,N-dimethylformamide (3 ml), 1-ethyl-3-(3'-dimethylaminopropyl)carbodiimide hydrochloride (102 mg) was added, and the admixture was stirred at room temperature for 14 hours. The reaction mixture was partitioned between water and ethyl acetate, and the ethyl acetate layer was washed with brine and then dried with anhydrous sodium sulfate. The solvent was removed by reduced-pressure distillation and the resulting crystallized product was washed with ethyl acetate to obtain 32 mg of the title compound (yield: 38%).

$^1$H-NMR (CDCl$_3$, 500 MHz): δ 4.04 (s, 3H), 4.05 (s, 3H), 6.48 (d, J=4.9 Hz, 1H), 7.22 (d, J=8.5 Hz, 2H), 7.41 (s, 1H), 7.55 (s, 1H), 7.76 (d, J=8.5 Hz, 2H), 7.76 (d, J=8.6 Hz, 2H), 8.02 (d, J=7.9 Hz, 2H), 8.13 (brs, 1H), 8.49 (d, J=5.5 Hz, 1H)

Mass spectrometry data (FD-MS, m/z): 468 (M$^+$)

Example 88

N-{4-[6,7-Dimethoxy-4-quinolyl)oxy]phenyl}-(4-cyclohexylphenyl)carboxamide [158]

6,7-Dimethoxy-4-(4-aminophenoxy)quinoline (52 mg) and commercially available 4-cyclohexylbenzoic acid (109 mg) were dissolved in N,N-dimethylformamide (3 ml), 1-ethyl-3-(3'-dimethylaminopropyl)carbodiimide hydrochloride (110 mg) was added, and the admixture was stirred at room temperature for 14 hours. The reaction mixture was then purified in the same manner as described in Example 51 to obtain 54 mg of the title compound (yield: 64%).

$^1$H-NMR (CDCl$_3$, 500 MHz): δ 1.25~1.86 (m, 10H), 2.55 (m, 1H), 4.01 (s, 3H), 4.03 (s, 3H), 6.46 (d, J=5.5 Hz, 1H), 7.16 (d, J=8.5 Hz, 2H), 7.27 (d, J=7.9 Hz, 2H), 7.39 (s, 1H), 7.55 (s, 1H), 7.75 (d, J=9.2 Hz, 2H), 7.83 (d, J=8.6 Hz, 2H), 8.46 (d, J=5.5 Hz, 1H)

Mass spectrometry data (FD-MS, m/z): 482 (M$^+$)

Example 89

N-{3-[6,7-Dimethoxy-4-quinolyl)oxy]phenyl}-(4-t-butylphenyl)carboxamide [159]

6,7-Dimethoxy-4-(3-aminophenoxy)quinoline (54 mg) and commercially available 4-t-butyl benzoic acid (102 mg) were dissolved in N,N-dimethylformamide (3 ml), 1-ethyl-3-(3'-dimethylaminopropyl)carbodiimide hydrochloride (106 mg) was added, and the admixture was stirred at room temperature for 6 hours. The reaction mixture was then purified in the same manner as described in Example 51 to obtain 29 mg of the title compound (yield: 35%).

$^1$H-NMR (CDCl$_3$, 500 MHz): δ 1.34 (s, 9H), 4.01 (s, 3H), 4.04 (s, 3H), 6.55 (d, J=4.9 Hz, 1H), 6.97 (d, J=7.3 Hz, 1H), 7.29~7.68 (m, 7H), 7.8 5 (d, J=7.9 Hz, 2H), 8.48 (d, J=4.9 Hz, 1H), 8.59 (brs, 1H)

Mass spectrometry data (FD-MS, m/z): 456 (M$^+$)

Example 90

N-{3-[6,7-Dimethoxy-4-quinolyl)thio]phenyl}-(4-t-butylphenyl)carboxamide [160]

6,7-Dimethoxy-4-(3-aminophenylthio)quinoline (62 mg) and commercially available 4-t-butyl benzoic acid (109 mg) were dissolved in N,N-dimethylformamide (3 ml), 1-ethyl-3-(3'-dimethylaminopropyl)carbodiimide hydrochloride (112 mg) was added, and the admixture was stirred at room temperature for 25 hours. The reaction mixture was then purified in the same manner as described in Example 51 to obtain 54 mg of the title compound (yield: 57%).

$^1$H-NMR (CDCl$_3$, 500 MHz): 61.31 (s, 9H), 4.00 (s, 3H), 4.01 (s, 3H), 6.83 (d, J=4.9 Hz, 1H), 7.20~7.9 9 (m, 9H), 8.06 (m, 1H), 8.39 (d, J=4.9 Hz, 1H), 8.60 (brs, 1H)

Mass spectrometry data (FD-MS, m/z): 472 (M$^+$)

Example 91

N-{4-[6,7-Dimethoxy-4-quinolyl)thio]phenyl}-(4-butylphenyl)carboxamide [161]

6,7-Dimethoxy-4-(4-aminophenoxy)quinoline (62 mg) and commercially available 4-butyl benzoic acid (104 mg) were dissolved in N,N-dimethylformamide (3 ml), 1-ethyl-3-(3'-dimethylaminopropyl)carbodiimide hydrochloride (117 mg) was added, and the admixture was stirred at room temperature for 21 hours. The reaction mixture was then purified in the same manner as described in Example 51 to obtain 21 mg of the title compound (yield: 22%).

$^1$H-NMR (CDCl$_3$, 500 MHz) δ 0.94 (t, J=7.3 Hz, 3H), 1.38 (m, 2H), 1.63 (m, 2H), 2.69 (t, J=7.9 Hz, 2H), 4.03 (s, 3H) 4.05 (s, 3H), 6.72 (d, J=4.9 Hz, 1H), 7.30 (d, J=7.9 Hz, 2H), 7.39 (s, 1H), 7.42 (s, 1H), 7.57 (d, J=8.5 Hz, 2H), 7.78 (d, J=8.5 Hz, 2H), 7.81 (d, J=7.9 Hz, 2H), 8.08 (s, 1H), 8.42 (d, J=5.5 Hz, 1H)

Mass spectrometry data (FD-MS, m/z): 472 (M$^+$)

Example 92

N-{4-[6,7-Dimethoxy-4-quinolyl)oxy]phenyl}-N'-(4-methoxythiophenyl)urea [163]

6,7-Dimethoxy-4-(4-aminophenoxy)quinoline (53 mg) was dissolved in toluene (3 ml) with heat, 4-methylthiophenyl isocyanate (0.2 ml) was added, and the admixture was refluxed with heat for 8 minutes. The separated crystals were filtered and washed with toluene to obtain 62 mg of the title compound (yield: 76%).

$^1$H-NMR (DMSO-d$_6$, 500 MHz): 2.44 (s, 3H), 3.94 (s, 3H), 3.95 (s, 3H), 6.44 (d, J=4.9 Hz, 1H), 7.19 (d, J=9.2 Hz, 2H), 7.23 (d, J=8.5 Hz, 2H), 7.38 (s, 1H), 7.44 (d, J=9.2 Hz, 2H), 7.52 (s, 1H), 7.58 (d, J=8.6 Hz, 2H), 8.46 (d, L=4.9 Hz, 1H), 8.70 (s, 1H), 8.79 (s, 1H) Mass spectrometry data (FD-MS, m/z): 461 (M$^+$)

Example 93

N-(3-Ethoxycarbonylphenyl)-N'-{4-[(6,7-dimethoxy-4-quinolyl)oxy]phenyl}urea [164]

6,7-Dimethoxy-4-(4-aminophenoxy)quinoline (53 mg) was dissolved in toluene (5 ml) with heat, 3-ethoxycarbonylphenyl isocyanate (284 mg) was added, and the admixture was refluxed with heat for 1 hour. The resulting residue was purified by column chromatography on silica gel eluting with chloroform/acetone (10/1) to obtain 18 mg of the title compound (yield: 20%).

$^1$H-NMR (CDCl$_3$, 500 MHz): 1.38 (m, 3H), 3.98 (s, 3 H), 4.05 (s, 3H), 4.3 5 (m, 2 H), 6.45 (d, J=5.5 Hz, 1H), 7.12 (d, J=9.2 Hz, 2H), 7.40 (s, 1H), 7.47 (d, J=9.2 Hz, 2H), 7.47 (d, J=8.6 Hz, 2H), 7.58 (s, 1H), 7.96 (d, J=9.2 Hz, 2H), 8.05 (s, 1H), 8.17 (s, 1H), 8.47 (d, J=5.5 Hz, 1H)

Mass spectrometry data (FD-MS, m/z): 487 (M$^+$)

Example 94

N-(4-Chlorophenyl)-N'-{4-[(6,7-dimethoxy-4-quinolyl)oxy]phenyl}urea [165]

6,7-Dimethoxy-4-(4-aminophenoxy)quinoline (52 mg) was dissolved in toluene (5 ml) with heat, 4-chlorophenyl isocyanate (0.2 ml) was added, and the admixture was refluxed with heat for 1 hour. The separated crystals were filtered and washed with toluene to obtain 43 mg of the title compound (yield: 55%).

$^1$H-NMR (DMSO-d$_6$, 500 MHz): δ 3.94 (s, 3H), 3.95 (s, 3H), 6.44 (d, J=5.5 Hz, 1H), 7.20 (d, J=9.2 Hz, 2H), 7.32 (d, J=8.5 Hz, 2H), 7.38 (s, 1H), 7.49 (d, J=9.2 Hz, 2H), 7.51 (s, 1H), 7.58 (d, J=9.2 Hz, 2H), 8.46 (d, J=4.9 Hz, 1H), 8.83 (brs, 1H), 8.83 (brs, 1H)

Mass spectrometry data (FD-MS, m/z): 449 (M$^+$), 451 (M$^+$+2)

Example 95

N-(2-Isopropylphenyl)-N'-{4-[(6,7-dimethoxy-4-quinolyl)oxy]phenyl}urea [166]

6,7-Dimethoxy-4-(4-aminophenoxy)quinoline (44 mg) was dissolved in toluene (5 ml) with heat, 2-isopropylphenyl isocyanate (0.2 ml) was added, and the admixture was refluxed with heat for 80 minutes. The resulting residue was purified by column chromatography on silica gel eluting with chloroform/acetone (10/1) to obtain 14 mg of the title compound (yield: 20%).

$^1$H-NMR (CDCl$_3$, 500 MHz): δ 1.21 (m, 6H), 3.21 (m, 1H), 4.04 (s, 3H), 4.04 (s, 3H), 6.42 (m, 1H), 6.63 (m, 1H), 7.09–7.55 (m, 11H), 8.46 (m, 1H)

Mass spectrometry data (FD-MS, m/z): 457 (M$^+$)

Example 96

N-{4-[(6,7-Dimethoxy-4-quinolyl)oxy]phenyl}-N'-phenylurea [167]

6,7-Dimethoxy-4-(4-aminophenoxy)quinoline (51 mg) was dissolved in toluene (5 ml) with heat, phenyl isocyanate (0.2 ml) was added, and the admixture was refluxed with heat for 50 minutes. The resulting residue was purified by column chromatography on silica gel eluting with chloroform/acetone (10/1) to obtain 21 mg of the title compound (yield: 41%).

$^1$H-NMR (CDCl$_3$, 500 MHz): δ 4.04 (s, 3H), 4.04 (s, 3H), 6.61 (m, 1H), 7.05 (m, 1H), 7.36~7.44 (m, 10H), 7.99 (s, 1H), 8.31 (s, 1H), 8.36 (m, 1H)

Mass spectrometry data (FD-MS, m/z): 431 (M$^+$)

Example 97

N-{4-[(6,7-Dimethoxy-4-quinolyl)oxy]phenyl}-N'-(2-nitrophenyl)urea [168]

6,7-Dimethoxy-4-(4-aminophenoxy)quinoline (83 mg) was dissolved in toluene (8 ml) with heat, 4-nitrophenyl isocyanate (370 mg) was added, and the admixture was refluxed with heat for 40 minutes. The deposited crystals were filtered and washed with toluene to obtain 58 mg of the title compound (yield: 45%).

$^1$H-NMR (DMSO-d$_6$, 500 MHz): δ 3.94 (s, 3H), 3.95 (s, 3H), 6.46 (d, J=5.5 Hz, 1H), 7.22 (m, 1H), 7.23 (d, J=9.2 Hz, 2H), 7.38 (s, 1H), 7.51 (s, 1H), 7.62 (d, J=9.2 Hz, 2H), 7.71 (m, 1H), 8.11 (m, 1H), 8.31 (m, 1H), 8.46 (d, J=5.5 Hz, 1H), 9.62 (s, 1H), 9.96 (s, 1H)

Mass spectrometry data (FD-MS, m/z): 460 (M$^+$)

Example 98

N-(2-Aminophenyl)-N'-{4-[(6,7-dimethoxy-4-quinolyl)oxy]phenyl}urea [169]

N-{4-[(6,7-Dimethoxy-4-quinolyl)oxy]phenyl)-}-(2-nitrophenyl)urea (42 mg) was dissolved in N,N- dimethylformamide/ethyl acetate (12 ml/6 ml), 20% palladium hydroxide-carbon (70 mg) was added, and the admixture was stirred at room temperature under hydrogen for 3 hours. The reaction mixture was filtered using Celite, after which the filtrate was washed with brine and then dried with anhydrous sodium sulfate. The solvent was removed by reduced-pressure distillation to obtain 39 mg of the title compound (yield: 100%).

$^1$H-NMR (DMSO-$d_6$, 500 MHz): δ 3.94 (s, 3H), 3.95 (s, 3H), 4.77 (br s, 2H), 6.44 (d, J=5.5 Hz, 1H), 6.58 (m, 1H), 6.75 (m, 1H), 6.85 (m, 1H), 7.18 (d, J=8.5 Hz, 2H), 7.34 (m, 1H), 7.38 (s, 1H), 7.52 (s, 1H), 7.58 (d, J=9.2 Hz, 2H), 8.29 (s, 1H), 8.46 (d, J=4.9 Hz, 1H), 8.92 (s, 1H)

Mass spectrometry data (FD-MS, m/z): 430 (M$^+$)

Example 99

N-{4-[(6,7-Dimethoxy-4-quinolyl)oxy]phenyl}-N'-(3-nitrophenyl)urea [170]

6,7-Dimethoxy-4-(4-aminophenoxy)quinoline (83 mg) was dissolved in toluene (6 ml) with heat, 3-nitrophenyl isocyanate (384 mg) was added, and the admixture was refluxed with heat for 40 minutes. The resulting residue was purified by column chromatography on silica gel eluting with chloroform/acetone (10/1) to obtain 44 mg of the title compound (yield: 34%).

$^1$H-NMR (DMSO-$d_6$, 500 MHz): δ 3.99 (s, 3H), 4.04 (s, 3H), 6.43 (d, J=4.9 Hz, 1H), 7.10 (d, J=9.2 Hz, 2H), 7.38 (m, 2H), 7.47 (d, J=8.6 Hz, 2H), 7.57 (s, 1H), 7.81 (m, 2H), 8.19 (s, 1H), 8.31 (s, 1H), 8.46 (d, J=4.9 Hz, 1H), 8.59 (s, 1H)

Mass spectrometry data (FD-MS, m/z): 460 (M$^+$)

Example 100

N-{4-[(6,7-Dimethoxy-4-quinolyl)oxy]phenyl}-N'-octylurea [171]

6,7-Dimethoxy-4-(4-aminophenoxy)quinoline (51 mg) was dissolved in toluene (5 ml) with heat, octyl isocyanate (0.2 ml) was added, and the admixture was refluxed with heat for 2 hours. The resulting residue was purified by column chromatography on silica gel eluting with chloroform/acetone (10/1) to obtain 32 mg of the title compound (yield: 41%).

$^1$H-NMR (CDCl$_3$, 500 MHz): δ 0.87 (m, 3H), 1.26~1.30 (m, 10H), 1.53 (m, 2H), 3.27 (m, 2H), 4.03 (s, 3H), 4.03 (s, 3H), 5.04 (m, 1H), 6.44 (d, J=5.5 Hz, 1H), 6.97 (s, 1H), 7.10 (d, J=8.6 Hz, 2H), 7.41 (s, 1H), 7.42 (d, J=8.6 Hz, 2H), 7.55 (s, 1H), 8.46 (d, J=4.9 Hz, 1H)

Mass spectrometry data (FD-MS, m/z): 451 (M$^+$)

Example 101

N-(3-Aminophenyl)-N'-{4-[(6,7-dimethoxy-4-quinolyl)oxy]phenyl}urea [172]

N-{4-[(6,7-Dimethoxy-4-quinolyl)oxy]phenyl}-N'-(3-nitrophenyl)urea (28 mg) was dissolved in N,N-dimethylformamide/ethyl acetate (5 ml/2.5 ml), 20% palladium hydroxide-carbon (97 mg) was added, and the admixture was stirred at room temperature under hydrogen for 3 hours. The reaction mixture was filtered using Celite, the filtrate was washed with brine and then dried with anhydrous sodium sulfate. The solvent was then removed by reduced-pressure distillation to obtain 13 mg of the title compound (yield: 51%).

$^1$H-NMR (CDCl$_3$, 500 MHz): δ 4.02 (s, 3H), 4.03 (s, 3H), 6.41 (m, 1H), 6.41 (d, J=5.5 Hz, 1H), 6.61 (m, 1H), 6.90 (s, 1H), 7.05 (m, 1H), 7.09 (d, J=8.5 Hz, 2H), 7.40 (s, 1H), 7.43 (m, 1H), 7.47 (d, J=8.5 Hz, 2H), 7.55 (s, 1H), 8.03 (s, 1H), 8.44 (d, J=5.5 Hz, 1H)

Mass spectrometry data (FD-MS m/z): 430 (M$^+$)

Example 102

N-Allyl-N'-{4-[(6,7-dimethoxy-4-quinolyl)oxy]phenyl}urea [173]

6,7-Dimethoxy-4-(4-aminophenoxy)quinoline (50 mg) was dissolved in N,N-dimethylformamide (5 ml), allyl isocyanate (0.2 ml) was added, and the admixture was stirred at 80° C. for 15 hours with heat. Water was added to the reaction mixture, the admixture was extracted 2 times with ethyl acetate, and the organic layer was washed with brine and then dried with anhydrous sodium sulfate. The solvent was removed by reduced-pressure distillation and the resulting residue was purified by column chromatography on silica gel eluting with chloroform/acetone (10/1) to obtain 61 mg of the title compound (yield: 96%).

$^1$H-NMR (CDCl$_3$, 500 MHz): δ 3.90 (m, 2H), 4.03 (s, 3H), 4.03 (s, 3H), 5.12 (d, J=10.4 Hz, 1H), 5.23 (d, J=1.77 Hz, 1H), 5.62 (s, 1H), 5.88 (m, 1H), 6.41 (d, J=4.9 Hz, 1H), 7.08 (d, J=8.5, 2H), 7.39 (s, 1H), 7.44 (d, J=8.5 Hz, 2H), 7.54 (s, 1H), 7.75 (s, 1H), 8.44 (d, J=5.5 Hz, 1H)

Mass spectrometry data (FD-MS, m/z): 379 (M$^+$)

Example 103

N-{4-[(6,7-Dimethoxy-4-quinolyl)oxy]phenyl}-N'-(1-naphthyl)urea [174]

6,7-Dimethoxy-4-(4-aminophenoxy)quinoline (50 mg) was dissolved in toluene (5 ml) with heat, 1-naphthyl isocyanate (0.2 ml) was added, and the admixture was refluxed with heat for 20 minutes. The resulting residue was purified by column chromatography on silica gel eluting with chloroform/acetone (10/1) to obtain 41 mg of the title compound (yield: 52%).

$^1$H-NMR (DMSO-$d_6$, 500 MHz): δ 3.95 (s, 3H), 3.95 (s, 3H), 6.45 (d, J=5.5 Hz, 1H), 7.21 (d, J=9.2 Hz, 2H), 7.38 (s, 1H), 7.48–7.65 (m, 7H), 7.92~8.15 (m, 3H), 8.46 (d, J=4.9 Hz, 1H), 8.80 (s, 1H), 9.20 (s, 1H)

Mass spectrometry data (FD-MS, m/z): 465 (M$^+$)

Example 104

N-(2-Biphenyl)-N'-{4-[(6,7-dimethoxy-4-quinolyl)oxy]phenyl}urea [175]

6,7-Dimethoxy-4-(4-aminophenoxy)quinoline (52 mg) was dissolved in toluene (5 ml) with heat, 2-biphenyl isocyanate (0.2 ml) was added, and the admixture was refluxed with heat for 30 minutes. The resulting residue was purified by column chromatography on silica gel eluting with chloroform/acetone (10/1) to obtain 56 mg of the title compound (yield: 64%).

$^1$H-NMR (CDCl$_3$, 500 MHz): δ 3.97 (s, 3H), 4.04 (s, 3H), 6.35 (d, J=5.5 Hz, 1H), 6.96 (s, 1H), 7.40 (d, J=9.2 Hz, 2H), 7.14~7.39 (m, 11H), 7.54 (s, 1H), 7.89 (brs, 1H), 8.08 (d, J=8.6 Hz, 1H), 8.33 (d, J=5.5 Hz, 1H)

Mass spectrometry data (FD-MS, m/z): 491 (M$^+$)

Example 105

N-(4-Ethylphenyl)-N'-{4-[(6,7-dimethoxy-4-quinolyl)oxy]phenyl}urea [188]

6,7-Dimethoxy-4-(4-aminophenoxy)quinoline (51 mg) was dissolved in toluene (5 ml) with heat, 4-ethylphenyl isocyanate (0.2 ml) was added, and the admixture was refluxed with heat for 90 minutes. The resulting residue was purified by column chromatography on silica gel eluting with chloroform/acetone (10/1) to obtain 42 mg of the title compound (yield: 56%).

$^1$H-NMR (CDCl$_3$, 500 MHz): δ 1.18 (m, 3H), 2.58 (m, 2H), 3.99 (s, 3H), 4.02 (s, 3H), 6.39 (d, J=5.5 Hz, 1H), 7.07 (d, J=9.2 Hz, 2H), 7.11 (d, J=7.9 Hz, 2H), 7.25 (d, J=8.5 Hz, 2H), 7.40 (s, 1H), 7.42 (d, J=8.5 Hz, 2H), 7.55 (s, 1H), 7.60 (s, 1H), 7.81 (s, 1H), 8.43 (d, J=4.9 Hz, 1H)

Mass spectrometry data (FD-MS, m/z): 443 (M$^+$)

Example 106

N-Benzoyl-N'-{4-[(6,7-dimethoxy-4-quinolyl)oxy]phenyl}urea [189]

6,7-Dimethoxy-4-(4-aminophenoxy)quinoline (52 mg) was dissolved in toluene (5 ml) with heat, benzoyl isocyanate (0.2 ml) was added, and the admixture was refluxed with heat for 50 minutes. The resulting residue was purified by column chromatography on silica gel eluting with chloroform/acetone (10/1) to obtain 11 mg of the title compound (yield: 15%).

$^1$H-NMR (CDCl$_3$, 500 MHz): δ 4.06 (s, 3H), 4.07 (s, 3H), 6.49 (d, J=4.9 Hz, 1H), 7.20 (d, J=9.2 Hz, 2H), 7.43 (s, 1H), 7.54 (m, 2H) 7.58 (s, 1H), 7.65 (m, 1H), 7.71 (d, J=9.2 Hz, 2H), 8.04 (d, J=7.9 Hz, 2H), 8.50 (d, J=5.5 Hz, 1H), 9.53 (s, 1H), 11.04 (s, 1 H)

Mass spectrometry data (FD-MS, m/z): 443 (M$^+$)

Example 107

N-Ethoxycarbonyl-N'-{4-[(6,7-Dimethoxy-4-quinolyl)oxy]phenyl}urea [190]

6,7-Dimethoxy-4-(4-aminophenoxy)quinoline (52 mg) was dissolved in toluene (5 ml) with heat, ethoxycarbonyl isocyanate (0.2 ml) was added, and the admixture was refluxed with heat for 15 minutes. The resulting residue was purified by column chromatography on silica gel eluting with chloroform/acetone (10/1) to obtain 20 mg of the title compound (yield: 28%).

$^1$H-NMR (CDCl$_3$, 500 MHz): δ 1.37 (t, J=7.3 Hz, 3H), 4.10 (s, 3H), 4.17 (s, 3H), 4.31 (q, J=7.3 Hz, 2H), 6.70 (d, J=6.1 Hz, 1H), 7.20 (d, J=8.6 Hz, 2 H), 7.64 (s, 1H), 7.72 (d, J=9.2 Hz, 2 H), 8.12 (s, 1H), 8.50 (d, J=6.7 Hz, 1H), 10.08 (s, 1H)

Mass spectrometry data (FD-MS, m/z): 411 (M$^+$)

Example 108

N-{4-[(6,7-Dimethoxy-4-quinolyl)oxy]phenyl}-N'-(2-methylphenyl)urea [56]

6,7-Dimethoxy-4-(4-aminophenoxy)quinoline (51 mg) was dissolved in toluene (5 ml) with heat, 2-methylphenyl isocyanate (0.2 ml) was added, and the admixture was refluxed with heat for 15 minutes. The resulting residue was purified by column chromatography on silica gel eluting with chloroform/acetone (10/1) to obtain 61 mg of the title compound (yield: 82%).

$^1$H-NMR (CDCl$_3$, 500 MHz): δ 2.20 (s, 3H), 4.00 (s, 3H), 4.03 (s, 3H), 4.31 (q, J=7.3 Hz, 2H), 6.40 (d, J=5.5 Hz, 1H), 7.05–7.20 (m, 6H), 7.39 (s, 1H), 7.42 (d, J=8.5 Hz, 2H), 7.55, (s, 1H), 7.60 (d, J=7.9 Hz, 2H), 7.80 (s, 1H), 8.45 (d, J=5.5 Hz, 1H)

Mass spectrometry data (FD-MS, m/z): 429 (M$^+$)

Example 109

N-{4-[(6,7-Dimethoxy-4-quinolyl)oxy]phenyl}-N'-(3-methylphenyl)urea [55]

6,7-Dimethoxy-4-(4-aminophenoxy)quinoline (51 mg) was dissolved in toluene (5 ml) with heat, 3-methylphenyl isocyanate (0.2 ml) was added, and the admixture was refluxed with heat for 15 minutes. The resulting residue was purified by column chromatography on silica gel eluting with chloroform/acetone (10/1) to obtain 41 mg of the title compound (yield: 56%).

$^1$H-NMR (CDCl$_3$, 500 MHz): δ 2.32 (s, 3H), 4.02 (s, 3H), 4.04 (s, 3H), 6.43 (d, J=5.5 Hz, 1H), 6.93 (d, J=7.3 Hz, 1H) 7.10~7.22 (m, 6H), 7.41 (s, 1H), 7.44~7.47 (m, 3H), 7.56 (s, 1H), 8.46 (d, J=5.5 Hz, 1H)

Mass spectrometry data (FD-MS m/z): 429 (M$^+$)

Example 110

N-(2-Fluorophenyl)-N'-{4-[(6,7-dimethoxy-4-quinolyl)oxy]phenyl}urea [60]

6,7-Dimethoxy-4-(4-aminophenoxy)quinoline (51 mg) was dissolved in toluene (5 ml) with heat, 2-fluorophenyl isocyanate (0.2 ml) was added, and the admixture was refluxed with heat for 15 minutes. The resulting residue was purified by column chromatography on silica gel eluting with chloroform/acetone (10/1) to obtain 54 mg of the title compound (yield: 73%).

$^1$H-NMR (CDCl$_3$, 500 MHz): δ 4.01 (s, 3H), 4.04 (s, 3H), 6.44 (d, J=5.5 Hz, 1H), 6.97~7.04 (m, 2H), 7.10~7.12 (m, 3H), 7.42 (s, 1H), 7.49 (d, J=9.2 Hz, 2H), 7.57 (s, 1H), 7.73 (s, 1H), 8.17 (m, 1H), 8.35 (s, 1H), 8.48 (d, J=5.5 Hz, 1H)

Mass spectrometry data (FD-MS, m/z): 433 (M$^+$)

Example 111

N-{4-[(6,7-Dimethoxy-4-quinolyl)oxy]phenyl}-N'-propylurea [194]

6,7-Dimethoxy-4-(4-aminophenoxy)quinoline (54 mg) was dissolved in N,N-dimethylformamide (3 ml), propyl isocyanate (0.2 ml) was added, and the admixture was stirred at 80° C. for 24 hours. Water was added to the reaction mixture, the admixture was extracted 2 times with ethyl acetate, and the organic layer was then washed with brine and dried with anhydrous sodium sulfate. The solvent was removed by reduced-pressure distillation and the resulting residue was purified by column chromatography on silica gel eluting with chloroform/acetone (10/1) to obtain 59 mg of the title compound (yield: 84%).

$^1$H-NMR (CDCl$_3$, 500 MHz): δ 0.93 (m, 3H), 1.55 (m, 2H), 3.24 (m, 2H), 4.02 (s, 3H), 4.02 (s, 3H), 5.47 (t, J=5.5 Hz, 1H), 6.41 (d, J=4.9 Hz, 1H), 7.08 (d, J=8.5 Hz, 2H), 7.39 (s, 1H), 7.43 (d, J=9.2 Hz, 2H), 7.55 (s, 1H), 7.60 (brs, 1H), 8.44 (d, J=5.5 Hz, 1H)

Mass spectrometry data (FD-MS, m/z): 381 (M$^+$)

Example 112

N-{4-[(6,7-Dimethoxy-4-quinolyl)oxy]phenyl}-N'-(4-phenylcarbonylphenyl)urea [195]

6,7-Dimethoxy-4-(4-aminophenoxy)quinoline (54 mg) was suspended in toluene (5 ml), triphosgene (53 mg) was added, and the admixture was refluxed with heat for 20 minutes. 4-Aminobenzophenone (85 mg) was added to the reaction mixture, and the admixture was refluxed for 1 hour with heat. After the addition of aqueous sodium hydrogen carbonate, the reaction mixture was extracted 2 times with ethyl acetate, and the organic layer was then washed with brine and dried with anhydrous sodium sulfate. The solvent was removed by reduced-pressure distillation and the resulting residue was purified by column chromatography on silica gel eluting with chloroform/acetone (10/1) to obtain 19 mg of the title compound (yield: 21%).

$^1$H-NMR (CDCl$_3$, 500 MHz): δ 4.01 (s, 3H), 4.04 (s, 3H), 6.44 (d, J=4.9 Hz, 1H), 7.12 (d, J=9.2 Hz, 2H), 7.41 (s, 1H), 7.46~7.80 (m, 12H), 8.14 (s, 1H), 8.30 (s, 1H), 8.47 (d, J=5.5 Hz, 1H)

Mass spectrometry data (FD-MS, m/z): 519 (M$^+$)

Example 113

N-Hexyl-N'-{4-[(6,7-dimethoxy-4-quinolyl)oxy]phenyl}urea [196]

6,7-Dimethoxy-4-(4-aminophenoxy)quinoline (52 mg) was dissolved in N,N-dimethylformamide (3 ml), hexyl isocyanate (0.2 ml) was added, and the admixture was stirred at 60° C. for 15 hours. After the addition of water, the reaction mixture was extracted 2 times with ethyl acetate, and the organic layer was then washed with brine and dried with anhydrous sodium sulfate. The solvent was removed by reduced-pressure distillation, and the resulting residue was purified by column chromatography on silica gel eluting with chloroform/acetone (10/1) to obtain 63 mg of the title compound (yield: 84%).

$^1$H-NMR (CDCl$_3$, 500 MHz): δ 0.85 (m, 3H), 1.25~1.47 (m, 6H), 1.50 (m, 2H), 3.26 (q, d=6.7 Hz, 2H), 4.02 (s, 3H), 4.02 (s, 3H), 5.68 (brs, 1H), 6.40 (d, J=5.5 Hz, 1H) 7.07 (d, J=9.2 Hz, 2H), 7.39 (s, 1H), 7.44 (d, J=9.2 Hz, 2H), 7.55 (s, 1H), 7.94 (s, 1H), 8.43 (d, J=4.9 Hz, 1H)

Mass spectrometry data (FD-MS, m/z): 423 (M$^+$)

Example 114

N-(5-Indanyl)-N'-{4-[(6,7-dimethoxy-4-quinolyl)oxy]phenyl}urea [197]

6,7-Dimethoxy-4-(4-aminophenoxy)quinoline (51 mg) was suspended in toluene (5 ml), triphosgene (54 mg) was added, and the admixture was refluxed with heat for 12 minutes. 4-Aminoindan (36 mg) was added, and the admixture was refluxed with heat for 36 minutes. After the addition of aqueous sodium hydrogen carbonate, the reaction mixture was extracted 2 times with ethyl acetate, and the organic layer was then washed with brine and dried with anhydrous sodium sulfate. The solvent was removed by reduced-pressure distillation and the resulting residue was purified by column chromatography on silica gel eluting with chloroform/acetone (10/1) to obtain 13 mg of the title compound (yield: 16%).

$^1$H-NMR (CDCl$_3$, 500 MHz): δ 2.04 (m, 2H), 2.82~2.86 (m, 4H), 4.01 (s, 3H), 4.03 (s, 3H), 6.40 (d, J=5.5 Hz, 1H), 7.03 (m, 1H), 7.08 (d, J=8.5 Hz, 2H), 7.13 (m, 1H), 7.32 (s, 1H), 7.40~7.57 (m, 6H), 8.44 (d, J=4.9 Hz, 1H)

Mass spectrometry data (FD-MS, m/z): 455 (M$^+$)

Example 115

N-(3,4-Dimethoxyphenyl)-N'-{4-[(6,7-dimethoxy-4-quinolyl)oxy]phenyl}urea [198]

3,4-Dimethoxyaniline (42 mg) was dissolved in toluene (5 ml), triphosgene (24 mg) was added, and the admixture was refluxed with heat for 22 minutes. 6,7-Dimethoxy-4-(4-aminophenoxy)quinoline (52 mg) was added, and the admixture was refluxed with heat for 18 minutes. After the addition of aqueous sodium hydrogen carbonate, the reaction mixture was extracted 2 times with ethyl acetate, and the organic layer was then washed with brine and dried with anhydrous sodium sulfate. The solvent was removed by reduced-pressure distillation and the resulting residue was purified by column chromatography on silica gel eluting with chloroform/acetone (10/1) to obtain 15 mg of the title compound (yield: 18%).

$^1$H-NMR (CDCl$_3$, 500 MHz): δ 3.84 (s, 3H), 3.85 (s, 3H), 4.01 (s, 3H), 4.04 (s, 3H), 6.43 (d, J=4.9 Hz, 1H), 6.75~6.80 (m, 2H), 7.10 (d, J=9.2 Hz, 2H), 7.16 (s, 1H), 7.38 (s, 1H), 7.41 (s, 1H), 7.45 (d, J=8.5 Hz, 2H), 7.56 (s, 1H), 7.59 (s, 1H), 8.46 (d, J=4.9 Hz, 1H)

Mass spectrometry data (FD-MS, m/z): 475 (M$^+$)

Example 116

N-(3,4-Ethylenedioxyphenyl)-N'-{4-[(6,7-dimethoxy-4-quinolyl)oxy]phenyl}urea [199]

3,4-Ethylenedioxyaniline (80 mg) was dissolved in toluene (5 ml), triethylamine (0.5 ml) and then triphosgene (50 mg) were added, and the admixture was refluxed with heat for 1 hour. 6,7-Dimethoxy-4-(4-aminophenoxy)quinoline (52 mg) was added, and the admixture was refluxed with heat for 100 minutes. After the addition of aqueous sodium hydrogen carbonate, the reaction mixture was extracted 2 times with ethyl acetate, and the organic layer was then washed with brine and dried with anhydrous sodium sulfate. The solvent was removed by reduced-pressure distillation, and the resulting residue was purified by column chromatography on silica gel eluting with chloroform/acetone (10/1) to obtain 62 mg of the title compound (yield: 74%).

$^1$H-NMR (DMSO-d$_6$, 500 MHz): δ 3.94 (s, 3H), 3.94 (s, 3H), 4.19~4.21 (m, 4H), 6.43 (d, J=4.9 Hz, 1H), 6.74~6.78 (m, 2H), 7.09 (s, 1H), 7.17 (d, J=9.2 Hz, 2H), 7.37 (s, 1H), 7.51 (s, 1H), 7.56 (d, J=8.5 Hz, 2H), 8.45 (d, J=4.9 Hz, 1H), 8.47 (s, 1H), 8.69 (s, 1H)

Mass spectrometry data (FD-MS, m/z): 473 (M$^+$)

Example 117

N-Methyl-N-{4-[(6,7-dimethoxy-4-quinolyl)oxy]phenyl}-N'-(4-methoxyphenyl)urea [200]

Formic acid (0.13 ml) was added to acetic anhydride (0.27 ml), and the admixture was stirred at 60° C. for 2 hours. A solution of 6,7-Dimethoxy-4-(4-aminophenoxy)quinoline (303 mg) in tetrahydrofuran (8 ml) was added to the reaction mixture, and the admixture was stirred at room temperature for 45 minutes. After the addition of aqueous sodium hydrogen carbonate, the reaction mixture was extracted 2 times with ethyl acetate, and the organic layer was then washed with brine and dried with anhydrous sodium sulfate. The solvent was removed by reduced-pressure distillation and the resulting residue was purified by column chromatography on silica gel eluting with chloroform/acetone (10/1) to obtain 327 mg of 6,7-dimethoxy-4-(4-formylaminophenoxy)quinoline.

6,7-Dimethoxy-4-(4-formylaminophenoxy)quinoline (317 mg) thus obtained was dissolved in tetrahydrofuran (9 ml), lithium aluminum hydride (181 mg) was added, and the admixture was stirred at room temperature for 2 hours. After the addition of aqueous ammonium chloride, the reaction mixture was extracted 2 times with ethyl acetate, and the organic layer was then washed with brine and dried with anhydrous sodium sulfate. The solvent was removed by reduced-pressure distillation and the resulting residue was purified by column chromatography on silica gel eluting with chloroform/acetone (10/1) to obtain 239 mg of 6,7-dimethoxy-4-(4-methylaminophenoxy)quinoline.

6,7-Dimethoxy-4-(4-methylaminophenoxy)quinoline (49 mg) thus obtained was dissolved in toluene (5 ml) with heat, 4-methoxyphenyl isocyanate (0.2 ml) was added, and the admixture was refluxed with heat for 12 hours. The resulting residue was purified by column chromatography on silica gel eluting with chloroform/acetone (10/1) to obtain 47 mg of the title compound (yield: 51%).

$^1$H-NMR (CDCl$_3$, 500 MHz): δ 3.38 (s, 3H), 3.77 (s, 3H), 4.05 (s, 3H), 4.06 (s, 3H), 6.14 (brs, 1H), 6.59 (d, J=5.5 Hz, 1H), 6.82 (d, J=9.2 Hz, 2H), 7.21 (d, J=9.2 Hz, 2H), 7.29 (d, J=9.2 Hz, 2H), 7.44 (d, J=8.6 Hz, 2H), 7.45 (s, 1H), 7.52 (s, 1H), 8.55 (d, J=5.5 Hz, 1H)

Mass spectrometry data (FD-MS, m/z): 459 (M$^+$)

Example 118

N-Methyl-N-phenyl-N'-{4-[(6,7-dimethoxy-4-quinolyl)oxy]phenyl}urea [201]

6,7-Dimethoxy-4-(4-aminophenoxy)quinoline (72 mg) was suspended in toluene (7 ml), triphosgene (52 mg) was added, and the admixture was refluxed with heat for 3 hours. N-Methylaniline (0.05 ml) was added to the reaction mixture, and the admixture was refluxed for 1 hour with heat. After the addition of aqueous sodium hydrogen carbonate, the reaction mixture was extracted 2 times with ethyl acetate, and the organic layer was then washed with brine and dried with anhydrous sodium sulfate. The solvent was removed by reduced-pressure distillation and the resulting residue was purified by column chromatography on silica gel eluting with chloroform/acetone (10/1) to obtain 48 mg of the title compound (yield: 46%).

$^1$H-NMR (CDCl$_3$, 500 MHz): δ 3.37 (s, 3H), 4.04 (s, 3H), 4.04 (s, 3H), 6.32 (brs, 1H), 6.41 (d, J=4.9 Hz, 1H), 7.07 (d, J=9.2 Hz, 2H), 7.37~7.53 (m, 8H), 7.54 (s, 1H), 8.45 (d, J=5.5 Hz, 1H)

Mass spectrometry data (FD-MS, m/z): 429 (M$^+$)

Example 119

N-Methyl-N-(4-methoxyphenyl)-N'-methyl-N'-{4-[(6,7-dimethoxy-4-quinolyl)oxy]phenyl}urea [202]

N-(4-Methoxyphenyl)-N'-{4-[(6,7-dimethoxy-4-quinolyl)oxy]phenyl}urea (99 mg) was dissolved in N,N-dimethylformamide (3 ml), sodium hydride (42 mg) was added, and the admixture was stirred at room temperature for 20 minutes, methyl iodide (0.03 ml) was added, and the admixture was stirred at the same temperature for 1 hour. After the addition of aqueous ammonium chloride, the reaction mixture was extracted 2 times with ethyl acetate, and the organic layer was then washed with brine and dried with anhydrous sodium sulfate. The solvent was removed by reduced-pressure distillation and the resulting residue was purified by column chromatography on silica gel eluting with chloroform/acetone (10/1) to obtain 91 mg of the title compound (yield: 87%).

$^1$H-NMR (CDCl$_3$, 500 MHz): δ 3.23 (s, 3H), 3.24 (s, 3H), 3.75 (s, 3H), 4.05 (s, 3H), 4.06 (s, 3H), 6.27 (d, J=5.5 Hz, 1H), 6.69 (d, J=8.5 Hz, 2H), 6.81 (d, J=9.2 Hz, 2H), 6.89 (d, J=9.2 Hz, 2H), 6.91 (d, J=9.2 Hz, 2H), 7.42 (s, 1H), 7.51 (s, 1H), 8.53 (d, J=4.9 Hz, 1H)

Mass spectrometry data (FD-MS m/z): 473 (M$^+$)

Example 120 (Reference Example)

3,4-Dichlorophenyl 4-methoxyphenyl ketone

To commercially available nitromethane (10 ml) were added commercially available anisole (1.081 g), commercially available 3,4-dichlorobenzoyl chloride (2.095 g) and commercially available ytterbium(III) trifluoromethanesulfonate (620 mg), and the admixture was stirred at 60° C. for 8 hours. The reaction mixture was partitioned between water and chloroform, and the chloroform layer was then dried with anhydrous magnesium sulfate. After removing the solvent by reduced-pressure distillation, the resulting residue was purified by column chromatography on silica gel eluting with hexane/ethyl acetate to obtain 270 mg of the title compound (yield: 10%).

$^1$H-NMR (CDCl$_3$, 500 MHz): δ 3.90 (s, 3H), 6.98 (d, J=9.2 Hz, 2H), 7.56 (s, 1H), 7.58 (d, J=1.8 Hz, 1H), 7.79 (d, J=9.2 Hz, 2H), 7.84 (d, J=1.8 Hz, 1H)

Mass spectrometry data (FD-MS, m/z): 280 (M$^+$) 282 (M$^+$+2)

Example 121 (Reference Example)

3,4-Dichlorophenyl 4-hydroxyphenyl ketone 3,4-Dichlorophenyl 4-methoxyphenyl ketone (235 mg) obtained in Example 120 was dissolved in dichloromethane (2 ml), a solution of 1.0 M boron tribromide in dichloromethane (7 ml) was added while cooled in ice, and the admixture was stirred at room temperature for two days. The reaction mixture was then poured into ice water and partitioned between water and chloroform. The chloroform layer was dried with anhydrous magnesium sulfate. After removing the solvent by reduced-pressure distillation, the resulting residue was purified by column chromatography on silica gel eluting with hexane/ethyl acetate to obtain 173 mg of the title compound (yield: 77%).

$^1$H-NMR (DMSO-d$_6$, 500 MHz): δ 6.91 (d, J=8.5 Hz, 2H), 7.62 (dd, J=1.8, 8.6 Hz, 1H), 7.68 (d, J=8.5 Hz, 2H), 7.80 (d, J=7.9 Hz, 1H), 7.85 (d, J=1.8 Hz, 1H), 10.55 (s, 1H)

Mass spectrometry data (FD-MS, m/z): 266 (M$^+$), 268 (M$^+$+2)

Example 122

{4-[(6,7-Dimethoxy-4-quinolyl)oxy]phenyl}(3,4-dichlorophenyl)methanone [177]

Under argon, 3,4-dichlorophenyl 4-hydroxyphenyl ketone (154 mg) obtained in Example 121 and 4-dimethylaminopyridine (77 mg) were added to xylene (5 ml), and the admixture was stirred at room temperature for 3 hours. 4-Chloro-6,7-dimethoxyquinoline (129 mg) was added, and the admixture was refluxed with heat for 21 hours. The reaction mixture was partitioned between saturated aqueous sodium hydrogen carbonate and chloroform, the chloroform layer was then dried with anhydrous magnesium sulfate. After removing the solvent by reduced-pressure distillation, the resulting residue was purified by thin layer chromatography on silica gel eluting with hexane/acetone (2/1) to obtain 81 mg of the title compound (yield: 31%).

$^1$H-NMR (CDCl$_3$, 500 MHz): δ 4.03 (s, 3H), 4.07 (s, 3H), 6.68 (d, J=5.5 Hz, 1H), 7.28 (d, J=8.5 Hz, 2H), 7.46 (s, 1H), 7.47 (s, 1H), 7.60 (d, J=8.5 Hz, 1H), 7.66 (dd, J=1.8, 8.6 Hz, 1H), 7.90 (d, J=9.2 Hz, 2H), 7.91 (d, J=1.8 Hz, 1H), 8.60 (d, J=4.9 Hz, 1H)

Mass spectrometry data (FD-MS, m/z): 453 (M$^+$), 455 (M$^+$+2)

Example 123 (Reference Example)

4-(4-Hydroxybenzoyl)benzonitrile

4-Tri-n-butyltin-1-methoxymethylphenol (1.282 g) obtained in Example 22 and commercially available 4-cyanobenzoyl chloride (497 mg) were dissolved in chloroform (5 ml), commercially available bis(triphenylphosphine)palladium(II) chloride (8 mg) was added, and the admixture was refluxed with heat for 11 hours. The reaction mixture was partitioned in the same manner as described in Example 23, and the resulting ether layer was dried with anhydrous magnesium sulfate. After removing the solvent by reduced-pressure distillation, the resulting residue (859 mg) was dissolved in tetrahydrofuran (2 ml), water (5 ml) and 6 N aqueous hydrochloric acid (12 ml) were added, and the admixture was refluxed with heat for 4 hours. The reaction mixture was partitioned between brine and chloroform, and the chloroform layer was then dried with anhydrous magnesium sulfate. After removing the solvent by reduced-pressure distillation, the resulting residue was purified by chromatography on silica gel eluting with hexane/ethyl acetate to obtain 250 mg of the title compound (yield: 37%).

$^1$H-NMR (DMSO-d$_6$, 500 MHz): 66.91 (d, J=9.2 Hz, 2H), 7.67 (d, J=8.5 Hz, 2H), 7.80 (d, J=7.9 Hz, 2H), 8.01 (d, J=8.6 Hz, 2H), 10.57 (s, 1H)

Mass spectrometry data (FD-MS m/z): 223 (M$^+$)

Example 124

4-{4-[(6,7-Dimethoxy-4-quinolyl)oxy]benzoyl}benzonitrile [178]

Under argon, 4-(4-hydroxybenzoyl)benzonitrile (230 mg) obtained in Example 123 and 4-dimethylaminopyridine (138 mg) were added to xylene (5 ml), and the admixture was stirred at room temperature for 1 hour. 4-Chloro-6,7-dimethoxyquinoline (230 mg) was added, and the admixture was refluxed with heat for 20 hours. The reaction mixture was partitioned between saturated aqueous sodium hydrogen carbonate and chloroform, and the chloroform layer was then dried with anhydrous magnesium sulfate. After removing the solvent by reduced-pressure distillation, the resulting residue was purified by chromatography on silica gel eluting with hexane/ethyl acetate and then by thin layer chromatography on silica gel eluting with chloroform/ethyl acetate (5/1) to obtain 199 mg of the title compound (yield: 47%).

$^1$H-NMR (CDCl$_3$, 500 MHz): δ 4.03 (s, 3H), 4.06 (s, 3H), 6.68 (d, J=5.5 Hz, 1H), 7.29 (d, J=8.5 Hz, 2H), 7.45 (s, 1H), 7.46 (s, 1H), 7.82 (d, J=7.9 Hz, 2H), 7.90 (d, J=8.6 Hz, 2H), 7.91 (d, J=8.5 Hz, 2H), 8.60 (d, J=5.5 Hz, 1H)

Mass spectrometry data (FD-MS, m/z): 410 (M$^+$)

Example 125 (Reference Example)

4-Methoxyphenyl 2-methylphenyl ketone

To commercially available nitromethane (10 ml) were added commercially available anisole (1.081 g), commercially available 2-methylbenzoyl chloride (1.546 g) and commercially available ytterbium(III) trifluoromethanesulfonate (620 mg), and the admixture was stirred at 60° C. for 7 hours. The reaction mixture was treated in the same manner as described in Example 120 to obtain 1.679 g of the title compound (yield: 74%).

Mass spectrometry data (FD-MS, m/z): 226 (M$^+$)

Example 126 (Reference Example)

4-Hydroxyphenyl 2-methylphenyl ketone

4-Methoxyphenyl 2-methylphenyl ketone (1.660 g) obtained in Example 125 was dissolved in chloroform (10 ml), a solution of 1.0 M boron tribromide in dichloromethane (29 ml) was added while cooled in ice, and the admixture was stirred at room temperature overnight. A solution of 1.0 M boron tribromide in dichloromethane (15 ml) was further added, and the admixture was stirred at room temperature for 2 days. The reaction mixture was then treated in the same manner as described in Example 121 to obtain 1.501 g of the title compound (yield: 96%).

$^1$H-NMR (CDCl$_3$, 500 MHz): δ 2.30 (s, 3H), 6.87 (d, J=8.5 Hz, 2H), 7.22~7.29 (m, 3H), 7.37 (td, J=1.2, 7.3 Hz, 1H), 7.73 (d, J=8.5 Hz, 2H)

Mass spectrometry data (FD-MS, m/z): 212 (M$^+$)

Example 127

{4-[(6,7-Dimethoxy-4-quinolyl)oxy]phenyl}(2-methylphenyl)methanone [180]

Under argon, 4-hydroxyphenyl 2-methylphenyl ketone (1.334 g) obtained in Example 126 and 4-dimethylaminopyridine (845 mg) were added to xylene (15 ml), and the admixture was stirred at room temperature for 1 hour. 4-Chloro-6,7-dimethoxyquinoline (1.406 g) was added, and the admixture was refluxed with heat for 23 hours. The reaction mixture was partitioned between saturated aqueous sodium hydrogen carbonate and chloroform, and the chloroform layer was then dried with anhydrous magnesium sulfate. After removing the solvent by reduced-pressure distillation, the resulting residue was purified by chromatography on silica gel eluting with hexane/ethyl acetate and then with chloroform, followed by thin layer chromatography on silica gel eluting with hexane/acetone (2/1), to obtain 1.258 g of the title compound (yield: 50%).

$^1$H-NMR (CDCl$_3$, 500 MHz): δ 2.37 (s, 3H), 4.02 (s, 3H), 4.06 (s, 3H), 6.65 (d, J=4.9 Hz, 1H), 7.23 (d, J=8.6 Hz, 2H), 7.25~7.35 (m, 3H), 7.39~7.42 (m, 1H), 7.45 (s, 1H), 7.46 (s, 1H), 7.91 (d, J=8.5 Hz, 2H), 8.57 (d, J=5.5 Hz, 1H)

Mass spectrometry data (FD-MS, m/z): 399 (M$^+$)

Example 128

{3-[(6,7-Dimethoxy-4-quinolyl)oxy]phenyl}phenylmethanone [181]

A mixture of 4-chloro-6,7-dimethoxyquinoline (112 mg) and commercially available 3-hydroxybenzophenone (297 mg) was stirred at 170° C. for 10 minutes, the reaction mixture was then purified by thin layer chromatography on silica gel eluting with hexane/acetone (2/1) to obtain 126 mg of the title compound (yield: 65%).

$^1$H-NMR (CDCl$_3$, 90 MHz): δ 4.4 (s, 3H), 4.05 (s, 3H), 6.53 (d, J=5.3 Hz, 1H), 7.34~7.88 (m, 11H), 8.53 (d, J=5.3 Hz, 1H)

Mass spectrometry data (FD-MS, m/z): 385 (M$^+$)

Example 129 (Reference Example)

2-Furoyl 4-hydroxyphenyl ketone

4-Tri-n-butyltin-1-methoxymethylphenol (1.282 g) obtained in Example 22 and commercially available 2-furoyl chloride (392 mg) were dissolved in chloroform (5 ml), commercially available bis(triphenylphosphine)palladium (II) chloride (8 mg) was added, and the admixture was refluxed for 11 hours. The reaction mixture was partitioned in the same manner as described in Example 23, and the resulting ether layer was dried with anhydrous magnesium sulfate. After removing the solvent by reduced-pressure distillation, the resulting residue (662 mg) was dissolved in tetrahydrofuran (2 ml), water (5 ml) and 6 N aqueous hydrochloric acid (12 ml) were added, and the admixture was refluxed for 3 hours with heat. The reaction mixture was treated in the same manner as described in Example 123 to obtain 218 mg of the title compound (yield: 39%).

$^1$H-NMR (DMSO-$d_6$, 500 MHz): δ 6.76 (dd, J=1.2, 3.1 Hz, 1H), 6.91 (d, J=8.5 Hz, 2H), 7.33 (d, J=3.1 Hz, 1H), 7.87 (d, J=8.5 Hz, 2H), 8.06 (d, J=1.2 Hz, 1H), 10.39 (s, 1H)

Mass spectrometry data (FD-MS, m/z): 188 (M$^+$)

Example 130

2-Furoyl-{4-[(6,7-dimethoxy-4-quinolyl)oxy] phenyl}methanone [182]

Under argon, 2-furoyl 4-hydroxyphenyl ketone (205 mg) obtained in Example 129 and 4-dimethylaminopyridine (146 mg) were added to xylene (5 ml), and the admixture was stirred at room temperature for 1 hour. 4-Chloro-6,7-dimethoxyquinoline (244 mg) was added, and the admixture was then refluxed with heat for 20 hours. The reaction mixture was partitioned between saturated aqueous sodium hydrogen carbonate and chloroform, and the chloroform layer was dried with anhydrous magnesium sulfate. After removing the solvent by reduced-pressure distillation, the resulting residue was purified by chromatography on silica gel eluting with hexane/ethyl acetate and then with chloroform, followed by thin layer chromatography on silica gel eluting with chloroform/ethyl acetate (5/1), to obtain 192 mg of the title compound (yield: 47%).

$^1$H-NMR (CDCl$_3$, 500 MHz): δ 4.03 (s, 3H), 4.07 (s, 3H), 6.63 (dd, J=1.8, 3.7 Hz, 1H), 6.65 (d, J=5.5 Hz, 1H), 7.28 (d, J=8.5 Hz, 2H), 7.32 (d, J=3.7 Hz, 1H), 7.47 (s, 1H), 7.48 (s, 1H), 7.73 (d, J=1.8 Hz, 1H), 8.14 (d, J=9.2 Hz, 2H), 8.58 (d, J=5.5 Hz, 1H)

Mass spectrometry data (FD-MS, m/z): 375 (M$^+$)

Example 131 (Reference Example)

4-Methoxyphenyl 3-methylphenyl ketone

To commercially available nitromethane (5 ml) were added commercially available anisole (541 mg), commercially available 3-methylbenzoyl chloride (773 mg) and commercially available scandium(III) trifluoromethanesulfonate (49 mg), and the admixture was stirred at 60° C. overnight. The reaction mixture was partitioned between water and chloroform, and the chloroform layer was dried with anhydrous magnesium sulfate. After removing the solvent by reduced-pressure distillation, the resulting residue was purified by column chromatography on silica gel eluting with hexane/acetone to obtain 635 mg of the title compound (yield: 56%).

Mass spectrometry (FD-MS, m/z): 226 (M$^+$)

Example 132 (Reference Example)

4-Hydroxyphenyl 3-methylphenyl ketone

4-Methoxyphenyl 3-methylphenyl ketone (603 mg) obtained in Example 131 was dissolved in dichloromethane (3 ml), a 1.0 M boron tribromide-dichloromethane solution (11 ml) was added while cooled in ice, and the admixture was stirred at room temperature for 22 hours, after which the reaction mixture was treated in the same manner as described in Example 121 to obtain 316 mg of the title compound (yield: 56%).

$^1$H-NMR (DMSO-$d_6$, 500 MHz): δ 2.38 (s, 3H), 6.89 (d, J=8.6 Hz, 2H), 7.37~7.47 (m, 4H), 7.65 (d, J=8.6 Hz, 2H), 10.42 (s, 1H)

Mass spectrometry data (FD-MS, m/z): 212 (M$^+$)

Example 133

{4-[(6,7-Dimethoxy-4-quinolyl)oxy]phenyl}(3-methylphenyl)methanone [183]

Under argon, 4-hydroxyphenyl 3-methylphenyl ketone (307 mg) obtained in Example 132 and 4-dimethylaminopyridine (194 mg) were added to xylene (5 ml), and the admixture was stirred at room temperature for 1 hour. 4-Chloro-6,7-dimethoxyquinoline (324 mg) was added, and the admixture was then refluxed with heat for 23 hours. The reaction mixture was treated in the same manner as described in Example 122 to obtain 262 mg of the title compound (yield: 45%).

$^1$H-NMR (CDCl$_3$, 500 MHz): δ 2.44 (s, 3H), 4.03 (s, 3H), 4.06 (s, 3H), 6.66 (d, J=4.9 Hz, 1H), 7.27 (d, J=8.6 Hz, 2H), 7.38 (t, J=7.3 Hz, 1H), 7.41 (d, J=7.3 Hz, 1H), 7.46 (s, 1H), 7.49 (s, 1H), 7.59 (d, J=7.3 Hz, 1H), 7.64 (s, 1H), 7.93 (d, J=8.6 Hz, 2H), 8.57 (d, J=5.5 Hz, 1H)

Mass spectrometry data (FD-MS, m/z): 399 (M$^+$)

Example 134 (Reference Example)

4-Hydroxyphenyl 4-nitrophenyl ketone

4-Tri-n-butyltin-1-methoxymethylphenol (1.282 g) obtained in Example 22 and commercially available 4-nitrobenzoyl chloride (557 mg) were dissolved in chloroform (5 ml), commercially available bis (triphenylphosphine)palladium(II) chloride (8 mg) was added, and the admixture was refluxed with heat for 23 hours. The reaction mixture was partitioned in the same manner as described in Example 23, and the resulting ether layer was dried with anhydrous magnesium sulfate. After removing the solvent by reduced-pressure distillation, the resulting residue (1.047 g) was dissolved in tetrahydrofuran (4 ml), water (5 ml) and 6 N aqueous hydrochloric acid (15 ml) were added, and the admixture was refluxed with heat overnight. The reaction mixture was treated in the same manner as described in Example 123 to obtain 398 mg of the title compound (yield: 55%).

$^1$H-NMR (DMSO-$d_6$, 500 MHz): δ 6.92 (d, J=8.6 Hz, 2H), 7.69 (d, J=8.6 Hz, 2H), 7.89 (d, J=8.5 Hz, 2H), 8.36 (d, J=8.5 Hz, 2H), 10.62 (s, 1H)

Mass spectrometry data (FD-MS, m/z): 243 (M$^+$)

Example 135

{4-[(6,7-Dimethoxy-4-quinolyl)oxy]phenyl}(4-nitrophenyl)methanone [184]

Under argon, 4-hydroxyphenyl 4-nitrophenyl ketone (370 mg) obtained in Example 134 and 4-dimethylaminopyridine (204 mg) were added to xylene (5 ml), and the admixture was stirred at room temperature for 1 hour. 4-Chloro-6,7-dimethoxyquinoline (340 mg) was added, and the mixture was then refluxed with heat for 23 hours. The reaction mixture was treated in the same manner as described in Example 130 to obtain 238 mg of the title compound (yield: 36%).

$^1$H-NMR (CDCl$_3$, 500 MHz): δ 4.63 (s, 3H), 4.07 (s, 3H), 6.69 (d, J=4.9 Hz, 1H), 7.29 (d, J=8.5 Hz, 2H), 7.44 (s, 1H), 7.47 (s, 1H), 7.93 (d, J=9.2 Hz, 2H), 7.96 (d, J=8.5 Hz, 2H), 8.37 (d, J=8.5 Hz, 2H), 8.60 (d, J=5.5 Hz, 1H)

Mass spectrometry data (FD-MS, m/z): 430 (M$^+$)

Example 136 (Reference Example)

4-Hydroxyphenyl 3,4-methylenedioxyphenyl ketone

4-Tri-n-butyltin-1-methoxymethylphenol (1.282 g) obtained in Example 22 and commercially available piperonyloyl chloride (664 mg) were dissolved in chloroform (5 ml), commercially available bis(triphenylphosphine) palladium(II) chloride (8 mg) was added, and the admixture was refluxed with heat overnight. The reaction mixture was partitioned in the same manner as described in Example 23, and the resulting ether layer was dried with anhydrous magnesium sulfate. After removing the solvent by reduced-pressure distillation, the resulting residue (1.030 g) was dissolved in tetrahydrofuran (2 ml), water (5 ml) and 6 N aqueous hydrochloric acid (12 ml) were added, and the admixture was refluxed with heat 10.5 hours. The reaction mixture was treated in the same manner as described in Example 123 to obtain 212 mg of the title compound (yield: 29%).

$^1$H-NMR (DMSO-d$_6$, 500 MHz): δ 6.15 (s, 2H), 6.88 (d, J=8.6 Hz, 2H), 7.04 (d, J=7.9 Hz, 1H), 7.21 (d, J=1.2 Hz, 1H), 7.24 (dd, J=1.8, 7.9 Hz, 1H), 7.62 (d, J=9.2 Hz, 2H), 10.34 (s, 1H)

Mass spectrometry data (FD-MS, m/z): 242 (M$^+$)

Example 137

{4-[(6,7-Dimethoxy-4-quinolyl)oxy]phenyl}(3,4-methylenedioxyphenyl)methanone [185]

Under argon, 4-hydroxyphenyl 3,4-methylenedioxyphenyl ketone (202 mg) obtained in Example 136 and 4-dimethylaminopyridine (112 mg) were added to xylene (2 ml), and the admixture was stirred at room temperature for 1 hour. 4-Chloro-6,7-dimethoxyquinoline (187 mg) was added, and the admixture was refluxed with heat for 20 hours. The reaction mixture was treated in the same manner as described in Example 124 to obtain 135 mg of the title compound (yield: 38%).

$^1$H-NMR (CDCl$_3$, 500 MHz): δ 4.04 (s, 3H), 4.06 (s, 3H), 6.09 (s, 2H), 6.64 (d, J=4.9 Hz, 1H), 6.89 (d, J=7.9 Hz, 1H), 7.26 (d, J=8.5 Hz, 2H), 7.38 (d, J=1.8 Hz, 1H), 7.41 (dd, J=1.8, 7.9 Hz, 1H), 7.46 (s, 1H), 7.49 (s, 1H), 7.88 (d, J=8.5 Hz, 2H), 8.57 (d, J=4.9 Hz, 1H)

Mass spectrometry data (FD-MS, m/z): 429 (M$^+$)

Example 138 (Reference Example)

3-Trifluoromethylphenyl 4-methoxyphenyl ketone

To commercially available nitromethane (10 ml) were added commercially available anisole (1.081 g), commercially available 3-(trifluoromethyl)benzoyl chloride (2.086 g) and commercially available ytterbium(III) trifluoromethanesulfonate (620 mg), and the admixture was stirred at 60° C. overnight. The reaction mixture was treated in the same manner as described in Example 120 to obtain 719 mg of the title compound (yield: 26%).

$^1$H-NMR (CDCl$_3$, 500 MHz): δ 3.91 (s, 3H), 6.99 (d, J=9.2 Hz, 2H), 7.60~7.64 (m, 1H), 7.80~7.83 (m, 1H), 7.82 (d, J=8.5 Hz, 2H), 7.93~7.94 (m, 1H), 8.01 (s, 1H)

Mass spectrometry data (FD-MS, m/z): 280 (M$^+$)

Example 139 (Reference Example)

3-Trifluoromethylphenyl 4-hydroxyphenyl ketone

3-Trifluoromethylphenyl 4-methoxyphenyl ketone (657 mg) obtained in Example 138 was dissolved in N,N-dimethylformamide (35 ml), sodium thiomethoxide (411 ml) was added, and the admixture was refluxed with heat under argon for 7 hours. The reaction mixture was treated in the same manner as described in Example 33 to obtain 454 mg of the title compound (yield: 73%).

$^1$H-NMR (CDCl$_3$, 500 MHz): δ 5.85 (s, 1H), 6.94 (d, J=9.2 Hz, 2H), 7.62 (t, J=7.3 Hz, 1H), 7.78 (d, J=9.2 Hz, 2H), 7.83 (d, J=7.3 Hz, 1H), 7.93 (d, J=7.3 Hz, 1H), 8.01 (s, 1H)

Example 140

(3-Trifluoromethylphenyl){4-[(6,7-dimethoxy-4-quinolyl)oxy]phenyl}methanone [186]

Under argon, 3-trifluoromethylphenyl 4-hydroxyphenyl ketone (432 mg) obtained in Example 139 and 4-chloro-6,7-dimethoxyquinoline (363 mg) were dissolved in diethylene glycol dimethyl ether (10 ml), and the solution was then refluxed at 160° C. for 11 hours. The reaction mixture was partitioned between saturated aqueous sodium hydrogen carbonate and chloroform, and the chloroform layer was dried with anhydrous magnesium sulfate. After removing the solvent by reduced-pressure distillation, the resulting residue was purified by chromatography on silica gel eluting with hexane/ethyl acetate and then by thin layer chromatography on silica gel eluting with chloroform/ethyl acetate (5/1) to obtain 204 mg of the title compound (yield: 28%).

$^1$H-NMR (CDCl$_3$, 500 MHz): δ 4.03 (s, 3H) 4.07 (s, 3H), 6,69 (d, J=4.9Hz, 1H), 7.30 (d, J=9.2Hz, 2H), 7.47 (s, 2H), 7.66 (t, J=7.9Hz, 1H), 7.87 (d, J=7.9Hz, 1H), 7.92 (d, J=9.2Hz, 2H), 8.00 (d, J=7.9Hz, 1H), 8.08 (s, 1H), 8.60 (d, J=4.9Hz, 1H)

Mass spectrometry data (FD-MS, m/z): 453 (M$^+$)

Example 141 (Reference Example)

4-Cyclohexylcarbonyl-1-methoxybenzene

To commercially available nitromethane (5 ml) were added commercially available anisole (0.5 ml), commercially available cyclohexanecarbonyl chloride (0.63 ml) and commercially available ytterbium(III) trifluoromethanesulfonate (288 mg), and the admixture was stirred at 60° C. for 3 hours. The reaction mixture was partitioned between water and chloroform, and the chloroform layer was washed with saturated aqueous sodium hydrogen carbonate and brine and then dried with anhydrous sodium sulfate. After removing the solvent by reduced-pressure distillation, the resulting residue was purified by chromatography on silica gel eluting with chloroform to obtain 517 mg of the title compound (yield: 51%).

$^1$H-NMR (CDCl$_3$, 500 MHz) δ 1.21~1.88 (m, 10H), 3.19~3.25 (m, 1H), 3.87 (s, 3H), 6.93 (d, J=9.2Hz, 2H), 7.94 (d, J=9.2Hz, 2H)

Mass spectrometry data (FAB-MS, m/z): 219 (M$^+$+1)

Example 142 (Reference Example)

4-Cyclohexylcarbonyl-1-hydroxybenzene

4-Cyclohexylcarbonyl-1-methoxybenzene (517 mg) obtained in Example 141 was dissolved in N,N- dimethylformamide (20 ml), sodium thiomethoxide (538 mg) was added, and the admixture was refluxed with heat for 1 hour under argon. The reaction mixture was partitioned between water and ethyl acetate, and the ethyl acetate layer was washed with brine and then dried with anhydrous sodium sulfate. After removing the solvent by reduced-pressure distillation, the resulting residue was purified by chromatography on silica gel eluting with hexane/acetone to obtain 487 mg of the title compound (yield: 93%).

$^1$H-NMR (CDCl$_3$, 500 MHz): δ 1.23~1.88 (m, 10H), 3.19~3.25 (m, 1H), 6.06 (brs, 1H) 6.89 (d, J=8.6Hz, 2H), 7.90 (d, J=8.6Hz, 1H)

Mass spectrometry data (FD-MS, m/z): 204 (M$^+$)

Example 143

4-Cyclohexylcarbonyl-1-[(6,7-dimethoxy-4-quinolyl)oxy]benzene [187]

Under argon, 4-cyclohexylcarbonyl-1-hydroxybenzene (273 mg) obtained in Example 142 and 4-chloro-6,7-dimethoxyquinoline (100 mg) were dissolved in diethylene glycol dimethyl ether (0.2 ml), and the solution was refluxed at 160° C. for 30 minutes. The reaction mixture was partitioned between saturated aqueous sodium hydrogen carbonate and chloroform, and the chloroform layer was washed with brine and then dried with anhydrous magnesium sulfate. After removing the solvent by reduced-pressure distillation, the resulting residue was purified by chromatography on silica gel eluting with hexane/acetone and then with chloroform/methanol to obtain 58 mg of the title compound (yield: 33%).

$^1$H-NMR (CDCl$_3$, 500 MHz): δ 1.21~1.93 (m, 10H), 3.24~3.29 (m, 1H), 4.03 (s, 3H), 4.06 (s, 3H), 6.60 (d, J=5.5Hz, 1H), 7.24 (d, J=8.5Hz, 2H), 7.45 (s, 1H), 7.47 (s, 1H), 8.05 (d, J=8.5Hz, 2H), 8.55 (d, J=5.5Hz, 1H)

Mass spectrometry data (FD-MS, m/z): 392 (M$^+$+1)

Example 144 (Reference Example)

2-Trifluoromethylphenyl 4-methoxyphenyl ketone

To commercially available nitromethane (10 ml) were added commercially available anisole (1.081 g), commercially available 2-(trifluoromethyl)benzoyl chloride (2.086 g) and commercially available ytterbium(III) trifluoromethanesulfonate (620 mg), and the admixture was stirred at 60° C. for 6 hours. The reaction mixture was partitioned between water and chloroform, abd the chloroform layer was then dried with anhydrous magnesium sulfate. After removing the solvent by reduced-pressure distillation, the resulting residue was purified by chromatography on silica gel eluting with hexane/ethyl acetate to obtain 1.402 g of the title compound (yield: 50%).

$^1$H-NMR (CDCl$_3$, 500 MHz): 3.88 (s, 3H) 6.93 (d, J=9.2Hz, 2H), 7.37~7.39 (m, 1H), 7.60~7.63 (m, 2H), 7.75 (d, J=9.2Hz, 2H), 7.73~7.78 (m, 1H)

Mass spectrometry data (FD-MS, m/z): 280 (M$^+$)

Example 145 (Reference Example)

2-Trifluoromethylphenyl 4-hydroxyphenyl ketone

2-Trifluoromethylphenyl 4-methoxyphenyl ketone (1.402 g) obtained in Example 144 was dissolved in N,N-dimethylformamide (15 ml), sodium thiomethoxide (877 mg) was added, and the admixture was refluxed with heat for 4 hours under argon. The reaction mixture was treated in the same manner as described in Example 33 to obtain 1.050 g of the title compound (yield: 79%).

$^1$H-NMR (CDCl$_3$, 500 MHz): δ 5.88 (s, 1H), 6.87 (d, J=8.5Hz, 2H), 7.37~7.38 (m, 1H), 7.58~7.63 (m, 2H), 7.71 (d, J 9.2Hz, 2H), 7.76~7.78 (m, 1H)

Mass spectrometry data (FD-MS, m/z) 266 (M$^+$)

Example 146

(2-Trifluoromethylphenyl){4-[(6,7-dimethoxy-4-quinolyl)oxy]phenyl}methanone [35]

Under argon, 2-trifluoromethylphenyl 4-hydroxyphenyl ketone (959 mg) obtained in Example 145 and 4-dimethylaminopyridine (484 mg) were added to xylene (7 ml), and the admixture was stirred at room temperature for 1 hour. 4-Chloro-6,7-dimethoxyquinoline (805 mg) was added, and the admixture was then refluxed with heat overnight. The reaction mixture was treated in the same manner as described in Example 130 to obtain 899 mg of the title compound (yield: 55%).

$^1$H-NMR (CDCl$_3$, 500 MHz): δ 4.01 (s, 3H), 4.06 (s, 3H), 6,67 (d, J=5.5Hz, 1H), 7.22 (d, J=9.2Hz, 2H), 7.42 (s, 1H), 7.42~7.44 (m, 1H), 7.45 (s, 1H), 7.62~7.68 (m, 2H), 7.80~7.81 (m, 1H), 7.87 (d, J=8.6Hz, 2H), 8.58 (d, J=5.5Hz, 1H)

Mass spectrometry data (FD-MS, m/Z): 453 (M$^+$)

Example 147 (Reference Example)

4-n-Butylphenyl 4-methoxyphenyl ketone

To commercially available nitromethane (10 ml) were added commercially available anisole (1.081 g), commercially available 4-(n-butyl)benzoyl chloride (1.967 g) and commercially available ytterbium(III) trifluoromethanesulfonate (620 mg), and the admixture was stirred at 60° C. for 6 hours. The reaction mixture was treated in the same manner as described in Example 120 to obtain 863 mg of the title compound (yield: 32%).

$^1$H-NMR (CDCl$_3$, 500 MHz): δ 0.95 (t, J=7.3Hz, 3H), 1.38 (tq, J=7.3, 7.3Hz, 2H), 1.64 (quint, J=7.3Hz, 2H), 2.69 (t, J=7.3Hz, 2H), 3.89 (s, 3H), 6.96 (d, J=9.2Hz, 2H), 7.27 (d, J=8.6Hz, 2H), 7.69 (d, J=8.6Hz, 2H), 7.82 (d, J=9.2Hz, 2H)

Mass spectrometry data (FD-MS, m/z): 268 (M$^+$)

Example 148 (Reference Example)

4-n-Butylphenyl 4-hydroxyphenyl ketone 4-n-Butylphenyl 4-methoxyphenyl ketone (863 mg) obtained in Example 147 was dissolved in N,N-dimethylformamide (50 ml), sodium thiomethoxide (563 mg) was added, and the admixture was refluxed with heat for 7 hours under argon. The reaction mixture was treated in the same manner as described in Example 33 to obtain 787 mg of the title compound (yield: 96%).

$^1$H-NMR (CDCl$_3$, 500 MHz): δ 0.95 (t, J=7.3Hz, 3H), 1.38 (tq, J=7.3, 7.3Hz, 2H), 1.64 (septet, J=7.3Hz, 2H), 2.69 (t, J=7.9Hz, 2H), 6.35 (s, 1H), 6.92 (d, J=8.5, 2H), 7.28 (d, J=7.9Hz, 2H), 7.69 (d, J=8.6Hz, 2H), 7.77 (d, J=8.5Hz, 2H)

Mass spectrometry data (FD-MS, m/z): 254 (M$^+$)

Example 149

(4-n-Butylphenyl){4-[(6,7-dimethoxy-4-quinolyl)oxy]phenyl}methanone [40]

Under argon, 4-n-butylphenyl 4-hydroxyphenyl ketone (727 mg) obtained in Example 148 and 4-chloro-6,7- dimethoxyquinoline (639 mg) were dissolved in diethylene glycol dimethyl ether (10 ml), and the solution was then refluxed with heat at 180° C. for 10 hours. The reaction mixture was partitioned between saturated aqueous sodium hydrogen carbonate and chloroform, and the chloroform layer was then dried with anhydrous magnesium sulfate. After removing the solvent by reduced-pressure distillation, the resulting residue was purified by chromatography on silica gel eluting with hexane/ethyl acetate and then with chloroform, followed by chromatography on silica gel eluting with hexane/acetone to obtain 400 mg of the title compound (yield: 32%).

$^1$H-NMR (CDCl$_3$, 500 MHz) δ 0.95 (t, J=7.3Hz, 3H), 1.38 (tq, J=7.3, 7.3Hz, 2H), 1.62~1.68 (m, 2H), 2.71 (t, J=7.3Hz, 2H), 4.04 (s, 3H), 4.07 (s, 3H), 6.65 (d, J=4.9Hz, 1H), 7.26 (d, J=8.5Hz, 2H), 7.31 (d, J=7.9Hz, 2H), 7.46 (s, 1H), 7.49 (s, 1H), 7.76 (d, J=7.9Hz, 2H), 7.92 (d, J=8.5Hz, 2H), 8.58 (d, J=5.5Hz, 1H)

Mass spectrometry data (FD-MS, m/z): 440 (M$^+$−1)

Example 150 (Reference Example)

3-Fluorophenyl 4-methoxyphenyl ketone

To commercially available nitromethane (5 ml) were added commercially available anisole (541 mg), commercially available 3-fluorobenzoyl chloride (793 mg) and commercially available scandium(III) trifluoromethanesulfonate (49 mg), and the admixture was stirred at 60° C. for 3 days. The reaction mixture was partitioned between water and chloroform, and the chloroform layer was then dried with anhydrous magnesium sulfate. After removing the solvent by reduced-pressure distillation, the resulting residue was purified by chromatography on silica gel eluting with hexane/acetone to obtain 585 mg of the title compound (yield: 51%).

Mass spectrometry data (FAB-MS, m/z): 231 (M$^+$+1)

Example 151 (Reference Example)

4-Hydroxyphenyl 3-fluorophenyl ketone

3-Fluorophenyl 4-methoxyphenyl ketone (580 mg) obtained in Example 150 was dissolved in dichloromethane (5 ml), a solution of 1.0 M boron tribromide in dichloromethane (23 ml) was added while cooled in ice, and the admixture was stirred at room temperature for 3 days. The reaction mixture was treated in the same manner as described in 121 to obtain 402 mg of the title compound (yield: 74%).

$^1$H-NMR (DMSO-d$_6$, 500 MHz) 6.91 (d, J=8.5Hz, 2H), 7.44~7.49 (m, 3H), 7.57~7.61 (m, 1H), 7.68 (d, J=8.5Hz, 2H), 10.51 (brs, 1H)

Mass spectrometry data (FAB-M S, m/z): 217 (M$^+$+1)

Example 152

{4-[(6,7-Dimethoxy-4-quinolyl)oxy]phenyl})(3-fluorophenyl)methanone [176]

Under argon, 4-hydroxyphenyl 3-fluorophenyl ketone (373 mg) obtained in Example 151 and 4-dimethylaminopyridine (232 mg) were added to xylene (5 ml), and the admixture was stirred at room temperature for 3 hours. 4-Chloro-6,7-dimethoxyquinoline (386 mg) was added, and the mixture was then refluxed with heat for 21 hours. The reaction mixture was partitioned between saturated aqueous sodium hydrogen carbonate and chloroform, and the chloroform layer was then dried with anhydrous magnesium sulfate. After removing the solvent by reduced-pressure distillation, the resulting residue was purified by chromatography on silica gel eluting with hexane/acetone and then with chloroform, followed by thin layer chromatography on silica gel eluting with chloroform/ethyl acetate (5/1), to obtain 484 mg of the title compound (yield: 70%).

$^1$H-NMR (CDCl$_3$, 500 MHz): δ 4.04 (s, 3H), 4.07 (s, 3H), 6.67 (d, J=4.9Hz, 1H), 7.28 (d, J=7.9Hz, 2H), 7.31~7.33 (m, 1H), 1.46 (s, 1H), 7.47 (s, 1H), 7.48~7.53 (m, 2H), 7.59~7.61 (m, 1H), 7.93 (d, J=8.6Hz. 2H), 8.59 (d, J-5.5Hz, 1H)

Mass spectrometry data (FD-MS, m/z): 403 (M$^+$)

Example 153

N-{4-[(6,7-Dimethoxy-4-quinazolinyl)oxy]phenyl)-N'-(2-methoxyphenyl)urea [113]

6,7-Dimethoxy-4-(4-aminophenoxy)quinazoline (100 mg) was dissolved in toluene (10 ml) with heat, 2-methoxyphenyl isocyanate (0.36 ml) was added, and the admixture was refluxed with heat for 40 minutes. After removing the solvent by distillation, the resulting residue was purified by column chromatography on silica gel eluting with chloroform/methanol (100/1) and then with chloroform/acetone (5/1) to obtain 112 mg of the title compound (yield: 75%).

$^1$H-NMR (DMSO-d$_6$, 500 MHz): δ 3.90 (s, 3H), 3.98 (s, 3H), 3.99 (s, 3H), 6.90 (t, J=7.9Hz, 1H), 6.96 (t, J=7.9Hz, 1H), 7.03 (t, J=7.9Hz, 1H), 7.23 (d, J=9.2Hz, 2H), 7.39 (s, 1H), 7.55 (d, J=9.2Hz, 2H), 7.57 (s, 1H), 8.15 (d, J=7.9Hz, 1H), 8.25 (s, 1H), 8.55 (s, 1H) 9.44 (s, 1H)

Mass spectrometry data (FD-MS m/z): 446 (M$^+$)

Example 154

N-{4-[(6,7-Dimethoxy-4-quinazolinyl)oxy]phenyl}-N'-(3-methoxyphenyl)urea [114]

6,7-Dimethoxy-4-(4-aminophenoxy)quinazoline (100 mg) was dissolved in toluene (10 ml) with heat, 3-methoxyphenyl isocyanate (0.36 ml) was added, and the admixture was refluxed with heat for 40 minutes. After removing the solvent by distillation, the resulting residue was purified by column chromatography on silica gel eluting with chloroform/methanol (100/1) and then with chloroform/acetone (5/1) to obtain 31 mg of the title compound (yield: 21%).

$^1$H-NMR (DMSO-d$_6$, 500 MHz): δ 3.74 (s, 3H), 3.98 (s, 3H), 3.99 (s, 3H), 6.56 (d, J=7.9Hz, 1H), 6.96 (d, J=7.9Hz, 1H), 7.15~7.25 (m, 4H), 7.38 (s, 1H), 7.53~7.60 (m, 3H), 8.55 (s, 1H), 8.76 (s, 1H) 8.81 (s, 1H)

Mass spectrometry data (FD-MS, m/z) 446 (M$^+$)

Example 155

N-{4-[(6,7-Dimethoxy-4-quinazolinyl)oxy]phenyl}-N'-(4-methoxyphenyl)urea [99]

6,7-Dimethoxy-4-(4-aminophenoxy)quinazoline (81 mg) was dissolved in toluene (5 ml) with heat, 4-methoxyphenyl isocyanate (0.29 ml) was added, and the admixture was refluxed with heat for 40 minutes. The separated solid was filtered and washed with toluene to obtain 60 mg of the title compound (yield: 49%).

$^1$H-NMR (CDCl$_3$, 500 MHz): δ 3.79 (s, 3H), 4.06 (s, 3H), 4.07 (s, 3H), 6.48 (s, 1H), 6.64 (s, 1H), 6.91 (d, J=9.2Hz,

2H), 7.20 (d, J=8.6Hz, 2H), 7.27 (d, J=8.6Hz, 2H), 7.32 (s, 1H), 7.47 (d, J=9.2Hz, 2H), 7.55 (s, 1H), 8.60 (s, 1H)

Mass spectrometry data (FAB-MS, m/z): 447 (M$^+$+1)

Example 156

N-{4-[(6,7-Dimethoxy-4-quinazolinyl)oxy]phenyl}-N'-(2-fluorophenyl)urea [116]

6,7-Dimethoxy-4-(4-aminophenoxy)quinazoline (100 mg) was dissolved in toluene (10 ml) with heat, 2-fluorophenyl isocyanate (0.30 ml) was added, and the admixture was refluxed with heat for 40 minutes. The separated solid was filtered and washed with toluene to obtain 96 mg of the title compound (yield: 66%).

$^1$H-NMR (DMSO-d$_6$, 500 MHz): δ 3.98 (s, 3H), 3.99 (s, 3H), 7.00~7.04 (m, 1H), 7.13~7.17 (m, 1H), 7.23~7.27 (m, 3H), 7.39 (s, 1H), 7.54~7.57 (m, 3H), 8.10~8.20 (m, 1H), 8.55 (s, 1H), 8.65 (s, 1H), 9.26 (s, 1H)

Mass spectrometry data (FD-MS, m/z): 434 (M$^+$)

Example 157

N-(4-[(6,7-Dimethoxy-4-quinazolinyl)oxy]phenyl)-N'-n-butylurea [220]

6,7-Dimethoxy-4-(4-aminophenoxy)quinazoline (100 mg) was dissolved in toluene (10 ml) with heat, n-butyl isocyanate (0.29 ml) was added, and the admixture was refluxed with heat for 40 minutes. After removing the solvent by distillation, the resulting residue was purified by column chromatography on silica gel eluting with chloroform/acetone (5/1) to obtain 75 mg of the title compound (yield: 56%).

$^1$H-NMR (DMSO-d$_6$, 500 MHz): δ 0.90 (t, J=7.3Hz, 3H), 1.28–1.46 (m, 4H), 3.09 (q, J=6.7Hz, 2H), 3.97 (s, 3H), 3.99 (s, 3H), 6.23 (brs, 1H), 7.14 (d, J=9.2Hz, 2H), 7.37 (s, 1 H), 7.47 (d, J=9.2Hz, 2H), 7.55 (s, 1H), 8.53 (s, 1H), 8.58 (brs, 1H)

Mass spectrometry data (FD-MS, m/z): 396 (M$^+$)

Example 158

N-{4-[6,7-Dimethoxy-4-quinolyl)oxy]phenyl}-(4-tert-butylphenyl)carboxamide [213]

6,7-Dimethoxy-4-(4-aminophenoxy)quinoline (54 mg) and commercially available 4-tert-butylbenzoic acid (102 mg) were dissolved in N,N-dimethylformamide (3 ml), 1-ethyl-3-(3'-dimethylaminopropyl)carbodiimide hydrochloride (106 mg) was added, and the admixture was stirred at room temperature for 6 hours, after which the reaction mixture was purified in the same manner as described in Example 51 to obtain 29 mg of the title compound (yield: 35%).

$^1$H-NMR (CDCl$_3$, 90 MHz): (1.36 (s, 9H), 4.05 (s, 3H), 4.08 (s, 3H), 6.48 (d, J=5.3Hz, 1H), 7.1~8.1 (m, 11H) 8.49 (d, J=5.3Hz, 1H)

Mass spectrometry data (FD-MS, m/z): 456 (M$^+$)

Example 159

N-(4-[(6,7-Dimethoxy-4-quinolyl)oxy]phenyl)-N-methyl-(4-t-butylphenyl)carboxamide [156]

N-(4-[6,7-Dimethoxy-4-quinolyl)oxy]phenyl)-(4-t-butylphenyl)carboxamide (100 mg) obtained in Example 158 was dissolved in N,N-dimethylformamide (3 ml), sodium hydride (10 mg) was added, and the admixture was stirred at 0° C. for 1 hour, methyl iodide (31 mg) was added, and the admixture was stirred for a further 3 hours. The reaction mixture was purified in the same manner as described in Example 51 to obtain 48 mg of the title compound (yield: 46%).

$^1$H-NMR (CDCl$_3$, 90 MHz): δ 1.28 (s, 9H), 3.54 (s, 3H), 4.04 (s, 3H), 4.05 (s, 3H), 6.32 (d, J=5.3Hz, 1H), 7.0~7.3 (m, 8H), 7.42 (s, 1H), 7.50 (s, 1H), 8.47 (d, J=5, 3Hz, 1H)

Mass spectrometry data (FD-MS, m/z): 470 (M$^+$)

Example 160

N-(4-t-Butylphenyl)-{4-[(6,7-dimethoxy-4-quinolyl)oxy]phenyl}carboxamide [155]

4-[6,7-Dimethoxy-4-quinolyl)oxybenzoic acid (54 mg) and commercially available 4-tert-butylaniline (102 mg) were dissolved in N,N-dimethylformamide (3 ml), 1-ethyl-3-(3'-dimethylaminopropyl)carbodiimide hydrochloride (106 mg) was added, and the admixture was stirred at room temperature for 6 hours, after which the reaction mixture was purified in the same manner as described in Example 51 to obtain 29 mg of the title compound (yield: 35%).

$^1$H-NMR (CDCl$_3$, 90 MHz): δ 1.34 (s, 9H), 4.03 (s, 3H), 4.06 (s, 3H), 6.57 (d, J=5.3Hz, 1H), 7.2~8.1 (m, 11H), 8.55 (d, J=5.3Hz, 1H)

Mass spectrometry dada (FD-MS, m/z): 456 (M$^+$)

Example 161 (Reference Example)

2- (6, 7-Dimethoxy-4-quinolyl)-2-(4-bromophenyl)acetonitrile

Commercially available 4-bromophenylacetonitrile (4.3 g) was dissolved in toluene (10 ml) and the temperature was lowered to 0° C., after which sodium hydride (1.0 g) was added, the temperature was raised to 50° C., and the admixture was then stirred for 1 hour. Next, 6,7-dimethoxy-4-chloroquinoline (2.2 g) was added, and the admixture was stirred for 15 hours, after which water was poured and the mixture was extracted with ethyl acetate. After drying with anhydrous sodium sulfate and removing the solvent by distillation, the resulting residue was purified by column chromatography on silica gel eluting with hexane/ethyl acetate (2/1) to obtain 850 mg of the title compound (yield: 22%).

$^1$H-NMR (CDCl$_3$, 90 MHz): δ 3.66 (s, 3H), 3.80 (s, 3H), 5.40 (s, 1H), 6.74 (s, 1H), 6.9~7.4 (m, 6H), 8.54 (d, J=4.6Hz, 1H)

Mass spectrometry data (FD-MS, m/z): 382 (M$^+$), 384 (M$^+$+2)

Example 162 (Reference Example)

6,7-Dimethoxy-4-(4-bromophenylmethyl)quinoline 2-(6,7-Dimethoxy-4-quinolyl)-2-(4-bromophenyl)acetonitrile (850 mg) obtained in Example 161 was dissolved in 60% aqueous sulfuric acid (5 ml), and the solution was refluxed with heat for 1 hour and then poured into a container with ice and aqueous ammonia. The solution was neutralized with hydrochloric acid and extracted with methylene chloride. After drying with anhydrous sodium sulfate and removing the solvent by distillation, the resulting residue was purified by column chromatography on silica gel eluting with chloroform/methanol (100/1) to obtain 260 mg of the title compound (yield: 33%).

$^1$H-NMR (CDCl$_3$, 90 MHz): δ 3.90 (s, 3H), 4.02 (s, 3H), 4.31 (s, 2H), 6.9~7.5 (m, 7H), 8.63 (d, J=4.4Hz, 1H)

Mass spectrometry data (FD-MS, m/z): 357 (M$^+$), 359 (M$^+$+2)

Example 163 (Reference Example)

6,7-Dimethoxy-4-(4-tri-n-butylstanniophenylmethyl) quinoline

Under argon, 6,7-dimethoxy-4-(4-bromophenylmethyl) quinoline (250 mg) obtained in Example 162 was dissolved in tetrahydrofuran (4 ml), and the solution was cooled to −78° C., a solution of 2.5 M n-butyllithium in hexane (0.3 ml) was added dropwise, and the admixture was stirred for 1 hour. An solution of tri-n-butyltin chloride in tetrahydrofuran (1 ml) was then added dropwise, and the admixture was stirred at −78° C. for 2 hours. After adding water, extracting with ethyl acetate and drying with anhydrous sodium sulfate, the solvent was removed by distillation, and the resulting residue was purified by column chromatography on silica gel eluting with hexane/ethyl acetate (3/1) to obtain 85 mg of the title compound (yield: 22%).

$^1$H-NMR (CDCl$_3$, 90 MHz): δ 0.7~1.6 (m, 27H), 3.88 (s, 3H), 4.02 (s, 3H), 4.34 (s, 2H), 7.0~7.5 (m, 7H), 8.63 (d, J=4.6Hz, 1H)

Example 164

(4-[(6,7-Dimethoxy-4-quinolyl)methyl]phenyl](4-t-butylphenyl)methanone [162]

6,7-Dimethoxy-4-tri-n-butylstanniophenylmethyl) quinoline (82 mg) obtained in Example 162, commercially available 4-t-butylbenzoyl chloride (31 mg) and a catalytic amount of commercially available bis(triphenylphosphine)palladium(II) chloride were dissolved in chloroform (3 ml), and the admixture was stirred for 15 hours under reflux with heat. After the addition of water, the admixture was extracted with methylene chloride, and the organic layer was washed with brine and saturated aqueous potassium fluoride and then dried with anhydrous sodium sulfate. After removing the solvent by distillation, the resulting residue was purified by thin layer chromatography on silica gel eluting with hexane/ethyl acetate (2/1) to obtain 6 mg of the title compound (yield: 10%).

$^1$H-NMR (CDCl$_3$, 90 MHz): δ 1.36 (s, 9H), 3.91 (s, 3H), 4.03 (s, 3H), 4.45 (s, 2H), 7.0~7.9 (m, 11H), 8.66 (d, J=4.4Hz, 1H)

Mass spectrometry data (FAB-MS, m/z): 440$^+$+1)

Example 165

N-(4-Fluorophenyl)-N'-(4-[(6,7-dimethoxy-4-quinolyl)oxy]phenyl)thiourea [203]

6,7-Dimethoxy-4-(4-aminophenoxy)quinoline (100 mg) was dissolved in toluene (10 ml) with heat, 4-fluorophenylthio isocyanate (52 mg) was added, and the admixture was refluxed with heat for 24 hours. After removing the solvent by distillation, the resulting residue was purified by column chromatography on silica gel eluting with chloroform/methanol (100/1) to obtain 32 mg of the title compound (yield: 21%).

$^1$H-NMR (DMSO-d$_6$, 500 MHz): δ 3.93 (s, 3H), 3.95 (s, 3H), 6.50 (d, J=4.9Hz, 1H), 7.15~7.25 (m, 4H), 7.40 (S, 1H), 7.47~7.50 (m, 3H), 7.59 (d,. J=8.6Hz, 2H), 8.50 (d, J=5.5Hz, 1H), 9.80 (brs, 1H), 9.84 (brs, 1H)

Mass spectrometry data (FAB-MS, m/z 450 (M$^+$+1)

Example 166

1-(4-Fluorophenyl)-2-cyano-3-{4-[(6,7-dimethoxy-4-quinolyl)oxy]phenyl}guanidine [204]

N-(4-Fluorophenyl)-N'-(4-[(6,7-dimethoxy-4-quinolyl)oxy]phenyl)thiourea (33 mg) obtained in Example 165, dicyclohexylcarbodiimide (31 mg) and a catalytic amount of diisopropylethyl amine were dissolved in methylene chloride (10 ml). To this solution, a solution of cyanamide (16 mg) in THF (1 ml) was added, and the admixture was stirred at room temperature overnight. After removing the solvent by distillation, the resulting residue was purified by column chromatography on silica gel eluting with chloroform/methanol (100/1) to obtain 34 mg of the title compound (yield: 99%).

$^1$H-NMR (CDCl$_3$, 90 MHz): δ 4.03 (s, 3H) 4.05 (s, 3H), 6.50 (d, J=5.1Hz, 1H), 6.8~7.6 (m, 10H), 8.52 (d, J=5.3Hz, 1H)

Mass spectrometry data (FD-MS, m/z): 457 (M$^+$)

Example 167

N-(2-Fluorophenyl)-N'-{4-[(6,7-dimethoxy-4-quinolyl)oxy]phenyl}thiourea [205]

6,7-Dimethoxy-4-(4-aminophenoxy)quinoline (100 mg) was dissolved in toluene (10 ml) with heat, 2-fluorophenylthio isocyanate (0.05 ml) was added, and the admixture was refluxed with heat for 24 hours. After removing the solvent by distillation, the resulting residue was purified by column chromatography on silica gel eluting with chloroform/methanol (100/1) to obtain 66 mg of the title compound (yield: 42%).

$^1$H-NMR (CDCl$_3$, 90 MHz): δ 4.03 (s, 3H) 4.05 (s, 3H), 6.53 (d, J=5.3Hz, 1H), 7.1~8.0 (m, 10H), 8.53 (d, J=5.1Hz, 1H)

Mass spectrometry data (FAB-MS, m/z): 450 (M$^+$+1)

Example 168

1-(2-Fluorophenyl)-2-cyano-3-{4-[(6,7-dimethoxy-4-quinolyl)oxy]phenyl}guanidine [206]

N-(2-Fluorophenyl)-N'-(4-[(6,7-dimethoxy-4-quinolyl)oxy]phenyl}thiourea (42 mg) obtained in Example 167, dicyclohexylcarbodiimide (37 mg) and a catalytic amount of diisopropylethyl amine were dissolved in methylene chloride (10 ml). To this solution, a solution of cyanamide (20 mg) in THF (1 ml) was added, and the admixture was stirred at room temperature overnight. After removing the solvent by distillation, the resulting residue was purified by column chromatography on silica gel eluting with chloroform/methanol (100/1) to obtain 41 mg of the title compound (yield: 99%).

$^1$H-NMR (CDCl$_3$, 90 MHz): δ 4.04 (s, 3H), 4.06 (s, 3H) 6.53 (d, J=5.3Hz, 1H), 7.1~7.6 (m, 10H), 8.47 (d, J 5.3Hz, 1H)

Mass spectrometry data (FD-MS, m/z): 457 (M$^+$+1)

Example 169

N-(2-Methoxyphenyl)-N'-{4-[(6,7-dimethoxy-4-quinolyl)oxy]phenyl}thiourea [207]

6,7-Dimethoxy-4-(4-aminophenoxy)quinoline (100 mg) was dissolved in toluene (10 ml) with heat, 2-methoxyphenylthio isocyanate (0.05 ml) was added, and the admixture was refluxed with heat for 24 hours. After removing the solvent by distillation, the resulting residue was purified by column chromatography on silica gel eluting with chloroform/methanol (100/1) to obtain 78 mg of the title compound (yield: 50%).

$^1$H-NMR (CDCl$_3$, 90 MHz): δ 3.86 (s, 3H), 4.04 (s, 3H), 4.05 (s, 3H), 6.52 (d, J=5.3Hz, 1H), 6.9~8.1 (m, 10H), 8.52 (d, J=5.1Hz, 1H)

Mass spectrometry data (FAB-MS, m/z): 462 (M$^+$+1)

Example 170

N-(2-Methylphenyl)-N'-{4-[(6,7-dimethoxy-4-quinolyl)oxy]phenyl}thiourea [209]

6,7-Dimethoxy-4-(4-aminophenoxy)quinoline (80 mg) was dissolved in toluene (10 ml) with heat, 2-methylphenylthio isocyanate (0.04 ml) was added, and the admixture was refluxed with heat for 24 hours. After removing the solvent by distillation, the resulting residue was purified by column chromatography on silica gel eluting with chloroform/methanol (100/1) to obtain 31 mg of the title compound (yield: 26%).

$^1$H-NMR (CDCl$_3$, 90 MHz): 2.38 (s, 3H), 4.03 (s, 3H), 4.04 (s, 3H), 6.50 (d, J=5.3Hz, 1H), 7.1~7.8 (m, 10H), 8.50 (d, J=5.3Hz, 1H)

Mass spectrometry data (FD-MS, m/z): 445 (M$^+$)

Example 171

N-(3-Methylphenyl)-N'-{4-[(6,7-dimethoxy-4-quinolyl)oxy]phenyl)thiourea [211]

6,7-Dimethoxy-4-(4-aminophenoxy)quinoline (81 mg) was dissolved in toluene (10 ml) with heat, 3-methylphenylthio isocyanate (0.04 ml) was added, and the admixture was refluxed with heat for 15 minutes. After removing the solvent by distillation, the resulting residue was purified by column chromatography on silica gel eluting with chloroform/methanol (100/1) to obtain 66 mg of the title compound (yield: 55%).

$^1$H-NMR (CDCl$_3$, 90 MHz): δ 2.40 (s, 3H), 4.03 (s, 3H), 4.05 (s, 3H), 6.52 (d, J=5.1Hz, 1H), 7.1~7.8 (m, 10H), 8.51 (d, J=5.3Hz, 1H)

Mass spectrometry data (FD-MS m/z): 445 (M$^+$)

Example 172

1-(2-Methylphenyl)-2-cyano-3-{4-[(6,7-dimethoxy-4-quinolyl)oxy]phenyl}guanidine [210]

N-(2-Methylphenyl)-N'-{4-[(6,7-dimethoxy-4-quinolyl)oxy]phenyl}thiourea (24 mg) obtained in Example 170, dicyclohexylcarbodiimide (45 mg) and a catalytic amount of diisopropylethyl amine were dissolved in methylene chloride (7 ml), to which a solution of cyanamide (28 mg) in THF (1 ml) was added, and the admixture was stirred at room temperature overnight. After removing the solvent by distillation, the resulting residue was purified by column chromatography on silica gel eluting with chloroform/methanol (100/1) to obtain 18 mg of the title compound (yield: 76%).

$^1$H-NMR (CDCl$_3$, 500 MHz): δ 2.36 (s, 3H), 4.03 (s, 3H), 4.04 (s, 3H), 6.46 (d, J=5.5Hz, 1H), 7.30~7.45 (m, 9H), 7.50 (s, 1H), 8.49 (d, J=4.9Hz, 1H)

Mass spectrometry data (FD-MS, m/z): 453 (M$^+$)

Example 173

1-(3-Methylphenyl)-2-cyano-3-{4-[(6,7-dimethoxy-4-quinolyl)oxy]phenyl}guanidine [212]

N-(3-Methylphenyl)-N'-{4-[(6,7-dimethoxy-4-quinolyl)oxy]phenyl}thiourea (18 mg) obtained in Example 171, dicyclohexylcarbodiimide (35 mg) and a catalytic amount of diisopropylethyl amine were dissolved in methylene chloride (6 ml), to which a solution of cyanamide (23 mg) in THF (1 ml) was added, and the admixture was stirred at room temperature overnight. After removing the solvent by distillation, the resulting residue was purified by column chromatography on silica gel eluting with chloroform/methanol (100/1) to obtain 19 mg of the title compound (yield: 95%).

$^1$H-NMR (CDCl$_3$, 500 MHz): δ 2.38 (s, 3H), 4.03 (s, 3H), 4.04 (s, 3H), 6.48 (d, J=5.5Hz, 1H), 7.10~7.45 (m, 9H), 7.51 (s, 1H), 8.48 (d, J=5.5Hz, 1H)

Mass spectrometry mass (FD-MS, m/z): 453 (M$^+$)

Example 174

4-Hydroxyphenyl 3-trifluoroxyphenyl ketone (Reference Example)

4-Tri-n-butyltin-1-methoxymethylphenol (1.3 g) obtained in Example 22 and commercially available 4-(trifluoromethoxy)benzoyl chlorobenzoyl chloride (674 mg) were dissolved in chloroform (5 ml), commercially available bis(triphenylphosphine)palladium(II) chloride (8 mg) was added, and the admixture was refluxed overnight. The reaction mixture was partitioned in the same manner as described in Example 23, and the ether layer was dried with anhydrous magnesium sulfate. After removing the solvent by reduced-pressure distillation, the resulting residue (2.0 g) was dissolved in tetrahydrofuran (4 ml), water (5 ml) and 6 N aqueous hydrochloric acid (15 ml) were added, and the admixture was refluxed for 8 hours. The reaction mixture was partitioned between water and chloroform, and the chloroform layer was dried with magnesium sulfate. After removing the solvent by reduced-pressure distillation, the resulting residue was purified by column chromatography on silica gel eluting with hexane/ethyl acetate to obtain 2.1 g of the title compound.

Mass spectrometry data (FD-M S, m/z): 282 (M$^+$)

Example 175

(4-Trifluoromethoxyphenyl){4-[(6,7-dimethoxy-4-quinolyl)oxy]phenyl}methanone [284]

4-Hydroxyphenyl 3-trifluoroxyphenyl ketone (581 mg) obtained in Example 174 and commercially available 4-dimethylaminopyridine (277 mg) were added to xylene (20 ml), and the admixture was stirred at room temperature under argon. After 1 hour, 4-chloro-6,7-dimethoxyquinoline (460 mg) was added, and the admixture was refluxed with heat for 24 hours. The reaction mixture was partitioned between saturated aqueous sodium hydrogen carbonate and chloroform, and the chloroform layer was then dried with anhydrous magnesium sulfate. After removing the solvent by reduced-pressure distillation, the resulting residue was purified by chromatography on silica gel eluting with hexane/ethyl acetate and then with chloroform, followed by thin layer chromatography on silica gel eluting with chloroform/ethyl acetate (5/1), to obtain 470 mg of the title compound (yield: 49%).

$^1$H-NMR (CDCl$_3$, 500 MHz): (4.03 (s, 3H) 4.07 (s, 3H), 6.66 (d, J=4.5Hz, 1H), 7.28 (d, J=8.5Hz, 2H), 7.35 (d, J=8.7Hz, 2H), 7.46 (s, 1H), 7.47 (s, 1H), 7.89 (d, J=8.5Hz, 2H), 7.92 (d, J=9.2Hz, 2H), 8.59 (d, J=4.5Hz, 1H)

Mass spectrometry data (FD-MS, m/z): 469 (M$^+$)

Example 176

4-Methoxyphenyl 4-iodophenyl ketone (Reference Example)

To commercially available nitromethane (10 ml) were added commercially available anisole (1.08 g), commercially available 4-iodobenzoyl chloride (2.67 g) and commercially available ytterbium(III) trifluoromethanesulfonate (620 mg), and the admixture was stirred at 60° C. overnight. The reaction mixture was partitioned between water and chloroform, and the chloroform layer was then dried with anhydrous magnesium sulfate. After removing the solvent by reduced-pressure distillation, the resulting residue was purified by column chromatography on silica gel eluting with hexane/ethyl acetate to obtain 722 mg of the title compound (yield: 21%).

Mass spectrometry data (FD-MS, m/z): 338 (M$^+$)

Example 177

4-Hydroxyphenyl 4-iodophenyl ketone (Reference Example)

4-Methoxyphenyl 4-iodophenyl ketone (722 mg) obtained in Example 176 was dissolved in dichloromethane (20 ml), a solution of 1.0 M boron tribromide in dichloromethane (9 ml) was added while cooled in ice, and the admixture was stirred at room temperature overnight. The reaction mixture was then poured into ice water and partitioned between water and chloroform. The chloroform layer was dried with anhydrous magnesium sulfate and the solvent was removed by reduced-pressure distillation. The resulting residue was purified by column chromatography on silica gel eluting with hexane/ethyl acetate to obtain 380 mg of the title compound (yield: 55%).

$^1$H-NMR (DMSO-d$_6$, 500 MHz): δ 6.89 (d, J=8.6Hz, 2H), 7.44 (d, J=8.5Hz, 2H), 7.65 (d, J=8.6Hz, 2H), 7.92 (d, J=8.5Hz, 2H), 10.47 (s, H)

Mass spectrometry data (FAB-MS, m/z): 325 (M$^+$+1)

Example 178

{4-[(6,7-Dimethoxy-4-quinolyl)oxy]phenyl}(4-iodophenyl)methanone [285]

Under argon, 4-hydroxyphenyl 4-iodophenyl ketone (380 mg) obtained in Example 177 and 4-dimethylaminopyridine (158 mg) were added to xylene (11 ml), and the admixture was stirred at room temperature. After 2 hours, 4-chloro-6,7-dimethoxyquinoline (262 mg) was added, and the admixture was refluxed with heat overnight. The reaction mixture was partitioned between saturated aqueous sodium hydrogen carbonate and chloroform, and the chloroform layer was then dried with anhydrous magnesium sulfate. After removing the solvent by reduced-pressure distillation, the resulting residue was purified by chromatography on silica gel eluting with hexane/ethyl acetate and then with chloroform/ethyl acetate, followed by thin layer chromatography on silica gel eluting with chloroform/ethyl acetate (5/1), to obtain 459 mg of the title compound (yield: 77%).

$^1$H-NMR (CDCl$_3$, 50 MHz): δ 4.03 (s, 3H), 4.07 (s, 3H), 6.66 (d, J=4.9Hz, 1H), 7.27 (d, J=7.6Hz, 2H), 7.46 (s, 1H), 7.4 7 (s, 1H), 7.5 4 (d, J 8.6Hz, 2H), 7.88 (d, J=7.9Hz, 2H), 7.90 (d, J=8.6Hz, 2H), 8.58 (d, J=5.5Hz, 1H)

Mass spectrometry data (FD-MS m/z): 511 (M$^+$)

Example 179

4-Methoxyphenyl 4-bromophenyl ketone (Reference Example)

To commercially available nitromethane (10 ml) were added commercially available anisole (1.08 g), commercially available 4-bromobenzoyl chloride (2.20 g) and commercially available ytterbium(III) trifluoromethanesulfonate (620 mg), and the admixture was stirred at 60° C. overnight. The reaction mixture was partitioned between water and chloroform, and the chloroform layer was then dried with anhydrous magnesium sulfate. After removing the solvent by reduced-pressure distillation, the resulting residue was purified by column chromatography on silica gel eluting with hexane/ethyl acetate to obtain 1.65 g of the title compound (yield: 57%).

$^1$H-NMR (CDCl$_3$, 500 MHz): δ 3.89 (s, 3H), 6.97 (d, J=8.6Hz, 2H), 7.62 (d, J=1.8Hz, 2H), 7.62 (d, J=1.8Hz, 2H), 7.80 (d, J=9.2Hz, 2H)

Mass spectrometry data (FD-MS, m/z: 290 (M$^+$), 292 (M$^+$+2)

Example 180

4-Hydroxyphenyl 4-bromophenyl ketone (Reference Example)

4-Methoxyphenyl 4-bromophenyl ketone (1.65 g) obtained in Example 122 was dissolved in dichloromethane (20 ml), a solution of 1.0 M boron tribromide in dichloromethane (23 ml) was added while cooled in ice, and the admixture was stirred at room temperature overnight. The reaction mixture was then poured into ice water and partitioned between water and chloroform. The chloroform layer was dried with anhydrous magnesium sulfate and the solvent was removed by reduced-pressure distillation. The resulting residue was purified by column chromatography on silica gel eluting with hexane/ethyl acetate to obtain 1.34 g of the title compound (yield: 85%).

$^1$H-NMR (DMSO-d$_6$, 500 MHz): δ 6.90 (d, J=8.5Hz, 2H), 7.61 (d, J=8.5Hz, 2H), 7.66 (d, J=8.6Hz, 2H), 7.74 (d, J=8.5Hz, 2H), 10.46 (brs, 1H)

Mass spectrometry data (FD-MS, m/z): 276 (M$^+$), 278 (M$^+$+2)

Example 181

{4-[(6,7-Dimethoxy-4-quinolyl)oxy]phenyl}(4-bromophenyl)methanone [286]

Under argon, 4-hydroxyphenyl 4-bromophenyl ketone (1.182 g) obtained in Example 123 and 4-dimethylaminopyridine (573 mg) were added to xylene (37 ml), and the admixture was stirred at room temperature. After 30 minutes, 4-chloro-6,7-dimethoxyquinoline (954 mg) was added, and the admixture was refluxed with heat overnight. The reaction mixture was partitioned between saturated aqueous sodium hydrogen carbonate and chloroform, and the chloroform layer was then dried with anhydrous magnesium sulfate. After removing the solvent by reduced-pressure distillation, the resulting residue was purified first by chromatography on silica gel eluting with chloroform/ethyl acetate and then by thin layer chromatography on silica gel eluting with chloroform/ethyl acetate (5/1) to obtain 1.574 g of the title compound (yield: 79%).

$^1$H-NMR (CDCl$_3$, 50 MHz): δ 4.05 (s, 3H), 4.66 (s, 3H), 6.66 (d, J=4.9Hz, 1H), 7.27 (d, J=8.6Hz, 2H), 7.46 (s, 1H), 7.47 (s, 1H), 7.65 (d, J=7.9Hz, 2H), 7.70 (d, J=8.5Hz, 2H), 7.90 (d, J=8.6Hz, 2H), 8.58 (d, J=5.5Hz, 1 H)

Mass spectrometry data FD-MS, m/z): 463 (M$^+$), 465 (M++2)

Example 182

{4-[(6,7-Dimethoxy-4-quinolyl)oxy]phenyl}[4-(N-methylpiperazino)phenyl]methanone [287]

Under argon, 4-hydroxyphenyl 4-bromophenyl ketone (232 mg) obtained in Example 180 was added to toluene (5 ml), and commercially available N-methylpiperazine (61 mg), sodium t-butoxide (67 mg), bis (triphenylphosphine) palladium(II) chloride (7 mg) were further added, and the admixture was stirred at 100° C. for 17 hours. The reaction mixture was partitioned between brine and chloroform, and the chloroform layer was then dried with anhydrous magnesium sulfate. After removing the solvent by reduced-pressure distillation, the resulting residue was purified by thin layer chromatography on silica gel eluting with chloroform/methanol (10/1) to obtain 53 mg of the title compound (yield: 22%).

$^1$H-NMR (CDCl$_3$, 500 MHz): δ 2.37 (s, 3H), 2.58 (t, J=5.5Hz, 4H), 3.41 (t, J=5.5Hz, 4H) 4.04 (s, 3H), 4.06 (s, 3H), 6.63 (d, J=4.9Hz, 1H), 6.9 2 (d, J=9.2Hz, 2H), 7.2 5 (d, J=8.5Hz, 2H), 7.45 (s, 1H), 7.51 (s, 1H), 7.81 (d, J=8.5Hz, 2H), 7.87 (d, J=8.6Hz, 2H), 8.56 (d, J=4.9Hz, 1H)

Mass spectrometry data (FD-MS, m/z): 483 (M$^+$)

Example 183

{4-[(6,7-Dimethoxy-4-quinolyl)oxy]phenyl}[4-morpholinophenyl]methanone [288]

Under argon, 4-hydroxyphenyl 4-bromophenyl ketone (232 mg) obtained in Example 180 was added to toluene (5 ml), and commercially available morpholine (52 mg), sodium t-butoxide (67 mg), bis (triphenylphosphine) palladium(II) chloride (7 mg) were further added, and the admixture was stirred at 100° C. overnight. The reaction mixture was partitioned between brine and chloroform, and the chloroform layer was then dried with anhydrous magnesium sulfate. After removing the solvent by reduced-pressure distillation, the resulting residue was purified by thin layer chromatography on silica gel eluting with chloroform/ethyl acetate (5/1) to obtain 32 mg of the title compound (yield: 14%).

$^1$H-NMR (CDCl$_3$, 500 MHz): δ 3.34 (t, J=4.9Hz, 4H), 3.88 (t, K=4.9Hz, 4H), 4.04 (s, 3H), 4.07 (s, 3H), 6.64 (d, J=5.5Hz, 1H), 6.92 (d, J=9.2Hz, 2H), 7.26 (d, J=7.3Hz, 2H), 7.83 (d, J=9.2Hz, 2H), 7.87 (d, J=8.5Hz, 2H), 8.56 (d, J=5.5Hz, 1H), 7.49 (s, 1H), 7.51 (s, 1H)

Mass spectrometry data (FD-MS, m/z): 470 (M$^+$)

Example 184

(4-[{6,7-Dimethoxy-4-quinolyl)oxy]phenyl)[4-pyrrolidinophenyl]methanone [289]

Under argon, 4-hydroxyphenyl 4-bromophenyl ketone (232 mg) obtained in Example 180 was added to toluene (5 ml), and commercially available pyrrolidine (43 mg), sodium t-butoxide (67 mg), bis (triphenylphosphine) palladium(II) chloride (7 mg) were further added, and the admixture was stirred at 100° C. overnight. The reaction mixture was partitioned between brine and chloroform, and the chloroform layer was then dried with anhydrous magnesium sulfate. After removing the solvent by reduced-pressure distillation, the resulting residue was purified by thin layer chromatography on silica gel eluting with chloroform/ethyl acetate (5/1) to obtain 45 mg of the title compound (yield: 20%).

$^1$H-NMR (CDCl$_3$, 500 MHz): δ 2.05~2.08 (m, 4 H), 3.38~3.41 (m, 4H), 4.04 (s, 3H), 4.06 (s, 3H), 6.57 (d, J=9.2Hz, 2H), 6.62 (d, J=4.9Hz, 1H), 7.24 (d, J=8.6Hz, 2H), 7.45 (s, 1H), 7.52 (s, 1H), 7.82 (d, J=9.2Hz, 2H), 7.84 (d, J=8.5Hz, 2H), 8.55 (d, J=4.9Hz, 1H)

Mass spectrometry data (FD-MS, m/z): 454 (M$^+$)

Example 185

{4-[(6,7-Dimethoxy-4-quinolyl)oxy]phenyl}[4-piperidinophenyl]methanone [290]

Under argon, 4-hydroxyphenyl 4-bromophenyl ketone (232 mg) obtained in Example 180 was added to toluene (5 ml), and commercially available piperidine (51 mg), sodium t-butoxide (67 mg), bis (triphenylphosphine)palladium(II) chloride (7 mg) were further added, and the admixture was stirred at 100° C. overnight. The reaction mixture was partitioned between brine and chloroform, and the chloroform layer was then dried with anhydrous magnesium sulfate. After removing the solvent by reduced-pressure distillation, the resulting residue was purified by thin layer chromatography on silica gel eluting with chloroform/ethyl acetate (5/1) to obtain 75 mg of the title compound (yield: 32%)).

$^1$H-NMR (CDCl$_3$, 500 MHz): δ 1.68 (brs, 6H), 3.38~3.39 (m, 4H), 4.04 (s, 3H), 4.06 (s, 3H), 6.63 (d, J=4.9Hz, 1H), 6.89 (d, J=8.6Hz, 2H), 7.25 (d, J=8.5Hz, 2H), 7.45 (s, 1H), 7.52 (s, 1H), 7.80 (d, J=9.2Hz, 2H), 7.86 (d, J=8.6Hz, 2H), 8.56 (d, J=4.9Hz, 1H)

Mass spectrometry data (FD-MS, m/z): 468 (M$^+$)

Example 186

N-(2-Methoxy-4-biphenyl)-N'-(4-[(6,7-dimethoxy-4-quinolyl)oxy]phenyl urea [222]

6,7-Dimethoxy-4-(4-aminophenoxy)quinoline (52 mg) was suspended in toluene (5 ml), after the addition of triethylamine (1 ml), triphosgene (52 mg) was added, and the admixture was refluxed with heat for 2 minutes 2-Methoxy-4-biphenylamine (103 mg) was added to the reaction mixture, and the admixture was refluxed with heat for 13 minutes. After the addition of aqueous sodium hydrogen carbonate, the reaction mixture was extracted 2 times with ethyl acetate, and the organic layer was then washed with brine and dried with anhydrous sodium sulfate. The solvent was removed by reduced-pressure distillation, and the resulting residue was purified by column chromatography on silica gel eluting with chloroform/acetone (10/1) to obtain 89 mg of the title compound (yield: 98%).

$^1$H-NMR (CDCl$_3$, 500 MHz) δ 3.67 (s, 3H), 4.00 (s, 3H), 4.04 (s, 3H) 6.44 (d, J=5.5Hz, 1H), 6.86 (d, J=8.5Hz, 1H), 7.10 (d, J=8.6Hz, 2H), 7.21~7.37 (m, 4H), 7.43 (s, 1H), 7.53~7.59 (m, 5H), 7.79 (s, H), 8.41 (s, 1H), 8.48 (d, J=4.9Hz, 1H), 8.53 (d, J=2.4Hz, 1H)

Mass spectrometry data (FD-MS, m/z): 521 (M$^+$)

Example 187

N-(2,6-Diisopropylphenyl)-N'-{4-[(6,7-dimethoxy-4-quinolyl)oxy]phenyl}urea [223]

6,7-Dimethoxy-4-(4-aminophenoxy)quinoline (54 mg) was suspended in toluene (5 ml), after the addition of triethylamine (1 ml), triphosgene (53 mg) was added, and the admixture was refluxed with heat for 8 minutes. 2,6-Diisopropylaniline (0.05 ml) was added to the reaction mixture, and the admixture was refluxed with heat for 15 minutes. After the addition of aqueous sodium hydrogen carbonate, the reaction mixture was extracted 2 times with ethyl acetate, and the organic layer was then washed with brine and dried with anhydrous sodium sulfate. The solvent was removed by reduced-pressure distillation, and the resulting residue was purified by column chromatography on silica gel eluting with chloroform/acetone (10/1) to obtain 69 mg of the title compound (yield: 76%).

$^1$H-NMR (CDCl$_3$, 500 MHz): (1.26 (m, 12H), 3.39 (m, 2H), 4.03 (s, 3H), 4.04 (s, 3H), 6.09 (brs, 1H), 6.28 (brs, 1H), 6.42 (d, J=5.5Hz, 1H), 7.08 (d, J=8.5Hz, 2H), 7.2 6 (m, 1H), 7.29~7.40 (m, 5H), 7.53 (s, 1H), 8.46 (d, J=4.9Hz, 1H)

Mass spectrometry data (FD-MS, m/z): 499 (M$^+$)

Example 188

N-(2-Chloro-4-nitrophenyl)-N'-{4-[(6,7-dimethoxy-4-quinolyl)oxy]phenyl}urea [224]

6,7-Dimethoxy-4-(4-aminophenoxy)quinoline (104 mg) was dissolved in toluene (10 ml) with heat, 2-chloro-4-nitrophenyl isocyanate (150 mg) was added, and the admixture was refluxed with heat for 10 minutes. The separated crystals were filtered and then washed with toluene to obtain 172 mg of the title compound (yield: 100%).

$^1$H-NMR (DMSO-d$_6$, 500 MHz): δ 3.94 (s, 3H), 3.95 (s, 3H), 6.46 (d, J=5.5Hz, 1H), 7.24 (d, J=9.2Hz, 2H), 7.38 (s, 1H), 7.51 (s, 1H), 7.62 (d, J=8.6Hz, 2H), 8.23 (, 1H), 8.35 (m, 1H), 8.46 (d, J=5.5Hz, 1H), 8.57 (m, 1H), 8.84 (brs, 1H), 9.85 (brs, 1H)

Mass spectrometry data (FD-MS, m/z): 494 (M$^+$), 496 (M$^+$+2)

Example 189

N-(3-Chloro-2-methoxyphenyl)-N'-{4-[(6,7-dimethoxy-4-quinolyl)oxy]phenyl}urea [225]

6,7-Dimethoxy-4-(4-aminophenoxy)quinoline (58 mg) was dissolved in toluene (5 ml) with heat, 3-chloro-2-methoxyphenyl isocyanate (0.1 ml) was added, and the admixture was refluxed with heat for 22 minutes. The resulting residue was purified by column chromatography on silica gel eluting with chloroform/acetone (10/1) to obtain 75 mg of the title compound (yield: 80%).

$^1$H-NMR (CDCl$_3$, 500 MHz): δ 3.73 (s, 3H), 4.02 (s, 3H), 4.05 (s, 3H), 6.47 (d, J=5.5Hz, 1H), 7.01~7.06 (m, 2H), 7.15 (d, J=8.5Hz, 2H), 7.4 3 (s, 1H), 7.52 (d, J=9.2Hz, 2H), 7.57 (s, 1H), 7.81 (s, 1H), 8.16~8.19 (m, 2H), 8.50 (d, J=5.5Hz, 1H)

Mass spectrometry data (FD-MS, m/z): 479 (M$^+$) 481 (M$^+$+2)

Example 190

N-(2-Chloro-6-methylphenyl)-N'-{4-[(6,7-dimethoxy-4-quinolyl)oxy]phenyl}urea [226]

6,7-Dimethoxy-4-(4-aminophenoxy)quinoline (52 mg) was dissolved in toluene (5 ml) with heat, 2-chloro-6-methylphenyl isocyanate (0.1 ml) was added, and the admixture was refluxed with heat for 17 minutes. The separated crystals were filtered and then washed with toluene to obtain 61 mg of the title compound (yield: 74%).

$^1$H-NMR (DMSO-d$_6$, 500 MHz): δ 2.2 8 (s, 3H), 3.94 (s, 3H), 3.94 (s, 3H), 6.43 (d, J=4.9Hz, 1H), 7.18 (d, J=9.2Hz, 2H), 7.20~7.36 (m, 3 H), 7.38 (s, 1H), 7.52 (s, 1H), 7.59 (d, J=9.2Hz, 2H), 7.98 (s, 1H), 8.45 (d, J=5.5Hz, 1H), 9.03 (s, 1H)

Mass spectrometry data (FD-MS, m/z): 463 (M$^+$) 465 (M$^+$+2)

Example 191

N-(3-Chloro-6-methoxyphenyl)-N'-{4-[(6,7-dimethoxy-4-quinolyl)oxy]phenyl}urea [227]

6,7-Dimethoxy-4-(4-aminophenoxy)quinoline (52 mg) was dissolved in toluene (5 ml) with heat, 3-chloro-6-methoxyphenyl isocyanate (111 mg) was added, and the admixture was refluxed with heat for 29 minutes. The resulting residue was purified by column chromatography on silica gel eluting with chloroform/acetone (10/1) to obtain 84 mg of the title compound (yield: 100%).

$^1$H-NMR (CDCl$_3$, 500 MHz): δ 3.60 (s, 3H), 3.99 (s, 3H), 4.05 (s, 3H), 6.46 (d, J=4.9Hz, 1H), 6.69 (d, J=8.5Hz, 1H), 6.90 (m, 1H), 7.11 (d, J=9.2Hz, 2H), 7.4 2 (s, 1H), 7.5 3 (d, J=8.5Hz, 2H), 7.58 (s, 1H), 7.82 (s, 1H), 8.32 (m, 1H), 8.48 (d, J=5.5Hz, 1H), 8.52 (s, 1H)

Mass spectrometry data (FED-MS, m/z): 479 (M$^+$), 481 (M$^+$+2)

Example 192

N-(4-Chloro-3-nitrophenyl)-N'-{4-[(6,7-dimethoxy-4-quinolyl)oxy]phenyl}urea [228]

6,7-Dimethoxy-4-(4-aminophenoxy)quinoline (52 mg) was dissolved in toluene (5 ml) with heat, 4-chloro-3-nitrophenyl isocyanate (224 mg) was added, and the admixture was refluxed with heat for 8 minutes. The separated crystals were filtered and then washed with toluene to obtain 125 mg of the title compound (yield: 75%).

$^1$H-NMR (DMSO-d$_6$, 500 MHz): δ 3.93 (s, 3H), 3.95 (s, 3H), 6.46 (d, J=4.9Hz, 1H), 7.21 (d, J=8.5Hz, 2H), 7.38 (s, 1H), 7.51 (s, 1H), 7.60 (d, J=8.5Hz, 2H), 7.65 (s, 1H), 7.67 (s, 1H), 8.31 (s, 1H), 8.46 (d, J=4.9Hz, 1H), 9.01 (s, 1H), 9.27 (s, 1H)

Mass spectrometry data (FD-MS m/z): 463 (M$^+$) 465 (M$^+$+2)

Example 193

N-(2,4-Dichlorophenyl)-N'-{4-[(6,7-dimethoxy-4-quinolyl)oxy]phenyl}urea [229]

6,7-Dimethoxy-4-(4-aminophenoxy)quinoline (53 mg) was dissolved in toluene (5 ml) with heat, 2,4-dichlorophenyl isocyanate (115 mg) was added, and the admixture was refluxed with heat for 20 minutes. The separated crystals were filtered and then washed with toluene to obtain 74 mg of the title compound (yield: 85%).

$^1$H-NMR (DMSO-d$_6$, 500 MHz): δ 3.94 (s, 3H), 3.95 (s, 3H), 6.45 (d, J=4.9Hz, 1H), 7.22 (d, J=8.6Hz, 2H), 7.39 (s, 1H), 7.40 (m, 1H), 7.51 (s, 1H), 7.59 (d, J=9.2Hz, 2H), 7.62 (m, 1 H), 8.21 (d, J=9.2Hz, 1H), 8.40 (s, 1H), 8.46 (d, J=5.5Hz, 1H), 9.56 (s, 1H)

Mass spectrometry data (FD-MS, m/z): 483 (M$^+$)

Example 194

N-(2,6-Dichlorophenyl)-N'-{4-[(6,7-dimethoxy-4-quinolyl)oxy]phenyl}urea [230]

6,7-Dimethoxy-4-(4-aminophenoxy)quinoline (52 mg) was dissolved in toluene (5 ml) with heat, 2,6-dichlorophenyl isocyanate (125 mg) was added, and the admixture was refluxed with heat for 12 minutes. The separated crystals were filtered and then washed with toluene to obtain 81 mg of the title compound (yield: 96%).

$^1$H-NMR (DMSO-d$_6$, 500 MHz): δ 3.94 (s, 3H) 3.94 (s, 3H), 6.43 (d, J=5.5Hz, 1H), 7.14~7.20 (m, 2H), 7.32 (dd, J=7.9, 7.9Hz, 1H), 7.38 (s, 1H) 7.51~7.54 (m, 3H), 7.60 (d, J=9.2Hz, 2H), 8.23 (s, 1H), 8.45 (d, J=5.5Hz, 1H), 9.09 (s, 1H)

Mass spectrometry data (FD-MS, m/z): 483 (M$^+$)

Example 195

N-{4-[(6,7-dimethoxy-4-quinolyl)oxy]phenyl)-N'-[1-(1-naphthyl)ethyl]urea [231]

6,7-Dimethoxy-4-(4-aminophenoxy)quinoline (54 mg) was dissolved in toluene (5 ml) with heat, 1-(1-naphthyl)

ethyl isocyanate (0.05 ml) was added, and the admixture was refluxed with heat for 100 minutes. The resulting residue was purified by column chromatography on silica gel eluting with chloroform/acetone (10/1) to obtain 65 mg of the title compound (yield: 72%).

$^1$H-NMR (DMSO-d$_6$, 500 MHz): δ 1.55 (d, J=6.7Hz, 3H), 3.93 (s, 3H), 3.94 (s, 3H), 4.62 (m, 1H), 6.39 (d, J=4.9Hz, 1H), 6.79 (s, 1H), 7.11 (d, J=9.2H z, 2H), 7.36 (s, 1H), 7.49~7.58 (m, 7H), 7.83 (m, 1H), 7.94 (m, 1H), 8.17 (m, 1H), 8.42 (d, J=5.5Hz, 1H), 8.52 (s, 1H)

Mass spectrometry data (FD-MS, m/z): 493 (M$^+$)

Example 196

N-(2-n-Butylphenyl)-N'-(4-[(6,7-dimethoxy-4-quinolyl)oxy]phenyl}urea [232]

6,7-Dimethoxy-4-(4-aminophenoxy)quinoline (119 mg) was suspended in toluene (12 ml), after the addition of triethylamine (2.4 ml), triphosgene (133 mg) was added, and the admixture was refluxed with heat for 2 minutes. 2-n-Butylphenylamine (0.13 ml) was added to the reaction mixture, and the admixture was refluxed with heat for 10 minutes. After the addition of aqueous sodium hydrogen carbonate, the reaction mixture was extracted 2 times with chloroform, and the organic layer was then washed with brine and dried with anhydrous sodium sulfate. The solvent was removed by reduced-pressure distillation, and the resulting residue was purified by column chromatography on silica gel eluting with chloroform/acetone (4/1) to obtain 130 mg of the title compound (yield: 69%).

$^1$H-NMR (DMSO-d$_6$, 500 MHz): δ 0.92 (t, J=7.5Hz, 3H), 1.32~1.40 (m, 2H), 1.50~1.57 (m, 2H), 2.59 (t, J=8.9Hz, 2H), 3.93 (s, 3H), 3.94 (s, 3H), 6.44 (d, J=4.9Hz, 1H), 6.98~7.02 (m, 1H), 7.12∫7.17 (m, 2H), 7.19 (d, J=8.9Hz, 2H), 7.51 (s, 1H), 7.58 (s, 1H), 7.59 (d, J=8.5Hz, 2H), 7.71~7.75 (m, 1H), 7.89 (s, 1H), 8.46 (d, J=4.9Hz, 1H), 9.11 (s, 1H)

Mass spectrometry data (FD-MS, m/z): 471 (M$^+$)

Example 197

N-(3-Ethoxycarbonylphenyl)-N'-{4-[(6,7-dimethoxy-4-quinolyl)oxy]phenyl}urea [233]

6,7-Dimethoxy-4-(4-aminophenoxy)quinoline (131 mg) was dissolved in toluene (10 ml) with heat, after the addition of triethylamine (2 ml), triphosgene (213 mg) was added, and the admixture was refluxed with heat for 2 minutes. Ethyl 3-aminobenzoate (0.1 ml) was added to the reaction mixture, and the admixture was refluxed with heat for 7 minutes. After the addition of aqueous sodium hydrogen carbonate, the reaction mixture was extracted 2 times with ethyl acetate, and the organic layer was then washed with brine and dried with anhydrous sodium sulfate. The solvent was removed by reduced-pressure distillation, and the resulting residue was purified by column chromatography on silica gel eluting with chloroform/acetone (10/1) to obtain 214 mg of the title compound (yield: 100%).

$^1$H-NMR (CDCl$_3$, 500 MHz): δ 1.36 (t, J=7.3Hz, 3H), 4.02 (s, 3H), 4.05 (s, 3H), 4.36 (q, J=7.3Hz, 2H), 6.45 (d, J=5.5Hz, 1H), 7.13 (d, J=9.2Hz, 2H), 7. 8~7.45 (m, 4H), 7.48 (d, J=9.2Hz, 2H), 7.5 6 (s, 1H), 7.75 (d, J=7.3Hz, 1H), 7.80 (d, J=7.9Hz, 1H), 7.90 (s, 1H), 8.48 (d, J=4.9Hz, 1H)

Mass spectrometry data (FD-MS, m/z): 487 (M$^+$)

Example 198

N-(2,3-Dichlorophenyl)-N'-{4-[(6,7-dimethoxy-4-quinolyl)oxy]phenyl}urea [234]

6,7-Dimethoxy-4-(4-aminophenoxy)quinoline (52 mg) was dissolved in toluene (5 ml) with heat, 2,3-dichlorophenyl isocyanate (0.05 ml) was added, and the admixture was refluxed with heat for 20 minutes. The reaction solution was purified by column chromatography on silica gel eluting with chloroform/acetone (10/1) to obtain 84 mg of the title compound (yield: 100%).

$^1$H-NMR (CDCl$_3$, 500 MHz): δ 4.00 (s, 3H), 4.05 (s, 3H), 6.45 (d, J=5.5Hz, 1H), 7.11~7.17 (m, 4H), 7.41 (s, 1H), 7.53 (d, J=9.2Hz, 2H), 7.57 (s, 1H), 7.91 ( s, 1H), 8.22 (d, J=8.5Hz, 1H), 8.48 (d, J=5.5Hz, 1H), 9.12 (s, 1H)

Mass spectrometry data (FD-MS, m/z): 483 (M$^+$)

Example 199

N-(2,4-Dichlorophenyl)-N'-(4-[(6,7-dimethoxy-4-quinolyl)oxy]phenyl}urea [235]

6,7-Dimethoxy-4-(4-aminophenoxy)quinoline (58 mg) was dissolved in toluene (5 ml) with heat, 2,4-dichlorophenyl isocyanate (93 mg) was added, and the admixture was refluxed with heat for 20 minutes. The reaction solution was purified by column chromatography on silica gel eluting with chloroform/acetone (10/1) to obtain 69 mg of the title compound (yield: 73%).

$^1$H-NMR (CDCl$_3$, 500 MHz): (4.04 (s, 3H), 4.06 (s, 3H), 6.47 (d, J=4.9Hz, 1H), 6.98 (d d, J=2.4, 8.5Hz, 1H), 7.19 (d, J=8.5Hz, 2H), 7.25 (s, 1H), 7.29 (s, 1H), 7.39 (s, 1H), 7.43 (s, 1H), 7.52 (d, J=8.5Hz, 2H), 7.56 (s, 1H), 8.40 (d, J=2.4Hz, 1H), 8.50 (d, J=4.9Hz, 1H)

Mass spectrometry data (FD-MS, m/z): 483 (M$^+$)

Example 200

N-(3,4-Dichlorophenyl)-N'-[4-[(6,7-dimethoxy-4-quinolyl)oxy]phenyl}urea [236]

6,7-Dimethoxy-4-(4-aminophenoxy)quinoline (51 mg) was dissolved in toluene (5 ml) with heat, 3,4-dichlorophenyl isocyanate (102 mg) was added, and the admixture was refluxed with heat for 8 minutes. The separated crystals were filtered and then washed with toluene to obtain 71 mg of the title compound (yield: 84%).

$^1$H-NMR (DMSO-d$_6$, 500 MHz): δ 3.94 (s, 3H), 3.95 (s, 3H), 6.44 (d, J=4.9Hz, 1H), 7.14~7.24 (m, 2H), 7.34 (m, 1H), 7.38 (s, 1H), 7.50~7.52 (m, 2H), 7.59 (d, J=9.2Hz, 2H) 7.88 (s, 1H), 8.46 (d, J=4.9Hz, 1H), 8.92 (s, 1H), 9.00 (s, 1H)

Mass spectrometry data (FD-MS, m/z): 483 (M$^+$)

Example 201

N-(3,5-Dichlorophenyl)-N'-{4-[(6,7-dimethoxy-4-quinolyl)oxy]phenyl}urea [237]

6,7-Dimethoxy-4-(4-aminophenoxy)quinoline (53 mg) was dissolved in toluene (5 ml) with heat, 3,5-dichlorophenyl isocyanate (76 mg) was added, and the admixture was refluxed with heat for 8 minutes. The separated crystals were filtered and then washed with toluene to obtain 75 mg of the title compound (yield: 87%).

$^1$H-NMR (DMSO-d$_6$, 500 MHz): δ 3.93 (s, 3H), 3.94 (s, 3H), 6.44 (d, J=4.9Hz, 1H), 7.15 (s, 1H), 7.20 (d, J=9.2Hz, 2H), 7.38 (s, 1H), 7.51 (s, 1H), 7.54 (s, 1H), 7.54 (s, 1H), 7.59 (d, J=9.2Hz, 2H), 8.46 (d, J=4.9Hz, 1H) 9.00 (brs, 1H), 9.07 (brs, 1H)

Mass spectrometry data (FD-MS, m/z): 483 (M$^+$)

Example 202

N-(4-Chloro-2-nitrophenyl)-N'-{4-[(6,7-dimethoxy-4-quinolyl)oxy]phenyl}urea [238]

6,7-Dimethoxy-4-(4-aminophenoxy)quinoline (123 mg) was dissolved in toluene (12 ml) with heat, 4-chloro-2- nitrophenyl isocyanate (172 mg) was added, and the admixture was refluxed with heat for 14 minutes. The separated crystals were filtered and then washed with toluene to obtain 174 mg of the title compound (yield: 85%).

$^1$H-NMR (DMSO-d$_6$, 500 MHz): δ 3.94 (s, 3H), 3.95 (s, 3H), 6.46 (d, J=4.9Hz, 1H), 7.23 (d, J=7.3Hz, 2H), 7.39 (s, 1H), 7.51 (s, 1H), 7.62 (d, J=7.3Hz, 2H), 7.79 (d, J=9.2Hz, 1H), 8.14 (s, 1H), 8.35 (d, J=9.2Hz, 1H), 8.46 (d, J=5.5Hz, 1H), 9.62 (s, 1H), 10.0 (s, 1H)

Mass spectrometry data (FD-MS, m/z): 494 (M$^+$), 496 (M$^+$+2)

Example 203

N-(2-Amino-4-chlorophenyl)-N'-{4-[(6,7-dimethoxy-4-quinolyl)oxy]phenyl}urea [239]

N-(4-Chloro-2-nitrophenyl)-N'-{4-[(6,7-dimethoxy-4-quinolyl)oxy]phenyl}urea (158 mg) was dissolved in chloroform/methanol/water (10 ml/70 ml/5 ml), sodium thiosulfate (1.01 g) was added, and the admixture was stirred at 60° C. for 37 minutes. The reaction mixture was extracted 2 times with chloroform, and the organic layer was then washed with brine and dried with anhydrous sodium sulfate. The solvent was removed by reduced-pressure distillation, and the resulting residue was purified by column chromatography on silica gel eluting with chloroform/acetone (10/1) to obtain 33 mg of the title compound (yield: 22%).

$^1$H-NMR (DMSO-d$_6$, 500 MHz): δ 3.94 (s, 3H), 3.95 (s, 3H), 5.09 (brs, 2H), 6.43 (d, J=4.9 Hz, 1H), 6.57 (m, 1H), 6.78 (d, J=2.4Hz, 1H), 7.17 (d, J=9.2Hz, 2H), 7.34 (d, J=8.6Hz, 1H), 7.38 (s, 1H), 7.51 (s, 1H), 7.57 (d, J=8.5Hz, 2H), 7.77 (s, 1H), 8.45 (d, J=4.9Hz, 1H), 8.89 (s, 1H)

Example 204

N-{4-[(6,7-dimethoxy-4-quinolyl)oxy]phenyl}-N'-(2-pyridinecarbonyl)urea [240]

6,7-Dimethoxy-4-(4-aminophenoxy)quinoline (75 mg) was dissolved in toluene (7 ml) with heat, after the addition of triethylamine (1.4 ml), triphosgene (201 mg) was added, and the admixture was refluxed with heat for 1 minute. 2-Pyridinecarboxamide (102 mg) was added to the reaction mixture, and the admixture was refluxed with heat for 3 hours. After the addition of aqueous sodium hydrogen carbonate, the reaction mixture was extracted 2 times with ethyl acetate, and the organic layer was then washed with brine and dried with anhydrous sodium sulfate. The solvent was removed by reduced-pressure distillation, and the resulting residue was purified by column chromatography on silica gel eluting with chloroform/acetone (10/1) to obtain 86 mg of the title compound (yield: 77%).

$^1$H-NMR (CDCl$_3$, 500 MHz): δ 4.06 (s, 3H), 4.06 (s, 3H), 6.49 (d, J=4.9Hz, 1H), 7.20 (d, J=9.2Hz, 2H), 7.4 3 (m, 1H), 7.57 (s, 1H), 7.59 (m, 1H), 7.71 (d, J=9.2Hz, 2H), 7.97 (m, 1H), 8.28 (d, J=7.9Hz, 1H), 8.50 (brs, 1H), 8.68 (d, J=4.9Hz, 1H), 10.1 (brs, 1H), 10.7 (brs, 1H)

Mass spectrometry data (FD-MS, m/z): 444 (M$^+$)

Example 205

N-(3-Chloro-4,6-dimethoxyphenyl)-N'-{4-[(6,7-dimethoxy-4-quinolyl)oxy]phenyl}urea [241]

6,7-Dimethoxy-4-(4-aminophenoxy)quinoline (54 mg) was dissolved in toluene (5 ml) with heat, 3-chloro-4,6-dimethoxyphenyl isocyanate (76 mg) was added, and the admixture was refluxed with heat for 18 minutes. The reaction solution was purified by column chromatography on silica gel eluting with chloroform/acetone (10/1) to obtain 93 mg of the title compound (yield: 100%)

$^1$H-NMR (CDCl$_3$, 500 MHz): δ 3.76 (s, 3H), 3.87 (s, 3H), 4.02 (s, 3H), 4.05 (s, 3H), 6.46 (d, J=5.5Hz, 1H), 6.49 (s, 1H), 7.13 (d, J=8.5Hz, 2H), 7.20 (s, 1H), 7.42 (s, 1H), 7.50 (d, J=8.5Hz, 2H), 7.57 (s, 1H), 7.59 (s, 1H), 8.12 (s, 1H), 8.48 (d, J=5.5Hz, 1H)

Mass spectrometry data (FD-MS, m/z): 509 (M$^+$), 511 (M$^+$+2)

Example 206

N-(4-Chloro-2-methylphenyl)-N'-{4-[(6,7-dimethoxy-4-quinolyl)oxy]phenyl}urea [242]

6,7-Dimethoxy-4-(4-aminophenoxy)quinoline (55 mg) was dissolved in toluene (5 ml) with heat, 4-chloro-2-methylphenyl isocyanate (90 mg) was added, and the admixture was refluxed with heat for 26 minutes. The separated crystals were filtered and then washed with toluene to obtain 69 mg of the title compound (yield: 80%).

$^1$H-NMR (DMSO-d$_6$, 500 MHz): δ 2.26 (s, 3H), 3.94 (s, 3H), 3.94 (s, 3H), 6.44 (m, 1H), 7.18~7.20 (m, 3H), 7.25 (s, H), 7.38 (s, 1H), 7.51 (s, 1H), 7.59 (d, J=9.2Hz, 2H), 7.87 (m, 1H), 7.99 (s, 1H), 8.45 (m, 1H), 9.15 (s, 1H)

Mass spectrometry data (FD-MS; m/z): 463 (M$^+$), 465 (M$^+$+2)

Example 207

N-(2-Chloro-3-methylphenyl)-N'-{4-[(6,7-dimethoxy-4-quinolyl)oxy]phenyl}urea [243]

6,7-Dimethoxy-4-(4-aminophenoxy)quinoline (52 mg) was dissolved in toluene (5 ml) with heat, 2-chloro-3-methylphenyl isocyanate (0.2 ml) was added, and the admixture was refluxed with heat for 12 minutes. The reaction solution was purified by column chromatography on silica gel eluting with chloroform/acetone (10/1) to obtain 30 mg of the title compound (yield: 37%).

$^1$H-NMR (CDCl$_3$, 500 MHz): 62.28 (s, 3H), 4.00 (s, 3H), 4.03 (s, 3H), 6.41 (d, J=4.9Hz, 1H), 7.09~7.15 (m, 4H), 7.37 (s, 1H), 7.39 (s, 1H), 7.42 (d, J=8.5Hz, 2H), 7.55 (s, 1H), 7.61 (s, 1H), 7.72 (s, 1H), 8.44 (d, J=5.5Hz, 1H)

Mass spectrometry data (FD-MS, m/z) 463 (M$^+$), 465 (M$^+$+2)

Example 208

N-(3-Amino-4-chlorophenyl)-N'-{4-[(6,7-dimethoxy-4-quinolyl)oxy]phenyl}urea [244]

N-(4-Chloro-3-nitrophenyl)-N'-{4-[(6,7-dimethoxy-4-quinolyl)oxy]phenyl}urea (100 mg) was dissolved in chloroform/methanol/water (5ml/15ml/3ml), sodium thiosulfate (358 mg) was added, and the admixture was stirred at 60° C. for 20 minutes. The reaction mixture was extracted 2 times with chloroform, and the organic layer was then washed with brine and dried with anhydrous sodium sulfate. The solvent was removed by reduced-pressure distillation, and the resulting residue was purified by column chromatography on silica gel eluting with chloroform/acetone (10/1) to obtain 39 mg of the title compound (yield: 41%).

$^1$H-NMR (DMSO-d$_6$ 500 MHz): δ 3.94 (s, 3H), 3.95 (s, 3H), 5.30 (brs, 1H), 6.45 (d, J=5.5Hz, 1H), 6.64 (m, 1H), 7.02 (m, 1H), 7.06 (d, J=8.6Hz, 1H), 7.20 (d, J=9.2Hz, 2H), 7.39 (s, 1H), 7.52 (s, 1H), 7.57 (d, J=8.6Hz, 2H), 8.47 (d, J=4.9Hz, 1H), 8.56 (s, 1H), 8.73 (s, 1H)

Mass spectrometry (FD-MS, m/z): 465 (M$^+$+1)

Example 209

N-(3-Methoxypropyl)-N'-{4-[(6,7-dimethoxy-4-quinolyl)oxy]phenyl}urea [245]

6,7-Dimethoxy-4-(4-aminophenoxy)quinoline (51 mg) was dissolved in toluene (5 ml) with heat, after the addition of triethylamine (1 ml), triphosgene (54 mg.) was added, and the admixture was refluxed with heat for 2 minutes. 3-Methoxypropylamine (0.05 ml) was added to the reaction mixture, and the admixture was refluxed with heat for 12 minutes. After the addition of aqueous sodium hydrogen carbonate, the reaction mixture was extracted 2 times with ethyl acetate, and the organic layer was then washed with brine and dried with anhydrous sodium sulfate. The solvent was removed by reduced-pressure distillation, and the resulting residue was purified by column chromatography on silica gel eluting with chloroform/acetone (10/1) to obtain 51 mg of the title compound (yield: 72%).

$^1$H-NMR (CDCl$_3$, 500 MHz): δ 1.82 (m, 2H), 3.31 (s, 3H), 3.39 (m, 2H), 3.50 (t, J=4.5Hz, 2H), 4.03 (s, 3H), 4.04 (s, 3H), 5.65 (brs, 1H), 6.44 (d, J=4.9Hz, 1H), 7.10 (d, J=8.7Hz, 2H), 7.4 1~7.55 (m, 4H), 7.55 (s, 1H), 8.46 (d, J=5.5Hz, 1H)

Mass spectrometry data (FD-MS, m/z) 411 (M$^+$)

Example 210

N-(2-Methoxyethyl)-N'-{4-[(6,7-dimethoxy-4-quinolyl)oxy]phenyl}urea [246]

6,7-Dimethoxy-4-(4-aminophenoxy)quinoline (52 mg) was dissolved in toluene (5 ml) with heat, after the addition of triethylamine (1 ml), triphosgene (54 mg) was added, and the admixture was refluxed with heat for 3 minutes. 3-Methoxyethylamine (0.05 ml) was added to the reaction mixture, and the admixture was refluxed with heat for 8 minutes. After the addition of aqueous sodium hydrogen carbonate, the reaction mixture was extracted 2 times with ethyl acetate, and the organic layer was then washed with brine and dried with anhydrous sodium sulfate. The solvent was removed by reduced-pressure distillation, and the resulting residue was purified by column chromatography on silica gel eluting with chloroform/acetone (10/1) to obtain 63 mg of the title compound (yield: 91%).

$^1$H-NMR (CDCl$_3$, 500 MHz): δ 3.36 (s, 3H), 3.36~3.53 (m, 4H), 4.03 (s, 3H), 4.03 (s, 3H), 5.81 (brs, 1H), 6.43 (d, J=5.5Hz, 1H), 7.87 (d, J=8.5Hz, 2H), 7.40 (s, 1H), 7.45 (d, J=9.2Hz, 2H), 7.55 (s, 1H), 7.92 (s, 1H), 8.45 (d, J=4.9Hz, 1H)

Mass spectrometry data (FAB-MS, m/z): 398 (M$^+$+1)

Example 211

N-(4-[(6,7-Dimethoxy-4-quinolyl)oxy]phenyl)-N'-(2-pyridylmethyl)urea [247]

6,7-Dimethoxy-4-(4-aminophenoxy)quinoline (52 mg) was dissolved in toluene (5 ml) with heat, after the addition of triethylamine (1 ml), triphosgene (54 mg) was added, and the admixture was refluxed with heat for 2 minutes. 2-Pyridylmethylamine (0.05 ml) was added to the reaction mixture, and the admixture was refluxed with heat for 12 minutes. After the addition of aqueous sodium hydrogen carbonate, the reaction mixture was extracted 2 times with ethyl acetate, and the organic layer was then washed with brine and dried with anhydrous sodium sulfate. The solvent was removed by reduced-pressure distillation, and the resulting residue was purified by column chromatography on silica gel eluting with chloroform/acetone (10/1) to obtain 76 mg of the title compound (yield: 100%).

$^1$H-NMR (CDCl$_3$, 500 MHz): δ 4.00 (s, 3H), 4.01 (s, 3H), 4.58 (d, J=5.5Hz, 2H), 6.39 (d, J=5.5Hz, 1H), 6.66 (m, 1H), 7.05 (d, J=9.2Hz, 2H), 7.18 (m, 1H), 7.34 (d, J=7.9Hz, 1H), 7.39 (s, 1H), 7.45 (d, J=9.2Hz, 2H), 7.54 (s, 1H), 7.66 (m, 1H), 8.40 (brs, 1H), 8.43 (d, J=5.5Hz, 1H), 8.47 (d, J=4.9Hz, 1H)

Mass spectrometry data (FD-MS, m/z) 430 (M$^+$)

Example 212

N-[(4-tert-Butylphenyl)methyl]-N'-{4-[(6,7-dimethoxy-4-quinolyl)oxy]phenyl}urea [248]

6,7-Dimethoxy-4-(4-aminophenoxy)quinoline (50 mg) was dissolved in toluene (5 ml) with heat, after the addition of triethylamine (1 ml), triphosgene (55 mg) was added, and the admixture was refluxed with heat for 2 minutes. (4-tert-Butylphenyl)methylamine (0.05 ml) was added to the reaction mixture, and the admixture was refluxed with heat for 12 minutes. After the addition of aqueous sodium hydrogen carbonate, the reaction mixture was extracted 2 times with ethyl acetate, and the organic layer was then washed with brine and dried with anhydrous sodium sulfate. The solvent was removed by reduced-pressure distillation, and the resulting residue was purified by column chromatography on silica gel eluting with chloroform/acetone (10/1) to obtain 23 mg of the title compound (yield: 28%).

$^1$H-NMR (CDCl$_3$, 500 MHz): δ 3.99 (s, 3H), 4.01 (s, 3H), 4.38 (d, J=5.5Hz, 1H), 5.81 (brs, 1H), 6.38 (d, J=4.9Hz, 1H), 7.02 (d, J=9.2Hz, 2H), 7.20~7.40 (m, 7H), 7.52 (s, 1H), 7.64 (s, 1H), 8.40 (d, J=5.5Hz, 1H)

Mass spectrometry data (FD-MS, m/z): 485 (M$^+$)

Example 213

N-(4-[(6,7-Dimethoxy-4-quinolyl)oxy]phenyl)-N'-(3-pyridylmethyl) urea [249]

6,7-Dimethoxy-4-(4-aminophenoxy)quinoline (52 mg) was dissolved in toluene (5 ml) with heat, after the addition of triethylamine (1 ml), triphosgene (56 mg) was added, and the admixture was refluxed with heat for 2 minutes. 3-Pyridylmethylamine (0.05 ml) was added to the reaction mixture, and the admixture was refluxed with heat for 12 minutes After the addition of aqueous sodium hydrogen carbonate, the reaction mixture was extracted 2 times with ethyl acetate, and the organic layer was then washed with brine and dried with anhydrous sodium sulfate. The solvent was removed by reduced-pressure distillation, and the resulting residue was purified by column chromatography on silica gel eluting with chloroform/acetone (10/1) to obtain 71 mg of the title compound (yield: 93%).

$^1$H-NMR (DMSO-d$_6$, 500 MHz): δ 3.93 (s, 3H) 3.94 (s, 3H), 4.34 (d, J=5.5Hz, 2H), 6.40 (d, J=4.9Hz, 1H), 6.72 (t, J=6.1Hz, 1H), 7.12 (d, J=9.2Hz, 2H), 7.3 5 (m, 1H), 7.37 (s, 1H), 7.50 (s, 1H), 7.53 (d, J=9.2Hz, 2H), 7.72 (d, J=7.9Hz, 1H), 8.43~8.46 (m, 2H), 8.53 (s, 1 H), 8.7 3 (s, 1H)

Mass spectrometry data (FD-MS, m/z) 430 (M$^+$)

Example 214

N-{4-[(6,7-Dimethoxy-4-quinolyl)oxy]phenyl}-N'-4-pyridylmethyl) urea [250]

6,7-Dimethoxy-4-(4-aminophenoxy)quinoline (52 mg) was dissolved in toluene (5 ml) with heat, after the addition of triethylamine (1 ml), triphosgene (53 mg) was added, and the admixture was refluxed with heat for 2 minutes. 4-Pyridylmethylamine (0.05 ml) was added to the reaction mixture, and the admixture was refluxed with heat for 12 minutes. After the addition of aqueous sodium hydrogen carbonate, the reaction mixture was extracted 2 times with ethyl acetate, and the organic layer was then washed with brine and dried with anhydrous sodium sulfate. The solvent was removed by reduced-pressure distillation, and the resulting residue was purified by column chromatography on silica gel eluting with chloroform/acetone (10/1) to obtain 40 mg of the title compound (yield: 54%).

$^1$H-NMR (CDCl$_3$, 500 MHz): 4.01 (s, 3H), 4.03 (s, 3H), 4.43 (d, J=5.5Hz, 2H), 5.97 (m, 1H), 6.40 (d, J=5.5Hz, 1H), 7.08 (d, J=9.2Hz, 2H), 7.20 (d, J=5.5Hz, 2H), 7.38 (s, 1H), 7.42 (d, J38.6Hz, 2H), 7.54 (s, H), 7.81 (s, 1H), 8.42 (d, J=5.5Hz, 1H), 8.49 (d, J=6.1Hz, 2H)

Mass spectrometry data (FD-MS, m/z): 430 (M$^+$)

Example 215

N-{4-[(6,7-Dimethoxy-4-quinolyl)oxy]phenyl}-N'-[(4-dimethylaminophenyl)methyl]urea [251]

6,7-Dimethoxy-4-(4-aminophenoxy)quinoline (51 mg) was dissolved in toluene (5 ml) with heat, after the addition of triethylamine (1 ml), triphosgene (55 mg) was added, and the admixture was refluxed with heat for 2 minutes. (4-Dimethylaminophenyl)methylamine (104 mg) was added to the reaction mixture, and the admixture was refluxed with heat for 12 minutes. After the addition of aqueous sodium hydrogen carbonate, the reaction mixture was extracted 2 times with ethyl acetate, and the organic layer was then washed with brine and dried with anhydrous sodium sulfate. The solvent was removed by reduced-pressure distillation, and the resulting residue was purified by column chromatography on silica gel eluting with chloroform/acetone (10/1) to obtain 12 mg of the title compound (yield: 15%).

$^1$H-NMR (DMSO-d$_6$, 500 MHz): (2.87 (s, 6H), 3.93 (s, 3H), 3.94 (s, 3H), 4.18 (d, J=5.5Hz, 2H), 6.40~6.43 (m, 2H), 6.70 (d, J=9.2Hz, 2 H), 7.1 3 (d, J=8.6Hz, 2H), 7.14 (d, J=8.6Hz, 2H), 7.37 (s, H), 7.51 (s, 1H), 7.52 (d, J=9.2Hz, 2H), 8.44 (d, J=4.9Hz, 1H), 8.57 (s, 1H)

Mass spectrometry data (FD-MS, m/z): 472 (M$^+$)

Example 216

N-{4-[(6,7-Dimethoxy-4-quinolyl)oxy]phenyl}-N'-(3,5-dinitrophenyl) urea [252]

6,7-Dimethoxy-4-(4-aminophenoxy)quinoline (54 mg) was dissolved in toluene (5 ml) with heat, 3,5-dinitrophenyl isocyanate (81 mg) was added, and the admixture was refluxed with heat for 20 minutes. The reaction solution was purified by column chromatography on silica gel eluting with chloroform/acetone (10/1) to obtain 53 mg of the title compound (yield: 57%).

$^1$H-NMR (DMSO-d$_6$, 500 MHz): 3.94 (s, 3H), 3.95 (s, 3H), 6.46 (d, J=4.9Hz, 1H), 7.24 (d, J=9.2Hz, 2H), 7.39 (s, 1H), 7.51 (s, 1H), 7.64 (d, J=8.5Hz, 2H), 8.42 (s, 1H) 8.47 (d, J=4.9Hz, 1H), 8.77 (s, 1H), 8.77 (s, 1H), 9.21 (s, 1H), 9.73 (s, 1H)

Mass spectrometry data (FD-MS, m/z): 506 (M$^+$+1)

Example 217

N-(Cyclohexyl)-N'-{4-[(6,7-dimethoxy-4-quinolyl)oxy]phenyl}urea [253]

6,7-Dimethoxy-4-(4-aminophenoxy)quinoline (200 mg) was dissolved in toluene (5 ml) with heat, cyclohexyl isocyanate (340 mg) was added, and the admixture was stirred with heat at 80–90° C. for 30 minutes. After the addition of water, the reaction mixture was extracted 2 times with ethyl acetate, and the organic layer was then washed with brine and dried with anhydrous sodium sulfate. The solvent was removed by reduced-pressure distillation, and the resulting residue was purified by column chromatography on silica gel eluting with chloroform/acetone (10/1) to obtain 210 mg of the title compound (yield: 74%).

$^1$H-NMR (CDCl$_3$, 500 MHz): δ 1.11~1.22 (m, 2 H), 1.34~1.46 (m, 2H), 1.56~1.66 (m, 2H), 1.68~1.78 (m, 2H), 1.96~2.05 (m, 2H), 3.64~3.73 (m, 1H), 4.05 (s, 6H), 4.58 (d, J=7.9Hz, 1H), 6.36 (s, 1H), 6.46 (d, J=4.9Hz, 1H), 7.13 (d, J=8.6Hz, 2H), 7.42 (d, J=8.6Hz, 2H), 7.42 (s, 1H), 7.56 (s, 1H), 8.48 (d, J=4.9Hz, 1H)

Mass spectrometry data (FD-MS, m/z): 421 (M$^+$)

Example 218

N-(3, 4-Difluorophenyl)-N'-(4-[(6,7-dimethoxy-4-quinolyl)oxy]phenyl)urea [254]

6,7-Dimethoxy-4-(4-aminophenoxy)quinoline (50 mg) was dissolved in toluene (5 ml) with heat, after the addition of triethylamine (1 ml), triphosgene (55 mg) was added, and the admixture was refluxed with heat for 3 minutes. 3,4-Difluoroaniline (66 mg) was added to the reaction mixture, and the admixture was refluxed with heat for 20 minutes. After the addition of aqueous sodium hydrogen carbonate, the reaction mixture was extracted 2 times with ethyl acetate, and the organic layer was then washed with brine and dried with anhydrous sodium sulfate. The solvent was removed by reduced-pressure distillation, and the resulting residue was purified by column chromatography on silica gel eluting with chloroform/acetone (10/1) to obtain 63 mg of the title compound (yield: 83%).

$^1$H-NMR (CDCl$_3$, 500 MHz): 64.03 (s, 3H), 4.06 (s, 3H), 6.45 (d, J=5.5Hz, 1H), 6.96~7.02 (m, 1H), 7.02~7.10 (m, 1H), 7.11 (d, J=8.5Hz, 2H), 7.41~7.45 (m, 2H), 7.48 (d, J=8.6Hz, 2H), 7.5 8 (s, 1H), 7.72 (s, 1H), 7.74 (s, 1H), 8.44 (d, J=5.5H z, 1H)

Mass spectrometry data (FD-MS, m/z) 451 (M$^+$)

Example 219

N-(2,4,5-Trifluorophenyl)-N'-{4-[(6,7-dimethoxy-4-quinolyl)oxy]phenyl}urea [255]

6,7-Dimethoxy-4-(4-aminophenoxy)quinoline (50 mg) was dissolved in toluene (5 ml) with heat, after the addition of triethylamine (1 ml), triphosgene (55 mg) was added, and the admixture was refluxed with heat for 3 minutes. 2,4,5-Trifluoroaniline (75 mg) was added to the reaction mixture, and the admixture was refluxed with heat for 20 minutes. After the addition of aqueous sodium hydrogen carbonate, the reaction mixture was extracted 2 times with ethyl acetate, and the organic layer was then washed with brine and dried with anhydrous sodium sulfate. The solvent was removed by reduced-pressure distillation, and the resulting residue was purified by column chromatography on silica gel eluting with chloroform/acetone (10/1) to obtain 58 mg of the title compound (yield: 73%).

$^1$H-NMR (DMSO-d$_6$, 500 MHz): δ 3.94 (s, 3H), 3.95 (s, 3H), 6.45 (d, J=5.5Hz, 1H), 7.24 (d, J=8.6Hz, 2H), 7.40 (s, 1H), 7.52 (s, 1H), 7.59 (d, J=8.6Hz, 2H), 7.62~7.70 (m, 1H), 8.17~8.25 (m, 1H), 8.48 (d, J=4.9Hz, 1H), 8.76 (s, 1H), 9.23 (s, 1H)

Example 220

N-(2,4,6-Trifluorophenyl)-N'-{4-[(6,7-dimethoxy-4-quinolyl)oxy]phenyl}urea [256]

6,7-Dimethoxy-4-(4-aminophenoxy)quinoline (50 mg) was dissolved in toluene (5 ml) with heat, after the addition of triethylamine (1 ml), triphosgene (55 mg) was added, and the admixture was refluxed with heat for 3 minutes. 2,4,6-Trifluoroaniline. (75 mg) was added to the reaction mixture, and the admixture was refluxed with heat for 20 minutes. After the addition of aqueous sodium hydrogen carbonate, the reaction mixture was extracted 2 times with ethyl acetate, and the organic layer was then washed with brine and dried with anhydrous sodium sulfate. The solvent was removed by reduced-pressure distillation, and the resulting residue was purified by column chromatography on silica gel eluting with chloroform/acetone (10/1) to obtain 37 mg of the title compound (yield: 47%).

$^1$H-NMR (DMSO-$d_6$, 500 MHz): δ 3.94 (s, 3H), 3.95 (s, 3H), 6.4 3 (d, J=5.5Hz, 1H), 7.2 0 (d, J=8.6Hz, 2H), 7.29 (t, J=8.6Hz, 2H), 7.39 (s, 1H), 7.52 (s, 1H), 7.58 (d, J=8.6Hz, 2H), 8.07 (s, 1H), 8.46 (d, J=5.5Hz, 1H), 9.14 (s, 1H)

Mass spectrometry data (FD-MS, m/z): 469 (M$^+$)

Example 221

N-(2,3,4-Trifluorophenyl)-N'-{4-[(6,7-dimethoxy-4-quinolyl)oxy]phenyl}urea [257]

6,7-Dimethoxy-4-(4-aminophenoxy)quinoline (50 mg) was dissolved in toluene (5 ml) with heat, after the addition of triethylamine (1 ml), triphosgene (55 mg) was added, and the admixture was refluxed with heat for 3 minutes. 2,3,4-Trifluoroaniline (75 mg) was added to the reaction mixture, and the admixture was refluxed with heat for 20 minutes. After the addition of aqueous sodium hydrogen carbonate, the reaction mixture was extracted 2 times with ethyl acetate, and the organic layer was then washed with brine and dried with anhydrous sodium sulfate. The solvent was removed by reduced-pressure distillation, and the resulting residue was purified by column chromatography on silica gel eluting with chloroform/acetone (10/1) to obtain 18 mg of the title compound (yield: 23%).

$^1$H-NMR (DMSO-$d_6$, 500 MHz) δ 3.94 (s, 3H), 3.95 (s, 3H), 6.44 (d, J=4.9Hz, 1H), 7.23 (d, J=8.6Hz, 2H), 7.25~7.33 (m, 1H), 7.39 (s, 1 H), 7.52 (s, 1H), 7.59 (d, J=8.6Hz, 2H), 7.85~7.92 (m, 1H), 8.47 (d, J=5.5Hz, 1H), 8.73 (s, 1H), 9.21 (s, 1H)

Mass spectrometry data (FD-MS, m/z) 469 (M$^+$)

Example 222

N-(2,5-Dimethoxyphenyl)-N'-{4-[(6,7-dimethoxy-4-quinolyl)oxy]phenyl}urea [258]

6,7-Dimethoxy-4-(4-aminophenoxy)quinoline (56 mg) was dissolved in toluene (5 ml) with heat, after the addition of triethylamine (1 ml), triphosgene (66 mg) was added, and the admixture was refluxed with heat for 3 minutes. 2,5-Dimethoxyaniline (102 mg) was added to the reaction mixture, and the admixture was refluxed with heat for 10 minutes. After the addition of aqueous sodium hydrogen carbonate, the reaction mixture was extracted 2 times with ethyl acetate, and the organic layer was then washed with brine and dried with anhydrous sodium sulfate. The solvent was removed by reduced-pressure distillation, and the resulting residue was purified by column chromatography on silica gel eluting with chloroform/acetone (10/1) to obtain 81 mg of the title compound (yield: 90%).

$^1$H-NMR (CDCl$_3$, 500 MHz): δ 3.68 (s, 3H), 3.78 (s, 3H), 4.02 (s, 3H), 4.05 (s, 3H), 6.46 (d, J=5.5Hz, 1H), 6.53 (dd, J=3.1, 8.5 Hz, 1H), 6.76 (d, J=9.2Hz, 1H), 7.13 (d, J=9.2Hz, 2H), 7.4 3 (s, 1H) 7.52 (d, J=9.2Hz, 2H), 7.55 (s, 1H), 7.5 7 (s, 1H) 7.78 (s, 1H), 7.91 (d, J=3.1Hz, 1H), 8.49 (d, J=4.9Hz, 1H)

Mass spectrometry data (FD-MS, m/z): 475 (M$^+$)

Example 223

N-(3,5-Dimethoxyphenyl)-N'-{4-[(6,7-dimethoxy-4-quinolyl)oxy]phenyl}urea [259]

6,7-Dimethoxy-4-(4-aminophenoxy)quinoline (53 mg) was dissolved in toluene (5 ml) with heat, after the addition of triethylamine (1 ml), triphosgene (101 mg) was added, and the admixture was ref luxed with heat for 4 minutes. 3,5-Dimethoxyaniline (62 mg) was added to the reaction mixture, and the admixture was refluxed with heat for 13 minutes. After the addition of aqueous sodium hydrogen carbonate, the reaction mixture was extracted 2 times with ethyl acetate, and the organic layer was then washed with brine and dried with anhydrous sodium sulfate. The solvent was removed by reduced-pressure distillation, and the resulting residue was purified by column chromatography on silica gel eluting with chloroform/acetone (10/1) to obtain 85 mg of the title compound (yield: 100%)).

$^1$H-NMR (CDCl$_3$ 500 MHz): δ 3.73 (s, 6H), 4.00 (s, 3H), 4.03 (s, 3H), 6.18 (s, 1H), 6.42 (d, J=5.5Hz, 1H), 6.60 (s, 1H), 6.60 (s, 1H), 7.09 (d, J=8.6Hz, 2H), 7.40 (s, 1H), 7.45 (d, J=8.6Hz, 2H), 7.56 (s, 1H), 7.68 (s, 1H), 7.85 (s, 1H), 8.45 (d, J=5.5Hz, 1H)

Mass spectrometry data (FD-MS, m/z): 47 5 (M$^+$)

Example 224

N-(2,3-Difluorophenyl)-N'-{4-[(6,7-dimethoxy-4-quinolyl)oxy]phenyl}urea [260]

6,7-Dimethoxy-4-(4-aminophenoxy)quinoline (50 mg) was dissolved in toluene (5 ml) with heat, after the addition of triethylamine (1 ml), triphosgene (55 mg) was added, and the admixture was refluxed with heat for 3 minutes. 2,3-Difluoroaniline (51 mg) was added to the reaction mixture, and the admixture was refluxed with heat for 20 minutes. After the addition of aqueous sodium hydrogen carbonate, the reaction mixture was extracted 2 times with ethyl acetate, and the organic layer was then washed with brine and dried with anhydrous sodium sulfate. The solvent was removed by reduced-pressure distillation, and the resulting residue was purified by column chromatography on silica gel eluting with chloroform/acetone (10/1) to obtain 60 mg of the title compound (yield: 79%).

$^1$H-NMR (DMSO-$d_6$, 500 MHz): δ 3.94 (s, 3H), 3.95 (s, 3H), 6.45 (d, J=4.9Hz, 1H), 7.02~7.08 (m, 1H), 7.11~7.19 (m, 1H), 7.23 (d, J=9.2Hz, 2H), 7.39 (s, 1H), 7.52 (s, 1H), 7.59 (d, J=9.2Hz, 2H), 7.94~7.99 (m, 1H), 8.47 (d, J=4.9Hz, 1H), 8.78 (s, 1H), 9.25 (s, 1H)

Mass spectrometry data (FD-M S, m/z): 451 (M$^+$)

Example 225

N-(3,5-Difluorophenyl)-N'-{4-[(6,7-dimethoxy-4-quinolyl)oxy]phenyl}urea [261]

6,7-Dimethoxy-4-(4-aminophenoxy)quinoline (50 mg) was dissolved in toluene (5 ml) with heat, after the addition of triethylamine (1 ml), triphosgene (55 mg) was added, and the admixture was refluxed with heat for 3 minutes. 3,5-Difluoroaniline (66 mg) was added to the reaction mixture, and the admixture was refluxed with heat for 20 minutes. After the addition of aqueous sodium hydrogen carbonate, the reaction mixture was extracted 2 times with ethyl acetate, and the organic layer was then washed with brine and dried with anhydrous sodium sulfate. The solvent was removed by reduced-pressure distillation, and the resulting residue was purified by column chromatography on silica gel eluting with chloroform/acetone (10/1) to obtain 49 mg of the title compound (yield: 64%).

$^1$H-NMR (DMSO-d$_6$, 500 MHz): δ 3.94 (s, 3H), 3.95 (s, 3H), 6.45 (d, J=4.9Hz, 1H), 6.75~6.83 (m, 1H), 7.16~7.26 (m, 4H), 7.39 (s, 1H), 7.52 (s, 1H), 7.59 (d, J=8.6Hz, 2H), 8.47 (d, J=4.9Hz, 1H), 8.99 (s, 1H), 9.12 (s, 1H)

Mass spectrometry data (FD-MS, m/z): 451 (M$^+$)

Example 226

N-(2,3,6-Trifluorophenyl)-N'-{4-[(6,7-dimethoxy-4-quinolyl)oxy]phenyl}urea [262]

6,7-Dimethoxy-4-(4-aminophenoxy)quinoline (50 mg) was dissolved in toluene (5 ml) with heat, after the addition of triethylamine (1 ml), triphosgene (55 mg) was added, and the admixture was refluxed with heat for 3 minutes. 2,3,6-trifluoroaniline (53 mg) was added to the reaction mixture, and the admixture was refluxed with heat for 20 minutes. After the addition of aqueous sodium hydrogen carbonate, the reaction mixture was extracted 2 times with ethyl acetate, and the organic layer was then washed with brine and dried with anhydrous sodium sulfate. The solvent was removed by reduced-pressure distillation, and the resulting residue was purified by column chromatography on silica gel eluting with chloroform/acetone (10/1) to obtain 30 mg of the title compound (yield: 38%).

$^1$H-NMR (DMSO-d$_6$, 500 MHz): δ 3.93 (s, 3H), 3.94 (s, 3H), 6.44 (d, J=5.5Hz, 1H), 7.15~7.25 (m, 3H), 7.33~7.44 (m, 2H), 7.52 (s, 1H), 7.59 (d, J=8.6Hz, 2H), 8.41 (s, 1H), 8.46 (d, J=4.9Hz, 1H), 9.18 (s, 1H)

Mass spectrometry data (FD-MS, m/z): 469 (M$^+$)

Example 227

N-(2,6-Difluorophenyl)-N'-{4-[(6,7-dimethoxy-4-quinolyl)oxy]phenyl}urea [263]

6,7-Dimethoxy-4-(4-aminophenoxy)quinoline (50 mg) was dissolved in toluene (5 ml) with heat, 2,6-difluorophenyl isocyanate (104 mg) was added, and the admixture was refluxed with heat for 30 minutes. The separated crystals were filtered and then washed with toluene to obtain 57 mg of the title compound (yield: 74%).

$^1$H-NMR (DMSO-d$_6$, 500 MHz): δ 3.94 (s, 3H), 3.95 (s, 3H), 6.44 (d, J=4.9Hz, 1H), 7.13~7.25 (m, 4H), 7.28~7.38 (m, 1H), 7.39 (s, 1H), 7.52 (s, 1H), 7.59 (d, J=9.2Hz, 2H), 8.15 (s, 1H), 8.46 (d, J=5.5Hz, 1H), 9.09 (s, 1H)

Mass spectrometry data (FD-MS, m/z): 451 (M$^+$)

Example 228

N-(2,5-Bis(trifluoromethyl)phenyl]-N'-{4-[(6,7-dimethoxy-4-quinolyl)oxy]phenyl}urea [264]

6,7-Dimethoxy-4-(4-aminophenoxy)quinoline (50 mg) was dissolved in toluene (5 ml) with heat, after the addition of triethylamine (1 ml), triphosgene (55 mg) was added, and the admixture was refluxed with heat for 3 minutes. 2,5-Bis(trifluoromethyl)aniline (79 mg) was added to the reaction mixture, and the admixture was refluxed with heat for 20 minutes. After the addition of aqueous sodium hydrogen carbonate, the reaction mixture was extracted 2 times with ethyl acetate, and the organic layer was then washed with brine and dried with anhydrous sodium sulfate. The solvent was removed by reduced-pressure distillation, and the resulting residue was purified by column chromatography on silica gel eluting with chloroform/acetone (10/1) to obtain 30 mg of the title compound (yield: 32%).

$^1$H-NMR (DMSO-d$_6$, 500 MHz): δ 3.94 (s, 3H), 3.95 (s, 3H), 6.45 (d, J=4.9Hz, 1H), 7.24 (d, J=9.2Hz, 2H), 7.40 (s, 1H), 7.52 (s, 1H), 7.60~7.66 (m, 3H), 7.95 (d, J=7.9Hz, 1H), 8.38 (s, 1H), 8.46~8.52 (m, 2H), 9.70 (s, 1H)

Mass spectrometry data (FD-MS, m/z): 551 (M$^+$)

Example 229

N-(2,4-Dimethoxyphenyl)-N'-{4-[(6,7-dimethoxy-4-quinolyl)oxy]phenyl}urea [265]

6,7-Dimethoxy-4-(4-aminophenoxy)quinoline (51 mg) was dissolved in toluene (5 ml) with heat, after the addition of triethylamine (1 ml), triphosgene (72 mg) was added, and the admixture was refluxed with heat for 3 minutes. 2,4-Dimethoxyaniline (60 mg) was added to the reaction mixture, and the admixture was refluxed with heat for 11 minutes. After the addition of aqueous sodium hydrogen carbonate, the reaction mixture was extracted 2 times with ethyl acetate, and the organic layer was then washed with brine and dried with anhydrous sodium sulfate. The solvent was removed by reduced-pressure distillation, and the resulting residue was purified by column chromatography on silica gel eluting with chloroform/acetone (10/1) to obtain 44 mg of the title compound (yield: 53%).

$^1$H-NMR (CDCl$_3$, 500 MHz): δ 3.74 (s, 3H), 3.80 (s, 3H), 4.03 (s, 3H), 4.05 (s, 3H), 6.44~6.51 (m, 3H), 7.06 (s, 1H), 7.12 (d, J=9.2Hz, 2H), 7.43 (s, 1H), 7.49~7.51 (m, 3H), 7.57 (s, 1H), 7.86 (d, J=8.6Hz, 1H), 8.48 (d, J=5.5Hz, 1H)

Mass spectrometry data (FD-MS, m/z): 475 (M$^+$)

Example 230

N-(2-Chlorophenyl)-N'-{4-[(6,7-dimethoxy-4-quinolyl)oxy]phenyl}urea [266]

6,7-Dimethoxy-4-(4-aminophenoxy)quinoline (52 mg) was dissolved in toluene (5 ml) with heat, 2-chlorophenyl isocyanate (0.05 ml) was added, and the admixture was refluxed with heat for 30 minutes. The reaction solution was purified by column chromatography on silica gel eluting with chloroform/acetone (10/1) to obtain 64 mg of the title compound (yield: 81%).

$^1$H-NMR (CDCl$_3$, 500 MHz) δ 4.01 (s, 3H), 4.05 (s, 3H), 6.46 (d, J=4.9Hz, 1H), 6.98 (d d, J=7.3, 7.9Hz, 1H), 7.14 (d, J=8.6Hz, 2H), 7.26 (dd, J=7.3, 7.9Hz, 1H), 7.31 (d, J=7.9 Hz, 1H), 7.43 (s, 1H), 7.52 (d, J=9.2Hz, 2H), 7.57 (s, 1H), 7.57 (s, 1H), 8.24 (d, J=7.9Hz, 1H), 8.37 (s, 1H), 8.50 (d, J=5.5Hz, 1H)

Mass spectrometry data (FD-MS, m/z): 449 (M$^+$) 451 (M$^+$+2)

Example 231

N-(3-Chlorophenyl)-N'-{4-[(6,7-dimethoxy-4-quinolyl)oxy]phenyl}urea [267]

6,7-Dimethoxy-4-(4-aminophenoxy)quinoline (52 mg) was dissolved in toluene (5 ml) with heat, 2-chlorophenyl isocyanate (0.05 ml) was added, and the admixture was refluxed with heat for 30 minutes. The reaction solution was purified by column chromatography on silica gel eluting with chloroform/acetone (10/1) to obtain 72 mg of the title compound (yield: 93%).

$^1$H-NMR (CDCl$_3$, 500 MHz): δ 3.98 (s, 3H), 4.03 (s, 3H), 6.41 (d, J=4.9Hz, 1H), 6.99 (d, J=7.9Hz, 1H), 7.09 (d, J=8.5Hz, 2H), 7.16 (dd, J=7.9Hz, 7.9Hz, 1H), 7.23 (d, J=8.6Hz, 1H), 7.38 (s, 1H), 7.42~7.44 (m, 3H), 7.56 (s, 1H), 8.13 (s, 1H), 8.14 (s, 1H), 8.44 (d, J=5.5Hz, 1H)

Mass spectrometry data (FD-MS, m/z): 449 (M$^+$) 451 (M$^+$+2)

Example 232

N-(2,3-Dimethoxyphenyl)-N'-{4-[(6,7-dimethoxy-4-quinolyl)oxy]phenyl}urea [268]

6,7-Dimethoxy-4-(4-aminophenoxy)quinoline (52 mg) was dissolved in toluene (5 ml) with heat, after the addition of triethylamine (1 ml), triphosgene (74 mg) was added, and the admixture was refluxed with heat for 3 minutes. 2,3-Dimethoxyaniline (0.05 ml) was added to the reaction mixture, and the admixture was refluxed with heat for 11 minutes. After the addition of aqueous sodium hydrogen carbonate, the reaction mixture was extracted 2 times with ethyl acetate, and the organic layer was then washed with brine and dried with anhydrous sodium sulfate. The solvent was removed by reduced-pressure distillation, and the resulting residue was purified by column chromatography on silica gel eluting with chloroform/acetone (10/1) to obtain 83 mg of the title compound (yield: 100%).

$^1$H-NMR (CDCl$_3$, 500 MHz): (3.72 (s, 3H), 3.84 (s, 3H), 4.02 (s, 3H), 4.05 (s, 3H), 6.46 (d, J=5.5Hz, 1H), 6.62 (d, J=7.9Hz, 1H), 7.05 (dd, J=8.5, 8.5Hz, 1H), 7.13 (d, J=9.2Hz, 2H), 7.43 (s, 1H), 7.54 (d, J=8.6Hz, 2H), 7.58 (s, 1H), 7.85 (d, J=8.6Hz, 1H), 7.88 (s, 1H), 8.27 (s, 1H), 8.50 (d, J=5.5Hz, 1H)

Mass spectrometry data (FD-MS, m/z): 475 (M$^+$)

Example 233

N-(4-Hydroxyphenyl)-N'-{4-[(6,7-dimethoxy-4-quinolyl)oxy]phenyl}urea [269]

N-(4-Benzyloxyphenyl)-N'-{4-[(6,7-Dimethoxy-4-quinolyl)oxy]phenyl}urea (228 mg) was dissolved in N,N-dimethylformamide/ethyl acetate (15 ml/20 ml), after the addition of triethylamine (4 ml), 20% palladium hydroxide (1.18 g) was added, and the admixture was stirred at room temperature under hydrogen for 15 hours. The reaction mixture was filtered using Celite, after which the filtrate was concentrated, and the resulting residue was purified by column chromatography on silica gel eluting with chloroform/acetone (10/1) to obtain 188 mg of the title compound (yield: 100%).

$^1$H-NMR (DMSO-d$_6$, 500 MHz): δ 3.98 (s, 3H), 3.9 9 (s, 3H), 6.60 (d, J=5.5Hz, 1H), 6.68 (d, J=8.6Hz, 2H), 7.21 (d, J=8.5Hz, 2H), 7.22 (d, J=8.5Hz, 2H), 7.47 (s, 1H), 7.60 (d, J=9.2Hz, 2H), 7.61 (s, 1H), 8.58 (s, 1H), 8.59 (s, 1H), 8.98 (s, 1H), 9.03 (s, 1H)

Mass spectrometry data (FD-MS, m/z): 431 (M$^+$+1)

Example 234

N-(4-Acetoxyphenyl)-N'-{4-[(6,7-dimethoxy-4-quinolyl)oxy]phenyl}urea [270]

N-(4-Hydroxyphenyl)-N'-{4-[(6,7-dimethoxy-4-quinolyl)oxy]phenyl}urea (47 mg) was dissolved in methylene chloride (6 ml), after the addition of triethylamine (2 ml), acetic anhydride (0.5 ml) was added, and the admixture was stirred at room temperature for 15 hours. After the addition of aqueous sodium hydrogen carbonate, the reaction mixture was extracted 2 times with ethyl acetate, and the organic layer was then washed with brine and dried with anhydrous sodium sulfate. The solvent was removed by reduced-pressure distillation, and the resulting residue was purified by column chromatography on silica gel eluting with chloroform/acetone (10/1) to obtain 35 mg of the title compound (yield: 68%).

$^1$H-NMR (CDCl$_3$, 500 MHz): δ 2.31 (s, 3H), 4.01 (s, 3H), 4.04 (s, 3H), 6.43 (d, J=5.5Hz, 1H), 7.01 (d, J=8.6Hz, 2H), 7.11 (d, J=9.2Hz, 2H), 7.26 (brs, 1H), 7.32 (d, J=9.2Hz, 2H), 7.40 (s, 1H), 7.45 (d, J=9.2Hz, 1H), 7.56 (s, 1H), 7.5 6 (brs, 1H), 8.46 (d, J=4.9Hz, 1H)

Mass spectrometry data (FD-M S, m/z) 473 (M$^+$)

Example 235

N-(3,4,5-Trimethoxyphenyl)-N'-{4-[(6,7-dimethoxy-4-quinolyl)oxy]phenyl}urea [271]

6,7-Dimethoxy-4-(4-aminophenoxy)quinoline (52 mg) was dissolved in toluene (5 ml) with heat, after the addition of triethylamine (1 ml), triphosgene (66 mg) was added, and the admixture was refluxed with heat for 2 minutes. 3,4,5-Trimethoxyaniline (76 mg) was added to the reaction mixture, and the admixture was refluxed with heat for 19 minutes. After the addition of aqueous sodium hydrogen carbonate, the reaction mixture was extracted 2 times with ethyl acetate, and the organic layer was then washed with brine and dried with anhydrous sodium sulfate. The solvent was removed by reduced-pressure distillation, and the resulting residue was purified by column chromatography on silica gel eluting with chloroform/acetone (10/1) to obtain 76 mg of the title compound (yield: 87%).

$^1$H-NMR (CDCl$_3$, 500 MHz) δ 3.81 (s, 6H), 3.83 (s, 3H), 4.02 (s, 3H), 4.05 (s, 3H), 6.44 (d, J=4.9Hz, 1H), 6.69 (s, 2H), 7.12 (d, J=9.2Hz, 2H), 7.41 (s, 1H), 7.41 (brs, 1H), 7.48 (d, J=8.6Hz, 2H), 7.57 (s, 1H), 7.58 (s, 1H), 8.47 (d, J=4.9Hz, 1H)

Mass spectrometry data (FD-MS, m/z): 505 (M$^+$)

Example 236

N-(2,4-Difluorophenyl)-N'-{4-[(6,7-dimethoxy-4-quinolyl)oxy]phenyl}urea [272]

6,7-Dimethoxy-4-(4-aminophenoxy)quinoline (100 mg) was dissolved in toluene (10 ml) with heat, 2,4-difluorophenyl isocyanate (120 μl) was added, and the admixture was refluxed with heat for 30 minutes. The separated crystals were filtered and then washed with toluene to obtain 128 mg of the title compound (yield: 84%).

$^1$H-NMR (DMSO-d$_6$, 500 MHz): δ 3.94 (s, 3H), 3.95 (s, 3H), 6.46 (d, J=4.9Hz, 1H), 7.03~7.10 (m, 1H), 7.22 (d, J=9.2Hz, 2H), 7.28~7.35 (m, 1H), 7.39 (s, 1H), 7.52 (s, 1H), 7.59 (d, J=9.2Hz, 2H) 8.05~8.12 (m, 1H) 8.47 (d, J=5.5Hz, 1H), 8.52 (s, 1H), 9.15 (s, 1H)

Mass spectrometry data (FD-MS, m/z) 451 (M$^+$)

Example 237

N-(2,5-Difluorophenyl)-N'-{4-[(6,7-dimethoxy-4-quinolyl)oxy]phenyl}urea [273]

6,7-Dimethoxy-4-(4-aminophenoxy)quinoline (100 mg) was dissolved in toluene (10 ml) with heat, 2,5- difluorophenyl isocyanate (120 μl) was added, and the admixture was refluxed with heat for 30 minutes. The separated crystals were filtered and then washed with toluene to obtain 132 mg of the title compound (yield: 87%).

$^1$H-NMR (DMSO-d$_6$, 500MHz): δ 3.94 (s, 3H), 3.95 (s, 3H), 6.46 (d, J=5.5Hz, 1H), 6.80~6.87 (m, 1H), 7.23 (d, J=9.2Hz, 2H), 7.27~7.33 (m, 1H), 7.40 (s, 1H), 7.52 (s, 1H), 7.59 (d, J=8.6Hz, 2H), 8.03~8.08 (m, 1H), 8.47 (d, J=5.5Hz, 1H), 8.78 (s, 1H), 9.27 (s, 1H)

Mass spectrometry data (FD-MS, m/z): 45 1 (M$^+$)

Example 238

N-(4-Amino-2-chlorophenyl)-N'-{4-[(6,7-dimethoxy-4-quinolyl)oxy]phenyl}urea [274]

N-(4-Chloro-3-nitrophenyl)-N'-{4-[(6,7-dimethoxy-4-quinolyl)oxy]phenyl)urea (150 mg) was dissolved in chloroform/methanol/water (10 ml/13 ml/3 ml), sodium thiosulfate (501 mg) was added, and the admixture was stirred at 60° C. for 50 minutes. The reaction mixture was extracted 2 times with chloroform, and the organic layer was then washed with brine and dried with anhydrous sodium sulfate. The solvent was removed by reduced-pressure distillation, and the resulting residue was purified by column chromatography on silica gel eluting with chloroform/acetone (10/1) to obtain 48 mg of the title compound (yield: 34%).

$^1$H-NMR (DMSO-d$_6$, 500 MHz): δ 3.94 (s, 3H), 3.94 (s, 3H), 5.14 (brs, 2H), 6.43 (d, J=4.9 Hz, 1H), 6.51 (m, 1H), 6.65 (d, J=2.5Hz, 1H), 7.17 (d, J=9.2Hz, 2H), 7.38 (s, 1H), 7.48 (d, J=8.6Hz, 1H), 7.51 (s, 1H), 7.56 (d, J=8.5Hz, 2H), 7.83 (s, 1H), 8.45 (d, J=5.5Hz, 1H), 9.10 (s, 1H)

Mass spectrometry data (FD-MS, m/z): 464 (M.), 466 (M$^+$+2)

Example 239

N-{4-[(6,7-Dimethoxy-4-quinolyl)oxy]phenyl}-N'-[2-ethoxycarbonylphenyl]urea [275]

6,7-Dimethoxy-4-(4-aminophenoxy)quinoline (100 mg) was dissolved in toluene (10 ml) with heat, after the addition of triethylamine (1 ml), triphosgene (100 mg) was added, and the admixture was refluxed with heat for 2 minutes. Ethyl-2-aminobenzoate (84 mg) was added to the reaction mixture, and the admixture was refluxed with heat for 2 hours. After the addition of aqueous sodium hydrogen carbonate, the reaction mixture was extracted 2 times with ethyl acetate, and the organic layer was then washed with brine and dried with anhydrous sodium sulfate. The solvent was removed by reduced-pressure distillation, and the resulting residue was purified by column chromatography on silica gel eluting with chloroform/acetone (10/1) to obtain 86 mg of the title compound (yield: 52%).

$^1$H-NMR (DMSO-d$_6$, 90 MHz): δ 1.37 (t, J=7Hz, 3H), 3.94 (s, 3H), 3.94 (s, 3H), 4.38 (q, J=7 Hz, 2H), 6.4 7 (d, J=5Hz, 1H), 7.1~8.1 (m, 9H), 8.38 (d, J=9Hz, 1H), 8.47 (d, J=5Hz, 1H), 9.92 (s, 1H), 10.10 (s, 1H)

Mass spectrometry data (FD-MS, m/z): 487 (M$^+$)

Example 240

N-(2-Methylthiophenyl)-N'-{4-[(6,7-dimethoxy-4-quinolyl)oxy]phenyl}urea [276]

6,7-Dimethoxy-4-(4-aminophenoxy)quinoline (131 mg) was dissolved in toluene (13 ml) with heat, after the addition of triethylamine (2.6 ml), triphosgene (152 mg) was added, and the admixture was refluxed with heat for 2 minutes. 2-Methylthioaniline (0.11 ml) was added to the reaction mixture, and the admixture was refluxed with heat for 10 minutes. After the addition of aqueous sodium hydrogen carbonate, the reaction mixture was extracted 2 times with chloroform, and the organic layer was then washed with brine and dried with anhydrous sodium sulfate. The solvent was removed by reduced-pressure distillation, and the resulting residue was purified by column chromatography on silica gel eluting with chloroform/acetone (4/1) to obtain 29 mg of the title compound (yield: 14%).

$^1$H-NMR (DMSO-d$_6$, 500 MHz): δ 2.50 (s, 3H), 4.00 (s, 3H), 4.00 (s, 3H), 6.51 (d, J=5.5Hz, 1H), 7.08~7.15 (m, 1H), 7.25~7.35 (m, 3H), 7.45 (s, 1H), 7.48 (d, J=7.9Hz, 1H), 7.58 (s, 1H), 7.67 (d, J=8.5Hz, 2H), 7.99 (d, J=7.9Hz, 1H), 8.24 (s, 1H), 8.53 (d, J=5.5Hz, 1H), 9.61 (s, 1H)

Mass spectrometry data (FD-MS, m/z): 461 (M$^+$)

Example 241

N-[3,5-Bis(trifluoromethyl)phenyl]-N'-{4-[(6,7-dimethoxy-4-quinolyl)oxy]phenyl}urea [277]

6,7-Dimethoxy-4-(4-aminophenoxy)quinoline (50 mg) was dissolved in toluene (5 ml) with heat, after the addition of triethylamine (1 ml), triphosgene (55 mg) was added, and the admixture was refluxed with heat for 3 minutes. 3,5-Bis(trifluoromethyl)aniline (116 mg) was added to the reaction mixture, and the admixture was refluxed with heat for 20 minutes. After the addition of aqueous sodium hydrogen carbonate, the reaction mixture was extracted 2 times with ethyl acetate, and the organic layer was then washed with brine and dried with anhydrous sodium sulfate. The solvent was removed by reduced-pressure distillation, and the resulting residue was purified by column chromatography on silica gel eluting with chloroform/acetone (10/1) to obtain 54 mg of the title compound (yield: 58%).

$^1$H-NMR (DMSO-d$_6$, 500 MHz): δ 3.93 (s, 3H), 3.94 (s, 3H), 6.45 (d, J=5.5Hz, 1H), 7.23 (d, J=9.2Hz, 2H), 7.39 (s, 1H), 7.51 (d, J=9.2Hz, 2H), 7.62 (d, J=9.2Hz, 2H), 7.64 (s, 1H), 8.15 (s, J5.5Hz, 2H), 9.13 (s, 1H), 9.43 (s, 1H)

Mass spectrometry data (FD-M S, m/z): 551 (M$^+$)

Example 242

N-(3-Chloropropyl)-N'-{4-[(6,7-dimethoxy-4-quinolyl)oxy]phenyl}urea [278]

6,7-Dimethoxy-4-(4-aminophenoxy)quinoline (50 mg) was dissolved in toluene (5 ml) with heat, after the addition of triethylamine (1 ml), triphosgene (55 mg) was added, and the admixture was refluxed with heat for 3 minutes. 3-Chloropropylaniline (66 mg) was added to the reaction mixture, and the admixture was refluxed with heat for 20 minutes. After the addition of aqueous sodium hydrogen carbonate, the reaction mixture was extracted 2 times with ethyl acetate, and the organic layer was then washed with brine and dried with anhydrous sodium sulfate. The solvent was removed by reduced-pressure distillation, and the resulting residue was purified by column chromatography on silica gel eluting with chloroform/acetone (10/1) to obtain 26 mg of the title compound (yield: 37%).

$^1$H-NMR (DMSO-d$_6$500 MHz): δ 1.87~1.94 (m, 2H), 3.20~3.27 (m, 2H), 3.69 (t, J=6.1Hz, 2 H), 3.93 (s, 3H), 3.94 (s, 3H), 6.29 (t, J=6.1Hz, 1H), 6.41 (d, J=5.5Hz, 1H), 7.14 (d, J=9.2Hz, 2H), 7.38 (s, 1H), 7.50~7.5 5 (m, 3 H), 8.46 (d, J=4.9H z, 1H), 8.61 (s, 1H)

Mass spectrometry data (FD-MS, m/z 415 (M+)

Example 243

N-{5-[2-(4-fluoro)phenoxy]-pyridyl}-N'-(4-[(6,7-dimethoxy-4-quinolyl)oxy]phenyl}urea [279]

6,7-Dimethoxy-4-(4-aminophenoxy)quinoline (53 mg) was dissolved in toluene (5 ml) with heat, after the addition of triethylamine (1 ml), triphosgene (58 mg) was added, and the admixture was refluxed with heat for 4 minutes. 5-Amino-2-(4-fluoro)phenoxypyridine (95 mg) was added to the reaction mixture, and the admixture was refluxed with heat for 19 minutes. After the addition of aqueous sodium hydrogen carbonate, the reaction mixture was extracted 2 times with ethyl acetate, and the organic layer was then washed with brine and dried with anhydrous sodium sulfate. The solvent was removed by reduced-pressure distillation, and the resulting residue was purified by column chromatography on silica gel eluting with chloroform/acetone (10/1) to obtain 74 mg of the title compound (yield: 79%).

$^1$H-NMR (DMSO-d$_6$, 500 MHz): δ 3.94 (s, 3H), 3.95 (s, 3H), 6.44 (d, J=5.5Hz, 1H), 7.0 (d, J=8.5Hz, 1H), 7.12~7.24 (m, 6H), 7.38 (s, 1 H), 7.51 (s, 1H), 7.59 (d, J=9.2Hz, 2H), 8.01 (d, J=8.6Hz, 1H), 8.19 (d, J=2.4Hz, 1H), 8.46 (d, J=4.9Hz, 1H), 8.77 (s, 1H), 8.89 (s, 1H)

Mass spectrometry data (FD-MS, m/z): 526 (M+)

Example 244

N-{4-[(6,7-Dimethoxy-4-quinolyl)oxy]phenyl}-N'-(3-dimethylaminophenyl)urea [280]

6,7-Dimethoxy-4-(4-aminophenoxy)quinoline (52 mg) was dissolved in toluene (5 ml) with heat, after the addition of triethylamine (1 ml), triphosgene (55 mg) was added, and the admixture was refluxed with heat for 3 minutes. 3-Dimethylaminoaniline (69 mg) was added to the reaction mixture, and the admixture was refluxed with heat for 12 minutes. After the addition of aqueous sodium hydrogen carbonate, the reaction mixture was extracted 2 times with ethyl acetate, and the organic layer was then washed with brine and dried with anhydrous sodium sulfate. The solvent was removed by reduced-pressure distillation, and the resulting residue was purified by column chromatography on silica gel eluting with chloroform/acetone (10/1) to obtain 72 mg of the title compound (yield: 89%).

$^1$H-NMR (CDCl$_3$, 500 MHz) δ 2.92 (s, 6H), 4.0 (s, 3H), 4.03 (s, 3H), 6.41 (d, J=4.9Hz, 1H), 6.48 (d, J=8.6Hz, 1H), 6.56 (d, J=9.2Hz, 1H), 6.88 (s, 1H), 7.08 (d, J=9.2Hz, 2H), 7.14 (dd, J=7.9, 8.5Hz, 1H), 7.35 (s, 1H), 7.41 (s, 1H), 7.45 (d, J=9.2Hz, 2H), 7.55 (s, 1H), 7.67 (s, H), 8.45 (d, J=4.9Hz, 1H)

Mass spectrometry data (FD-MS, m/z): 458 (M+)

Example 245

N-(2-Hydroxyphenyl)-N'-{4-[(6,7-dimethoxy-4-quinolyl)oxy]phenyl}urea [281]

6,7-Dimethoxy-4-(4-aminophenoxy)quinoline (105 mg) was dissolved in toluene (10 ml) with heat, after the addition of triethylamine (2 ml), triphosgene (118 mg) was added, and the admixture was refluxed with heat for 2 minutes. 2-Aminophenol (77 mg) was added to the reaction mixture, and the admixture was refluxed with heat for 10 minutes. After the addition of aqueous sodium hydrogen carbonate, the reaction mixture was extracted with chloroform, and the organic layer was then washed with brine and dried with anhydrous sodium sulfate. The solvent was removed by reduced-pressure distillation, and the resulting residue was washed with chloroform and filtered to obtain 86 mg of the title compound (yield: 56%).

$^1$H-NMR (DMSO-d$_6$, 500 MHz): δ 3.94 (s, 3H), 3.95 (s, 3H), 6.45 (d, J=4.9Hz, 1H), 6.73~6.88 (m, 3H), 7.20 (d, J=8.6Hz, 2H), 7.39 (s, 1H), 7.52 (s, 1H), 7.59 (d, J=8.6Hz, 2H), 8.03~8.08 (m, 1H), 8.19 (s, 1H), 8.47 (d, J=5.5Hz, 1H), 9.46 (s, 1H), 9.95 (s, 1H)

Mass spectrometry data (FD-MS, m/z) 431 (M+)

Example 246

N-(3-Hydroxyphenyl)-N'-{4-[(6,7-dimethoxy-4-quinolyl)oxy]phenyl}urea [282]

6,7-Dimethoxy-4-(4-aminophenoxy)quinoline (115 mg) was dissolved in toluene (12 ml) with heat, after the addition of triethylamine (2 ml), triphosgene (113 mg) was added, and the admixture was refluxed with heat for 2 minutes. 3-Aminophenol (73 mg) was added to the reaction mixture, and the admixture was refluxed with heat for 10 minutes. After the addition of aqueous sodium hydrogen carbonate, the reaction mixture was extracted with chloroform, and the organic layer was then washed with brine and dried with anhydrous sodium sulfate. The solvent was removed by reduced-pressure distillation, and the resulting residue was washed with chloroform and filtered to obtain 95 mg of the title compound (yield: 60%).

$^1$H-NMR (DMSO-d$_6$, 500 MHz): δ 3.94 (s, 3H), 3.95 (s, 3H), 6.35~6.42 (m, 1H), 6.44 (d, J=4.9Hz, 1H), 6.77~6.85 (m, 1H), 6.98~7.08 (m, 2H), 7.20 (d, J=8.6Hz, 2H), 7.39 (s, 1H), 7.52 (s, 1H), 7.58 (d, J=8.6Hz, 2H), 8.47 (d, J=4.9Hz, 1H), 8.57 (s, 1H), 8.73 (s, 1H), 9.31 (s, 1H)

Mass spectrometry data (FD-MS, m/z): 431 (M+)

Example 247

N-(3-Hydroxycarbonylphenyl)-N'-{4-[(6,7-dimethoxy-4-quinolyl)oxy]phenyl}urea [283]

N-(3-Ethoxycarbonylphenyl)-N'-{4-[(6,7-dimethoxy-4-quinolyl)oxy]phenyl}urea (190 mg) obtained in Example 197 was dissolved in methanol (3 ml), 35% aqueous potassium hydroxide (5 ml) was added, and the admixture was stirred at room temperature for 30 minutes. After removing methanol by reduced-pressure distillation and neutralizing using dilute hydrochloric acid, the separated crystals were filtered to obtain 67 mg of the title compound (yield: 38%).

$^1$H-NMR (DMSO-d$_6$, 500 MHz): δ 3.94 (s, 3H) 3.95 (s, 3H), 6.45 (d, J=5.5Hz, 1H), 7.20 (d, J=8.6Hz, 2H), 7.38~7.65 (m, 7H), 8.13 (s, 1H), 8.46 (d, J=4.9H z, 1H), 8.88 (s, 1H), 8.97 (s, 1H)

Mass spectrometry data (FD-MS m/z 459 (M+)

Test Example 1

As for pharmacological action of the compounds of the present invention, inhibition of PDGF receptor autophosphorylation was studied using cultured rat mesangial cells which are known to have the PDGF receptor.

1. Cultivation of rat mesangial cells

Kidneys were taken out from Wistar-Kyoto rats (purchased from Charles River Japan, Inc.), and the glomeruli were isolated by the sieving method (Nephron, 22, 454 (1978)). The glomeruli were cultured in RPMI 1640 medium (hereinafter referred to as the medium) containing 10% fetal calf serum (hereinafter abbreviated to FCS) at 37° C. in an incubator in an atmosphere containing 5% carbon dioxide. The glomerulus-derived adhesive cells were subcultured several times to obtain mesangial cells. The mesangial cells subcultured more than 5 passages were used for the assay.

2. Evaluation of PDGF receptor autophosphorylation inhibition

The mesangial cells were seeded in 24-well flat-bottom microtiter plates and then cultured in the medium containing 10% FCS for 2 days. When the cells were grown to about $3 \times 10^4$ cells per well, the medium was changed to the medium containing 0.5% FCS, the cultivation was continued for another 3 days, and then cell growth was arrested. The culture medium was removed, the adhered cells were washed with 500 μl of the medium, and 250 μl of the medium containing 0.1% bovine serum albumin (hereinafter abbreviated to BSA) was then added. A test drug dissolved in 1.38 μl of dimethyl sulfoxide (hereinafter abbreviated to DMSO) was added to this culture medium, and the admixture was incubated at 37° C. for 1 hour. Recombinant human platelet-derived growth factor BB chain (hereinafter abbreviated to PDGF-BB) was dissolved in the medium containing 0.1% BSA, 25 μl per well of the solution was added at final 50 ng/ml, and the incubation was continued at 37° C. for 10 minutes. The medium was removed, the cells were washed with 500 μl of phosphate-buffered physiological saline (pH 7.4) (hereinafter abbreviated to PBS), and 50 μl of lysis buffer (Tris-buffered physiological saline, pH 7.4, containing 1% Triton X100, 2 mM sodium orthobanadate, and 1 mM ethylene-diamine-tetraacetic acid disodium (hereinafter abbreviated to EDTA) were added. The cells were allowed to stand at 4° C. for 30 minutes for lysis, and the resulting solution was thoroughly admixed with an equal amount of Tris-buffered physiological saline containing 1% sodium dodecyl sulfate (hereinafter abbreviated to SDS). An aliquot (20 μl) of the solution was subjected to SDS electrophoresis on 7.5% polyacrylamide gel. After the electrophoresis, proteins in the gel were electrically transferred to a PVDF filter, which was then subjected to Western blotting using monoclonal antibodies against phosphotyrosine. Bands of PDGF receptor (molecular weight: about 180 Kda) which were autophosphorylated due to the addition of PDGF-BB were quantitated by a densitometer. Autophosphorylation rates for individual wells with drugs were calculated by setting measurements for PDGF receptor autophosphorylation in the wells without drugs in the presence and absence of PDGF-BB as 100% and 0%, respectively.

PDGF receptor autophosphorylation inhibition rates were obtained at a series of different concentrations of individual test drugs, from which regression line formulas were determined to calculate PDGF receptor autophosphorylation 50% inhibition concentrations ($IC_{50}$s) for the test drugs.

The compounds of the present invention showed the PDGF receptor autophosphorylation 50% inhibition concentrations ($IC_{50}$s) of less than 100 μM.

As for representative examples of preferred compound groups of the present invention, test results for PDGF receptor autophosphorylation 50% inhibition concentrations ($IC_{50}$s) in mesangial cells are shown in Table 2.

TABLE 2

| Compound No. | $IC_{50}$ (μM) for PDGF receptor autophosphorylation inhibition |
|---|---|
| (2) | 0.44 |
| (6) | 0.45 |
| (8) | 0.10 |
| (16) | 0.05 |
| (29) | 0.80 |
| (32) | 0.30 |
| (43) | 0.005 |
| (44) | 0.006 |
| (45) | 0.014 |
| (46) | 0.021 |
| (47) | 0.043 |
| (49) | 0.018 |
| (50) | 0.067 |
| (51) | 0.009 |
| (52) | 0.03 |
| (53) | 0.010 |
| (54) | 0.003 |
| (55) | 0.003 |
| (56) | 0.004 |
| (57) | 0.006 |
| (58) | 0.002 |
| (59) | 0.004 |
| (60) | 0.004 |
| (63) | 0.40 |
| (66) | 0.13 |
| (67) | 0.11 |
| (68) | 0.44 |
| (69) | 0.05 |
| (74) | 0.34 |
| (75) | 0.18 |
| (79) | 0.34 |
| (94) | 0.023 |
| (113) | 0.004 |
| (114) | 0.004 |
| (131) | 0.003 |
| (133) | 0.007 |
| (135) | 0.043 |
| (138) | 0.014 |
| (139) | 0.005 |
| (163) | 0.005 |
| (165) | 0.010 |
| (166) | 0.011 |
| (167) | 0.004 |
| (168) | 0.006 |
| (169) | 0.004 |
| (170) | 0.018 |
| (172) | 0.010 |
| (173) | 0.016 |
| (174) | 0.002 |
| (175) | 0.006 |
| (188) | 0.006 |
| (189) | 0.011 |
| (190) | 0.021 |
| (192) | 0.004 |
| (194) | 0.014 |
| (195) | 0.079 |
| (196) | 0.031 |
| (197) | 0.010 |
| (198) | 0.011 |
| (199) | 0.003 |
| (200) | 0.004 |
| (220) | 0.009 |
| (224) | 0.087 |
| (225) | 0.047 |
| (226) | 0.011 |
| (227) | 0.073 |
| (228) | 0.055 |
| (229) | 0.037 |
| (230) | 0.034 |
| (231) | 0.019 |
| (232) | 0.018 |
| (233) | 0.013 |
| (234) | 0.024 |
| (235) | 0.043 |

TABLE 2-continued

| Compound No. | IC$_{50}$ ($\mu$M) for PDGF receptor autophosphorylation inhibition |
|---|---|
| (236) | 0.055 |
| (237) | 0.075 |
| (238) | 0.016 |
| (239) | 0.005 |
| (240) | 0.15 |
| (241) | 0.018 |
| (242) | 0.018 |
| (243) | 0.014 |
| (244) | 0.009 |
| (245) | 0.006 |
| (246) | 0.013 |
| (247) | 0.009 |
| (248) | 0.063 |
| (249) | 0.041 |
| (250) | 0.017 |
| (251) | 0.036 |
| (253) | 0.007 |
| (254) | 0.007 |
| (255) | 0.015 |
| (256) | 0.004 |
| (257) | 0.007 |
| (258) | 0.007 |
| (259) | 0.005 |
| (260) | 0.002 |
| (261) | 0.010 |
| (262) | 0.002 |
| (263) | 0.004 |
| (265) | 0.005 |
| (266) | 0.001 |
| (267) | 0.15 |
| (268) | 0.007 |
| (269) | 0.008 |
| (270) | 0.006 |
| (271) | 0.004 |
| (272) | 0.003 |
| (273) | 0.005 |
| (274) | 0.036 |
| (276) | 0.005 |
| (278) | 0.003 |
| (279) | 0.029 |
| (281) | 0.012 |
| (282) | 0.008 |
| (283) | 0.002 |
| (288) | 0.024 |
| (289) | 0.032 |
| (290) | 0.055 |

Test Example 2

Effect on nephritis associated with mesangial cell growth in rats

Groups of 6 Wistar-Kyoto male rats (7 weeks old, purchased from Charles River Japan, Inc.) were used. OX-7 (prepared according to Pathol. Int., 45, 409 (1995)), a monoclonal antibody against anti-rat Thy1.1, was injected intravenously into the tails of rats at a dose of 1.2 mg/kg to induce glomerulonephritis associated with mesangial cell growth and extracellular matrix accumulation. A test drug suspended in a vehicle, a 1% aqueous cremophor solution, was administered orally 2 times a day starting one day after an OX-7 injection for 8 consecutive days. On day 9, when pathological changes in glomeruli became markedly apparent, the rats were sacrificed and anatomized under anesthesia with ether, and left kidneys were taken out and fixed in formalin. The kidneys were embedded in paraffin and then sectioned thinly, and the sections were stained with a periodic acid-Schiff's reagent. The 20 glomeruli were arbitrarily selected for individual specimens thus prepared, and pathological sclerotic changes were scored as follows:

0: No pathological sclerotic changes were observed in glomeruli.

1: Pathological sclerotic changes were observed in less than 25% of glomeruli. 2: Pathological sclerotic changes were observed in 25–50% of glomeruli.

3: Pathological sclerotic changes were observed in 50–75% of glomeruli.

4: Pathological sclerotic changes were observed in 75–100% of glomeruli.

Average scores for sclerotic change of individual specimens were calculated to quantify the degree of glomerular sclerosis. Average scores of glomerular sclerosis for individual specimens of rat groups administered with the drug were compared with those for control groups administered with the vehicle only to calculate glomerular sclerosis inhibition rates (%). The significance of differences was determined by the Dunnet method after testing homoscedasticity according to the Bartlett method.

Glomerular sclerosis inhibition rates (%) for the compound number 32 are shown as follows:

| Dose | Glomerular sclerosis inhibition rate (%) | Significance of difference |
|---|---|---|
| 10 mg/kg | 11.7 | $p < 0.05$ |
| 30 mg/kg | 10.2 | $p < 0.05$ |
| 100 mg/kg | 13.7 | $p < 0.01$ |

From the results above, it was shown that the compound number 32 has an effect in inhibiting pathological sclerotic changes of glomeruli in nephrosis associated with mesangial cell growth.

Test Example 3

Antitumor activity

1. Antitumor effect of the compound number 43 against mouse leukemia cells (P388)

The compound number 43 exhibited the following effect on prolonging survival of mice injected with tumor cells.

P388 cells ($1 \times 10^5$ cells), mouse leukemia cells obtained from ATCC, were inoculated intraperitoneally into CDF$_1$ mice (obtained from Japan SLC, Inc.), and then the test compound was administered intraperitoneally for 9 consecutive days at the dose of 100 mg/kg. The drug-treated animals survived longer than control animals by 130%.

2. Antitumor effect of the compound number 43 against human glioma cells (GLO7)

The compound number 43 exhibited an antitumor effect in the nude mice human tumor xenograft model, a model which reflects clinical effect, as follows.

Human glioma, GLO7 (obtained from the Central Institute for Experimental Animals), was transplanted into nude mice. When the tumor had grown to a volume of about 100 mm$^3$, the nude mice were divided into several groups of 4 animals so as to equalize the average tumor volumes of each group. The test drug was administered orally to animals in experimental groups 2 times a day for 14 consecutive days at 100 mg/kg, and the vehicle was administered to control animals. The tumor growth inhibition rate (TGIR, %) was calculated from the equation: TGIR=$(1-Tx/Cx) \times 100$, in which Cx is the tumor volume in the control mice and Tx is the tumor volume in the drug-treated mice, on day X, when the initial tumor volume at the time treatment was commenced is set 1. During the test period of about 4 weeks, the maximum TGIR value was 76%, and thus an excellent antitumor effect was observed.

From the results above, the compound number 43 was revealed to have an antitumor activity.

3. Antitumor effect of the compounds of the present invention against human glioma (GLO7)

Each compounds exhibited an antitumor effect in the nude mice human tumor xenogroft model, a model which reflects clinical effect, as follows.

Analogously to 2, human glioma cells, GLO7 (obtained from the Central Institute for Experimental Animals), was transplanted into nude mice. When the tumor had grown to a volume of about 100 mm$^3$, the nude mice were divided into several groups of 4 animals so as to equalize the average tumor volumes of each group. The test drug was administered orally to animals in experimental groups once a day for 9 consecutive days at 50 mg/kg, and the vehicle was administered to control animals. The tumor growth inhibition rate (TGIR, %) was calculated from the equation: TGIR=(1-Tx/Cx)×100, in which Cx is the tumor volume in the control mice and Tx is the tumor volume in the drug-treated mice, on day X, when the initial tumor volume at the time treatment was commenced is set 1. Results are shown in Table 3.

TABLE 3

| Compound No. | Tumor growth inhibition rate (TGIR, %) |
|---|---|
| (44) | 78 |
| (45) | 68 |
| (52) | 86 |
| (56) | 52 |
| (57) | 64 |
| (58) | 57 |
| (59) | 82 |
| (165) | 70 |
| (168) | 56 |
| (173) | 54 |
| (190) | 50 |
| (191) | 50 |
| (194) | 59 |
| (225) | 58 |
| (227) | 78 |
| (229) | 81 |
| (235) | 78 |
| (236) | 84 |
| (237) | 74 |
| (242) | 62 |
| (244) | 73 |
| (254) | 85 |
| (255) | 86 |
| (260) | 52 |
| (262) | 87 |
| (264) | 63 |
| (267) | 65 |
| (272) | 84 |

4. Antitumor effect of compounds numbers 43 and 58 against various tumor cells

In the same manner as described in 2, various types of tumor cells (obtained from the Central Institute for Experimental Animals) were transplanted into nude mice. When the tumor had grown to a volume of about 100 mm$^3$, the animals were allocated to several groups each consisting of 4 animals so as to equalize the average tumor volume of each group. Test drugs were administered intraperitoneally to animals in experimental groups once a day for 9 consecutive days at 100 mg/kg, and the vehicle was administered to control animals. The resulting tumor growth inhibition rates (TGIR) are shown in Table 4.

TABLE 4

| Cells | Tumors | Tumor growth inhibition rate (TGIR, %) | |
|---|---|---|---|
| | | (43) | (58) |
| COL-1 | colon | 68 | 74 |
| St-4 | stomach | 78 | 86 |
| L-27 | lung | 83 | 96 |

The results above revealed that the compounds of the present invention had antitumor effect on various types of tumors.

Test Example 4

Effect on collagen-induced arthritis in mice

9–10 male DBA/IJNCrj mice (9 weeks old, purchased from Charles River Japan, Inc.) were used. An emulsion consisting of 5 ml of 0.3% bovine collagen type II (K-41, Collagen Gijyutsu-kenshukai, Japan), 15 mg of *Mycobacterium tuberculosis* H37Ra (obtained from Difco Labs.), 2.5 ml of physiological saline and 7.5 ml of Freund's incomplete adjuvant (Difco Labs.) was prepared, and then injected subcutaneously at the base of the tail (0.1 ml/animal) 2 times at 3 week intervals to induce arthritis. A test drug suspended in a vehicle, physiological saline containing 10% each of cremophor and DMSO, was administered intraperitoneally for 16 consecutive days, beginning one day before the second injection of the emulsion. Swelling of four legs, characteristic of the onset of arthritis, was investigated every day.

Effect of the compound number 43 on the incidence (%) of collagen-induced arthritis is shown as follows:

| Dose | Number of mice with arthritis/total mice | Incidence (%) |
|---|---|---|
| Vehicle only | 7/10 | 70 |
| 10 mg/kg | 1/9 | 11 |
| 100 mg/kg | 0/10 | 0 |

The results shown above revealed that the compound number 43 suppressed the incidence of collagen-induced arthritis.

Possible Industrial Use

Since the compounds of the present invention have inhibitory activity on abnormal cell growth, more specifically PDGF receptor autophosphorylation inhibitory activity, they are useful for treating numerous diseases such as leukemia, cancers, psoriasis, glomerulonephritis, organofibrosis, atherosclerosis, restenosis after percutaneous coronary angioplasty or bypass surgery and articular rheumatism. Therefore, the compounds can benefit greatly in treating humans and other animals which need these treatments.

What is claimed is:

1. A quinoline derivative, or a pharmaceutically acceptable salt thereof, wherein the derivative is represented by the following formula (I):

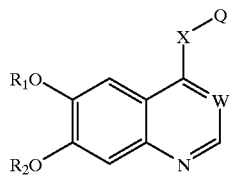

(1)

wherein $R_1$ and $R_2$ are each independently H, $C_1$–$C_5$-alkyl or together form $C_1$–$C_3$-alkylene, wherein W is CH, wherein X is O, S or $CH_2$, wherein Q is a group represented by the following formula (III), (IV) or (V):

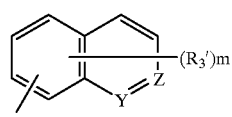

(III)

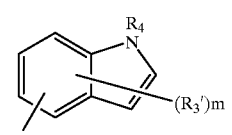

(IV)

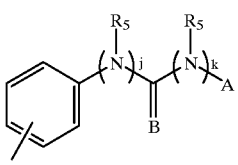

(V)

wherein m is 1, 2 or 3, wherein each $R_3'$ is independently OH, $C_1$–$C_5$-alkyl or $C_1$–$C_4$-alkoxy, wherein Y and Z are each independently N or CH, wherein $R_4$ is H, $C_1$–$C_5$-alkyl or $C_2$–$C_4$-acyl, wherein j and k are each independently 0 or 1, wherein each $R_5$ is independently H or $C_1$–$C_4$-alkyl, wherein A is $C_1$–$C_8$-alkyl, $C_1$–$C_5$-alkenyl, cyclic ($C_3$–$C_{10}$)-alkyl, $C_1$–$C_4$-alkoxycarbonyl, phenyl, naphthyl, furyl, thienyl, benzoyl, substituted benzoyl, $C_2$–$C_4$-acyl, or a 5- or 6-membered monocyclic or 9- or 10-membered bicyclic heteroaryl group, wherein the heteroaryl group has 1 or 2 nitrogen atoms, wherein B is O, S, NH, NCN, $NR_6$ or $NOR_6$, and wherein $R_6$ is $C_1$–$C_5$-alkyl, with the proviso that if X is $CH_2$, then Q is not a group represented by the formula (III) or (IV).

2. The derivative, or pharmaceutically acceptable salt thereof, according to claim 1, wherein the heteroaryl group has another heteroatom selected from the group consisting of N, O and S.

3. The derivative, or pharmaceutically acceptable salt thereof, according to claim 1, wherein, if A is alkyl, aryl or heteroaryl, then A has 1 to 5 substituents selected from the group consisting of CN, $NO_2$, OH, $NH_2$, halogen $C_1$–$C_5$-alkyl, cyclic ($C_3$–$C_{10}$) alkyl, $C_1$–$C_4$-alkoxy, $C_1$–$C_4$-alkoxycarbonyl, $C_1$–$C_5$-acyl, $C_1$–$C_5$-acyloxy, $C_1$–$C_3$-alkylenedioxy, $C_1$–$C_4$-alkylamino, di-($C_1$–$C_4$-alkyl)amino, $CO_2H$, $CONH_2$, N-($C_1$–$C_4$-alkyl)amido, N,N-di-($C_1$–$C_4$-alkyl)amido, $C_2$–$C_4$-alkylamido, trifluoromethyl, $C_1$–$C_4$-alkylthio, phenyl, substituted phenyl, phenoxy, substituted phenoxy, phenylthio, substituted phenylthio, phenyl($C_1$–$C_4$-alkyl), substituted phenyl($C_1$–$C_4$-alkyl), pyridyl, pyrazinyl, pyrimidinyl, pyridazinyl, pyrrolidinyl, piperidinyl, piperazinyl, homopyperazinyl, morpholinyl, quinolyl, quinazolinyl, benzoyl, substituted benzoyl and $C_2$–$C_4$-acyl.

4. The derivative, or pharmaceutically acceptable salt thereof, according to claim 1, wherein X is O or S, and Q is a group represented by the formula (III) or (IV).

5. The derivative, or pharmaceutically acceptable salt thereof, according to claim 4, wherein X is O.

6. The derivative, or pharmaceutically acceptable salt thereof, according to claim 1, wherein Q is a group represented by the formula (V).

7. The derivative, or pharmaceutically acceptable salt thereof, according to claim 1, wherein $R_1$ and $R_2$ are each independently $C_1$–$C_5$-alkyl, Q is a group represented by the formula (V), j and k are each O, and B is O, S or $NOR_6$.

8. The derivative, or pharmaceutically acceptable salt thereof, according to claim 2, wherein $R_1$ and $R_2$ are each independently $C_1$–$C_5$-alkyl, Q is a group represented by the formula (V), j is 0, k is 1, and $R_5$ is H or methyl.

9. The derivative, or pharmaceutically acceptable salt thereof, according to claim 1, wherein $R_1$ and $R_2$ are each independently $C_1$–$C_5$-alkyl, Q is a group represented by the formula (V), j is 1, k is 0, and $R_5$ is H or methyl.

10. The derivative, or pharmaceutically acceptable salt thereof, according to claim 1, wherein $R_1$ and $R_2$ are each independently $C_1$–$C_5$-alkyl, Q is a group represented by the formula (V), j and k are 1, and each $R_5$ is independently H or methyl.

11. The derivative, or pharmaceutically acceptable salt thereof, according to claim 1, wherein X is 0; $R_1$ and $R_2$ are methyl; Q is a group represented by the formula (V); j and k are each independently 0 or 1; $R_5$ is H; A is $C_1$–$C_5$-alkyl, cyclopentyl, cyclohexyl, cycloheptyl, allyl, $C_1$–$C_4$-alkoxycarbonyl, phenyl, naphthyl or benzoyl; and $R_6$ is methyl.

12. The derivative, or pharmaceutically acceptable salt thereof, according to claim 11, wherein, if A is alkyl, aryl or heteroaryl, then A has 1–5 substituents selected from the group consisting of OH, $CO_2H$, fluoro, chloro, bromo, iodo, nitro, amino, di-($C_1$–$C_4$-alkyl)amino, ethylenedioxy, acetoxy, methylthio, $C_1$–$C_4$-alkoxycarbonyl, trifluoromethyl, $C_1$–$C_4$-alkyl, $C_1$–$C_4$-alkoxy, pyridyl and phenyl.

13. The derivative, or pharmaceutically acceptable salt thereof, according to claim 1, wherein the derivative is:

6,7-dimethoxy-4-(1-naphthyloxy) quinoline,
6,7-dimethoxy-4-(2-naphthyloxy)quinoline,
6,7-dimethoxy-4-(5-methoxy-1-naphthyloxy)quinoline,
6,7-dimethoxy-4-(6-methoxy-2-naphthyloxy)quinoline,
6,7-dimethoxy-4-(7-methoxy-2-naphthyloxy)quinoline,
6,7-dimethoxy-4-(5-quinolyloxy)quinoline,
6,7-dimethoxy-4-(6-quinolyloxy)quinoline,
4-(4-indolyloxy)-6,7-dimethoxyquinoline, or
4-(5-indolyloxy)-6,7-dimethoxyquinoline.

14. A quinoline derivative, or a pharmaceutically acceptable salt thereof, wherein the derivative is represented by the following formula (VI):

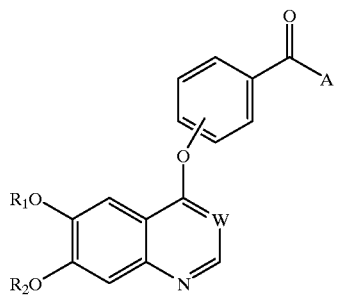

(VI)

wherein W is CH, wherein $R_1$ and $R_2$ are each independently $C_1$–$C_5$-alkyl, and wherein A is methyl, ethyl, propyl, isopropyl, butyl, isobutyl, s-butyl, t-butyl, pentyl, isopentyl, cyclopentyl, cyclohexyl, cycloheptyl, phenyl, naphthyl, furyl, thienyl, pyridyl or pyrimidinyl.

15. A quinoline derivative, or a pharmaceutically acceptable salt thereof, according to claim 14, wherein, if A is alkyl, aryl, or heteroaryl, then A has 1–5 substituents selected from the group consisting of fluoro, chloro, bromo, iodo, cyano, hydroxy, nitro, amino, methylamino, dimethylamino, diethylamino, dipropylamino, dibutylamino, trifluoromethyl, methyl, ethyl, propyl, isopropyl, butyl, isobutyl, s-butyl, t-butyl, methoxy, ethoxy, propoxy, isopropoxy, morpholino, pyrrolidino, piperidino and butoxy.

16. A quinoline derivative, or a pharmaceutically acceptable salt thereof, wherein the derivative is represented by the following formula (VII):

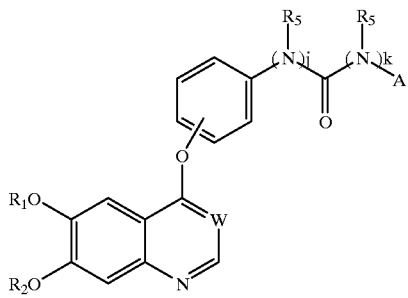

(VII)

wherein W is CH, wherein j is 0 and K is 1, or j is 1 and k is 0, wherein $R_1$ and $R_2$ are each independently $C_1$–$C_5$-alkyl, wherein $R_5$ is H or methyl, and wherein A is methyl, ethyl, propyl, isopropyl, butyl, isobutyl, s-butyl, t-butyl, pentyl, isopentyl, cyclopentyl, cyclohexyl, cycloheptyl, phenyl, naphthyl, furyl, thienyl, pyridyl or pyrimidinyl.

17. A quinoline derivative, or a pharmaceutically acceptable salt thereof, according to claim 16, wherein, if A is alkyl, aryl, or heteroaryl, then A has 1–5 substituents selected from the group consisting of fluoro, chloro, bromo, iodo, cyano, hydroxy, nitro, amino, methylamino, dimethylamino, diethylamino, dipropylamino, dibutylamino, trifluoromethyl, methyl, ethyl, propyl, isopropyl, butyl, isobutyl, s-butyl, t-butyl, methoxy, ethoxy, propoxy, isopropoxy and butoxy.

18. A quinoline derivative, or a pharmaceutically acceptable salt thereof, wherein the derivative is represented by the following formula (VIII):

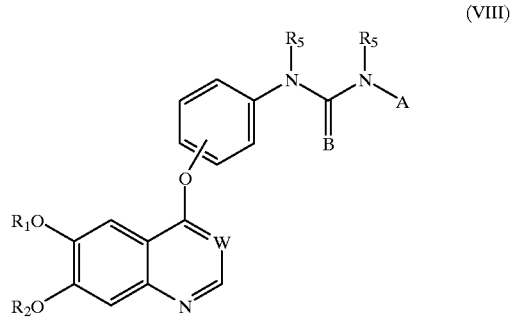

(VIII)

wherein W is CH, wherein $R_1$ and $R_2$ are each independently $C_1$–$C_5$-alkyl, each $R_5$ is independently H or methyl, wherein A is $C_1$–$C_6$-alkyl, $C_1$–$C_4$-alkenyl, cyclopentyl, cyclohexyl, cycloheptyl, $C_1$–$C_4$-alkoxycarbonyl, phenyl, naphthyl, furyl, thienyl, benzoyl, acetyl, pyridyl, pyrimidinyl, pyrrolidinyl, piperidinyl, piperazinyl, homopiperazinyl or morpholino, wherein B is O, S, NH, NCN, $NR_6$ or $NOR_6$, and wherein $R_6$ is methyl.

19. A quinoline derivative, or a pharmaceutically acceptable salt thereof, according to claim 18, wherein, if A is alkyl, aryl or heteroaryl, then A has 1–5 substituents selected from the group consisting of halogen, cyano, $CO_2H$, $CONH_2$, hydroxy, nitro, amino, $C_1$–$C_4$-alkylamino, di-($C_1$–$C_4$-alkyl)amino, $C_1$–$C_5$-acyloxy, $C_1$–$C_5$-acyl, $C_1$–$C_4$-alkylthio, trifluoromethyl, $C_1$–$C_5$-alkyl, $C_1$–$C_4$-alkoxyl, $C_1$–$C_4$-alkoxycarbonyl, N-($C_1$–$C_4$-alkyl)amido, N,N-di-($C_1$–$C_4$-alkyl)amido, $C_2$–$C_4$-alkylamido, ethylenedioxy, phenyl, phenoxy, substituted phenyl, benzoyl, pyridyl, pyrazinyl, pyrimidinyl, pyridazinyl, quinolyl and quinazolinyl.

20. A quinoline derivative, or a pharmaceutically acceptable salt thereof, wherein the derivative is represented by the following formula (IX):

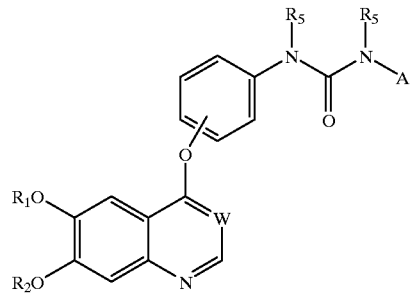

(IX)

wherein W is CH, wherein $R_1$ and $R_2$ are each independently $C_1$–$C_5$-alkyl, wherein each $R_5$ is independently H or methyl, and wherein A is $C_1$–$C_6$-alkyl, $C_1$–$C_4$-alkenyl, cyclopentyl, cyclohexyl, cycloheptyl, $C_1$–$C_4$-alkoxycarbonyl, phenyl, naphthyl, furyl, thienyl, benzoyl, acetyl, pyridyl, pyrimidinyl, pyrrolidinyl, piperidinyl, piperazinyl, homopiperazinyl or morpholino.

21. A quinoline derivative, or a pharmaceutically acceptable salt thereof, according to claim 20, wherein, if A is alkyl, aryl or heteroaryl, then A has 1–5 substituents selected from the group consisting of halogen, cyano, $CO_2H$, $CONH_2$, hydroxy, nitro, amino, $C_1$–$C_4$-alkylamino, di-($C_1$–$C_4$-alkyl)amino, $C_1$–$C_5$-acyloxy, $C_1$–$C_5$-acyl, $C_1$–$C_4$-alkylthio, trifluoromethyl, $C_1$–$C_5$-alkyl, $C_1$–$C_4$-alkoxyl, $C_1$–$C_4$-alkoxycarbonyl, N-($C_1$–$C_4$-alkyl)amido, N,N-di-($C_1$–$C_4$-alkyl)amido, $C_2$–$C_4$-alkylamido, ethylenedioxy, phenyl, phenoxy, substituted phenyl, benzoyl, pyridyl, pyrazinyl, pyrimidinyl, pyridazinyl, quinolyl and quinazolinyl.

22. A quinoline derivative, or a pharmaceutically acceptable salt thereof, wherein the derivative is represented by the following formula (X):

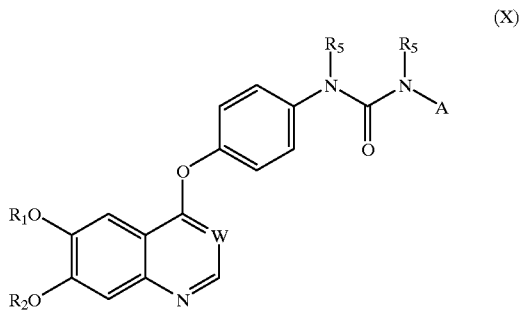

wherein $R_1$ and $R_2$ are each independently $C_1$–$C_5$-alkyl, wherein $R_5$ is each independently hydrogen or methyl, and wherein A is $C_1$–$C_5$-alkyl, cyclopentyl, cyclohexyl, cycloheptyl, allyl, $C_1$–$C_4$-alkoxycarbonyl, phenyl, naphthyl or benzoyl.

23. A quinoline derivative, or a pharmaceutically acceptable salt thereof, according to claim 22, wherein, if A is alkyl, aryl or heteroaryl, then A has 1–5 substituents selected from the group consisting of OH, CO2H, fluoro, chloro, bromo, iodo, nitro, amino, di-($C_1$–$C_4$-alkyl)amino, ethylenedioxy, acetoxy, methylthio, $C_1$–$C_4$-alkoxycarbonyl, trifluoromethyl, $C_1$–$C_4$-alkyl, pyridyl and phenyl.

24. The derivative, or pharmaceutically acceptable salt thereof, according to claim 22, wherein $R_1$ and $R_2$ are methyl, and each $R_5$ is H.

25. A quinoline derivative, or a pharmaceutically acceptable salt thereof, wherein the derivative is represented by the following formula (XI):

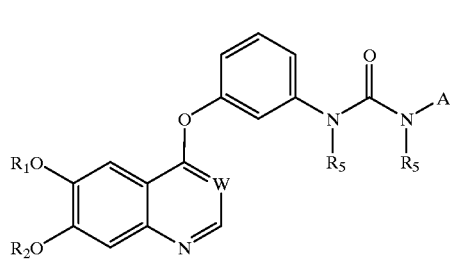

wherein $R_1$ and $R_2$ are each independently $C_1$–$C_5$-alkyl, wherein each $R_5$ is independently H or methyl, and wherein A is $C_1$–$C_5$-alkyl, cyclopentyl, cyclohexyl, cycloheptyl, allyl, $C_1$–$C_4$-alkoxycarbonyl, phenyl, naphthyl or benzoyl.

26. A quinoline derivative, or a pharmaceutically acceptable salt thereof, according to claim 25, wherein, if A is alkyl or aryl, then A has 1–5 substituents selected from the group consisting of OH, $CO_2H$, fluoro, chloro, bromo, iodo, nitro, amino, di-($C_1$–$C_4$-alkyl)amino, ethylenedioxy, acetoxy, methylthio, $C_1$–$C_4$-alkoxycarbonyl, trifluoromethyl, $C_1$–$C_4$-alkyl, $C_1$–$C_4$-alkoxy, pyridyl and phenyl.

27. The derivative, or pharmaceutically acceptable salt thereof, according to any one of claims 1, 11, 13, 14, 16, 18, and 20, wherein the derivative is:

(4-n-butylphenyl){4-[(6,7-dimethoxy-4-quinolyl)oxy]phenyl}methanone, (4-t-butylphenyl){4-[(6,7-dimethoxy-4-quinolyl)oxy]phenyl}methanone, (4-trifluoromethylphenyl){4-[(6,7-dimethoxy-4-quinolyl)oxy]phenyl}methanone, (4-t-butylphenyl){4-[(6,7-dimethoxy-4-quinolyl)methyl]phenyl}methanone, N-{4-[(6,7-dimethoxy-4-quinolyl)oxy]phenyl}-cyclohexanecarboxamide, N-{4-[(6,7-dimethoxy-4-quinolyl)oxy]phenyl}-(4-nitrophenyl)carboxamide, N-{4-[(6,7-dimethoxy-4-quinolyl)oxy]phenyl}-(N,N-dimethylaminophenyl)carboxamide, N-{4-[(6,7-dimethoxy-4-quinolyl)oxy]phenyl}-(4-acetylphenyl)carboxamide, N-{4-[(6,7-dimethoxy-4-quinolyl)oxy]phenyl}-(4-n-butylphenyl)carboxamide, N-{4-[(6,7-dimethoxy-4-quinolyl)oxy]phenyl}-(4-butoxyphenyl)carboxamide, N-{4-[(6,7-dimethoxy-4-quinolyl)oxy]phenyl}-(4-bromophenyl)carboxamide, N-{4-[(6,7-dimethoxy-4-quinolyl)oxy]phenyl}-cyclopentanecarboxamide, N-(4-n-butylphenyl)-N'-{4-[(6,7-dimethoxy-4-quinolyl)oxy]phenyl}urea, N-(4-t-butylphenyl)-N'-{4-[(6,7-dimethoxy-4-quinolyl)oxy]phenyl}urea, N-(2-trifluoromethylphenyl)-N'-{4-[(6,7-dimethoxy-4-quinolyl)oxy]phenyl}urea, N-(3-trifluoromethylphenyl)-N'-{4-[(6,7-dimethoxy-4-quinolyl)oxy]phenyl}urea, N-(4-trifluoromethylphenyl)-N'-{4-[(6,7-dimethoxy-4-quinolyl)oxy]phenyl}urea, N-(2-methoxyphenyl)-N'-{4-[(6,7-dimethoxy-4-quinolyl)oxy]phenyl}urea, N-(3-methoxyphenyl)-N'-{4-[(6,7-dimethoxy-4-quinolyl)oxy]phenyl}urea, N-(4-methoxyphenyl)-N'-{4-[(6,7-dimethoxy-4-quinolyl)oxy]phenyl}urea, N-(2-fluorophenyl)-N'-{4-[(6,7-dimethoxy-4-quinolyl)oxy]phenyl}urea, N-(3-fluorophenyl)-N'-{4-[(6,7-dimethoxy-4-quinolyl)oxy]phenyl}urea, N-(4-fluorophenyl)-N'-{4-[(6,7-dimethoxy-4-quinolyl)oxy]phenyl}urea, N-(4-acetylphenyl)-N'-{4-[(6,7-dimethoxy-4-quinolyl)oxy]phenyl}urea, N-{4-[(6,7-dimethoxy-4-quinolyl)oxy]phenyl}-N'-n-propylurea, N-n-butyl-N'-{4-[(6,7-dimethoxy-4-quinolyl)oxy]phenyl}phenylurea, {4-[(6,7-dimethoxy-4-quinolyl)oxy]phenyl}[4-morpholinophenyl]methanone, {4-[(6,7-dimethoxy-4-quinolyl)oxy]phenyl}[4-pyrrolidinophenyl]methanone, {4-[(6,7-dimethoxy-4-quinolyl)oxy]phenyl}[4-piperidinophenyl]methanone, N-(2,4-dichlorophenyl)-N'-{4-[(6,7-dimethoxy-4-quinolyl)oxy]phenyl}urea, N-(3,4-dichlorophenyl)-N'-{4-[(6,7-dimethoxy-4-quinolyl)oxy]phenyl}urea, N-(3,5-dichlorophenyl)-N'-{4-[(6,7-dimethoxy-4-quinolyl)oxy]phenyl}urea, N-(4-chloro-2-methylphenyl)-N'-{4-[(6,7-dimethoxy-4-quinolyl)oxy]phenyl}urea, N-(3-amino-4-chlorophenyl)-N -{4-[(6,7-dimethoxy-4-quinolyl)oxy]phenyl}urea, N-{4-[(6,7-dimethoxy-4-quinolyl)oxy]phenyl}-N'-(2-pyridylmethyl)urea, N-(3,4-difluorophenyl)-N'-{4-[(6,7-dimethoxy-4-quinolyl)oxy]phenyl}urea, N-(2,4,5-trifluorophenyl)-N'-{4-[(6,7-dimethoxy-4-quinolyl)oxy]phenyl}urea, N-(3-chlorophenyl)-N'-{4-[(6,7-dimethoxy-4quinolyl)oxy]phenyl}urea, or N-(4-hydroxyphenyl)-N'-{4-[(6,7-dimethoxy-4-quinolyl)oxy]phenyl}urea.

28. A pharmaceutical composition comprising a pharmaceutically acceptable carrier and the derivative, or a pharmaceutically acceptable salt thereof, according to claim 1.

29. A pharmaceutical composition comprising a pharmaceutically acceptable carrier and the derivative, or a pharmaceutically acceptable salt thereof, according to any of claims 1, 14, 16, 18, 20, 22, and 25 in an amount effective in inhibiting platelet-derived growth factor receptor autophosphorylation.

30. A pharmaceutical composition comprising a pharmaceutically acceptable carrier and the derivative, or a pharmaceutically acceptable salt thereof, according to any of claims 1, 14, 16, 18, 20, 22 and 25 in an amount effective in treating tumors.

31. A pharmaceutical composition comprising a pharmaceutically acceptable carrier and the derivative, or a pharmaceutically acceptable salt thereof, according to any of claims 1, 14, 16, 18, 20, 22 and 25 in an amount effective in treating psoriasis.

32. A pharmaceutical composition comprising a pharmaceutically acceptable carrier and the derivative, or a pharmaceutically acceptable salt thereof, according to any of claims 1, 14, 16, 18, 20, 22 and 25 in an amount effective in treating atherosclerosis.

33. A pharmaceutical composition comprising a pharmaceutically acceptable carrier and the derivative, or a pharmaceutically acceptable salt thereof, according to any of claims 1, 14, 16, 18, 20, 22 and 25 in an amount effective in treating restenosis after percutaneous coronary angioplasty or bypass surgery.

34. A pharmaceutical composition comprising a pharmaceutically acceptable carrier and the derivative, or a pharmaceutically acceptable salt thereof, according to any of claims 1, 14, 16, 18, 20, 22 and 25 in an amount effective in treating glomerulonephritis.

35. A pharmaceutical composition comprising a pharmaceutically acceptable carrier and the derivative, or a pharmaceutically acceptable salt thereof, according to any of claims 1, 14, 16, 18, 20, 22 and 25 in an amount effective in treating organofibrosis.

36. A pharmaceutical composition comprising a pharmaceutically acceptable carrier and the derivative, or a pharmaceutically acceptable salt thereof, according to any of claims 1, 14, 16, 18, 20, 22 and 25 in an amount effective in treating leukemia.

37. A pharmaceutical composition comprising a pharmaceutically acceptable carrier and the derivative, or a pharmaceutically acceptable salt thereof, according to any of claims 1, 14, 16, 18, 20, 22 and 25 in an amount effective in treating articular rheumatism.

38. A pharmaceutical composition comprising a pharmaceutically acceptable carrier and the derivative, or a pharmaceutically acceptable salt thereof, according to any of claims 7 and 14 in an amount effective in inhibiting platelet-derived growth factor receptor autophosphorylation.

39. A pharmaceutical composition comprising a pharmaceutically acceptable carrier and the derivative, or a pharmaceutically acceptable salt thereof, according to any of claims 10, 18, 20, 22, 24, and 25 in an amount effective in treating tumors.

40. A pharmaceutical composition comprising a pharmaceutically acceptable carrier and the derivative, or a pharmaceutically acceptable salt thereof, according to any of claims 10, 18, 20, 22, 24 and 25 in an amount effective in treating leukemia.

41. A pharmaceutical composition comprising a pharmaceutically acceptable carrier and the derivative, or a pharmaceutically acceptable salt thereof, according to any of claims 10, 18, 20, 22, 24 and 25 in an amount effective in treating articular rheumatism.

42. A method for treating a tumor comprising administering to a patient suffering from a tumor an effective amount of a quinoline derivative, or a pharmaceutically acceptable salt thereof, wherein the derivative is represented by the following formula (I):

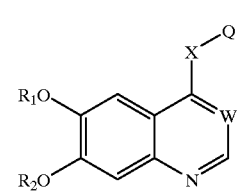

(1)

wherein $R_1$ and $R_2$ are each independently H, $C_1$–$C_5$-alkyl or together form $C_1$–$C_3$-alkylene, wherein W is CH, wherein X is O, S or $CH_2$, wherein Q is a group represented by the following formula (II), (III), (IV) or (V):

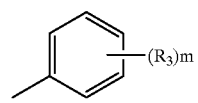

(II)

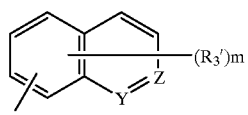

(III)

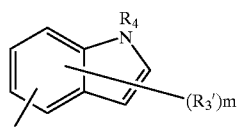

(IV)

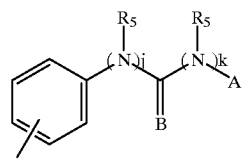

(V)

wherein m is 1, 2 or 3, wherein each $R_3$ is independently CN, OH, halogen, $C_1-C_5$-alkyl, $C_1-C_4$-alkoxy or $C_2-C_4$-acyl, wherein each $R_3'$ is independently OH, $C_1-C_5$-alkyl or $C_1-C_4$-alkoxy, wherein Y and Z are each independently N or CH, wherein $R_4$ is H, $C_1-C_5$-alkyl or $C_2-C_4$-acyl, wherein j and k are each independently 0 or 1, wherein each $R_5$ is independently H or $C_1-C_4$-alkyl, wherein A is $C_1-C_8$-alkyl, $C_1-C_5$-alkenyl, cyclic $(C_3-C_{10})$-alkyl, $C_1-C_4$-alkoxycarbonyl, phenyl, naphthyl, furyl, thienyl, benzoyl, substituted benzoyl, $C_2-C_4$-acyl, or a 5- or 6-membered monocyclic or 9- or 10-membered bicyclic heteroaryl group, wherein the heteroaryl group has 1 or 2 nitrogen atoms, wherein B is O, S, NH, NCN, $NR_6$ or $NOR_6$, and wherein $R_6$ is $C_1-C_5$-alkyl, with the proviso that if X is $CH_2$, then Q is not a group represented by the formula (II), (III) or (IV).

43. The method of claim 42, wherein the tumor is neoplastic.

44. A method for treating psoriasis comprising administering to a patient suffering from psoriasis an effective amount of a quinoline derivative, or a pharmaceutically acceptable salt thereof, wherein the derivative is represented by the following formula (I):

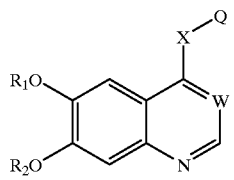

(1)

wherein $R_1$ and $R_2$ are each independently H, $C_1-C_5$-alkyl or together form $C_1-C_3$-alkylene, wherein W is CH, wherein X is O, S or $CH_2$, wherein Q is a group represented by the following formula (II), (III), (IV) or (V):

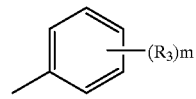

(II)

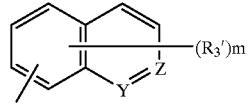

(III)

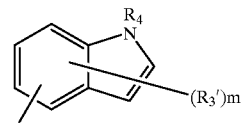

(IV)

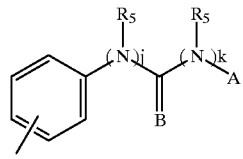

(V)

wherein m is 1, 2 or 3, wherein each $R_3$ is independently CN, OH, halogen, $C_1-C_5$-alkyl, $C_1-C_4$-alkoxy or $C_2-C_4$-acyl, wherein each $R_3'$ is independently OH, $C_1-C_5$-alkyl or $C_1-C_4$-alkoxy, wherein Y and Z are each independently N or CH, wherein $R_4$ is H, $C_1-C_5$-alkyl or $C_2-C_4$-acyl, wherein j and k are each independently 0 or 1, wherein each $R_5$ is independently H or $C_1-C_4$-alkyl, wherein A is $C_1-C_8$-alkyl, $C_1-C_5$-alkenyl, cyclic $(C_3-C_{10})$-alkyl, $C_1-C_4$-alkoxycarbonyl, phenyl, naphthyl, furyl, thienyl, benzoyl, substituted benzoyl, $C_2-C_4$-acyl, or a 5- or 6-membered monocyclic or 9- or 10-membered bicyclic heteroaryl group, wherein the heteroaryl group has 1 or 2 nitrogen atoms, wherein B is O, S, NH, NCN, $NR_6$ or $NOR_6$, and wherein $R_6$ is $C_1-C_5$-alkyl, with the proviso that if X is $CH_2$, then Q is not a group represented by the formula (II), (III) or (IV).

45. A method for treating atherosclerosis comprising administering to a patient suffering from atherosclerosis an effective amount of a quinoline derivative, or a pharmaceutically acceptable salt thereof, wherein the derivative is represented by the following formula (I):

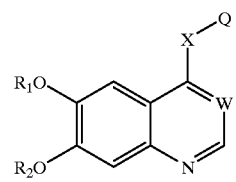

(1)

wherein $R_1$ and $R_2$ are each independently H, $C_1-C_5$-alkyl or together form $C_1-C_3$-alkylene, wherein W is CH, wherein X is O, S or $CH_2$, wherein Q is a group represented by the following formula (II), (III), (IV) or (V):

(II)
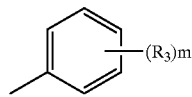

(III)
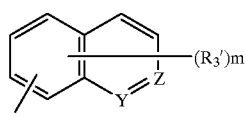

(IV)
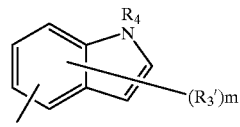

(V)
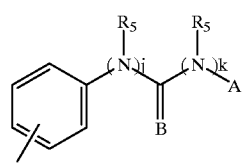

wherein m is 1, 2 or 3, wherein each $R_3$ is independently CN, OH, halogen, $C_1$–$C_5$-alkyl, $C_1$–$C_4$-alkoxy or $C_2$–$C_4$-acyl, wherein each $R_3'$ is independently OH, $C_1$–$C_5$-alkyl or $C_1$–$C_4$-alkoxy, wherein Y and Z are each independently N or CH, wherein $R_4$ is H, $C_1$–$C_5$-alkyl or $C_2$–$C_4$-acyl, wherein j and k are each independently 0 or 1, wherein each $R_5$ is independently H or $C_1$–$C_4$-alkyl, wherein A is $C_1$–$C_8$-alkyl, $C_1$–$C_5$-alkenyl, cyclic ($C_3$–$C_{10}$)-alkyl, $C_1$–$C_4$-alkoxycarbonyl, phenyl, naphthyl, furyl, thienyl, benzoyl, substituted benzoyl, $C_2$–$C_4$-acyl, or a 5- or 6-membered monocyclic or 9- or 10-membered bicyclic heteroaryl group, wherein the heteroaryl group has 1 or 2 nitrogen atoms, wherein B is O, S, NH, NCN, $NR_6$ or $NOR_6$, and wherein $R_6$ is $C_1$–$C_5$-alkyl, with the proviso that if X is $CH_2$, then Q is not a group represented by the formula (II), (III) or (IV).

46. A method for treating restenosis after percutaneous coronary angioplasty or bypass surgery comprising administering to a patient suffering from restenosis after percutaneous coronary angioplasty or bypass surgery an effective amount of a quinoline derivative, or a pharmaceutically acceptable salt thereof, wherein the derivative is represented by the following formula (I):

(1)
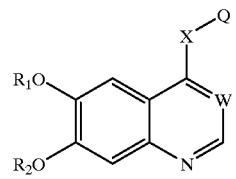

wherein $R_1$ and $R_2$ are each independently H, $C_1$–$C_5$-alkyl or together form $C_1$–$C_3$-alkylene, wherein W is CH, wherein X is O, S or $CH_2$, wherein Q is a group represented by the following formula (II), (III), (IV) or (V):

(II)
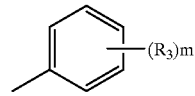

(III)
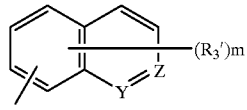

(IV)
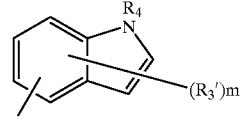

(V)
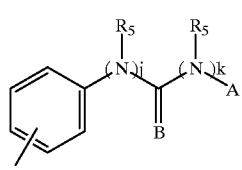

wherein m is 1, 2 or 3, wherein each $R_3$ is independently CN, OH, halogen, $C_1$–$C_5$-alkyl, $C_1$–$C_4$-alkoxy or $C_2$–$C_4$-acyl, wherein each $R_3'$ is independently OH, $C_1$–$C_5$-alkyl or $C_1$–$C_4$-alkoxy, wherein Y and Z are each independently N or CH, wherein $R_4$ is H, $C_1$–$C_5$-alkyl or $C_2$–$C_4$-acyl, wherein j and k are each independently 0 or 1, wherein each $R_5$ is independently H or $C_1$–$C_4$-alkyl, wherein A is $C_1$–$C_5$-alkyl, $C_1$–$C_5$-alkenyl, cyclic ($C_3$–$C_{10}$)-alkyl, $C_1$–$C_4$-alkoxycarbonyl, phenyl, naphthyl, furyl, thienyl, benzoyl, substituted benzoyl, $C_2$–$C_4$-acyl, or a 5- or 6-membered monocyclic or 9- or 10-membered bicyclic heteroaryl group, wherein the heteroaryl group has 1 or 2 nitrogen atoms, wherein B is O, S, NH, NCN, $NR_6$ or $NOR_6$, and wherein $R_6$ is $C_1$–$C_5$-alkyl, with the proviso that if X is $CH_2$, then Q is not a group represented by the formula (II), (III) or (IV).

47. A method for treating glomerulonephritis comprising administering to a patient suffering from glomerulonephritis an effective amount of a quinoline derivative, or a pharmaceutically acceptable salt thereof, wherein the derivative is represented by the following formula (I):

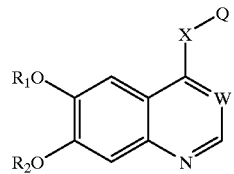

(1)

wherein $R_1$ and $R_2$ are each independently H, $C_1$–$C_5$-alkyl or together form $C_1$–$C_3$-alkylene, wherein W is CH, wherein X is O, S or $CH_2$, wherein Q is a group represented by the following formula (II), (III), (IV) or (V):

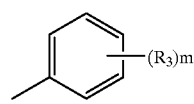

(II)

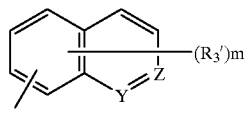

(III)

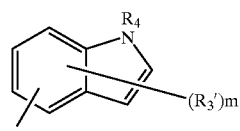

(IV)

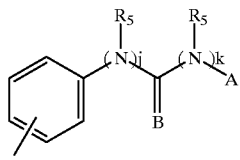

(V)

wherein m is 1, 2 or 3, wherein each $R_3$ is independently CN, OH, halogen, $C_1$–$C_5$-alkyl, $C_1$–$C_4$-alkoxy or $C_2$–$C_4$-acyl, wherein each $R_3'$ is independently OH, $C_1$–$C_5$-alkyl or $C_1$–$C_4$-alkoxy, wherein Y and Z are each independently N or CH, wherein $R_4$ is H, $C_1$–$C_5$-alkyl or $C_2$–$C_4$-acyl, wherein j and k are each independently 0 or 1, wherein each $R_5$ is independently H or $C_1$–$C_4$-alkyl, wherein A is $C_1$–$C_5$-alkyl, $C_1$–$C_5$-alkenyl, cyclic ($C_3$–$C_{10}$)-alkyl, $C_1$–$C_4$-alkoxycarbonyl, phenyl, naphthyl, furyl, thienyl, benzoyl, substituted benzoyl, $C_2$–$C_4$-acyl, or a 5- or 6-membered monocyclic or 9- or 10-membered bicyclic heteroaryl group, wherein the heteroaryl group has 1 or 2 nitrogen atoms, wherein B is O, S, NH, NCN, $NR_6$ or $NOR_6$, and wherein $R_6$ is $C_1$–$C_5$-alkyl, with the proviso that if X is $CH_2$, then Q is not a group represented by the formula (II), (III) or (IV).

48. A method for treating organofibrosis comprising administering to a patient suffering from organofibrosis an effective amount of a quinoline derivative, or a pharmaceutically acceptable salt thereof, wherein the derivative is represented by the following formula (I):

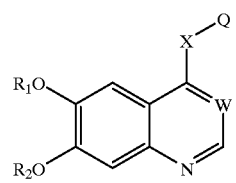

(1)

wherein $R_1$ and $R_2$ are each independently H, $C_1$–$C_5$-alkyl or together form $C_1$–$C_3$-alkylene, wherein W is CH, wherein X is O, S or $CH_2$, wherein Q is a group represented by the following formula (II), (III), (IV) or (V):

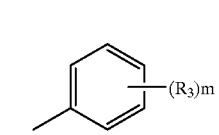

(II)

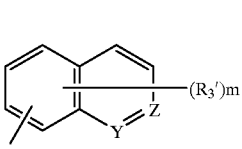

(III)

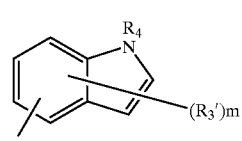

(IV)

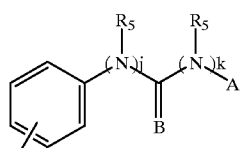

(V)

wherein m is 1, 2 or 3, wherein each $R_3$ is independently CN, OH, halogen, $C_1$–$C_5$-alkyl, $C_1$–$C_4$-alkoxy or $C_2$–$C_4$-acyl, wherein each $R_3'$ is independently OH, $C_1$–$C_5$-alkyl or $C_1$–$C_4$-alkoxy, wherein Y and Z are each independently N or CH, wherein $R_4$ is H, $C_1$–$C_5$-alkyl or $C_2$–$C_4$-acyl, wherein j and k are each independently 0 or 1, wherein each $R_5$ is independently H or $C_1$–$C_4$-alkyl, wherein A is $C_1$–$C_8$-alkyl, $C_1$–$C_5$-alkenyl, cyclic ($C_3$–$C_{10}$)-alkyl, $C_1$–$C_4$-alkoxycarbonyl, phenyl, naphthyl, furyl, thienyl, benzoyl, substituted benzoyl, $C_2$–$C_4$-acyl, or a 5- or 6-membered monocyclic or 9- or 10-membered bicyclic heteroaryl group, wherein the heteroaryl group has 1 or 2 nitrogen atoms, wherein B is O, S, NH, NCN, $NR_6$ or $NOR_6$, and wherein $R_6$ is $C_1$–$C_5$-alkyl, with the proviso that if X is $CH_2$, then Q is not a group represented by the formula (II), (III) or (IV).

49. A method for treating leukemia comprising administering to a patient suffering from leukemia an effective amount of a quinoline derivative, or a pharmaceutically acceptable salt thereof, wherein the derivative is represented by the following formula (I):

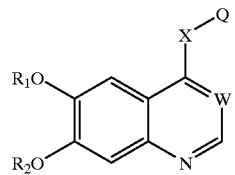

(1)

wherein $R_1$ and $R_2$ are each independently H, $C_1$–$C_5$-alkyl or together form $C_1$–$C_3$-alkylene,
wherein W is CH,
wherein X is O, S or $CH_2$,
wherein Q is a group represented by the following formula (II), (III), (IV) or (V):

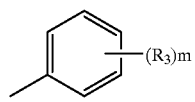

(II)

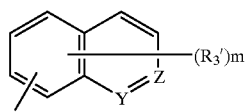

(III)

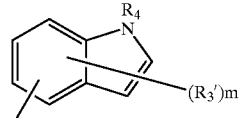

(IV)

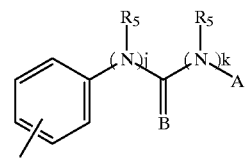

(V)

wherein m is 1, 2 or 3,
wherein each $R_3$ is independently CN, OH, halogen, $C_1$–$C_5$-alkyl, $C_1$–$C_4$-alkoxy or $C_2$–$C_4$-acyl,
wherein each $R_3'$ is independently OH, $C_1$–$C_5$-alkyl or $C_1$–$C_4$-alkoxy,
wherein Y and Z are each independently N or CH,
wherein $R_4$ is H, $C_1$–$C_5$-alkyl or $C_2$–$C_4$-acyl,
wherein j and k are each independently 0 or 1,
wherein each $R_5$ is independently H or $C_1$–$C_4$-alkyl,
wherein A is $C_1$–$C_8$-alkyl, $C_1$–$C_5$-alkenyl, cyclic $(C_3$–$C_{10})$-alkyl, $C_1$–$C_4$-alkoxycarbonyl, phenyl, naphthyl, furyl, thienyl, benzoyl, substituted benzoyl, $C_2$–$C_4$-acyl, or a 5- or 6-membered monocyclic or 9- or 10-membered bicyclic heteroaryl group,
wherein the heteroaryl group has 1 or 2 nitrogen atoms, wherein B is O, S, NH, NCN, $NR_6$ or $NOR_6$, and
wherein $R_6$ is $C_1$–$C_5$-alkyl,
with the proviso that if X is $CH_2$, then Q is not a group represented by the formula (II), (III) or (IV).

50. A method for treating articular rheumatism comprising administering to a patient suffering from articular rheumatism an effective amount of a quinoline derivative, or a pharmaceutically acceptable salt thereof, wherein the derivative is represented by the following formula (I):

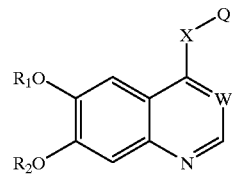

(1)

wherein $R_1$ and $R_2$ are each independently H, $C_1$–$C_5$-alkyl or together form $C_1$–$C_3$-alkylene,
wherein W is CH,
wherein X is O, S or $CH_2$,
wherein Q is a group represented by the following formula (II), (III), (IV) or (V):

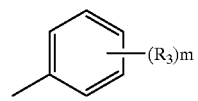

(II)

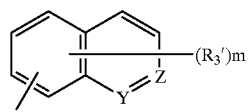

(III)

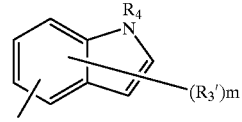

(IV)

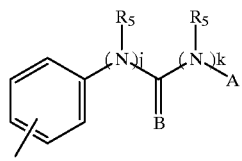

(V)

wherein m is 1, 2 or 3,
wherein each $R_3$ is independently CN, OH, halogen, $C_1$–$C_5$-alkyl, $C_1$–$C_4$-alkoxy or $C_2$–$C_4$-acyl,
wherein each $R_3'$ is independently OH, $C_1$–$C_5$-alkyl or $C_1$–$C_4$-alkoxy,
wherein Y and Z are each independently N or CH,
wherein $R_4$ is H, $C_1$–$C_5$-alkyl or $C_2$–$C_4$-acyl,
wherein j and k are each independently 0 or 1,
wherein each $R_5$ is independently H or $C_1$–$C_4$-alkyl,
wherein A is $C_1$–$C_5$-alkyl, $C_1$–$C_5$-alkenyl, cyclic $(C_3$–$C_{10})$-alkyl, $C_1$–$C_4$-alkoxycarbonyl, phenyl, naphthyl, furyl, thienyl, benzoyl, substituted benzoyl, $C_2$–$C_4$-acyl, or a 5- or 6-membered monocyclic or 9- or 10-membered bicyclic heteroaryl group, wherein the heteroaryl group has 1 or 2 nitrogen atoms,
wherein B is O, S, NH, NCN, $NR_6$ or $NOR_6$, and
wherein $R_6$ is $C_1$–$C_5$-alkyl, with the proviso that if X is $CH_2$, then Q is not a group represented by the formula (II), (III) or (IV).

51. The method according to any one of claims 42–50, wherein the heteroaryl group has another heteroatom selected from the group consisting of N, O and S.

52. The method according to any one of claims 42–40, wherein, if A is alkyl, aryl or heteroaryl, then A has 1 to 5 substituents selected from the group consisting of CN, $NO_2$, OH, $NH_2$, halogen $C_1$–$C_5$-alkyl, cyclic ($C_3$–$C_{10}$) alkyl, $C_1$–$C_4$-alkoxy, $C_1$–$C_4$-alkoxycarbonyl, $C_1$–$C_5$-acyl, $C_1$–$C_5$-acyloxy, $C_1$–$C_3$-alkylenedioxy, $C_1$–$C_4$-alkylamino, di-($C_1$–$C_4$-alkyl)amino, $CO_2H$, $CONH_2$, N-($C_1$–$C_4$-alkyl)amido, N,N-di-($C_1$–$C_4$-alkyl)amido, $C_2$–$C_4$-alkylamido, trifluoromethyl, $C_1$–$C_4$-alkylthio, phenyl, substituted phenyl, phenoxy, substituted phenoxy, phenylthio, substituted phenylthio, phenyl($C_1$–$C_4$-alkyl), substituted phenyl ($C_1$–$C_4$-alkyl), pyridyl, pyrazinyl, pyrimidinyl, pyridazinyl, pyrrolidinyl, piperidinyl, piperazinyl, homopyperazinyl, morpholinyl, quinolyl, quinazolinyl, benzoyl, substituted benzoyl and $C_2$–$C_4$-acyl.

* * * * *